United States Patent [19]

Hibino et al.

[11] Patent Number: 5,060,632

[45] Date of Patent: Oct. 29, 1991

[54] ENDOSCOPE APPARATUS

[75] Inventors: Hiroki Hibino; Yoshikatsu Nagayama; Mutsumi Yoshikawa, all of Hachioji; Toshiyuki Takara, Higashimurayama; Masahito Goto; Akira Suzuki, both of Hachioji; Sakae Takehana, Machida; Yoshinao Oaki, Hachioji; Koichi Hoshimitsu, Hachioji; Yoshisada Aoki, Hachioji; Yasuhiro Ueda, Kokubunji; Raifu Matsui, Hino, all of Japan

[73] Assignee: Olympus Optical Co., Ltd., Tokyo, Japan

[21] Appl. No.: 535,252

[22] Filed: Jun. 8, 1990

[30] Foreign Application Priority Data

| | | | |
|---|---|---|---|
| Sep. 5, 1989 | [JP] | Japan | 1-230235 |
| Oct. 18, 1989 | [JP] | Japan | 1-121980[U] |
| Mar. 20, 1990 | [JP] | Japan | 2-71086 |
| Mar. 22, 1990 | [JP] | Japan | 2-75142 |
| Apr. 20, 1990 | [JP] | Japan | 2-105821 |
| Apr. 20, 1990 | [JP] | Japan | 2-105822 |
| Apr. 20, 1990 | [JP] | Japan | 2-105823 |
| Apr. 20, 1990 | [JP] | Japan | 2-105824 |
| Apr. 20, 1990 | [JP] | Japan | 2-105825 |
| Apr. 20, 1990 | [JP] | Japan | 2-105826 |

[51] Int. Cl.[5] .................. A63B 1/04
[52] U.S. Cl. .................. 128/6; 358/98
[58] Field of Search .................. 128/4, 6; 358/98

[56] References Cited

U.S. PATENT DOCUMENTS

| | | | |
|---|---|---|---|
| 4,499,895 | 2/1985 | Takayama | 128/6 |
| 4,503,842 | 3/1985 | Takayama | 128/4 |
| 4,559,928 | 12/1985 | Takayama | 128/6 |
| 4,618,884 | 10/1986 | Nagasaki | 128/4 X |
| 4,870,951 | 10/1989 | Suzuki | 128/6 |

FOREIGN PATENT DOCUMENTS

| | | |
|---|---|---|
| 2504663C2 | 10/1982 | Fed. Rep. of Germany . |
| 55-126804 | 9/1980 | Japan . |
| 58-78635 | 5/1983 | Japan . |
| 59-33402 | 3/1984 | Japan . |
| 59-181122 | 10/1984 | Japan . |
| 1-37927 | 2/1989 | Japan . |
| 1-229218 | 9/1989 | Japan . |

*Primary Examiner*—William H. Grieb
*Attorney, Agent, or Firm*—Armstrong, Nikaido, Marmelstein, Kubovcik & Murray

[57] ABSTRACT

An endoscope apparatus comprises an elongate insert section including an observation window in the distal end portion and inserted into an object to be observed; an observation device for producing an endoscope image, the observation device including a focusing optical system which receives an incident light from the object through the observation window to focus the endoscope image; and a vibration device for vibrating at least a part of the insert section in a direction crossing the axial direction of the insert section, the vibration device including a vibration unit capable of vibrating in itself to vibrate at least the part of the insert section even under a condition that the insert section is not contact with the object.

29 Claims, 88 Drawing Sheets

FIG.13(a) SWITCH 10a ON OFF
FIG.13(b) SWITCH 10b ON OFF
FIG.13(c) SWITCH 10c ON OFF
FIG.13(d) JOY STICK 8 U D R L
FIG.13(e) JOY STICK 9 Push Pull R-ROTATION L-ROTATION
FIG.13(f) SWITCH 25a
PARALLEL MINUTE VIBRATION MODE
FIG.13(g) SWITCH 25c
LOW SPEED
HIGH SPEED
LOW SPEED
FIG.13(h) SWITCH 25d
NARROW ANGLE
WIDE ANGLE
FIG.13(i) SPEED CONTROL CIRCUIT 29a
FIG.13(j) ROTATING DIRECTION INDICATION CIRCUIT 30a H L

FIG.14(a) SWITCH 10a ON OFF
FIG.14(b) SWITCH 10b ON OFF
FIG.14(c) SWITCH 10c ON OFF
FIG.14(d) JOY STICK 8 U D R L
FIG.14(e) JOY STICK 9 Push Pull R-ROTATION L-ROTATION
FIG.14(f) SWITCH 25a
PARALLEL MINUTE VIBRATION MODE
FIG.14(g) SWITCH 25c
LOW SPEED
FIG.14(h) SWITCH 25d
NARROW ANGLE
FIG.14(i) SPEED CONTROL CIRCUIT 29a
FIG.14(j) ROTATING DIRECTION INDICATION CIRCUIT 30a H L

FIG.15(a) SWITCH 10a ON OFF
FIG.15(b) SWITCH 10b ON OFF
FIG.15(c) SWITCH 10c ON OFF
FIG.15(d) JOY STICK 8 U D R L
FIG.15(e) JOY STICK 9 Push Pull R-ROTATION L-ROTATION
FIG.15(f) SWITCH 25a
FIG.15(g) SWITCH 25c
FIG.15(h) SWITCH 25d
FIG.15(i) SPEED CONTROL CIRCUIT 29a
FIG.15(j) ROTATING DIRECTION INDICATION CIRCUIT 30a H L

FIG.15(p) 30d H L
ORTHOGONAL MINUTE VIBRATION MODE
LOW SPEED
NARROW ANGLE

FIG.17(a) SWITCH 10a ON OFF
FIG.17(b) SWITCH 10b ON OFF
FIG.17(c) SWITCH 10c ON OFF
FIG.17(d) JOY STICK 8 U D R L
FIG.17(e) JOY STICK 9 Push Pull R-ROTATION L-ROTATION
FIG.17(f) SWITCH 25a PARALLEL MINUTE VIBRATION MODE
FIG.17(g) SWITCH 25c ROTATION & BENDING NARROW ANGLE
FIG.17(h) SWITCH 25d ROTATION & BENDING LOW SPEED
FIG.17(i) SPEED CONTROL CIRCUIT 29a
FIG.17(j) ROTATING DIRECTION INDICATION CIRCUIT 30a H L

FIG.19(a) SWITCH 10a ON OFF
FIG.19(b) SWITCH 10b ON OFF
FIG.19(c) SWITCH 10c ON OFF
FIG.19(d) JOY STICK 8 U D R L
FIG.19(e) JOY STICK 9 Push Pull R-ROTATION L-ROTATION
FIG.19(f) SWITCH 25a
PARALLEL MINUTE VIBRATION MODE
FIG.19(g) SWITCH 25c
NARROW ANGLE
FIG.19(h) SWITCH 25d
LOW SPEED
FIG.19(i) SPEED CONTROL CIRCUIT 29a
FIG.19(j) ROTATING DIRECTION INDICATION CIRCUIT 30a H L

| INSERTED LENGTH | MIN. MOVING VIB. | SPEED | LENGTH |
|---|---|---|---|
| 0  50  100 ▭ | [ON] OFF | [L] M H | N M [W] |
| ROTATING ANGLE OF INSERT SECTION  L 90°— R 90° | MIN. ROTATING VIB. [ON] OFF | [L] M H | ANGLE N M [W] |
| BENDING ANGLE  U L—R 90° 180° D | MIN. BENDING VIB. [ON] OFF | [L] M H | N M [W] |

MODE

[PAR. MIN. VIB.]   ORTH. MIN. VIB.

LEFTWARD SWING    RIGHTWARD SWING

BENDING RESISTANCE

U
L ━╋━ R
D

FIG. 34
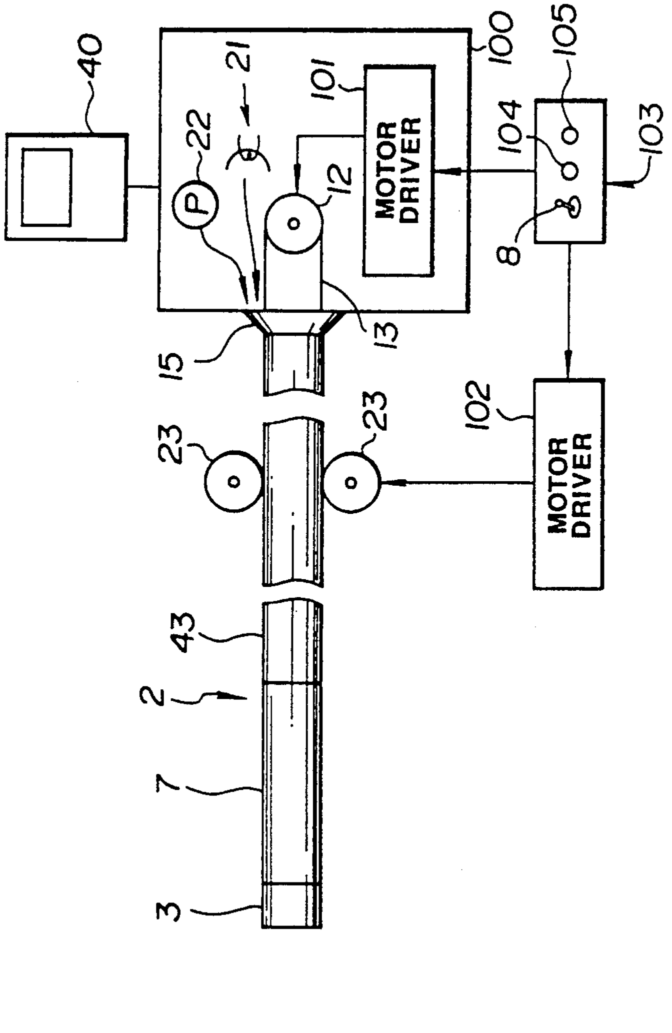
FIG. 35(a)
FIG. 35(b)
FIG. 35(c)
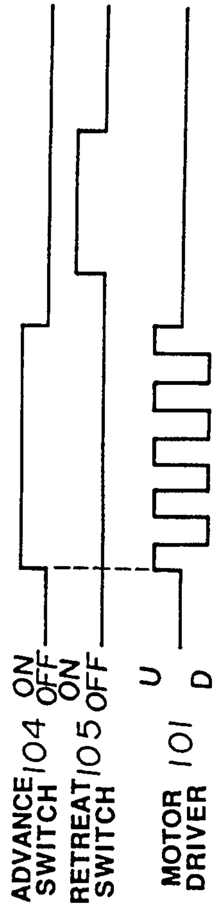

FIG.42(a) BENDING RESISTANCE DETECTION OUTPUT
FIG.42(b) SWITCH 10a ON OFF
FIG.42(c) SWITCH 10b ON OFF
FIG.42(d) SWITCH 10c ON OFF
FIG.42(e) JOY STICK 8 U D R L
FIG.42(f) JOY STICK 9 Push Pull R-ROTATION L-ROTATION
FIG.42(g) SWITCH 25a
FIG.42(h) SWITCH 25c
FIG.42(i) SWITCH 25d
FIG.42(j) SPEED CONTROL CIRCUIT 29a
FIG.42(k) ROTATING DIRECTION INDICATION CIRCUIT 30a H L

FIG.42(q) 30d H L
NARROW ANGLE
LOW SPEED

FIG.45(a) SWITCH 10a ON OFF
FIG.45(b) SWITCH 10a ON OFF
FIG.45(c) SWITCH 10a ON OFF
FIG.45(d) JOY STICK 8 U D R L
FIG.45(e) JOY STICK 9 Push Pull R-ROTATION L-ROTATION
FIG.45(f) SWITCH 25a
FIG.45(g) SWITCH 25c
FIG.45(h) SWITCH 25d
FIG.45(i) SPEED CONTROL CIRCUIT 29a
FIG.45(j) ROTATING DIRECTION INDICATION CIRCUIT 30a H L

FIG.45(p) 30d H L
PARALLEL MINUTE VIBRATION MODE
NARROW ANGLE
WIDE ANGLE
HIGH SPEED
LOW SPEED

ENDOSCOPE APPARATUS

BACKGROUND OF THE INVENTION

1. Field of the Invention

The present invention relates to an endoscope apparatus which can be inserted with improved operability.

2. Related Art Statement

Conventionally, there have widely been used endoscopes (scopes or fiber scopes) of which elongate insert sections can be inserted into the body cavities for diagnosing or examining internal organs of a living body and the like. In addition to the medical field, endoscopes have been used in the engineering field as well to observe or check objects such as interiors of pipes or machines of boilers, machinery, chemical plants, etc.

Further, various types of endoscopes using solid imaging devices, e.g., charge coupled devices (CCD's), as imaging means have also been practiced.

The endoscope comprises, for example, an elongate and flexible insert section, a larger-diameter grip section continuously provided at the rear end of the insert section, and so fourth. The insert section comprises a hard distal end component, a bendable portion continuously provided at the rear end of the distal end component and capable of bending upwards, downwards, rightwards and leftwards, for example, and a flexible pipe portion continuously provided at the rear end of the bendable portion.

The bendable portion has an outer covering member made of a bendable material such as rubber.

However, use of the bendable rubber is problematic in that when it strongly contacts an object to be examined, e.g., a wall of the body cavity, the contact resistance is increased, which makes it hard to further insert the insert section.

Meanwhile, Japanese Patent Laid-Open No. 229218/1989 discloses a technique which utilizes a fluid intermittently supplied to the insert section, for lifting a part of the insert section in an intermittent manner so as to vibrate the insert section. With this technique, however, since the fluid is jetted against the object to be examined and the resulting counteraction is utilized to vibrate the insert section, the object is subjected to a large impact and hence a problem arises when applied to medical endoscopes, in particular.

OBJECTS AND SUMMARY OF THE INVENTION

It is a principal object of the present invention to provide an endoscope apparatus which allows an insert section to be easily inserted even under a condition that the contact resistance between the insert section and an object to be examined is large, and which can reduce an impact against the object during the insertion.

In particular, the present invention has an object to facilitate insertion of the insert section into a bent location of the body cavity, especially, insertion thereof from the descending colon to the transverse colon.

Practically, the above objects are achieved by vibrating at least one part of the insert section even under a condition that the insert section is not in contact with the object.

The vibration is performed in the vertically (upward/downward) or horizontally (rightward/leftward) directions, in the form of swing motion in which the distal end draws a circle, or in the form of movement (advance/retreat) motion. By appropriately selecting those various forms of vibration, the above objects can be achieved.

A range of the vibration may be selected to cover the entire length of the insert section or only the distal end side thereof. In the case of having a bendable portion, the bendable portion may be vibrated. Also, the bendable portion may be vibrated while bending it.

The vibration of the insert section is advantageous in that if the insert section happens to make a loop when it is inserted from the descending colon to the horizontal colon region, a force for making the insert section straight is produced by vibrating the insert section, and hence the insert section can easily be inserted without causing a patient to suffer pain.

The endoscope apparatus of the present invention comprises an elongate insert section including an observation window in the distal end portion and inserted into an object to be observed; observation means for producing an endoscope image, the observation means including an focusing optical system which receives an incident light from the object through the observation window to focus the endoscope image; and vibration means for vibrating at least a part of the insert section in a direction crossing the axial direction of the insert section, the vibration means including a vibration unit capable of vibrating in itself to vibrate at least the part of the insert section even under a condition that the insert section is not contact with the object.

Other features and advantages of the present invention will be apparent in full from the following description.

BRIEF DESCRIPTION OF THE DRAWINGS

FIGS. 1 and 2 are concerned with a first embodiment of the present invention in which;

FIG. 1 is a block diagram showing the constitution of an endoscope apparatus, and FIG. 2 is a block diagram showing the constitution of an ultrasonic motor control circuit.

FIGS. 3 and 4 are concerned with a second embodiment of the present invention in which;

FIG. 3 is a diagrammatic view of a minute vibration control circuit, and

FIG. 4 is an explanatory chart of output signals from an output circuit of the minute vibration control circuit.

FIGS. 9 through 27 are concerned with a sixth embodiment of the present invention in which;

FIG. 9 is a block diagram showing the constitution of an endoscope apparatus, FIG. 10 is an explanatory view showing an appearance of the endoscope apparatus, FIG. 11 is a block diagram showing the constitution of a bending/movement (advance and retreat)/rotation control circuit, FIG. 12 is a timing chart for explaining operation of the endoscope apparatus during the normal bending process, FIG. 13 is a timing chart for explaining operation of the endoscope apparatus during the non-bending process in a parallel minute vibration mode, FIG. 14 is a timing chart for explaining operation of the endoscope apparatus during the bending process in a parallel minute vibration mode, FIG. 15 is a timing chart for explaining operation of the endoscope apparatus in an orthogonal minute vibration mode, FIG. 16 is a timing chart for explaining operation of the endoscope apparatus during a swing motion, FIG. 17 is a timing chart for explaining operation of the endoscope apparatus during the process of a minute rotating vibration and a minute bending vibration, FIG. 18 is a timing chart for explaining operation of the endoscope apparatus when conditions of the minute rotating vibration are changed, FIG. 19 is a timing chart for explaining operation of the endoscope apparatus during the process of a minute moving (advancing/retreating) vibration and a minute bending vibration, FIG. 20 is a timing chart for explaining operation of the endoscope apparatus when conditions of the minute moving vibration are changed, FIG. 21 is an explanatory view showing a minute vibration in the upward and downward directions, FIG. 22 is an explanatory view showing a minute vibration in the rightward and leftward directions, FIG. 23 is an explanatory view showing a rightward swing motion, FIG. 24 is an explanatory view showing a leftward swing motion, FIG. 25 is an explanatory view showing a minute moving (advancing/retreating) vibration, FIG. 26 is an explanatory view showing a minute rotating vibration, and FIG. 27 is an explanatory view showing a part of mode display section of a monitor.

FIGS. 28 and 29 are concerned with a seventh embodiment of the present invention in which;

FIG. 28 is a block diagram showing the constitution of an endoscope apparatus, and FIG. 29 is an explanatory view showing an appearance of the endoscope apparatus.

FIGS. 30 and 31 are concerned with an eighth embodiment of the present invention in which;

FIG. 30 is a block diagram showing the constitution of an endoscope apparatus, and FIG. 31 is an explanatory view showing an appearance of the endoscope apparatus.

FIGS. 32 and 33 are concerned with a ninth embodiment of the present invention in which;

FIG. 32 is a block diagram showing the constitution of an endoscope apparatus, and FIG. 33 is an explanatory view showing an appearance of the endoscope apparatus.

FIGS. 34 through 36 are concerned with a tenth embodiment of the present invention in which;

FIG. 34 is a block diagram showing the constitution of an endoscope apparatus,

FIG. 35 is a timing chart for explaining operation of this embodiment, and

FIG. 36 is an explanatory view showing an appearance of the endoscope apparatus.

FIGS. 37 and 38 are concerned with an eleventh embodiment of the present invention in which;

FIG. 37 is an explanatory view showing the constitution of an endoscope apparatus, and FIG. 38 is an explanatory view showing an appearance of the endoscope apparatus.

FIGS. 43 and 44 are concerned with a sixteenth embodiment of the present invention in which;

FIG. 43 is an explanatory view showing important components of a controller, and FIG. 44 is a timing chart for explaining operation of an endoscope apparatus.

FIGS. 49 through 53 are concerned with a twenty-first embodiment of the present invention in which;

FIG. 49 is a sectional view of an operating section of an endoscope apparatus and thereabout, FIG. 50 is an explanatory view schematically showing the constitution of the endoscope apparatus, FIG. 51 is a sectional view of a distal end component of an insert section of the endoscope, FIG. 52 is a perspective view of the operating section of the endoscope apparatus and thereabout, and FIG. 53 is an explanatory view showing the state that the operating section is gripped.

FIGS. 54 and 55 are concerned with a twenty-second embodiment of the present invention in which;

FIG. 54 is a sectional view of an operating section of an endoscope apparatus and thereabout, and FIG. 55 is an explanatory view schematically showing the constitution of the endoscope apparatus.

FIGS. 56 through 59 are concerned with three examples that driven members other than a bendable portion are driven by a motor mounted in an extended base section, in which;

FIG. 56 is an explanatory view schematically showing the constitution of an endoscope of the first example, FIG. 57 is a sectional view of a distal end component of insert section of the endoscope of the first example, FIG. 58 is an explanatory view showing a distal end component of insert section of an endoscope of the second example, and FIG. 59 is an explanatory view showing a distal end component of insert section of the endoscope of the third example.

FIGS. 62 through 66 are concerned with a twenty-third embodiment of the present invention in which;

FIG. 62 is a longitudinal sectional view of an endoscope's insert section,

FIG. 63 is a cross-sectional view of the endoscope's insert section,

FIG. 64 is an explanatory view showing the entire constitution of an endoscope apparatus, FIG. 65 is an explanatory view showing the configurative form of the insert section when a bendable portion is driven, and FIG. 66 is an explanatory view showing the state that the insert section is inserted into a tract of a living body.

FIGS. 67 and 68 are concerned with a twenty-fourth embodiment of the present invention in which;

FIG. 67 is an explanatory view showing the entire constitution of an endoscope apparatus, and FIG. 68 is an explanatory view showing the configurative form of an insert section when a bendable portion is driven.

FIGS. 69 through 75 are concerned with a twenty-fifth embodiment of the present invention in which;

FIG. 69 is an explanatory view showing the entire constitution of an endoscope apparatus, FIG. 70 is a perspective view showing a first example of a bending unit, FIG. 71 is a perspective view showing a second example of the bending unit, FIG. 72 is a perspective view showing a third example of the bending unit, FIG. 73 is an explanatory view showing important components of the bending unit of FIG. 72, FIG. 74 is a perspective view showing a fourth example of the bending unit, and FIG. 75 is a perspective view showing a fifth example of the bending unit.

FIGS. 76 through 88 are concerned with three examples of an endoscope apparatus using an oscillating wave motor which can perform bending operation even under a condition that load exceeding a certain value is applied:

FIGS. 76 through 82 are concerned with the first example in which;

FIG. 76 is a block diagram showing the constitution of the endoscope apparatus,

FIG. 77 is a block diagram showing a control mechanism of the ultrasonic motor,

FIG. 78 is a characteristic graph showing frequency characteristics of the ultrasonic motor, FIG. 79 is a characteristic graph showing the relationships between torque and revolution speed of the ultrasonic motor, FIGS. 80 and 81 are each a timing chart for explaining operation of a ring counter, and FIG. 82 is a graph showing waveforms of voltage supplied to the ultrasonic motor in a condition of FIG. 80;

FIGS. 83 and 84 are concerned with the second example in which;

FIG. 84 is a block diagram of a motor control circuit; and FIGS. 85 through 88 are concerned with the third example in which;

FIG. 85 is an explanatory view showing an endoscope's bendable portion,

FIG. 86 is a sectional view of a linear type ultrasonic motor,

FIG. 88 is an explanatory view showing a bending switch.

FIGS. 89 through 92 are concerned with the first example in which;

FIG. 89 is a sectional view of an endoscope's operating section,

FIG. 90 is a plan view of a bending operation device,

FIG. 91 is an explanatory view showing the entire of the endoscope apparatus, and FIG. 92 is an explanatory view showing the state that an endoscope's bendable portion is bent;

FIGS. 93 and 94 are concerned with the second example in which;

FIG. 93 is a sectional view of an endoscope's operating section, and

FIG. 94 is a plan view of a bending operation device;

FIG. 95 is a sectional view of an endoscope's operating section of the third example; and FIG. 96 is a sectional view of an endoscope's operating section of the fourth example.

FIGS. 97 through 100 are concerned with the first example in which;

FIG. 97 is an explanatory view showing the constitution of the endoscope apparatus, FIG. 98 is a sectional view taken along line A—A' in FIG. 97, FIG. 99 is a sectional view taken along line B—B' in FIG. 97, and FIG. 100 is a block diagram of a bent condition display control circuit;

FIGS. 101 through 103 are concerned with the second example in which;

FIG. 101 is an explanatory view showing the constitution of the endoscope apparatus, FIG. 102 is an explanatory view of the bent condition of an endoscope inserted into the body cavity of a patient, and FIG. 103 is an explanatory view of the endoscope of FIG. 102 as viewed from side;

FIGS. 104 through 107 are concerned with the third example in which;

FIG. 104 is an explanatory view showing principal components of this example,

FIG. 105 is an explanatory view of a bending operation mechanism using scissors gears, FIG. 106 is an explanatory view of a bending operation mechanism using an elastic member, and FIG. 107 is a side view as viewed in the direction of C—C′ in FIG. 106; and FIGS. 108 through 110 are concerned with the fourth example in which;

FIG. 108 is an explanatory view of a bendable portion,

FIG. 109 is an explanatory view showing important components of the endoscope apparatus, and FIG. 110 is a sectional view of an attachment portion of a bimorph piezoelectric element.

FIGS. 111 through 118 are concerned with six examples of the endoscope apparatus which can notify a temperature rise of a motor:

FIGS. 111 through 113 are concerned with the first example in which;

FIG. 111 is an explanatory view showing the constitution of the endoscope apparatus, FIG. 112 is a sectional view of a ultrasonic motor.

FIGS. 114 and 115 are concerned with the second example in which;

FIG. 114 is an explanatory view showing the constitution of the electronic endoscope apparatus.

FIG. 116 is an explanatory view showing the constitution of the endoscope apparatus of the third example;

FIG. 118 is a block diagram showing annunciator means of the fifth example.

FIGS. 119 through 121 are concerned with the first example in which;

FIG. 119 is an explanatory view showing a sprocket, a chain and thereabout in the operating section, FIG. 120 is an explanatory view showing the constitution of the endoscope apparatus, and FIG. 121 is a sectional view of a bending operation device in the operating section;

FIGS. 122 through 124 are concerned with the second example in which;

FIG. 122 is an explanatory view showing the constitution of the endoscope apparatus, FIG. 123 is a sectional view of a bending operation device in the operating section, and FIG. 124 is a plan view of a bending operation device in the operating section;

FIG. 125 is an explanatory view of a bending operation device of the third example; and FIG. 126 is an explanatory view of a bending operation device according to a modification of the third example.

FIGS. 127 through 130 are concerned with the first example in which;

FIG. 127 is a sectional view of a bending operation device of the first example, FIG. 128 is a sectional view taken along line D—D in FIG. 127, FIG. 129 is an explanatory view showing an arrangement of the bending operation device, and FIG. 130 is an explanatory view showing the constitution of the endoscope apparatus;

FIG. 131 is a sectional view of a bending operation device of the second example;

FIG. 132 is a sectional view of a bending operation device of the third example;

FIG. 133 is a sectional view of a bending operation device of the fourth example;

FIG. 134 is a sectional view of a bending operation device of the fifth example; and FIGS. 135 and 136 are each an explanatory view showing an arrangement example of two motors in the operating section.

DETAILED DESCRIPTION OF THE PREFERRED EMBODIMENTS

Figure 1:
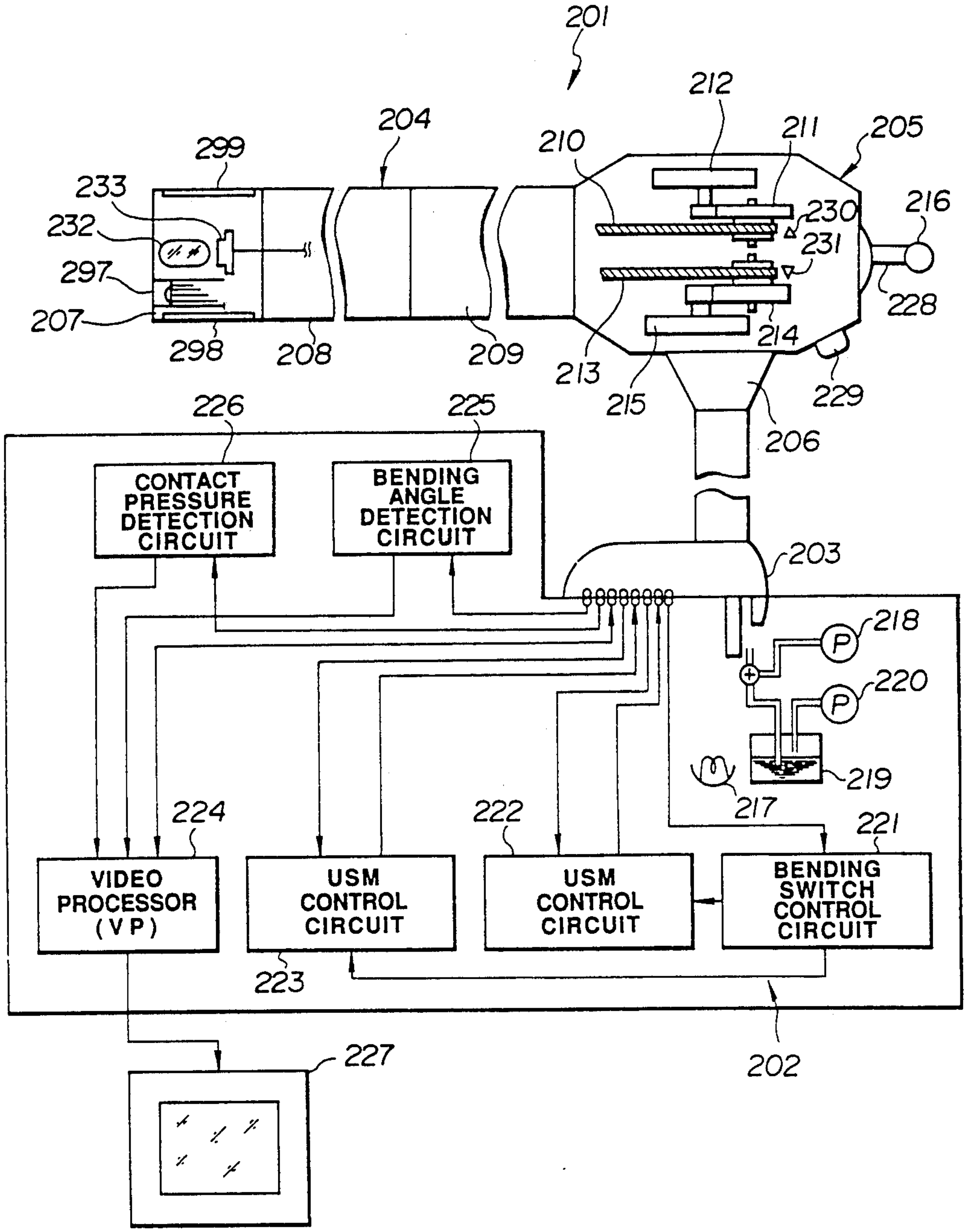
Figure 2:
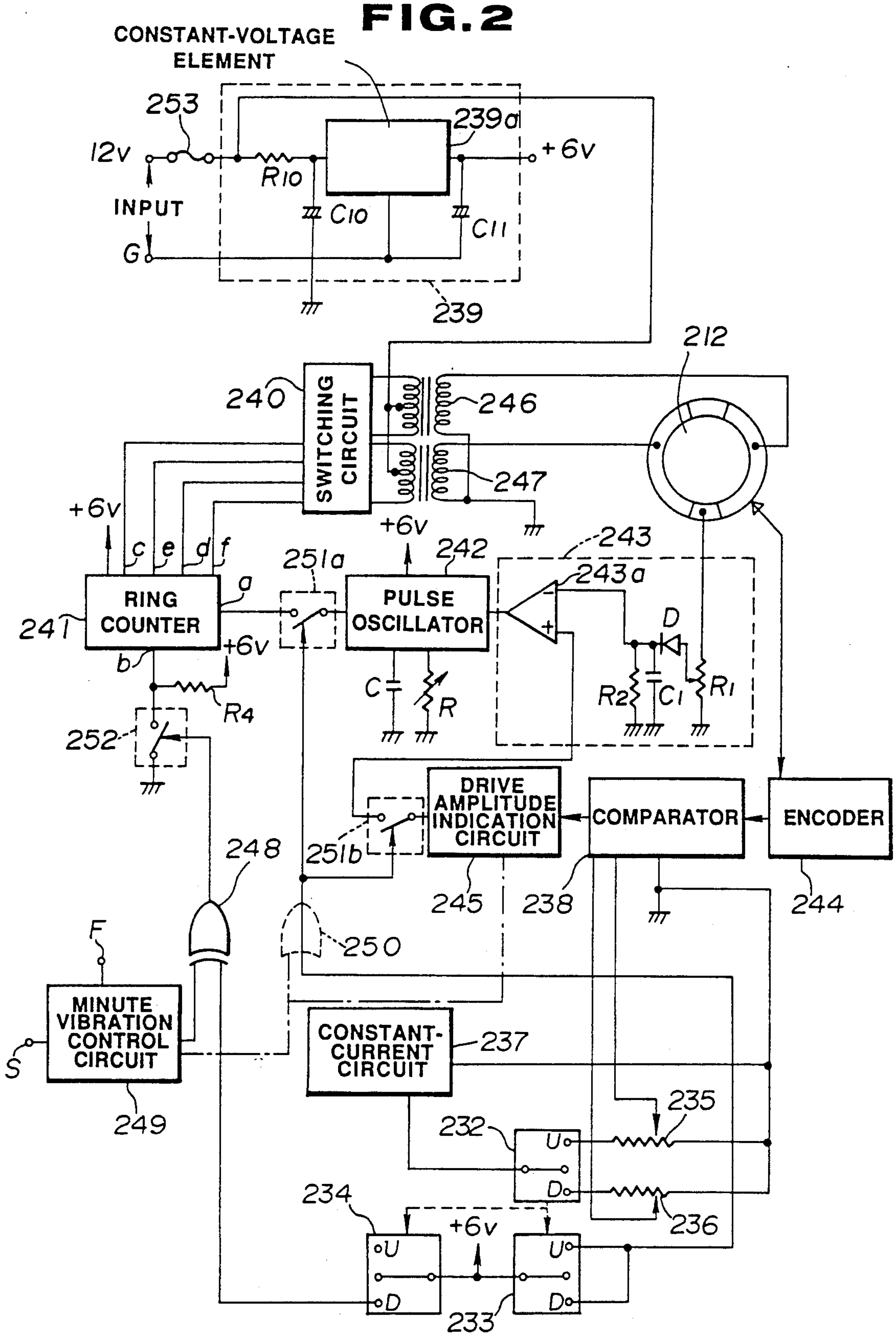

FIGS. 1 and 2 illustrate a first embodiment of the present invention.

As shown in FIG. 1, an endoscope apparatus, e.g., an electronic endoscope apparatus, comprises an endoscope 201 which is formed to be elongate so that it may be inserted into the body cavity by way of example, a universal control apparatus (hereinafter referred to as UCA) 202 to which a universal cable 206 of the endoscope 201 is connected via a connector 203, and a monitor 227 for providing an image of an object to be observed, such as any desired location in the body cavity, based on an output signal from a video processor (VP) 224 installed in the UCA 202.

The endoscope 201 comprises, for example, an elongate and flexible insert section 204, a larger-diameter grip section 205 continuously provided at the rear end of the insert section 204, the flexible universal cable 206 extended laterally from the grip section 205, and the connector 203 provided at the end of the universal cable 206. The insert section 204 comprises a hard distal end component 207 which incorporates an imaging device for picking up an object image, or the like, a bendable portion 208 continuously provided at the rear end of the distal end component 207 and capable of bending upwards, downwards, rightwards and leftwards, and a flexible pipe portion 209 continuously provided at the rear end of the bendable portion 208.

The distal end component 207 includes an objective lens 232 and a solid imaging device 233 disposed at a focus position of the objective lens 232. Connected to the solid imaging device 233 are signal lines (not shown) incorporated in the endoscope 201, these signal lines being connectable to the video processor 224 incorporated in the UCA 202 via the connector 203. In the distal end component 207, there is also disposed a contact pressure sensor 229 for detecting a contact pressure as developed when the bendable portion 208 is bent and the distal end component 208 is brought into contact with a wall of the body cavity or the like. Connected to the contact pressure sensor 299 are signal lines (not shown) incorporated in the endoscope 201, these signal lines being connectable to a contact pressure detection circuit 226 incorporated in the UCA 202 via the connector 203.

The grip section 205 incorporates a speed reduction gearing 211 to which a vertically (upwards/downwards) bending wire 210 is fixedly connected, an ultrasonic motor (hereinafter referred to as USM) 212 as a motor with its shaft coupled to the speed reduction gearing 211, a speed reduction gearing 214 to which a horizontally (rightwards/leftwards) bending wire 213 is fixedly connected, and an USM 215 with its shaft coupled to the speed reduction gearing 214. In the vicinity of the speed reduction gears 211, 214, there are respectively disposed rotation angle sensors 230, 231 each comprising a photo-reflector or the like. Connected to the rotation angle sensors 230, 231 are signal lines (not shown) incorporated in the universal cable 206, these signal lines being connectable to a bending angle detection circuit 225 incorporated in the UCA 202 via the connector 203. On the outer surface of the grip section 205, there are provided a bending switch 216 which controls the bending direction of the bendable portion 208, a switch 229 which affords a minute vibration to the bendable portion 208, an air-feed/water-feed button, a suction button, $CO_2$ gas feed button, and various switches for a forceps raising mechanism, as well as freezing, releasing and VTR-starting to control a video processor, the latter buttons and switches being not shown. Connected to the bending switch 216 are signal lines (not shown) incorporated in the universal cable 206, these signal lines being connectable to a bending switch control circuit 221 incorporated in the UCA 202 via the connector 203. Further, connected to the above switch 229 are signal lines (not shown) incorporated in the universal cable 206, these signal lines being connectable to USM control circuits 222, 223 incorporated in the UCA 202 via the connector 203.

A light guide fiber 298 is inserted through the insert section 204 of the endoscope 201 and the universal cable 206. The incident end of the light guide fiber 298 is connected to the connector 203. The emergent end of the light guide fiber 298 is located in the distal end component 207, and a light directing lens 297 is provided in opposite relation to the emergent end. An air-feed/water-feed tube, an appliance channel and so forth (not shown) are also incorporated in the endoscope 201.

The UCA 202 includes a lamp 217 for supplying a beam of illumination light to the light guide fiber 298, an air-feed pump 218 for feeding air to the air-feed/water-feed tube, a water-feed pump 220 for feeding water to the air-feed/water-feed tube, a tank 219 for storing water to be fed, the bending switch control circuit 221 for controlling the bending switch 216, the USM control circuits 222, 223 for controlling the USM's 212, 215, the video processor 224 for converting an image pick-up signal from the solid imaging device 233 and carrying out various steps of signal processing to output a video signal to the monitor 227, the bending angle detection circuit 225 for detecting an bending angle of the bendable portion 208 based on outputs of the rotation angle sensors 230, 231, and the contact pressure detection circuit 226 for processing a signal from the contact pressure sensor 299. Note that the UCA 202 may be constituted by interconnecting separate components electrically and physically.

The bending switch control circuit 221 has an input terminal to which the bending switch 216 is connected as mentioned above, and an output terminal which is connected to the USM control circuits 222, 223.

The bending angle detection circuit 225 has an input terminal to which the rotation angle sensors 230, 231 are connected as mentioned above, and an output terminal which is connected to the video processor 224.

The contact pressure detection circuit 226 has an input terminal to which the contact pressure sensor 299 is connected as mentioned above, and an output terminal which is connected to the video processor 224.

The USM control circuit 222 has an output terminal connected via the connector 203 to the USM 212 by signal lines (not shown) incorporated in the universal cable 206, and the USM control circuit 223 has an output terminal connected via the connector 203 to the USM 215 by signal lines (not shown) incorporated in the universal cable 206. The bending switch 216 is of the joy stick type comprising a switch operable by tilting a lever 228 upwards, downwards, rightwards or leftwards, for example, to control the bending direction of the bendable portion 208, and a variable resistor having its resistance value varied dependent on the tilting of the lever 228. The above switch for controlling the bending direction consists of a switch which controls the upward and downward bending directions, and a switch which controls the rightward and leftward bending directions. The switch for bending in the upward and downward directions and the switch for bending in the rightward and leftward directions have the structure allowing them to be operated simultaneously. Note that the lever 228 of the bending switch 216 is arranged such that it can be returned to a neutral position under an urging force produced by a spring or the like.

The circuit configuration of the USM control circuit 222 for controlling the USM 212 is shown in FIG. 2 in detail. The USM control circuit 223 for controlling the USM 215 is constituted and operates similarly to the USM control circuit 222, and hence its explanation is omitted. Note that the upward bending direction is indicated by "U" and the downward bending direction is indicated by "D". In the case of the USM control circuit 223, the following description should be read by taking "up" as "right", "down" as "left", U as R, D as L, the USM 212 as the USM 215, the speed reduction gearing 211 as the speed reduction gearing 214, and the bending wire 210 as the bending wire 213.

The bending switch 216 can be expressed by an equivalent circuit comprising switches 232, 233, 234 and variable resistors 235, 236. The switch 232 has a transfer terminal (hereinafter referred to as a T terminal) connected to one end of a constant-current circuit 237, a U terminal connected to one end of the variable resistor 235, and a D terminal connected to one end of the variable resistor 236. The other end of the constant-current circuit 237 is grounded. The variable resistor 235 has the other terminal grounded and a medium or tap point connected to a U speed setting input terminal of a comparator 238. The variable resistor 236 has the other terminal grounded and a medium or tap point connected to a D speed setting input terminal of the comparator 238. The comparator 238 is grounded at its grounding terminal. The switch 232 is arranged such that its T terminal does not contact the U and D terminals when the lever 228 of the bending switch 216 is at the neutral position. The switch 233 has a T terminal connected to an output terminal (+6 V) of a power supply circuit 239, and U and D terminals both connected to each of control terminals of switches 251*a* and 251*b*. The switch 233 is arranged such that its T terminal does not contact the U and D terminals when the lever 228 of the bending switch 216 is at the neutral position. The switch 234 has a T terminal connected to the output terminal (+6 V) of the power supply circuit 239, a U terminal left not connected or open, and a D terminal connected to a first input terminal of a logic circuit 248. The switch 234 is arranged such that its T terminal does not contact the U and D terminals when the lever 228 of the bending switch 216 is at the neutral position. Further, the switch 232, the switch 233 and the switch 234 are arranged such that their T terminals contact the corresponding U or D terminals at the same time.

The ultrasonic motor 212 is provided with an encoder 244 for detecting a rotation speed of the ultrasonic motor 212, an output terminal of the encoder 244 being connected to a detected speed input terminal of the comparator 238. One terminal of the ultrasonic motor 212 is connected to a first input terminal of a feedback circuit 243.

The comparator 238 has an output terminal connected to an indication input terminal of a drive amplitude indication circuit 245. An output terminal of the drive amplitude indication circuit 245 is connected to a second input terminal of the feedback circuit 243 via the switch **251*b***.

The first input terminal of the feedback circuit 243 is grounded via a variable resistor $R_1$. The variable resistor $R_1$ has a medium or tap terminal connected to an anode of a diode D of which cathode is connected to both an inverted input terminal of an operational amplifier **243*a* and one terminals of a capacitor $C_1$ and a resistor $R_2$. The other ends of capacitor $C_1$ and the resistor $R_2$ are grounded. A second input terminal of the feedback circuit 243 is connected to a non-inverted input terminal of the operational amplifier 243*a***.

An output terminal of the feedback circuit 243, i.e., an output terminal of the operational amplifier **243*a*, is connected to a control input terminal of a pulse oscillator 242, and an output terminal of the pulse oscillator 242 is connected to a clock terminal a of a ring counter 241 via a switch 251*a*. Further, the pulse oscillator 242 is connected to the output terminal (+6 V) of the power supply circuit 239, and a capacitor $C_3$ and a variable resistor $R_3$ both connected to the pulse oscillator 242** are grounded.

The ring counter 241 is of a 4-bit, right-and-left shift register of the serial-in/parallel-out type, and has a shift direction control terminal b which is connected to the output terminal (+6 V) of the power supply circuit 239 via a resistor $R_4$ and also grounded via a switch 252. The ring counter 241 has output terminals c–f connected to respective input terminals of a switching circuit 240, and a power supply terminal connected to the output terminal (+6 V) of the power supply circuit 239.

The switching circuit 240 is constituted by four sets of transistors or the like interconnected in the form of Darlington connection, for example. Output terminals of the switching circuit 240 are connected to opposite ends of a transformer 246 on the primary side and opposite ends of a transformer 247 on the primary side.

Medium or tap points of the transformers 246, 247 are connected to an output terminal (+12 V) of the power supply circuit 239. One ends of the transformers 246, 247 on the secondary side are connected to respective electrodes of the USM 212, and the other ends of the transformers 246, 247 on the secondary side are grounded.

A control terminal of the switch 252 is connected to an output terminal of the logic circuit 248. The first input terminal of the logic circuit 248 is connected to the D terminal of the switch 234 as mentioned above, and a second input terminal thereof is connected to an output terminal of a minute vibration control circuit 249 described later.

The minute vibration control circuit 249 has an input terminal connected to an S terminal and an input terminal connected to an F terminal. The S terminal is connected to the switch 229, and the F terminal is connected to a minute vibration frequency setting switch (not shown). The output of the minute vibration control circuit 249 is connected to the logic circuit 248 as mentioned above.

The logic circuit 248 is of an exclusive logical sum (EX-OR) gate, for example. When a logic signal from the minute vibration control circuit 249 connected to the second input terminal of the logic circuit 248 assumes a level "L", the logic circuit 248 directly issues at its output terminal a logic signal from the switch 234 connected to the first input terminal thereof. When the logic signal from the minute vibration control circuit 249 connected to the second input terminal of the logic circuit 248 assumes a level "H", the logic circuit 248 inverts the logic signal from the switch 234 connected to the first input terminal thereof and issues the inverted signal at the output terminal.

The power supply circuit 239 has an input terminal connected to a power supply (+12 V) via a fuse 253, the input terminal being connected to the output terminal (+12 V) thereof directly and to an input terminal of a constant-voltage element **239*a* via a resistor $R_{10}$, and also grounded via an electrolytic capacitor $C_{10}$. The constant-voltage element 239*a* has an output terminal grounded via an electrolytic capacitor $R_{10}$ and connected to the output terminal (+6 V) of the power supply circuit 239. The constant-voltage element 239*a*** is grounded at its grounding terminal.

Operation of the endoscope apparatus thus constituted will now be described.

The light radiated from the lamp 217 incorporated in the UCA 202 is introduced through the light guide fiber 298 and then emitted from the emergent end of the light guide fiber 298 disposed in the distal end component 207 of the endoscope apparatus 201 (see FIG. 1), for irradiating an object to be examined or so through the light directing lens 297. An image of the object irradiated by the light is focused by the objective lens 232 on the imaging surface of the solid imaging device 233 and converted to an image pick-up signal which is input through an image pick-up line (not shown) to the video processor 224 incorporated in the UCA 202. The solid imaging device 233 is supplied with a drive signal from the video processor 224.

The video processor 224 converts the image pick-up signal to a video signal and, simultaneously, combines both the bending angle from the bending angle detection circuit 225 and the contact pressure from the contact pressure detection circuit 226 with the video signal, followed by outputting it to the monitor 227. Thus, the monitor 227 displays the object image, the bending angle and the contact pressure.

When bending the bendable portion 208 upwards, the lever 228 of the bending switch 216 is operated in a predetermined specific direction.

This causes the T terminal of the switch 232 to contact the U terminal, whereupon a current of 1 mA, for example, flows from the constant-voltage circuit 237 through the variable resistor 235 to produce a voltage (hereinafter referred to as a speed setting voltage) dependent on tilting of the lever 228 at the tap point of the variable resistor 235. The speed setting voltage is then applied to the U speed setting input terminal of the comparator 238.

The encoder 244 performs F/V conversion to convert the revolution speed of the USM 212 to a voltage proportional to the revolution speed, and outputs the speed voltage converted from the revolution speed to the speed detection input terminal of the comparator 238.

The comparator 238 compares the above the speed setting voltage with the above speed voltage. When the speed voltage is lower than the speed setting voltage, the comparator 238 outputs a control signal for increasing the speed to the drive amplitude indication circuit 245. When the speed voltage is higher than the speed setting voltage, the comparator 238 outputs a control signal for decreasing the speed to the drive amplitude indication circuit 245.

Simultaneously, the T terminal of the switch 233 is caused to contact the U terminal, whereupon the output (+6 V) of the power supply circuit 239 is applied to the control terminals of the switch 251*a* and the switch 251*b* for turning on these switches 251*a*, 251*b*.

In response to the control signal applied from the comparator 238 to the indication input terminal, the drive amplitude indication circuit 245 outputs a drive amplitude indication signal to the feedback circuit 243 via the switch 251*b*.

Based on both the drive amplitude indication signal from the drive amplitude indication circuit 245 and the feedback signal from the USM 212, the feedback signal 243 outputs a frequency control signal to the pulse oscillator 242.

When the USM 212 is at rest, the pulse oscillator 242 oscillates itself at frequency 4 times the actuating frequency. Upon application of the frequency control signal, the pulse oscillator 242 is controlled by the frequency control signal to oscillate at frequency 4 times the drive frequency. The resulting clock signal of frequency 4 times the actuating or drive frequency is input to the clock terminal a of the ring counter 241 via the switch 251*a*.

On the other hand, the T terminal of the switch 234 is not caused to contact the D terminal, and a logic signal applied to the first input terminal of the logic circuit 248 assumes a level "L". Further, with the switch 229 being not depressed, a logic signal at the output terminal of the minute vibration control circuit 249 assumes a level "L", whereby a logic signal applied to the second input terminal of the logic circuit 248 assumes a level "L". Therefore, the logic circuit 248 issues a logic signal of level "L" at its output terminal, so that the switch 252 is turned off.

Since the switch 252 is turned off, i.e., a logic signal applied to the shift direction control terminal b assumes a level "H", the ring counter 241 now operates such that logic signals at the output terminals are turned to "H" in turns while being switched in the order of f, e, d, c, for example, and the respective high-level logic signals are applied to the switching circuit 240 successively.

In response to the logic signals from the ring counter 241, the switching circuit 240 causes the opposite ends of the transformers 246, 247 on the primary side to be grounded in turns by way of example.

A sine wave voltage of 100 Vrms, for example, is thereby produced on the secondary side of the transformers 246, 247 and supplied, as s drive voltage, to the USM 212.

This drive voltage is produced such that the voltage supplied from the ring counter 241 to one electrode of the USM 212 has a phase angle delayed or advanced 90 degrees from a phase angle of the voltage supplied to the other electrode.

The USM 212 is revolved with the drive voltage applied, and a drive force of the USM 212 is transmitted to the speed reduction gearing 211. The speed reduction gearing 211 pushes and pulls both ends of the bending wire 210 to bend the bendable portion 208 upwards.

When bending the bendable portion 208 downwards, the lever 228 of the bending switch 216 is operated in a predetermined specific direction.

This causes the T terminal of the switch 232 to contact the D terminal, whereupon a current of 1 mA, for example, flows from the constant-voltage circuit 237 through the variable resistor 236 to produce a voltage (hereinafter referred to as a speed setting voltage) dependent on tilting of the lever 228 at the tap point of the variable resistor 236. The speed setting voltage is then applied to the D speed setting input terminal of the comparator 238.

Simultaneously, the T terminal of the switch 233 is caused to contact the D terminal, whereupon the output (+6 V) of the power supply circuit 239 is applied to the control terminals of the switch 251*a* and the switch 251*b* for turning on these switches 251*a*, 251*b*.

Moreover, the T terminal of the switch 234 is caused to contact the D terminal, whereupon the output (+6 V) of the power supply circuit 239 is applied to the first input terminal of the logic circuit 248 so that the logic signal at the output terminal of the logic circuit 248 assumes a level "H" to turn on the switch 252.

Since the switch 252 is turned on, i.e., the logic signal applied to the shift direction control terminal b assumes a level "L", the ring counter 241 now operates such that the logic signals at the respective output terminals are turned to "H" in turns while being switched in the order of c, d, e, f, for example, and the respective high-level logic signals are applied to the switching circuit 240 successively.

The USM 212 is revolved with the drive voltage applied, and a drive force of the USM 212 is transmitted to the speed reduction gearing 211, as mentioned above. The speed reduction gearing 211 pushes andr pulls both ends of the bending wire 210 to bend the bendable portion 208 downwards.

Because operation of the remaining components is similar to that in the case of bending the bendable portion 208 upwards, the explanation about it is omitted.

Where it becomes hard to further insert the insert section 204, an operator can depress the aforesaid switch 229 while operating the lever 228 of the bending switch 216 to bend the bendable portion 208 in a desired direction.

This causes the minute vibration control circuit 249 to output the logic signal with duty ratio of 50%, for example, to the logic circuit 248 at frequency set by a minute vibration frequency setting switch which is connected to the F terminal.

Accordingly, the logic circuit 248 turns on/off the switch 252 at the aforesaid duty ratio. Upon the switch 252 turning on/off, the ring counter 241 outputs the logic signals for bending the bendable portion 208 upwards and the logic signals for bending the bendable portion 208 downwards repeatedly at the frequency set by the minute vibration frequency setting switch.

Thus, the bendable portion 208 repeats the upward bending and the downward bending repeatedly at a short cycle, resulting in an advantageous effect that the contact resistance exerted on the bendable portion 208 is reduced to facilitate the inserting operation. In addition, since the bendable portion 208 vibrates of itself in a direction crossing the axial direction of the insert section 204 even when the bendable portion 208 is not in contact with the inner wall of the body cavity, the impact against the inner wall of the body cavity is reduced.

Figure 3:
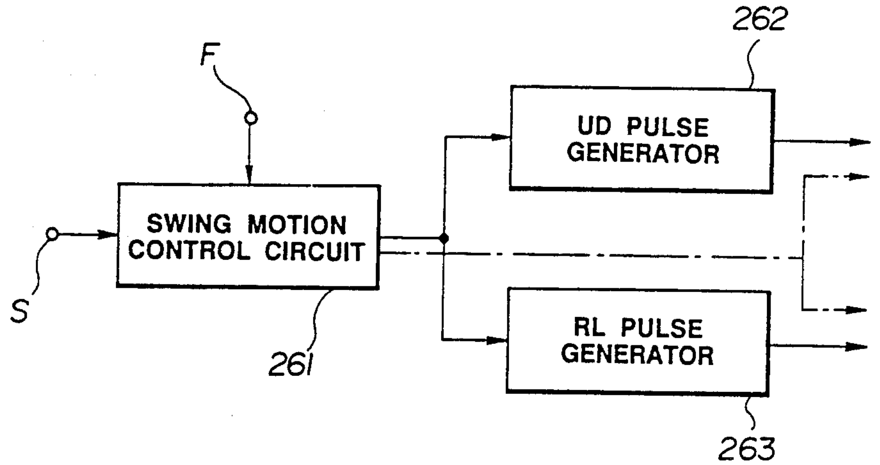
Figure 4:
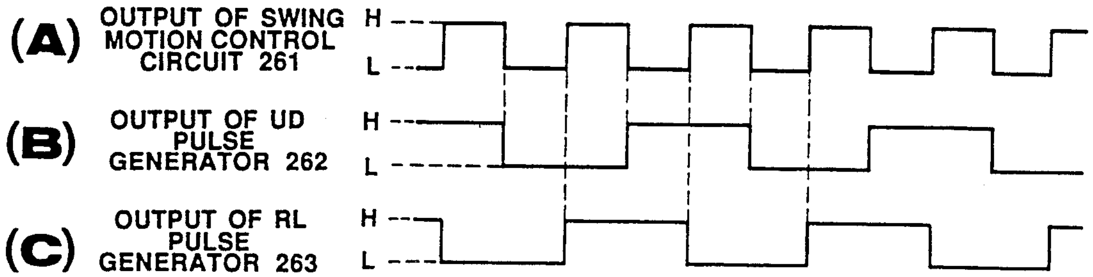

FIGS. 3 and 4 illustrate a second embodiment of the present invention. It is to be noted that an endoscope is constituted similarly to that in FIG. 1 explained above in connection with the first embodiment, and a USM control circuit 222 has the same configuration as that in FIG. 2 explained above in connection with the first embodiment except for that the minute vibration control circuit 249 is omitted.

A minute vibration control circuit is provided in the bending switch control circuit and, as shown in FIG. 3, comprises a swing motion control circuit 261, a UD pulse generator 262 having its input terminal to which an output terminal of the swing motion control circuit 261 is connected, and an RL pulse generator 263 having its input terminal to which an output terminal of the swing motion control circuit 261 is connected.

The swing motion control circuit 261 has an input terminal connected to an S terminal and an input terminal connected to an F terminal. The S terminal is connected to the switch 229 explained above in connection with the first embodiment, while the F terminal is connected to a frequency adjusting switch (not shown).

The UD pulse generator 262 has an output terminal connected to the second input terminal of the logic circuit 248 which is provided in the USM control circuit 222 explained above in connection with the first embodiment. The RL pulse generator 263 has an output terminal connected to the second input terminal of a logic circuit which is provided in the USM control circuit 223 explained above in connection with the first embodiment.

Operation of the minute vibration control circuit thus constituted will now be described.

When the insert section of the endoscope is inserted and subjected to the increased resistance against insertion as with the first embodiment, the operator operates the switch 229, whereupon the swing motion control circuit 261 outputs a pulse wave with duty ratio of 50% as shown in FIG. 4(A), for example. The UD pulse generator 262 outputs a pulse wave, as shown in FIG. 4(B), of which logic level is inverted in synchronism with falling of the output pulse wave from the swing motion control circuit 261 by way of example. The RL pulse generator 263 outputs a pulse wave, as shown in FIG. 4(C), of which logic level is inverted in synchronism with rising of the output pulse wave from the swing motion control circuit 261 by way of example.

The USM control circuit 222 explained above in connection with the first embodiment controls here the USM 212 with the output pulse wave from the UD pulse generator 262 in such a manner as to drive the bendable portion 208 in the vertical direction (i.e., upwards and downwards), and the USM control circuit 223 controls here the USM 215 with the output pulse wave from the RL pulse generator 263 in such a manner as to drive the bendable portion 208 in the horizontal direction (i.e., rightwards and leftwards).

Thus, since the output pulse wave from the UD pulse generator 262 and the output pulse wave from the RL pulse generator 263 have a phase difference of 90 degrees therebetween, the bendable portion 208 develops a bending or swing motion such that the tip end of the distal end component 207 draws a circle. This results in an advantageous effect that the contact resistance exerted on the bendable portion 208 is reduced to facilitate the inserting operation.

Figure 5:
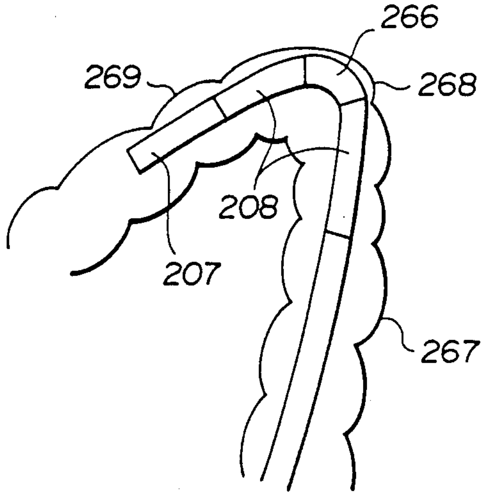
FIG. 5 is an explanatory view showing the state that a distal end component of an endoscope is inserted into a bending region of the spleen in a third embodiment of the present invention.

FIG. 5 illustrates a third embodiment of the present invention. It is to be noted that an endoscope apparatus of this embodiment is the same as that of the foregoing first and second embodiments except for omission of the switch 229, with the S terminals of the USM control circuits 222, 223 being connected to a contact pressure sensor described later. In FIG. 5, the same components as those mentioned above are designated by the same reference numerals and they are not be described here.

An insert section 204 of an endoscope 201 in this embodiment comprises, as shown in FIG. 5, a distal end component 207, a bendable portion 208 continuously provided at the rear end of the distal end component 207, and the flexible pipe portion 209 continuously provided at the rear end of the bendable portion 208.

A contact pressure sensor 266 is stuck onto the circumferential surface of the bendable portion 208 substantially at the center in the axial direction. Connected to the contact pressure sensor 266 is a signal line (not shown) which is in turn connected to the S terminal of the minute vibration control circuit 249 in the endoscope apparatus explained above in the first embodiment, or to the S terminal of the swing motion control circuit 261 in the endoscope apparatus explained above in the second embodiment.

With the above constitution, when the insert section 204 is inserted into the large intestine, for example, and then the tip end of the insert section 204 reaches a spleen bending region 268 at the joint between the descending colon region 267 and the transverse colon region 269 as shown in FIG. 5, the operator pushes the insert section 204 while operating the lever 228 of the bending switch 216, whereby the contact pressure sensor 266 is brought into contact with a wall of the body cavity. At the time the contact pressure detected by the contact pressure sensor 266 reaches a predetermined pressure, the minute vibration control circuit 250 or the swing motion control circuit 261 controls the bendable portion 208 to develop a minute vibration or swing motion in a like manner to the first embodiment or the second embodiment.

This results in an advantageous effect that the minute vibration or swing motion imparted to the bendable portion 208 facilitates passage of the insert section 204 through the spleen bending region 262.

In the first embodiment and the second embodiment, an OR circuit 250 and a control line indicating depression of the switch 229 may be additionally provided as indicated by chain lines in FIGS. 2 and 3, allowing the bendable portion 208 to develop the minute vibration or swing motion even when the lever 228 of the bending switch 216 is not operated.

FIG. 6 illustrates a fourth embodiment of the present invention.

Note that the same components or operating members in this embodiment as those in the first embodiment are designated by the same reference numerals and they are not described here.

Figure 6A:
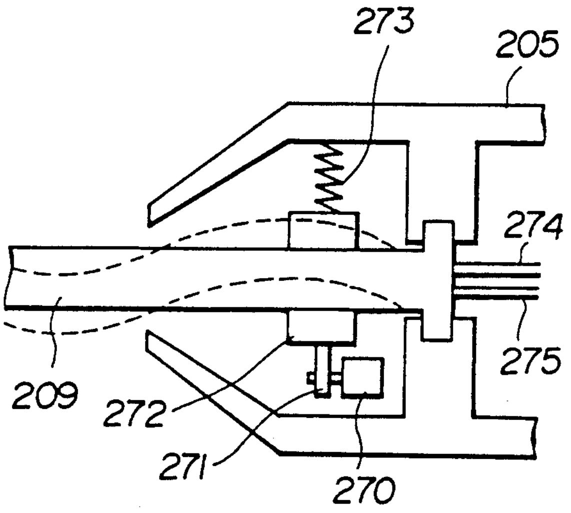
FIGS. 6(A) and 6(B) are explanatory views showing important components of a flexible pipe portion of the endoscope in a fourth embodiment of the present invention.
Figure 6B:
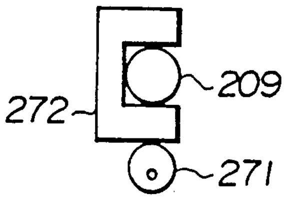

At the distal end of a grip section 205, as shown in FIG. 6(A), there is disposed a flexible pipe portion 209 which incorporates an image guide 274, a light guide 275, etc. extending therethrough. The inner end of the flexible pipe portion 209 is fixedly attached in the grip section 205. A motor 270 is disposed in the vicinity of a position where the flexible pipe portion 209 is fixedly attached in the grip section 205, and a cam 271 is eccentrically mounted on a shaft of the motor 270. Also, as shown in FIG. 6(B), a vibrating member 272, as an abutment portion held in abutment with the flexible pipe section 209, is disposed around the flexible pipe portion 209, and has one end held in contact with the cam 271 and the other end pressed by an urging force of a spring 273. The motor 270, the cam 271 and the spring 273 jointly constitute fluctuation means.

By driving the motor 270 to revolve, therefore, the vibrating member 272 is moved correspondingly in the vertical direction, for example, resulting in an advantageous effect that the flexible pipe portion 209 is forced to vibrate over its entire length for reducing the contact resistance.

FIG. 7 illustrates a fifth embodiment of the present invention.

Figure 7A:
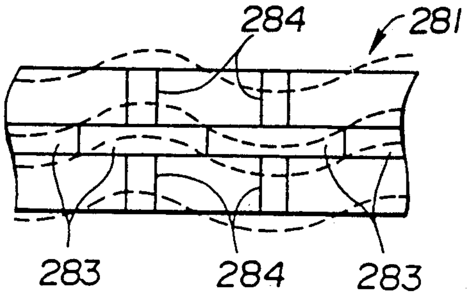
FIGS. 7(A) and 7(B) are explanatory views showing a flexible pipe portion of the endoscope in a fifth embodiment of the present invention.
Figure 7B:
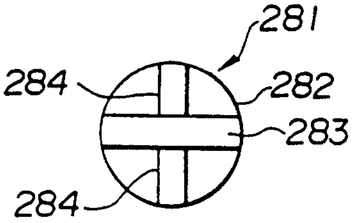

In a flexible pipe portion 281 of an endoscope, as shown in FIG. 7(B), there is disposed a bimorph 283 extending substantially throughout the diameter of a circular cross-section of the flexible pipe portion 281. A pair of posts 284 are fixed at their one ends to the bimorph 283 in orthogonal relation. The opposite ends of the posts 284 are fixed to an outer cover 282 of the flexible pipe portion 281. Also, as shown in FIG. 7(A), the above set of the bimorph 283 and the pair of posts 284 is disposed successively over the entire length of the flexible pipe portion 281.

Thus, by driving or energizing the bimorphs 283, vibrations of the bimorphs 283 are transmitted to the outer cover 282, resulting in an advantageous effect that the flexible pipe portion 281 is entirely vibrated to reduce the contact resistance.

The foregoing embodiments may also be applied to electronic endoscopes, endoscopes using image guides, and the like.

Figure 8:
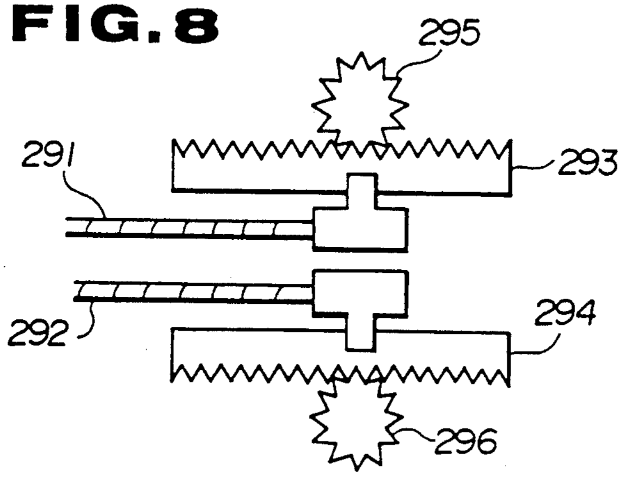
FIG. 8 is an explanatory view showing means to bend the bendable portion momentarily.

Meanwhile, the bending wires for bending the bendable portion may be arranged as shown in FIG. 8. More specifically, an upwards bending wire 291 is fixedly attached to a rack gear 293 and a downwards bending wire 292 is fixedly attached to a rack gear 294, allowing the bending wires 291, 292 to be tensioned independently of each other. A pinion gear 295 is rotated to tension the upwards bending wire 291, while the downwards bending wire 292 is tensioned by a pinion gear 296 or any other means. Then, the tension of the downwards bending wire 292 is released or made zero momentarily, so that the bendable portion is bent correspondingly by the resulting repulsion force to transmit this momentary motion to the flexible pipe portion.

Other operation and advantageous effect of the second through fifth embodiments are similar to those in the first embodiment.

FIGS. 9 through 27 illustrates a sixth embodiment of the present invention.

Figure 9:
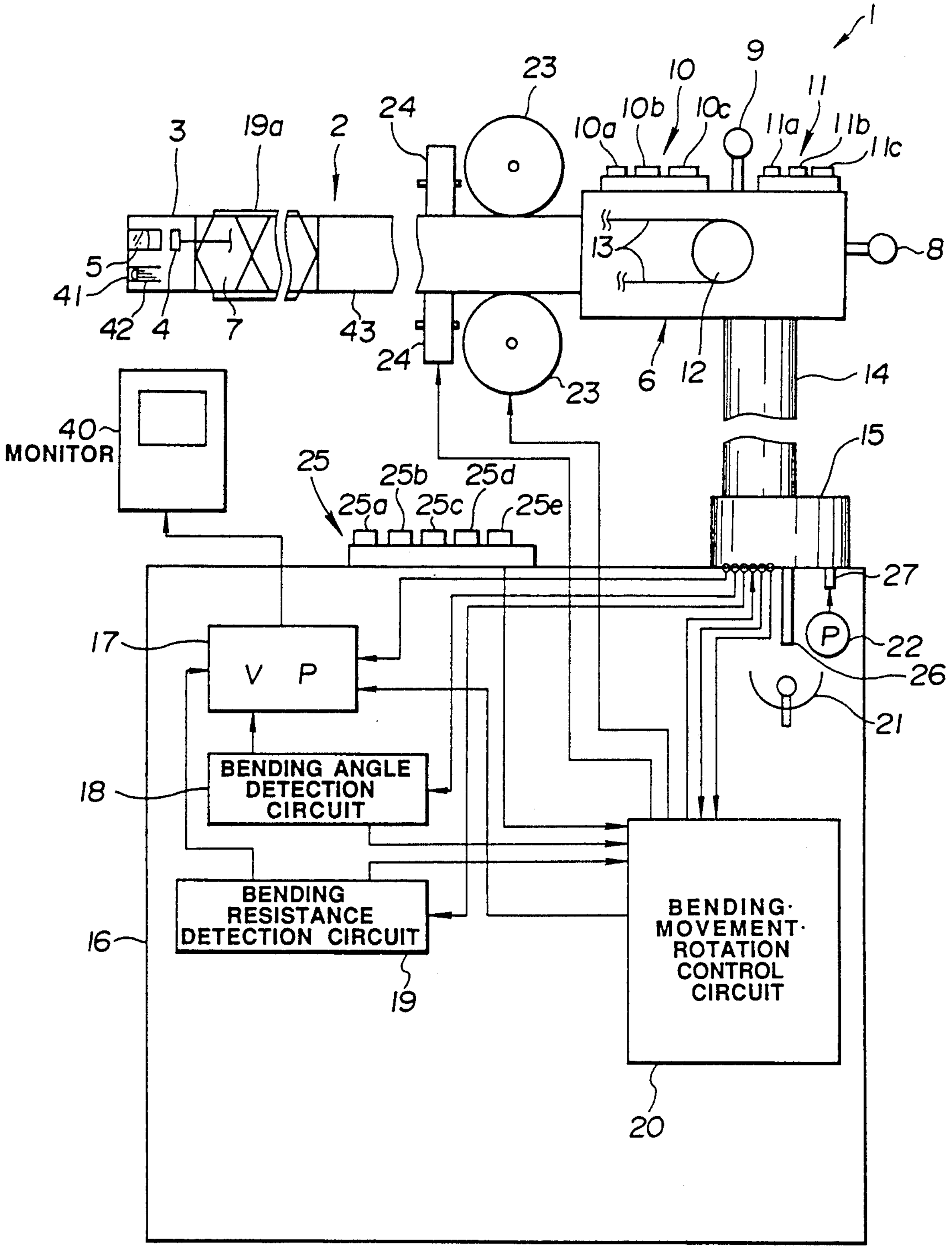
Figure 10:
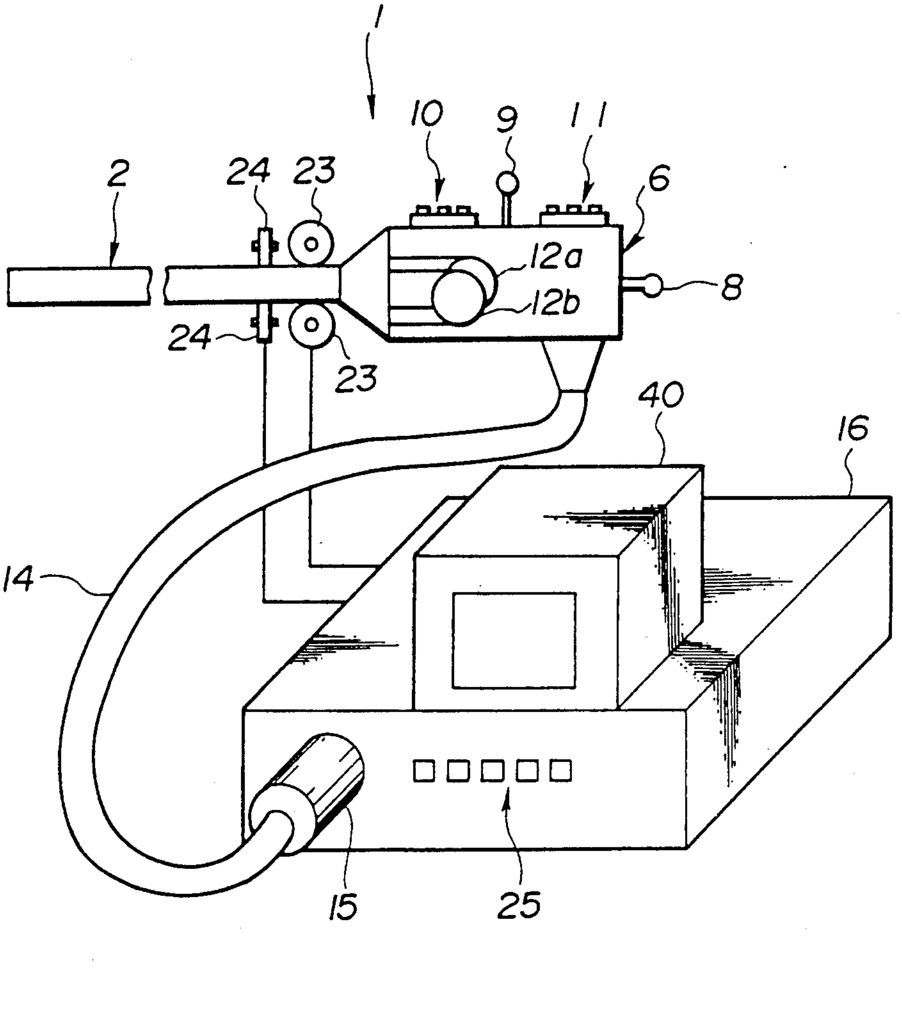

As shown in FIGS. 9 and 10, an endoscope apparatus of this embodiment comprises an endoscope 1, a controller 16 to which the endoscope 1 is connectable, and a monitor 40 connected to the controller 16.

The endoscope 1 comprises an elongate and flexible insert section 2, a larger-diameter operating section 6 continuously provided at the rear end of the insert section 2, and a universal cable 14 extended laterally from the operating section 6. A connector 15 detachably connected to the controller 16 is provided at the opposite end of the universal cable 14. The insert section 2 comprises a pliable portion 43 coupled with the operating section 6, a bendable portion 7 continuously provided at the front end of the pliable portion 43 and capable of bending, and a distal end component 3 continuously provided at the front end of the bendable portion 7.

In the distal end component 3, there are provided an observation window 5*a*, an illumination window 41*a*, and an air-feed/water-feed port (not shown). The observation window 5*a* includes an objective lens 5, and a solid imaging device 4 is disposed at a focus position of the objective lens 5. A signal line connected to the solid imaging device 4 is extended through the insert section 2, the operating section 6 and the universal cable 14, and connected to the connector 15. A light directing lens 41 is fitted in the illumination window 41*a*, and a light guide 42 is continuously provided at the rear end of the light directing lens 41. The light guide 42 is extended through the insert section 2, the operating section 6 and the universal cable 14, and the incident end of the light guide 42 is connected to a light guide pipe 26 extending from the connector 15. The air-feed/water-feed port is connected to an air-feed/water-feed tube which is inserted through the insert section 2, the operating section 6 and the universal cable 14, and connected to an air-feed pipe 27 extending from the connector 15.

A contact pressure sensor 19*a* is provided around the outer circumference of the bendable portion 7. A signal line connected to the contact pressure sensor 19*a* is extended through the insert section 2, the operating section 6 and the universal cable 14, and connected to the connector 15.

On the operating section 6, there are provided a joy stick 8 for bending the bendable portion 7, a joy stick 9 for moving (advancing/retreating) and rotating the insert section 2, and switches 10, 11 described later.

A pair of bending drive motors 12*a*, 12*b* are provided in the operating section 6. A bending wire 13 inserted through the insert section 2 is attached to the bending drive motor 12 (representing each of 12*a* and 12*b*), and the fore end of the bending wire 13 is secured to the distal end of the bendable portion 7. By revolving the bending drive motor 12, the bending wire 13 is pushed or pulled to bend the bendable portion 7 upwards, downwards, rightwards and leftwards. Further, an encoder 18*a* is attached to the bending drive motor 12. A signal line connected to the encoder 18*a* is extended through the insert section 2, the operating section 6 and the universal cable 14, and connected to the connector 15.

The controller 16 houses therein a video processor (hereinafter referred to as VP) 17 connected to the solid imaging device 4 via the connector 15, a bending angle detection circuit 18 connected to the encoder 18*a* via the connector 15, a bending resistance detection circuit 19 connected to the contact pressure sensor 19*a* via the connector 15, a bending/movement(advance and retreat)/rotation control circuit 20, a lamp 21, and a pump 22.

The VP 17 processes an output signal of the solid imaging device 4 into a video signal which is output to the monitor 40. Then, the monitor 40 displays an image of an object to be examined. Based on an output of the encoder 18*a*, the bending angle detection circuit 18 detects a bending angle of the bendable portion 7 and displays the detected bending angle on the monitor 40 via the VP 17. Information of the bending angle from the bending angle detection circuit 18 is also sent to the bending/movement/rotation control circuit 20. Based on an output of the contact pressure sensor 19*a* provided in the bendable portion 7, the bending resistance detection circuit 19 detects bending resistance and displays the detected bending resistance on the monitor 40 via the VP 17. Information of the bending resistance from the bending resistance detection circuit 19 is also sent to the bending/movement/rotation control circuit 20. The lamp 21 is so arranged as to impinge a beam of illumination light to the incident end of the light guide 42 within the light guide pipe 26. Further, the pump 22 is so arranged as to supply air to the air-feed pipe 27.

Figure 11:
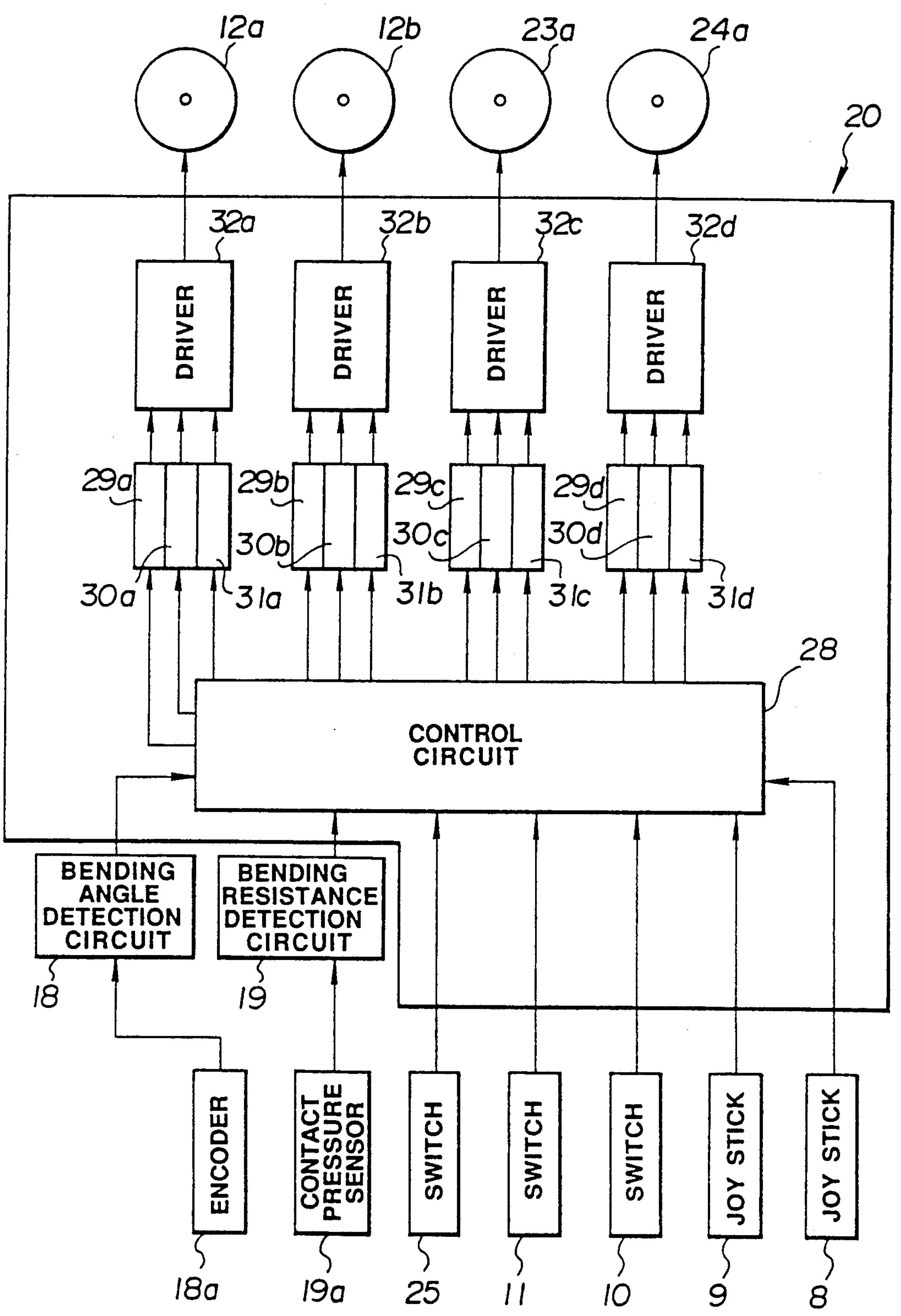

As shown in FIG. 11, the bending/movement/rotation control circuit 20 drives the bending drive motors 12*a*, 12*b*, a movement motor 23*a* for driving movement rollers 23 held against the periphery of the insert section 2, and a rotation motor 24*a* for driving rotation rollers 24 held against the periphery of the insert section 2. As shown in FIG. 10, a set of switches 25 are provided on the outer surface of the controller 16. Also, as shown in FIG. 11, the joy sticks 8, 9 and the switches 10, 11, 25 are connected to the bending/movement/rotation control circuit 20 so that the control circuit 20 can display the operating conditions of the joy sticks 8, 9 and the switches 10, 11, 25 on the monitor 40 via the VP 17.

In addition, as shown in FIG. 11, the bending/movement/rotation control circuit 20 includes a control circuit 28 for receiving information from the joy sticks 8, 9, the switches 10, 11, 25, the bending angle detection circuit 18, and the bending resistance detection circuit 19, drivers 32*a*, 32*b*, 32*c*, 32*d* for driving the motors 12*a*, 12*b*, 23*a*, 24*a*, respectively, and speed control circuits 29*a*–29*d*, rotating direction indication circuits 30*a*–30*d* and free/lock circuits 31*a*–31*d* for controlling the drivers 32*a*, 32*b*, 32*c*, 32*d* based on the information from the control circuit 28, respectively.

As shown in FIG. 9, the switch 10 comprises a minute bending vibration on/off switch 10*a*, a minute moving (advancing and retreating) vibration on/off switch 10*b*, and a minute rotating vibration on/off switch 10*c*. The switch 11 comprises a bending free/lock switch 11*a*, a movement free/lock switch 11*b*, and a rotation free/lock switch 11*c*. The switch 25 comprises a set of a minute bending vibration selector switch 25*a*, bending/movement/rotation/swing setting selector switch 25*b*, an angle specifying switch 25*c*, a speed specifying switch 25*d*, and an all-free switch 25*e*.

The angle specifying switch 25*c* is so arranged as to specify an angle or length of each minute vibration at three stages such as narrow angle (N), medium angle (M) and wide angle (W), for example. The speed specifying switch 25*d* is so arranged as to specify a speed of each minute vibration at three stages such as low speed (L), medium speed (M) and high speed (H), for example.

The joy sticks 8, 9 are arranged such that when their levers are tilted upwards, downwards, rightwards or leftwards, they output information of the direction and degree of respective tilting, and the output information is applied to the control circuit 28.

Operation of this embodiment will now be described. The endoscope apparatus of this embodiment enables various forms of operations by combining three types of motions such as bending, movement (advance and retreat) and rotation with three types of minute vibrations of bending, movement and rotation. The following typical operations will be described below in order with reference to FIGS. 12 through 20.

Figures 19K, 19M, 19O:
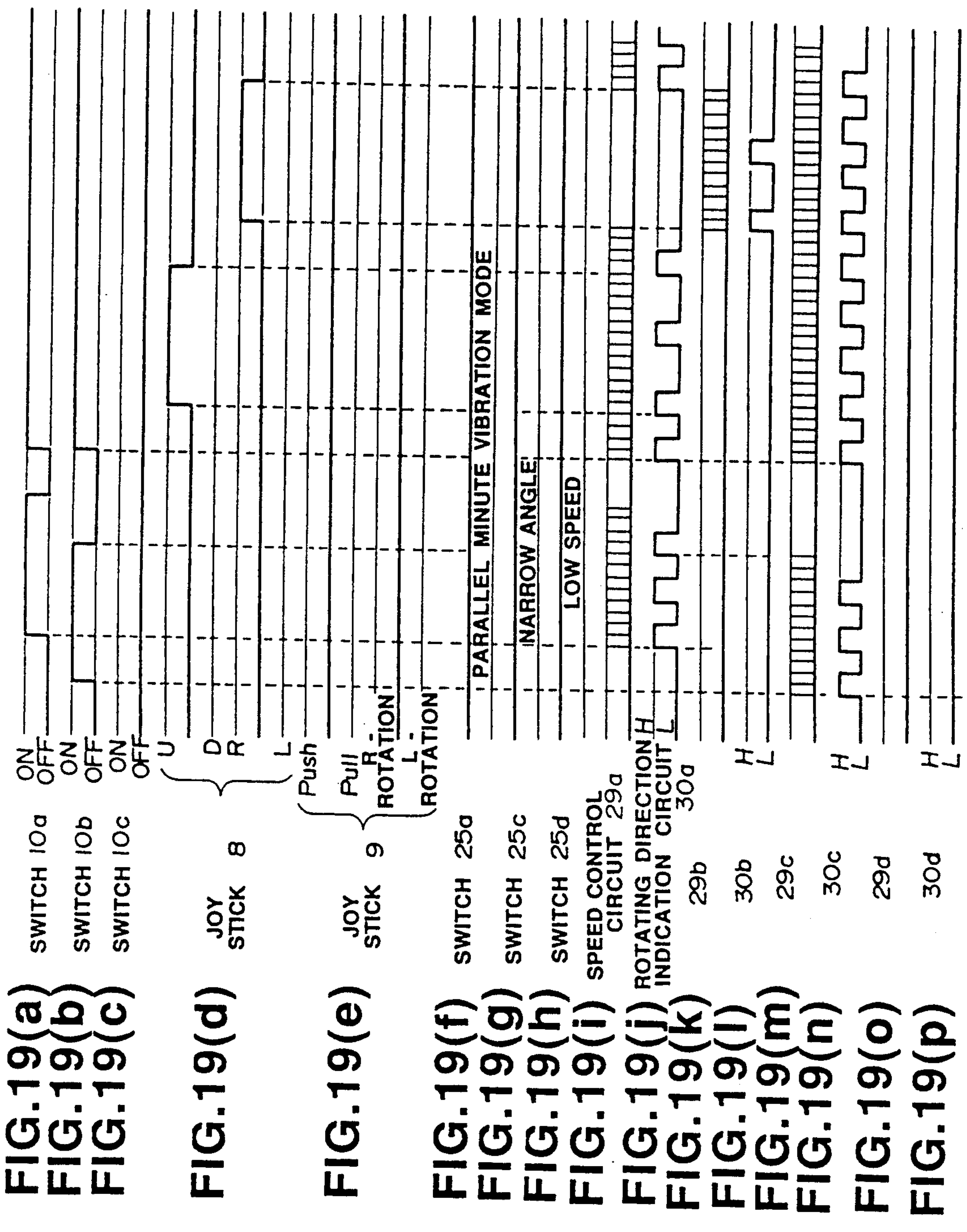
Figures 20A, 20B, 20C, 20D, 20E, 20F, 20G, 20H, 20I, 20J, 20K, 20L, 20M, 20N, 20O, 20P:
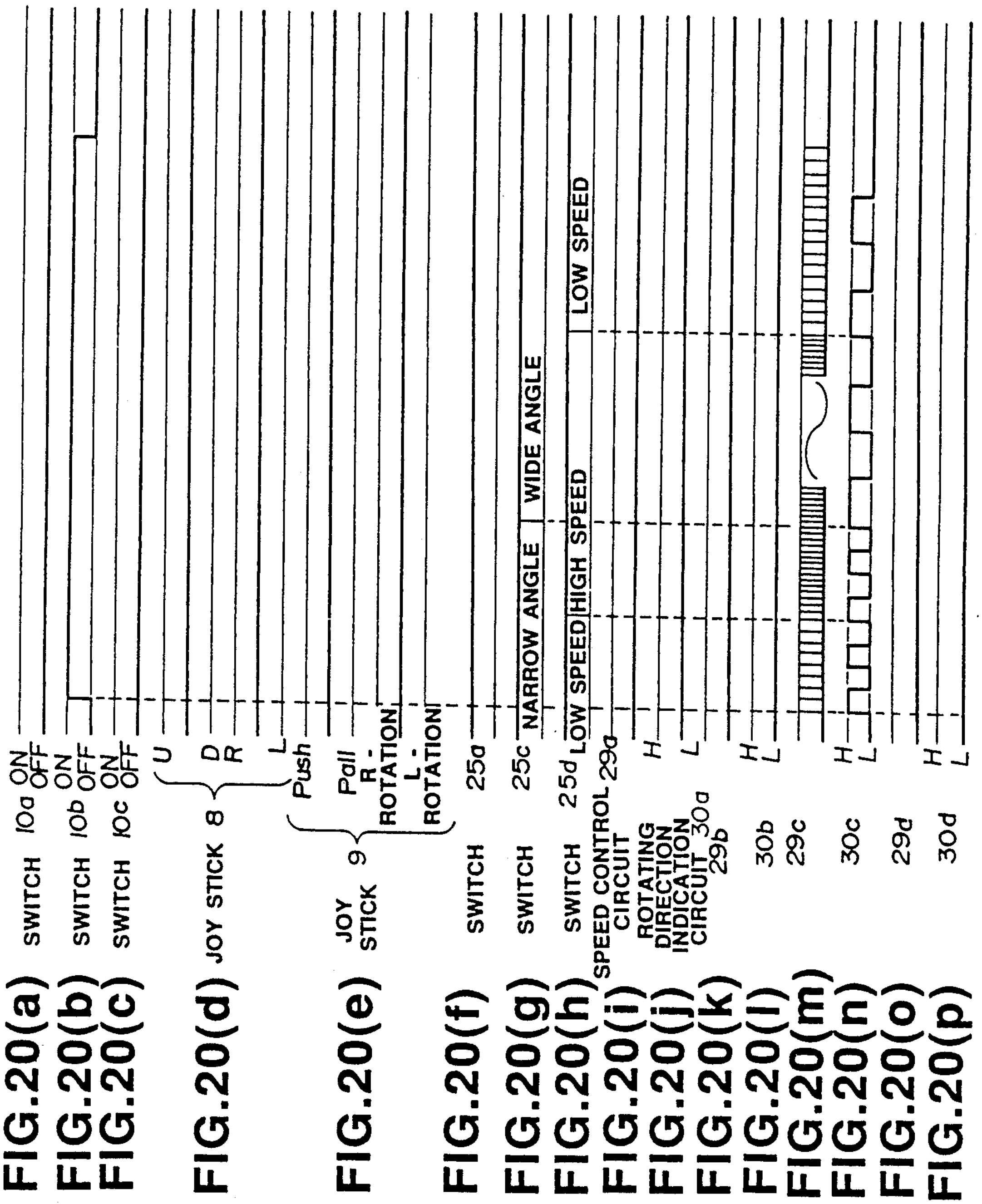
Figure 21:
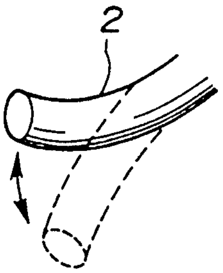
Figure 22:
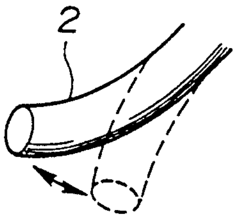
Figure 23:
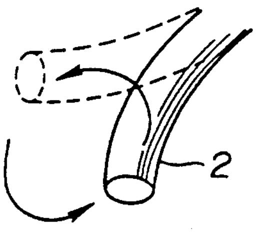
Figure 24:
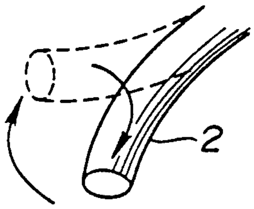

(I) Operation during normal bending process (FIG. 12)
(II) Operation during non-bending process in a parallel minute vibration mode (FIG. 13)
(III) Operation during bending process in a parallel minute vibration mode (FIG. 14)
(IV) Operation in an orthogonal minute vibration mode (FIG. 15)
(V) Operation based on swing motion, minute moving vibration and minute rotating vibration (FIG. 16)
(VI) Operation in a combination of minute rotating vibration and minute bending vibration (FIG. 17)
(VII) Operation upon change in conditions of minute rotating vibration (FIG. 18)
(VIII) Operation in a combination of minute moving vibration and minute bending vibration (FIG. 19)
(IX) Operation upon change in conditions of minute moving vibration (FIG. 20)

Figures 12A, 12B, 12C, 12D, 12E, 12F, 12G, 12H, 12I, 12J, 12K, 12L, 12M, 12N:
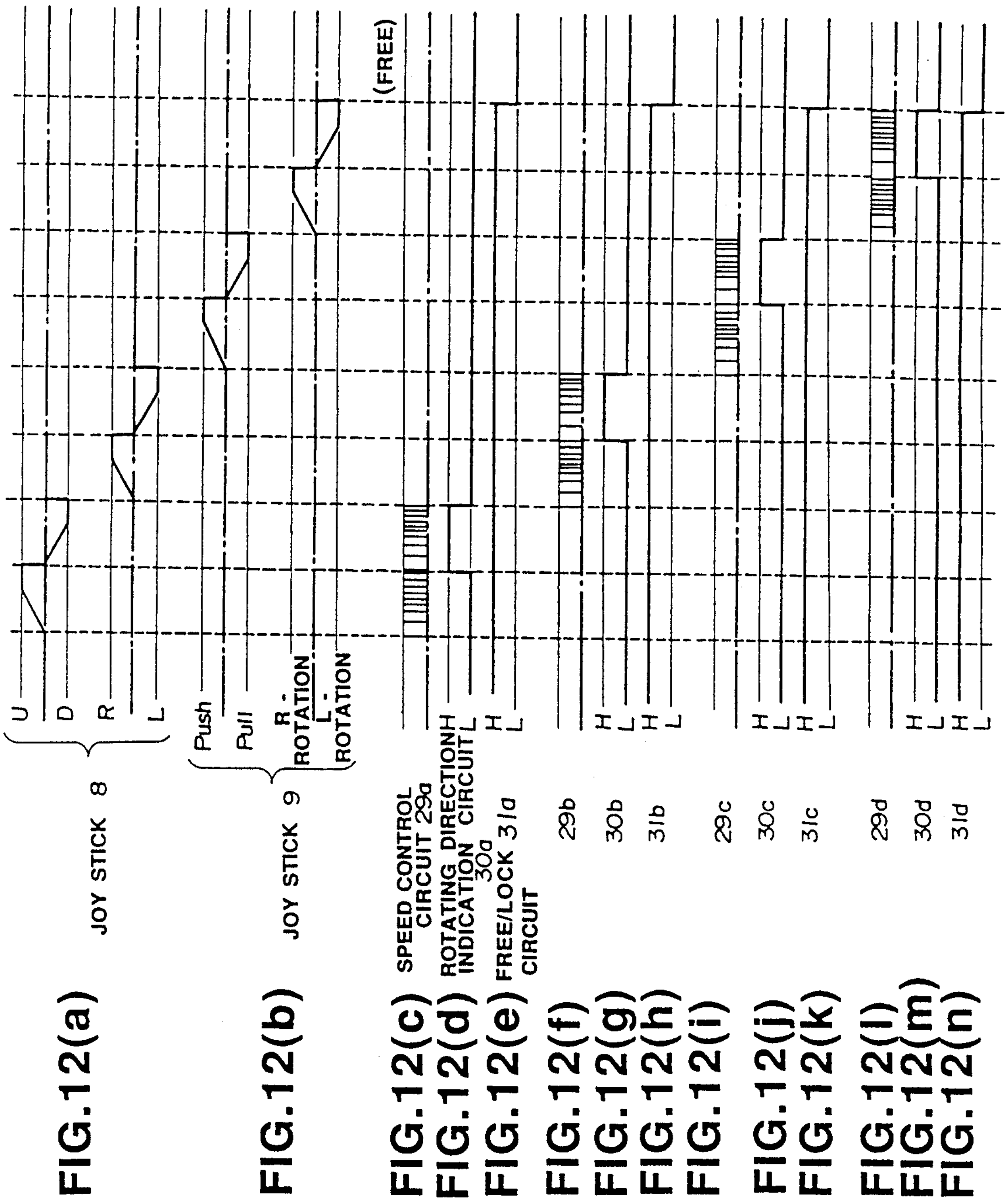

In FIG. 12, (*a*), (*b*) represent operations of the joy sticks 8, 9, respectively. (*c*) through (*e*) represent operations of the speed control circuit 29*a*, the rotating direction indication circuit 30*a* and the free/lock circuit 31*a* for the bending drive motor 12*a*, respectively. Likewise, (*f*) through (*h*) represent operations of the respective circuits 29*b*, 30*b*, 31*b* for the bending drive motor 12*b*; (*i*) through (*k*) represent operations of the respective circuits 29*c*, 30*c*, 31*c* for the movement motor 23*a*; and (*l*) through (*n*) represent operations of the respective circuits 29*d*, 30*d*, 31*d* for the rotation motor 24*a*.

Also, in FIGS. 13 through 20 (*a*) through (*c*) represent operations of the switches 10*a*–10*c*, respectively; (*d*), (*e*) represent operations of the joy sticks 8, 9, respectively; and (*f*) through (*h*) represent operations of the switches 25*a*, 25*c*, 25*d*, respectively. Furthermore, (i) and (j) represent operations of the speed control circuit 29*a* and the rotating direction indication circuit 30*a* for the bending drive motor 12*a*, respectively. Likewise, (k) and (l) represent operations of the respective circuits 29*b*, 30*b* for the bending drive motor 12*b*; (m) and (n) represent operations of the respective circuits 29*c*, 30*c* for the movement motor 23*a*; and (o) and (p) represent operations of the respective circuits 29*d*, 30*d* for the rotation motor 24*a*, respectively.

First, (I) operation during normal bending process will be described with reference to FIG. 12.

When the joy stick 8 is operated in the upward (hereinafter referred to as U) direction as shown at (a) in FIG. 12, the voltage dependent on a degree of the tilting is sent from the control circuit 28 to the speed control circuit 29*a*. The speed control circuit 29*a* outputs pulses of frequency dependent on the applied voltage value, as shown at (c). In other words, the speed control circuit 29*a* outputs pulses of lower frequency when the voltage is low, and pulses of higher frequency when it is high. The motor 12*a* is thereby revolved in a direction corresponding to the U direction at a speed gradually increased. Note that the motors 12*a*, 12*b*, 23*a*, 24*a* are each a stepping motor. The rotating direction indication circuit 30*a* outputs a high level (hereinafter referred to as H) when the joy stick 8 is operated in the downward (hereinafter referred to as D) direction, and a low level (hereinafter referred to as L, but with it in mind that L has meaning of low level for signals and meaning of left for directions) in other cases. As shown at (d), the rotating direction indication circuit 30*a* controls the motor 12*a* such that it revolves forwards when the output is at L, and it revolves backwards when the output is at H. The free/lock circuit 31*a* outputs L when the freely bending state is indicated by the free/lock switch 11*a* or the all-free switch 25*e*, and H in other cases. As shown at (e), the free/lock circuit 31*a* controls the motor 12*a* such that it is locked when the output is at H, and it is set free when the output is at L.

The foregoing similarly applies to the other D, rightward (hereinafter referred to as R) and leftward (hereinafter referred to as L) directions as shown at (a) and (c) through (h), and hence explanation with regard to those directions are omitted here.

Then, when the joy stick 9 is operated in the advance (designated by "Push" in the drawing), the voltage dependent on a degree of the tilting is sent from the control circuit 28 to the speed control circuit 29*a* as shown at (i), so that the motor 23*a* is revolved forwards and the insert section 2 is advanced by the movement rollers 23. As shown at (j), the rotating direction indication circuit 30*c* outputs H when the joy stick 9 is operated in the retreat (designated by "Pull" in the drawing) direction, and outputs L in other cases. It is to be noted that the retreating or pulling operation is also similarly performed as shown at (b) and (i) through (k), and hence is not explained here.

Next, when the joy stick 9 is operated in the R-rotating direction, the voltage dependent on a degree of the tilting is sent from the control circuit 28 to the speed control circuit 29*a* as shown at (l), so that the motor 24*a* is revolved forwards and the insert section 2 is rotated rightwards by the rotation rollers 23. As shown at (m), the rotating direction indication circuit 30*d* outputs H when the joy stick 9 is operated in the L-rotating direction, and outputs L in other cases. It is to be noted that the L-rotating operation is also similarly performed as shown at (b) and (l) through (n), and hence is not explained here.

When the free/lock switches 11*a*, 11*b*, 11*c* are operated together, the free/lock circuits 31*a*–31*d* output L to set the motors 12*a*, 12*b*, 23*a*, 24*a* free. The latter process also occurs when the all-free switch 25*e* is turned on.

Further, the minute bending vibration mode selector switch 25*a* is a switch for selecting the directions of minute vibration and the directions of swing motion by turns. More specifically, whenever depressed, the switch 25*a* cyclically selects one of the minute vibration in the same direction as the bending direction (hereinafter referred to as a parallel minute vibration), the minute vibration orthogonal to the bending direction (hereinafter referred to as an orthogonal minute vibration), the rightward swing motion, and the leftward swing motion. The bending/movement/rotation/swing setting selector switch 25*b* makes it possible to set a minute vibrating angle and a minute vibrating speed in the various forms of operations, whenever depressed. For example, when the operator desires to set an angle and a speed of the minute rotating vibration, the switch 25*b* is depressed two times to get into the rotation setting state, following which the speed specifying switch 25*d* and the angle specifying switch 25*c* are depressed so as to achieve the minute rotating vibration at a desired speed and angle. Incidentally, the switch 25*b* is arranged to cyclically select one of bending, movement, rotation and swing by turns.

Next, (II) operation during non-bending process in a parallel minute vibration mode will be described with reference to FIG. 13.

Figures 13K, 13M, 13O:
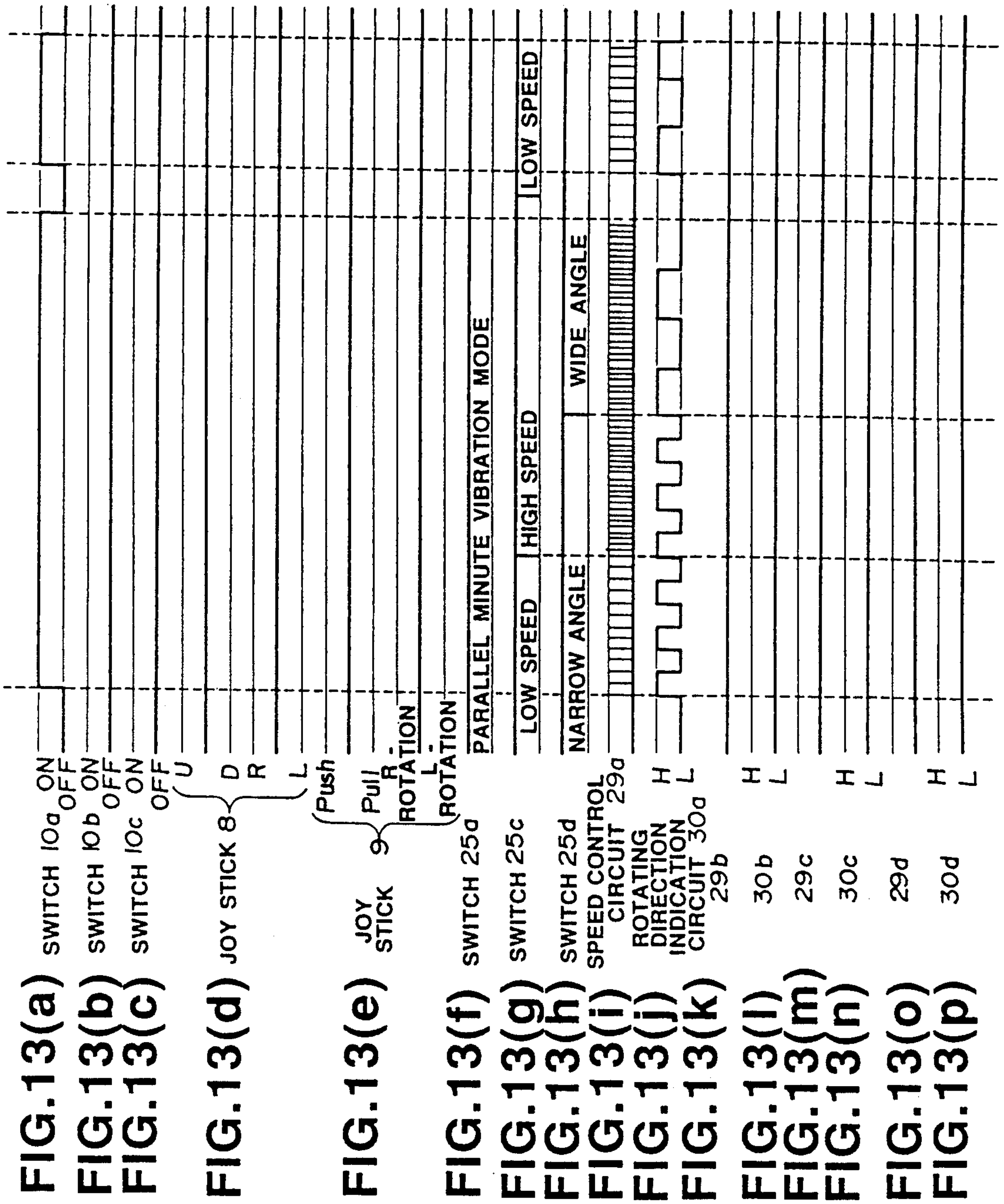

When the minute bending vibration switch 10*a* is turned on as shown at (a) in FIG. 13,, the bendable portion 7 develops a minute vibration (reciprocal motion) under conditions set by the switches 25*a*, 25*c*, 25*d*. More specifically, when the switch 25*a* is set to a parallel minute vibration mode as shown at (f), the switch 25*c* is set to a low speed as shown at (g), and the switch 25*d* is set to a narrow angle as shown at (h), the rotating direction indication circuit 30*a* for the UD motor 12*a* successively outputs H and L alternately as shown at (j), and the speed control circuit 29*a* outputs pulses with pulse width dependent on a speed value set by the switch 25*c* as shown at (i). Therefore, the motor 12*a* is repeatedly revolved forwards and backwards so that the bendable portion 7 develops a minute vibration in the UD directions. When the switch 25*c* is set to a high speed as shown at (g), the width of pulses output from the speed control circuit 29*a* is reduced as shown at (i), whereby the bendable portion 7 develops a minute vibration at a high speed. When the bending angle is set to a wide angle, the bendable portion 7 develops a minute vibration with larger amplitude.

Although in this embodiment the bending angle is set based on the output frequency of the rotating direction indication circuit 30*a* as shown at (j), the bending angle may be controlled by detecting an angle of revolution of the motor 12*a* from the output of the encoder 18*a*.

Further, when an orthogonal minute vibration mode is set by the switch 25*a*, the RL motor 12*b* is operated upon turning-on of the switch 10*a*, causing the bendable portion 7 to develop a minute vibration in the RL direction.

Note that the foregoing description corresponds to the case where the switch 10*a* is operated without operating the joy stick 8.

Next, (III) operation during bending process in a parallel minute vibration mode will be described with reference to FIG. 14. In other words, the case of depressing the switch 10*a* while operating the joy stick 8 will be described. For brevity of explanation, operation of the joy stick 8 will be limited to on/off control (namely, a degree of tilting of the joy stick 8 will not be taken into account), and the minute vibration will be limited to a low speed and a narrow angle in the following description. As with the foregoing operation in which the joy stick 8 is not operated, however, it is possible to selectively set the speed (high speed/low speed, etc.) and the angle (wide angle/narrow angle, etc.) by the switches 25*c*, 25*d*.

Figures 14K, 14M, 14O:
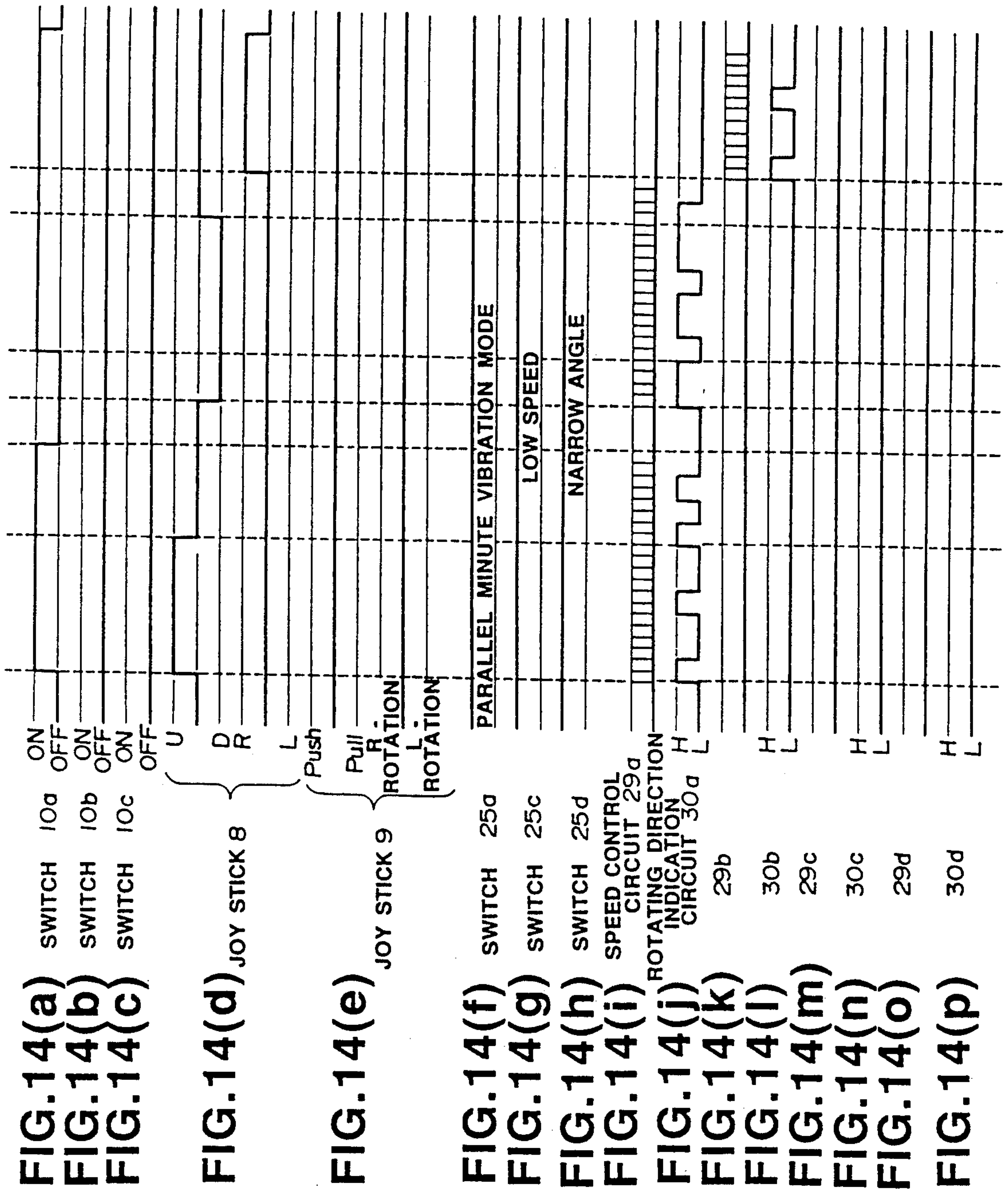

In the case of a parallel minute vibration mode being set as shown at (f) in FIG. 14, when the switch 10*a* is turned on and the joy stick 8 is operated in the U direction, the rotating direction indication circuit 30*a* outputs H and L alternately as shown at (j) such that L lasts longer than H. Thus, the driving period in the U direction is longer than that in the D direction. At this time, the speed control circuit 29*a* outputs pulses dependent on a specified speed as shown at (i). Accordingly, the bendable portion 7 is bent in the U direction while minutely vibrating in the UD directions.

When the joy stick 8 is turned off, i.e., returned to a neutral position, the bendable portion 7 develops just a minute vibration in the UD directions.

Further, when the joy stick 8 is turned toward the D side, the rotating direction indication circuit 30*a* outputs H and the speed control circuit 29*a* outputs pulses dependent on a specified speed, whereby the bendable portion 7 is bent toward the D side. On this occasion, when the switch 10*a* is turned on, the rotating direction indication circuit 30*a* outputs pulses with the duration of H being longer than that of L, and the speed control circuit 29*a* outputs pulses dependent on a specified speed. Accordingly, the bendable portion 7 is bent in the D direction while minutely vibrating in the UD directions.

Likewise, when the joy stick 8 is operated in the R direction, the bendable portion is bent in the R direction while minutely vibrating in the RL directions. Also, when the joy stick 8 is operated in the L direction, the bendable portion is bent in the L direction while minutely vibrating in the RL directions.

Next, (IV) operation in an orthogonal minute vibration mode will be described with reference to FIG. 15.

For brevity of explanation, operation of the joy stick 8 will be limited to on/off control and the minute vibration will be limited to a low speed and a narrow angle in the following description as well.

Figures 15K, 15M, 15O:
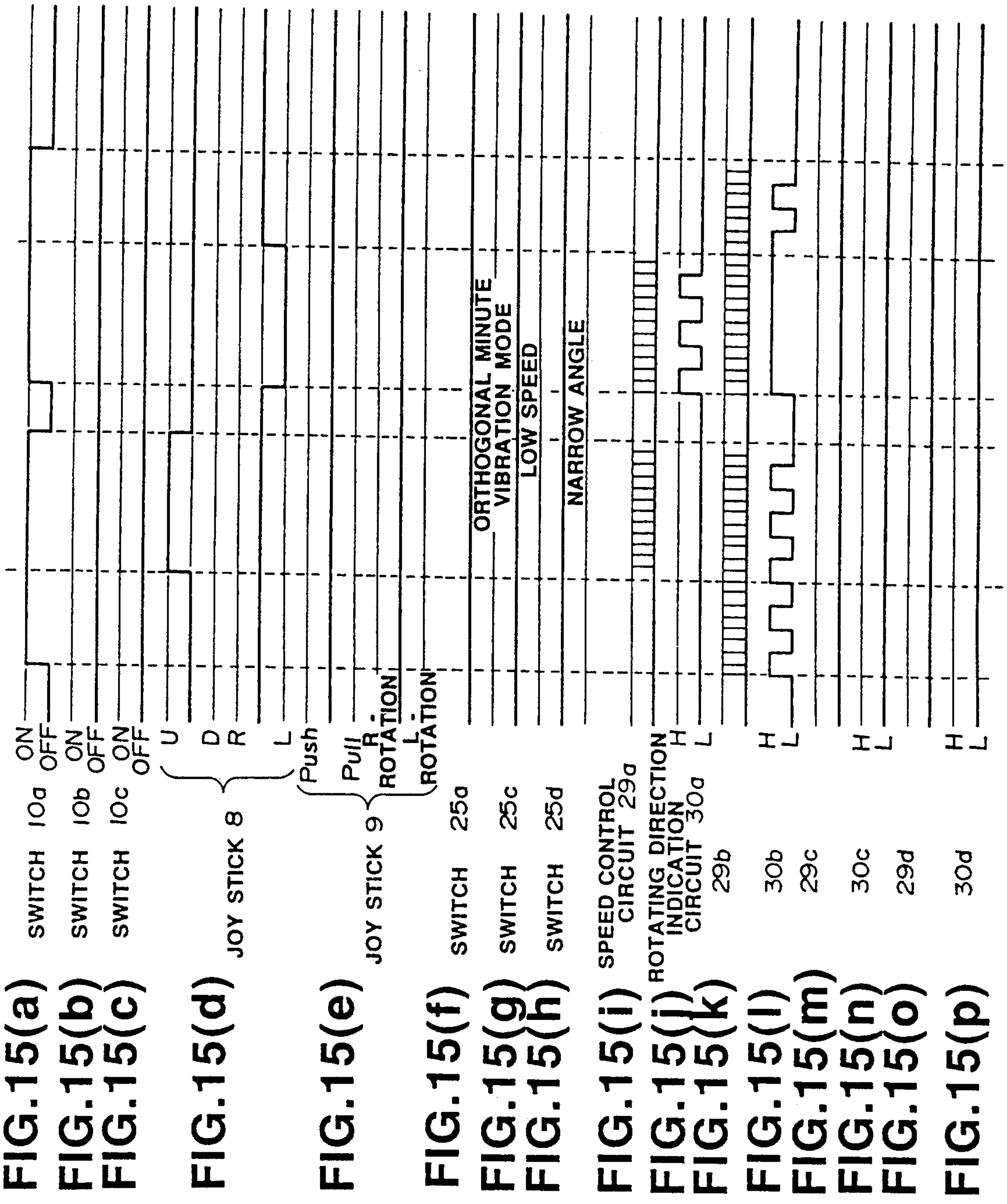

When the switch 10*a* is operated without operating the joy stick 8 as shown in at (a) and (d) in FIG. 15, the bendable portion 7 develops a minute vibration in the RL direction as mentioned above.

When the joy stick 8 is operated in the U direction under the above condition, the bendable portion 7 is bent in the U direction as shown at (i) and (j) while minutely vibrating in the RL directions as shown at (k) and (l). Likewise, when the joy stick 8 is operated in the D direction, the bendable portion 7 is bent in the D direction while minutely vibrating in the RL directions.

Further, when the joy stick 8 is operated in the L direction, the bendable portion 7 is bent in the L direction as shown at (k) and (l) while minutely vibrating in the UD directions as shown at (i) and (j). Likewise, when the joy stick 8 is operated in the R direction, the bendable portion 7 is bent in the R direction while minutely vibrating in the UD directions.

Although the foregoing explanation has been made as operating the joy stick in any one of the U, D, R and L direction, the joy stick may be operated to include either one of the UD directions and either one of the RL directions in a combined manner. In this case, the bendable portion 7 is bent in a direction intermediate between the two directions operated, while minutely vibrating in the UD and RL directions.

Figures 16A, 16B, 16C, 16D, 16E, 16F, 16G, 16H, 16I, 16J, 16K, 16L, 16M, 16N, 16O, 16P:
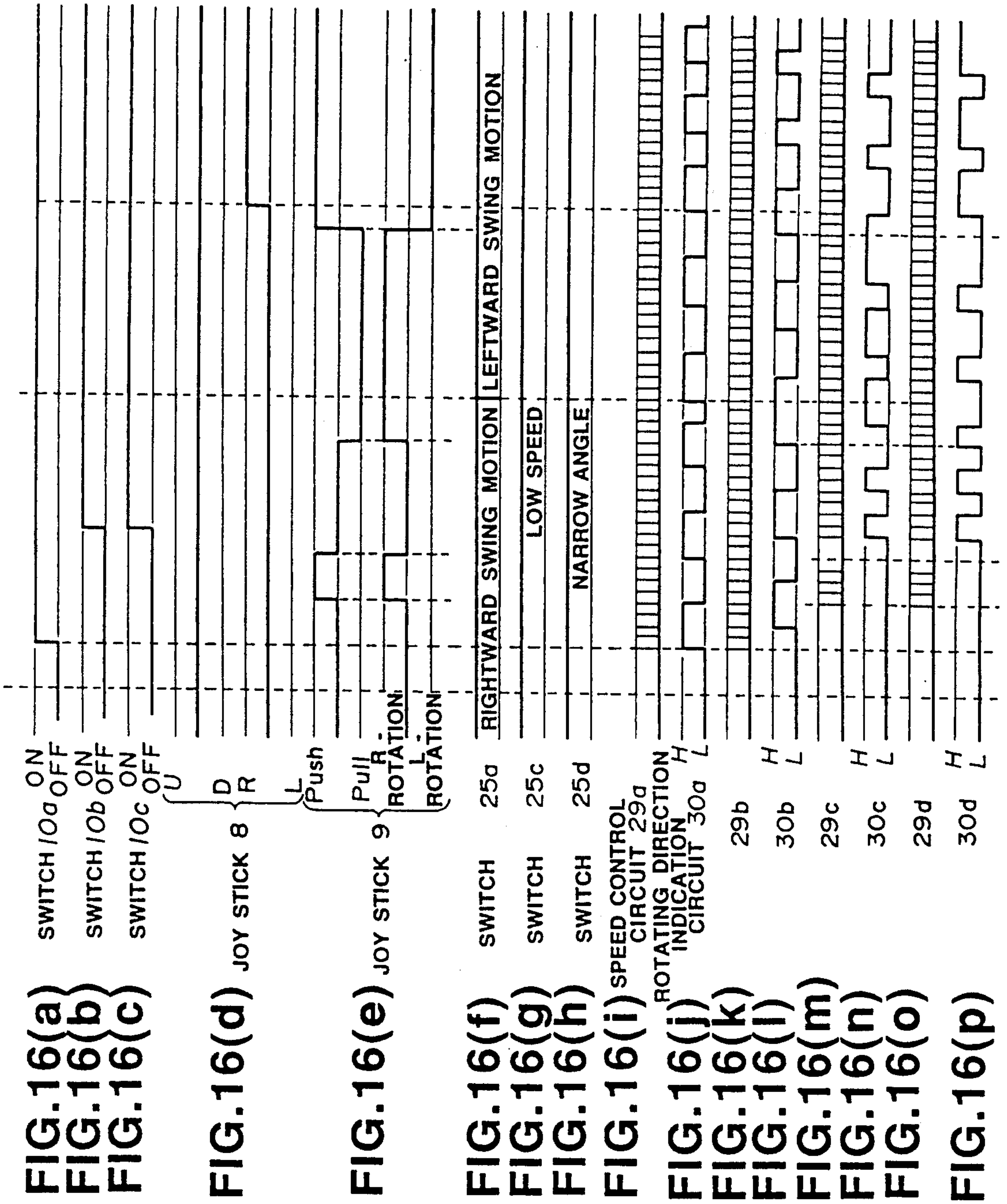

Next, (V) operation based on swing motion, minute moving vibration and minute rotating vibration will be described with reference to FIG. 16.

Here, the case of the switch 25*a* being set to a rightward swing motion mode or a leftward swing motion mode as shown at (f) will be explained, along with other cases of performing movement and rotation.

When the switch 10*a* is turned on as shown at (a), the speed control circuits 29*a*, 29*b* output pulses dependent on the speed set by the switch 25*c* as shown at (i) and (k). At this time, the rotating direction indication circuits 30*a*, 30*b* output respective trains of pulses which are 90 degrees out of phase, as shown at (j) and (l). Setting of the switch 25*a* determines whether a rightward or leftward swing motion. In the case of rightward swing, the output pulses of the rotating direction indication circuit 30*a* are ahead 90 degrees from those of the rotating direction indication circuit 30*b*. In the case of leftward swing, the phase relationship is reversed. The bendable portion 7 is thereby caused to develop the rightward or leftward swing motion. Note that this swing motion is also one form of the minute vibration (reciprocal motion). This is because the swing motion results from a combination of the linear minute vibration in the UD directions and the linear minute vibration in the RL directions. Accordingly, by appropriately setting a phase difference between two trains of the output pulses from the rotating direction indication circuits 30*a*, 30*b*, an elliptic swing motion can also be achieved.

When the joy stick 8 is operated in the R direction, for example, during the above swing motion, the rotating direction indication circuit 30*b* outputs pulses with the duration of H being shorter than that of L. This allows the bendable portion 7 to bend in the R direction while continuing the swing motion. As to the other directions, the bendable portion 7 is similarly bent while continuing the swing motion in the corresponding direction in which the joy stick 8 is operated. More detailed explanation is omitted here.

There will now be described minute moving and rotating vibrations. Note that the speed and angle (length) of movement and the speed and angle of rotation can be set by the switches 25*c*, 25*d* after setting the switch 25*b* to a movement or rotation mode. In an example of FIG. 16, the movement and the rotation are both set to a low-speed, narrow-angle mode.

Under a condition that the minute moving vibration switch 10*b* and the minute rotating vibration switch 10*c* are turned off as shown at (b) and (c), when the joy stick 9 is operated so as to include both the advance (Push) direction and the R-rotating direction (i.e., operated obliquely between the Push direction and the R-rotating direction) as shown at (e), the rotating direction indication circuits 30*c*, 30*d* output L as shown at (n) and (p), and the speed control circuits 29*c*, 29*d* output pulses in a low speed mode as shown at (m) and (o). Accordingly, the insert section 2 advances while rotating rightwards.

On the other hand, when the minute moving vibration switch 10*b* and the minute rotating vibration switch 10*c* are turned off as shown at (b) and (c), the rotating direction indication circuits 30*c*, 30*d* output pulses in a narrow angle mode as shown at (n) and (p). Then, the speed control circuits 29*c*, 29*d* output pulses in a low speed mode as shown at (m) and (o). Accordingly, the insert section 2 develops the minute moving vibration (minute movement) while continuing the minute rotating vibration (minute rotation).

Now, when the joy stick 9 is operated obliquely between the retreat (Pull) direction and the R-rotating direction during the combined operation of minute rotating vibration and minute moving vibration, the speed control circuits 29*c*, 29*d* output pulses in a low speed mode, the rotating direction indication circuit 30*c* outputs pulses with the duration of H being longer than that of L, and the rotating direction indication circuit 30*d* outputs pulses with the duration of L being longer than that of H. Accordingly, the insert section 2 rotates in the R direction while continuing the minute rotating vibration, and also retreats while continuing the minute moving vibration.

Likewise, when the joy stick 9 is operated obliquely between the advance (Push) direction and the L-rotating direction during the combined operation of minute rotating vibration and minute moving vibration, the insert section 2 rotates in the L direction while continuing the minute rotating vibration, and also advances while continuing the minute moving vibration.

Although the minute bending vibration, the minute rotating vibration and the minute moving vibration have been explained above, it is needless to say that these vibrations can be performed in any desired combination. It should also be understood that the bending operation can be added during the process of any minute vibration.

Figures 17K, 17M, 17O:
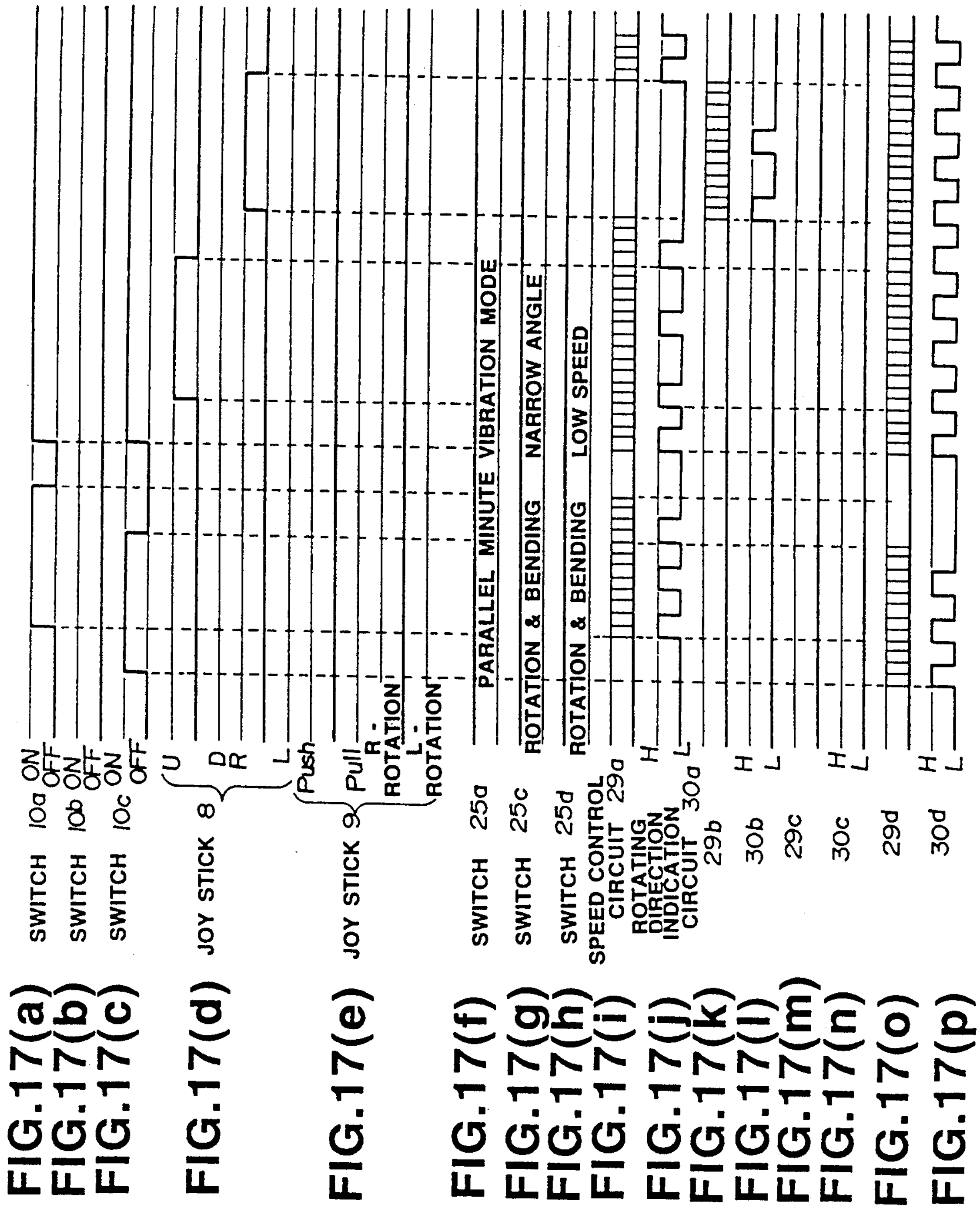

Next, (VI) operation in a combination of minute rotating vibration and minute bending vibration will be described with reference to FIG. 17. For brevity of explanation, the following shows an example in which a parallel minute vibration mode is set as shown at (f), and the minute rotating and bending vibrations are both set to a narrow-angle, low-speed mode.

When the minute bending vibration switch 10*a* and the minute rotating vibration switch 10*c* are turned on as shown at (a) and (c), the rotating direction indication circuits 30*a*, 30*d* output pulses in a narrow angle mode as shown at (j) and (p), and the speed control circuits 29*a*, 29*d* output pulses in a low speed mode as shown at (i) and (o). Accordingly, the insert section 2 develops the minute bending vibration while continuing the minute rotating vibration. Not that when the switch 10*a* or the switch 10*c* is solely operated, the minute bending vibration or the minute rotating vibration is performed independently as mentioned above.

Now, when the joy stick 8 is operated in the U direction as shown at (d) under a condition that the minute bending vibration switch 10*a* and the minute rotating vibration switch 10*c* are turned on, the rotating direction indication circuit 30*a* outputs pulses with the duration of L being longer than that of H as shown at (j). The remaining process is the same as that in the case where the joy stick 8 is not operated. Accordingly, the insert section 2 is bent in the U direction while continuing both the minute rotating vibration and the minute bending vibration. Likewise, when the joy stick 8 is operated in the D, R or L direction, the insert section 2 is bent in the D, R or L direction, respectively, while continuing both the minute rotating vibration and the minute bending vibration.

Figures 18A, 18B, 18C, 18D, 18E, 18F, 18G, 18H, 18I, 18J, 18K, 18L, 18M, 18N, 18O, 18P:
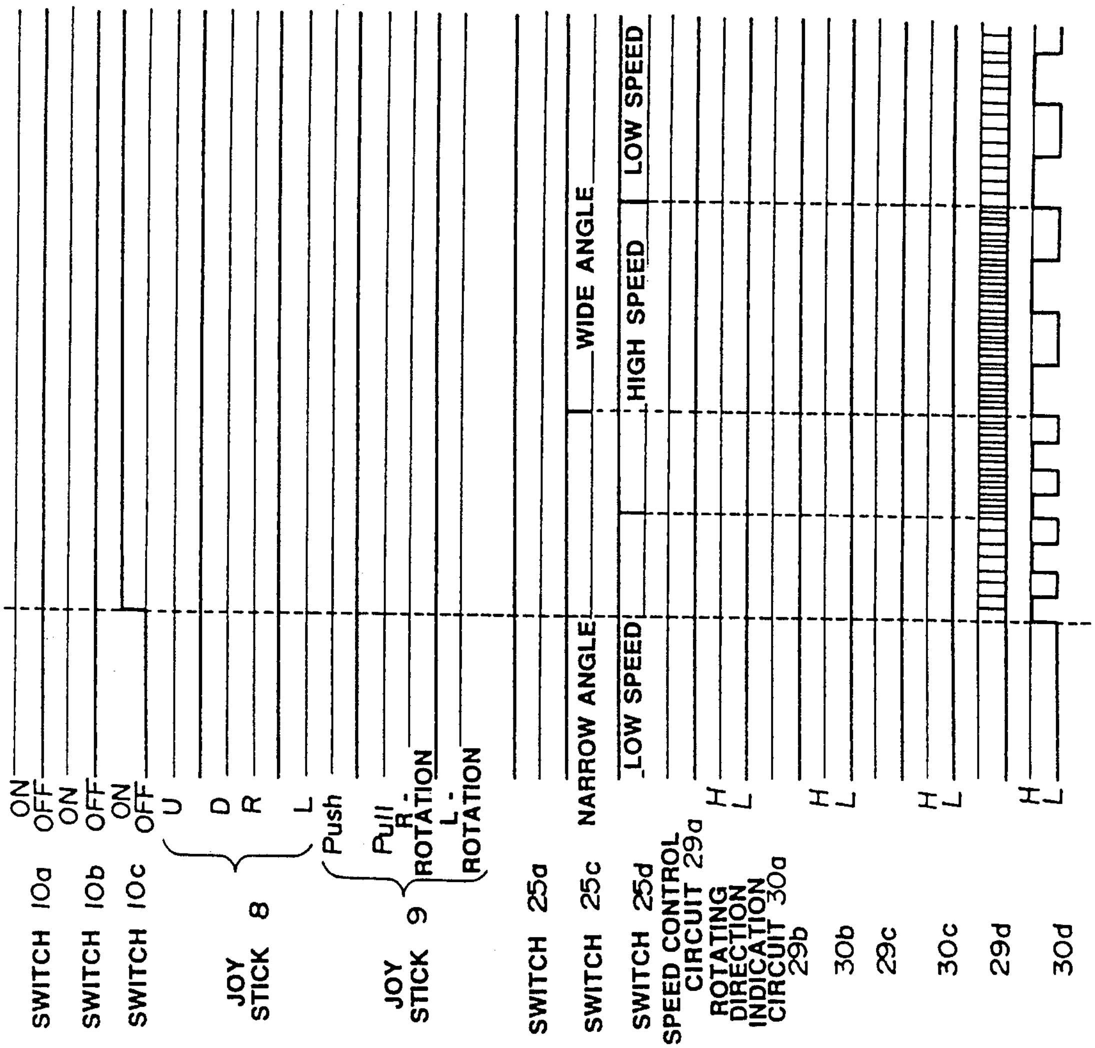

Next, (VII) operation upon change in conditions of minute rotating vibration will be described with reference to FIG. 18.

In a narrow-angle, low-speed mode as shown at (g) and (h), when the minute rotating vibration switch 10*c* is turned on as shown at (c), the rotating direction indication circuit 30*d* outputs pulses in a narrow angle mode as shown at (p), and the speed control circuit 29*d* outputs pulses in a low speed mode as shown at (o). Accordingly, the insert section 2 develops the minute rotating vibration in a narrow-angle, low-speed mode. Now, when the switch 25*d* is operated to select a high speed mode, the speed control circuit 29*d* outputs pulses in a high speed mode as shown at (o). Thus, the pulse frequency is increased. This causes the insert section 2 to develop the minute rotating vibration in a narrow-angle, high-speed mode.

Further, when the switch 25*c* is operated to select a wide angle mode, the rotating direction indication circuit 30*d* outputs pulses in a wide angle mode as shown at (p). Thus, the pulse frequency is decreased. This causes the insert section 2 to develop the minute rotating vibration in a wide-angle, high-speed mode. In addition, when the switch 25*d* is operated to select a low speed mode, the speed control circuit 29*d* outputs pulses in a low speed mode as shown at (o). This causes the insert section 2 to develop the minute rotating vibration in a wide-angle, low-speed mode.

Next, (VIII) operation in a combination of minute moving vibration and minute bending vibration will be described with reference to FIG. 19. For brevity of explanation, the following shows an example in which a parallel minute vibration mode is set as shown at (f), and the minute moving and bending vibrations are both set to a narrow-angle, low-speed mode.

When the minute bending vibration switch 10*a* and the minute moving vibration switch 10*b* are turned on as shown at (a) and (b), the rotating direction indication circuits 30*a*, 30*c* output pulses in a narrow angle mode as shown at (j) and (n), and the speed control circuits 29*a*, 29*c* output pulses in a low speed mode as shown at (i) and (m). Accordingly, the insert section 2 develops the minute bending vibration while continuing the minute moving vibration. Note that when the switch 10*a* or the switch 10*b* is solely operated, the minute bending vibration or the minute moving vibration is performed independently as mentioned above.

Now, when the joy stick 8 is operated in the U direction as shown at (d) under a condition that the minute bending vibration switch 10*a* and the minute moving vibration switch 10*b* are turned on, the rotating direction indication circuit 30*a* outputs pulses with the duration of L being longer than that of H as shown at (j). The remaining process is the same as that in the case where the joy stick 8 is not operated. Accordingly, the insert section 2 is bent in the U direction while continuing both the minute moving vibration and the minute bending vibration. Likewise, when the joy stick 8 is operated in the D, R or L direction, the insert section 2 is bent in the D, R or L direction, respectively, while continuing both the minute moving vibration and the minute bending vibration.

Next, (IX) operation upon change in conditions of minute moving vibration will be described with reference to FIG. 20.

In a narrow-angle, low-speed mode as shown at (g) and (h), when the minute moving vibration switch 10*b* is turned on as shown at (b), the rotating direction indication circuit 30*c* outputs pulses in a narrow angle mode as shown at (n), and the speed control circuit 29*c* outputs pulses in a low speed mode as shown at (m). Accordingly, the insert section 2 develops the minute moving vibration in a narrow-angle (short-distance), low-speed mode. Now, when the switch 25*d* is operated to select a high speed mode, the speed control circuit 29*c* outputs pulses in a high speed mode as shown at (m). Thus, the pulse frequency is increased. This causes the insert section 2 to develop the minute moving vibration in a narrow-angle (short-distance), high-speed mode.

Further, when the switch 25*c* is operated to select a wide angle mode, the rotating direction indication circuit 30*c* outputs pulses in a wide angle mode as shown at (n). Thus, the pulse frequency is decreased. This causes the insert section 2 to develop the minute moving vibration in a wide-angle (long-distance), high-speed mode. In addition, when the switch 25*d* is operated to select a low speed mode, the speed control circuit 29*c* outputs pulses in a low speed mode as shown at (m). This causes the insert section 2 to develop the minute moving vibration in a wide-angle (long-distance), low-speed mode.

FIGS. 21 through 26 show behavior of the minute bending vibration in the UD directions, the minute bending vibration in the RL directions, the rightward swing motion, the leftward swing motion, the minute moving vibration, and the minute rotating vibration, respectively.

Figure 27:
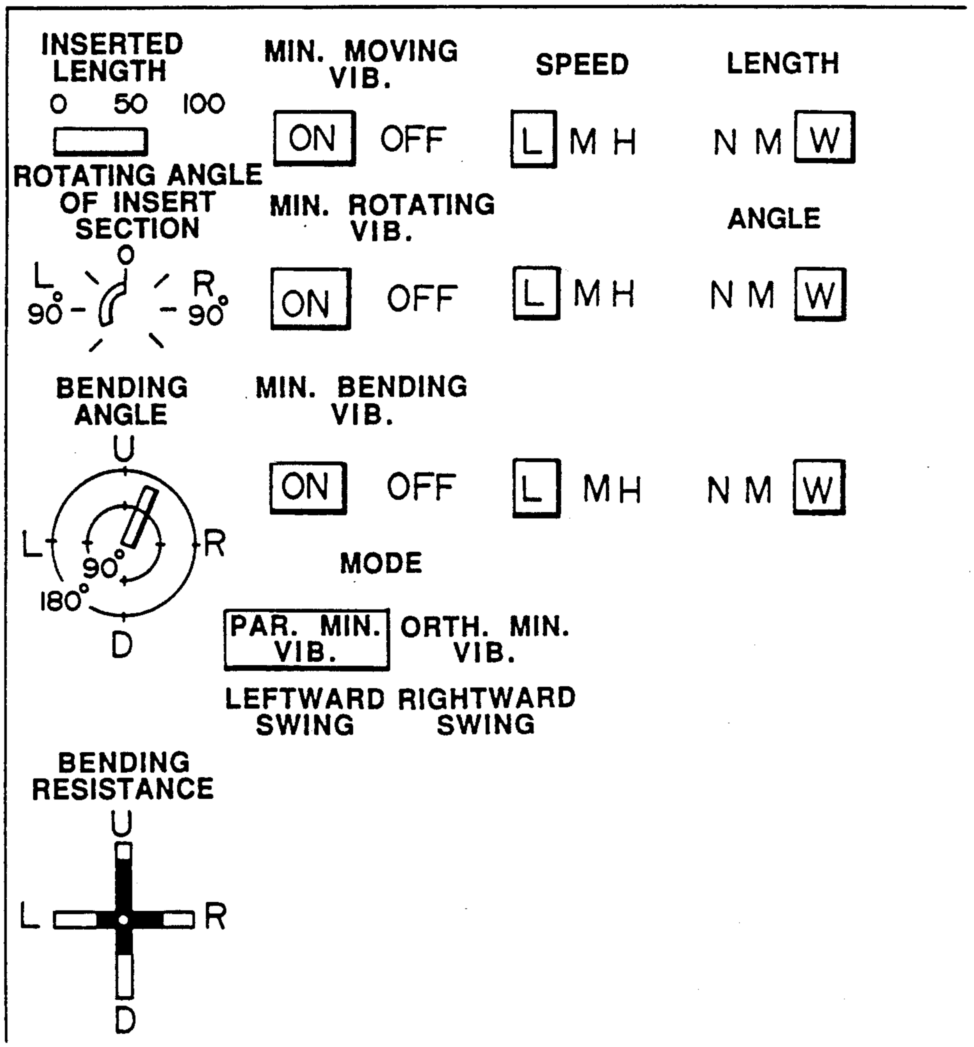

FIG. 27 shows a part of a mode display section on the screen of the monitor 40. More specifically, the mode display section displays the inserted length of the insert section 2, the rotating angle of the insert section 2, the bending angle of the bendable portion 7, and the bending resistance of the bendable portion 7. The mode display section also displays the on/off state of the minute moving vibration, the minute rotating vibration and the minute bending vibration, as well as the mode of the minute bending vibration (i.e., parallel minute vibration, orthogonal minute vibration, leftward swing motion or rightward swing motion). Further, the mode display section displays conditions of the speed (e.g., three stages L, M, H), length and angle (e.g., three stages N, M, W) of each minute vibration.

Moreover, the monitor is arranged such that if the output of the bending resistance detection circuit 19 exceeds a predetermined critical value, it gives an alarm and stops the respective minute vibrations of bending, movement and rotation.

With this embodiment, as described above, the insert section 2 is subjected to a minute vibration for reducing the contact resistance exerted on the insert section 2 and improving operability of insertion. Application of the minute bending vibration causes the rear part of the bendable portion 7 and hence the front end part of the pliable portion 43, to develop a minute vibration for reducing the contact resistance exerted on that parts.

During the minute bending vibration, since the insert section 2 vibrates of itself in a direction crossing the axial direction thereof even when it is not in contact with the inner wall of the body cavity, the impact against the inner wall of the body cavity is reduced.

Further, since conditions of the minute vibration can appropriately be selected for proper operation dependent on the state of an object to be examined, an object into which the insert portion is to be inserted, or the like, it is possible to reduce the bending resistance exerted on the insert section 2 inclusive of the bendable portion 7, without damaging the object to be examined, the inserted object or the like. This further improves operability of insertion.

In addition, since the angle (length) and the direction of each minute vibration can appropriately be chosen, conditions of the optimum minute vibration can be selected dependent on the size, configuration or other factor of a tract and cavity as the inserted object. Since the speed of each minute vibration can appropriately be chosen, it is also possible to select a proper speed in accordance with the kind of a disease.

As to the minute bending vibration, since the direction of the minute vibration can selectively be set parallel (i.e., in the same direction as) or orthogonal to the bending direction, and the rightward swing motion and the leftward swing motion can selectively be added, it is possible to select an optimum mode dependent on the state of a tract and cavity.

Since the respective minute vibrations are turned on/off by the switches 10*a*–10*c*, it is possible to turn off the minute vibration which may possibly perforate a diverticulum region of the organ wall, for example, thereby ensuring a high degree of safety. In an attempt to insert the insert section while closely observing the internal state of the object, for example, a clearer object image free from blur and noise can be obtained by turning off the minute vibration.

Further, since the minute bending vibration is performed by the motors 12*a*, 12*b* used for the bending, it is not required to provide a motor for the minute vibration separately from the bending motor, thereby avoiding an increase in size and weight of the endoscope.

In addition, the insert section 2 can be subjected to the minute moving vibration and/or the minute rotating vibration. Therefore, even when the minute bending vibration is hard to develop or has no effect, for example, the contact resistance exerted on the insert section 2 can be reduced to improve operability of insertion, by effecting the minute moving vibration and/or the minute rotating vibration.

In an orthogonal minute vibration mode of the minute bending vibration, the bending can surely be continued even when the bending has been ceased halfway. More specifically, in the case where the bending is ceased halfway, the bendable portion 7 is subjected to the tension in a direction opposite to the bending direction and, therefore, large actuating torque is required at the time of resuming the bending. Accordingly, the bending may become hard to resume and perform in such cases. Nevertheless, by imparting a minute vibration to the bendable portion 7 in a direction orthogonal to the bending direction, the bending can easily be resumed.

Since the bendable portion 7 can be bent while applying various forms of minute vibrations, it is possible to insert the bendable portion 7 along the bent tract and cavity while developing the desired minute vibration, and to improve operability of insertion through the bent object in particular.

Further, either one or both of movement and rotation of the insert section 2 can be performed by the joy stick 9, resulting in very good operability.

Since one or more of various forms of minute vibrations, i.e., the minute bending vibrations (parallel minute vibration, orthogonal minute vibration, rightward swing motion and leftward swing motion), the minute moving vibration of the insert section, and the minute rotating vibration of the insert section can be operated in a combined manner, it is possible to select the optimum dependent on the state of the tract and cavity.

Moreover, if the insert section 2 happens to make a loop when it is inserted from the descending colon region 267 to the transverse colon region 269 of the large intestine as shown in FIG. 5, for example, the loop can easily be removed because application of the minute vibration to the insert section 2 produces a force for making the insert section 2 straight. Thus, the insert section 2 can easily be inserted without causing a patient to suffer pain.

Each minute vibration is only needed to develop at least one cycle of minute vibration (reciprocal motion). It is preferable that the angle of each minute vibration except for the minute moving vibration is in a range of 1–180 degrees, the length of the minute moving vibration is in a range of 1–5 cm, the speed of each minute vibration except for the minute moving vibration is in a range of 1–90 degrees/sec, and the speed of the minute moving vibration is in a range of 1–50 mm/sec. However, the above respective ranges may appropriately be modified at the operator's discretion.

When, the minute vibration is set to an extremely high speed mode or an extremely wide angle mode, the resulting visual field and angle of view of the endoscope makes it very hard to observe the object image. In this case, the image quality can be improved by properly utilizing a freeze function so as to give intermittent display.

In addition, by displaying various minute vibration modes and other parameters on the same screen as the observed image, as shown in FIG. 27, conditions of the respective minute vibrations can be confirmed at a glance, resulting in more excellent operability.

The speed of each minute vibration may be changed gradually from a low speed to a high speed, or the angle of each minute vibration may be changed gradually from a narrow angle to a wide angle. Also, the minute bending vibration may be shifted from the vertical direction to the horizontal direction, or from the rightward swing motion to the leftward swing motion, etc.

Finally, the insert section 2 may be so arranged as to return to the state prior to the minute vibration, when the minute vibration switch is turned off.

Figure 28:
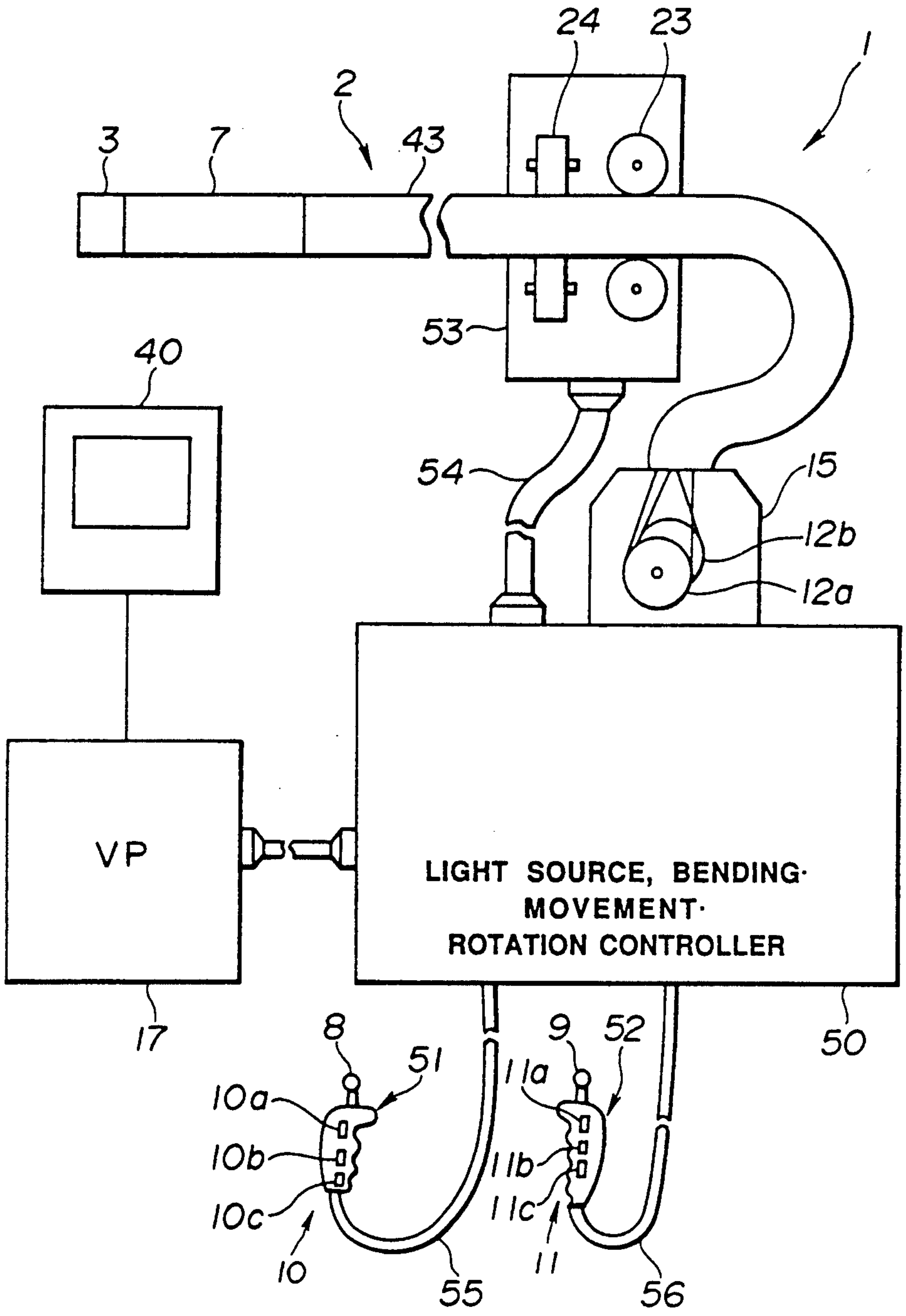
Figure 29:
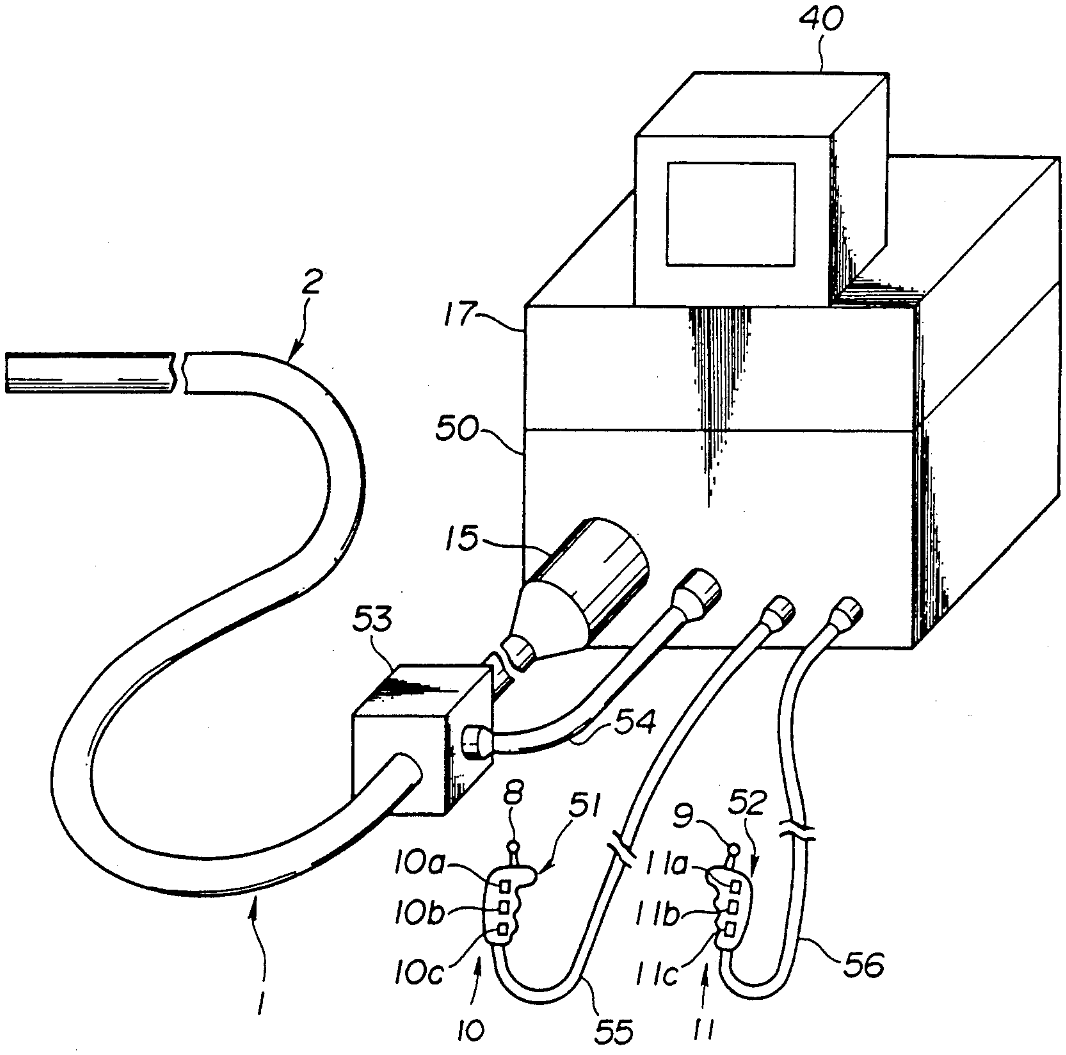

FIGS. 28 and 29 illustrate a seventh embodiment of the present invention.

Note that similar components as those in the sixth embodiment are designated by the same reference numerals, and are not described here.

As shown in FIG. 29, an endoscope apparatus of this embodiment comprises an endoscope 1, a light source and bending/movement/rotation controller 50 to which the endoscope 1 is connected, a VP 17 connected to the controller 50, a monitor 40 connected to the VP 17, and a movement/rotation device 53 attached to an insert section 2 of the endoscope 1.

The endoscope 1 of this embodiment includes no operating section, and a connector 15 is directly provided at the base end of the insert section 2. As will be seen from FIG. 28, motors 12*a*, 12*b* are provided in the connector 15. The connector 15 is connectable to the light source and bending/movement/rotation controller 50. This controller 50 includes the bending/movement/rotation control circuit 20, the bending angle detection circuit 18, the bending resistance detection circuit 19, the lamp 21, the pump 22, and the switch 25 in the above sixth embodiment. Thus, the controller 50 has the same structure as that of the controller 16 of the sixth embodiment except for omission of the VP 17. In this embodiment, the VP 17 is connectable to the controller 50. A bending operating unit 51 and a movement/rotation operating unit 52 are also connectable to the controller 50 via coupling cables 55, 56, respectively. The bending operating unit 51 includes a joy stick 8 and a switch 10, and the movement/rotation operating unit 52 includes a joy stick 9 and a switch 11.

The movement/rotation device 53 is attached to the insert section 2. The movement/rotation device 53 includes the movement rollers 23, the motor 23*a*, the rotation rollers 24, and the motor 24*a* in the sixth embodiment. The movement/rotation device 53 is connectable to the controller 50 via a coupling cable 54.

It is to be noted that connectors provided at the ends of the coupling cables between the respective components are capable of freely attaching and detaching.

With this embodiment, since the motors 12*a*, 12*b* are provided in the connector 15, it is not required to provide an operating section midway the insert section 2. This eliminates the need of gripping the heavy operating section which incorporates motors and others, and only requires to grip the lighter operating units 51, 52, thereby facilitating the operation.

Where the movement/rotation device 53 is not provided, it is possible to perform the bending alone. In this case, the bending can be performed by holding the operating unit 51 by the left hand and the insert section 2 by the right hand, for example.

In the case of providing the movement/rotation device 53, the operating units 51, 52 can be operated while holding them by the respective hands one to one, resulting in very excellent operability. By holding the bending operating unit 51 by the left hand and the movement/rotation operating unit 52 by the right hand, for example, the operator can perform the bending in a familiar manner, because this allotment of roles to the respective hands is approximate to that usually practiced during manual operation, i.e., the left hand manipulates a bending operating knob and the right hand moves and rotates (twists) the insert section.

Moreover, in the case of not providing the movement/rotation device 53, it is further possible to motorize only the bending operation. Of course, the minute bending vibration is also possible.

Other constitution, operation and advantageous effect are similar to those in the sixth embodiment.

Figure 30:
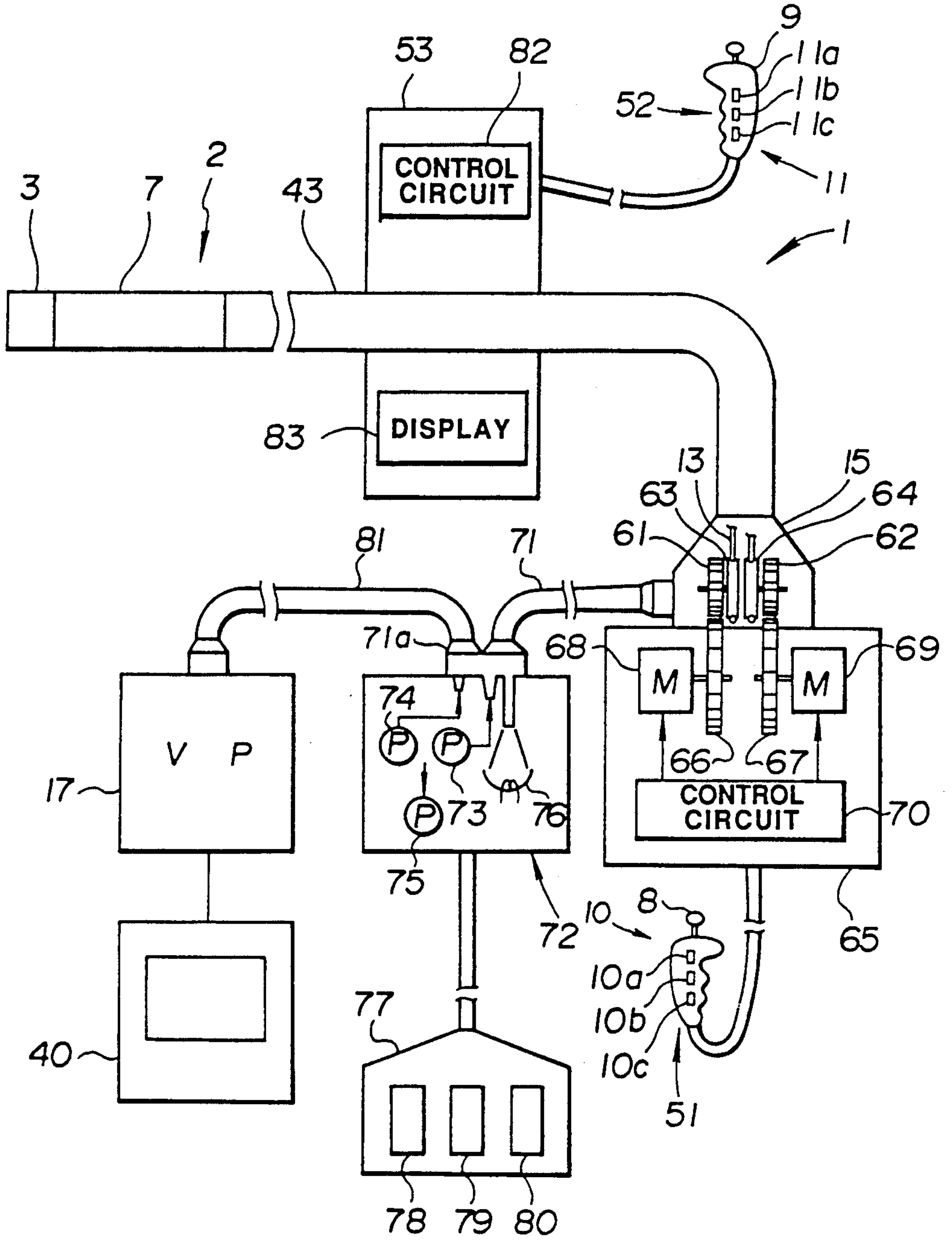
Figure 31:
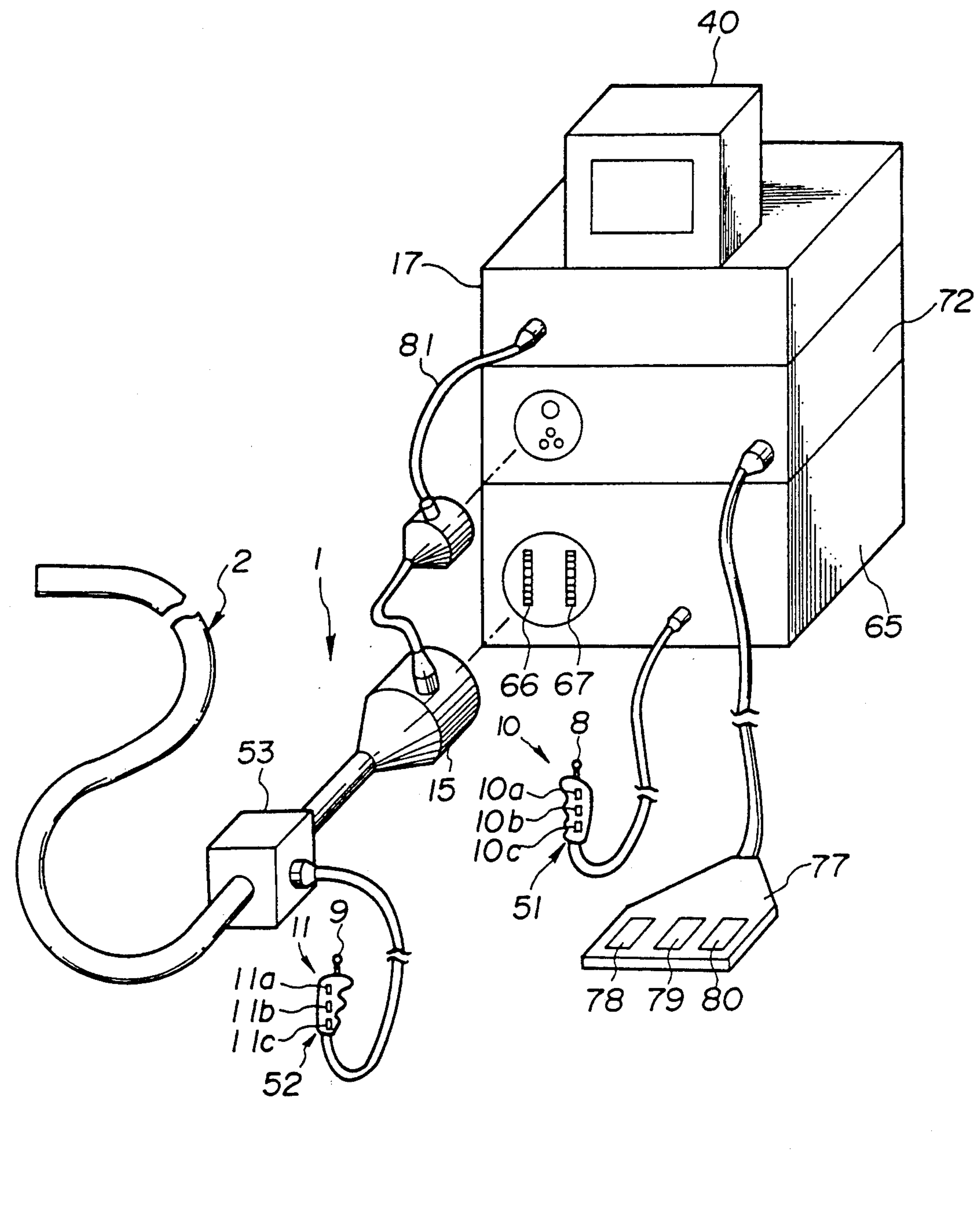

FIGS. 30 and 31 illustrate an eighth embodiment of the present invention.

Note that similar components to those in the sixth and seventh embodiments are designated by the same reference numerals, and are not described here.

As shown in FIG. 31, an endoscope apparatus of this embodiment comprises an endoscope 1, a bending device 65 connected to the endoscope 1, a light source unit 72, a VP 17, a monitor 40 connected to the VP 17, and a movement/rotation device 53 attached to an insert section 2.

The endoscope 1 of this embodiment include no operating section as with the seventh embodiment, and a connector 15 is directly provided at the base end of the insert section 2. As will be seen from FIG. 30, transmission gears 61, 62 are provided in the connector 15, and pulleys 63, 64 are mounted on rotary shafts of the transmission gears 61, 62, respectively. A bending wire 13 is attached to each of the pulleys 63, 64. On the other hand, the bending device 65 includes motors 68, 69, transmission gears 66, 67 mounted on output shafts of the motors 68, 69, respectively, and a control circuit 70 for controlling the motors 68, 69. In a condition that the connector 15 is connected to the bending device 65, the gears 61, 62 in the connector 15 come into mesh with the gears 66, 67 in the bending device 65, respectively. Also connected to the bending device 65 is a bending operating unit 51 similar to that in the seventh embodiment. The control circuit 70 drives the motors 68, 69 dependent on operation of the bending operating unit 51 to control the bending (inclusive of the minute bending vibration) as explained in the sixth embodiment.

The connector 15 is also connectable to the light source unit 72 via a coupling cable 71. The light source unit 72 incorporates an air-feed pump 73, a water-feed pump 74, a suction pump 74, and a lamp 76. A foot switch 77 is connected to the light source unit 72. Treading on pedals 78, 79, 80 of the foot switch 77 actuates air-feed, water-feed and suction, respectively.

A coupling cable 81 is extended from a connector 71*a* of the above cable 71 on the same side as the light source unit 72, and connectable to the VP 17.

Further, connected to the movement/rotation device 53 is a movement/rotation operating unit 52 similar to that in the seventh embodiment. The movement/rotation device 53 incorporates a control circuit 82 and has a display 83. The control circuit 82 drives movement motors 23*a* and rotation motors 24*a* dependent on operation of the movement/rotation operating unit 52 to control the movement and the rotation inclusive of the minute moving vibration and the minute rotating vibration explained in the sixth embodiment. The display 83 displays the inserted length of the insert section 2, the rotating angle of the insert section 2, the on/off state of the minute moving vibration, the speed (L, M, H) of the minute moving vibration, the length (N, M, W) of the minute moving vibration, the on/off state of the minute rotating vibration, the speed (L, M, H) of the minute rotating vibration, and the angle (N, M, W) of the minute rotating vibration.

Meanwhile, the monitor 40 displays the bending angle, the bending resistance, the on/off state of the minute bending vibration, the speed (L, M, H) of the minute bending vibration, and the angle (N, M, W) of the minute bending vibration.

With this embodiment, the provision of the foot switch 77 enables to control air-feed, water-feed and suction using the foot switch 77 even while gripping the operating units 51, 52 by the respective hands.

In the case of providing only the movement/rotation device 53 on a usual endoscope of the manually bending type, it is possible to motorize the operation of movement and rotation, and to develop the minute moving vibration and the minute rotating vibration.

With this embodiment, since the bending device 65 and the movement/rotation device 53 are separate units, it is possible to use either one or both of the devices 65, 53 in a sole or combined manner as required.

Furthermore, since the bending motors 12*a*, 12*b* are not present in the endoscope body, the endoscope can be reduced in weight and cost.

Other constitution, operation and advantageous effect are similar to those in the sixth and seventh embodiments.

Figure 32:
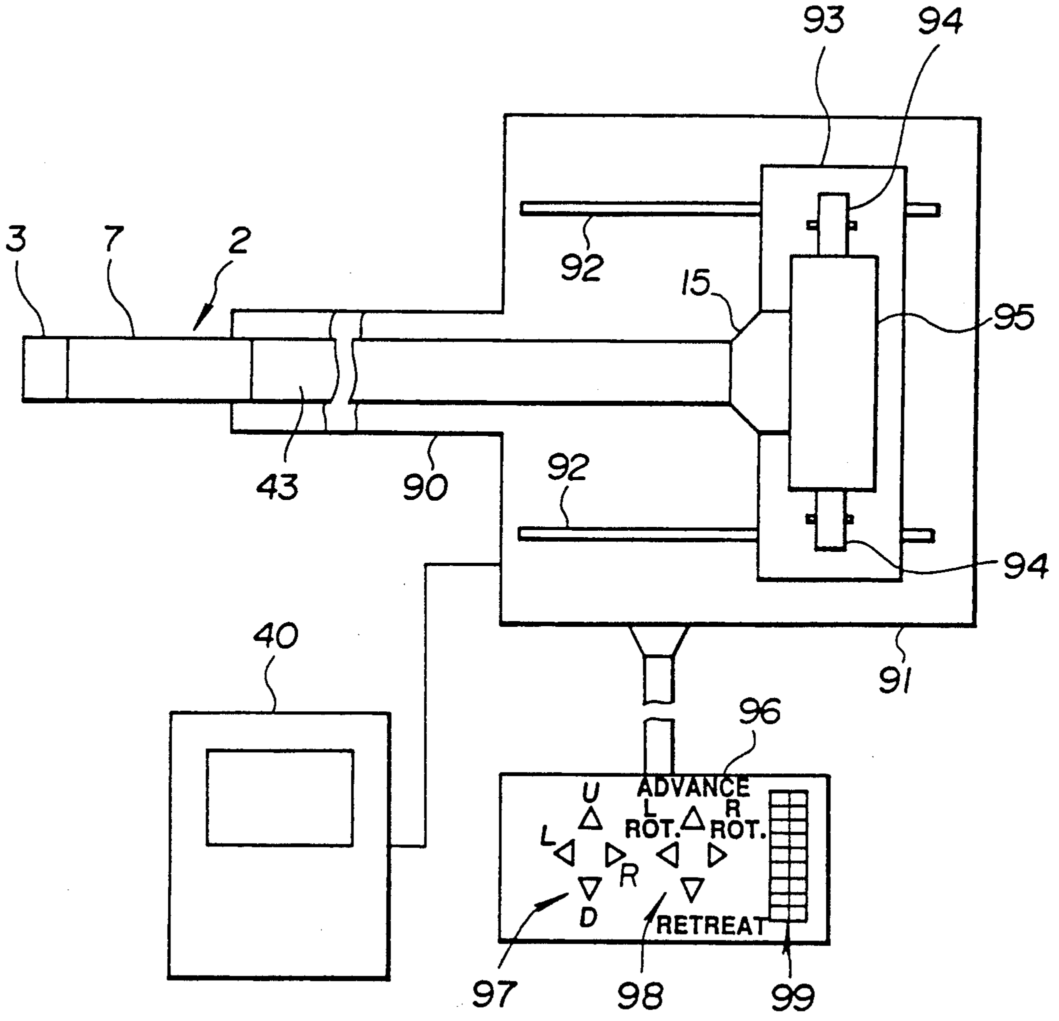
Figure 33:
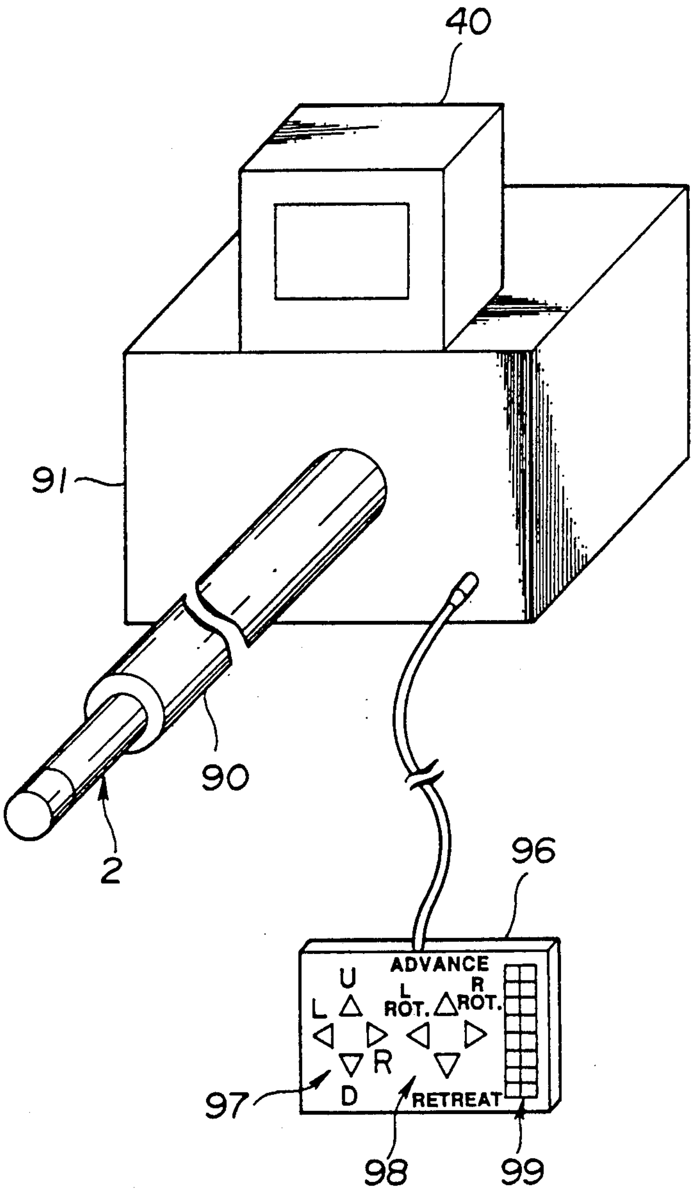

FIGS. 32 and 33 illustrate a ninth embodiment of the present invention.

Note that similar components to those in the sixth embodiment are designated by the same reference numerals, and are not described here.

In an endoscope apparatus of this embodiment, an insert section 2 is introduced to an insertion opening of an object to be examined using a pliable guide 90 which is cylindrical in shape. The base end of the guide 90 is connected to a centralized controller 91. In the controller 91, there are provided a pair of parallel rails 92, 92 extending in the axial direction of the insert section 2, and a base 93 movable to advance and retreat while being guided by the rails 92, 92. A rotatable drum 94 is provided on the base 93. A bending/light source/VP unit 95 is supported by the drum 94 in a rotatable manner.

The bending/light source/VP unit 95 incorporates the bending device 65, the light source unit 72 and the VP 17 in the eighth embodiment together. As with the seventh embodiment shown in FIG. 30, the connector 15 houses therein transmission gears and is freely connectable to the unit 95.

A control box 96 is detachably connected to the unit 95. On the control box 96, there are provided bending buttons 97 corresponding to the U, D, R and L directions, insert section movement/rotation buttons 98, and minute bending/moving/rotating vibration control switches 99.

The guide 90 has a cylindrical shape and can be split into two parts.

Operation of this embodiment when any one of the bending buttons 97 is depressed is similar to that in the eighth embodiment, and hence is not explained here. When one movement switch of the movement/rotation buttons 98 is depressed, the base 93 advances or retreats along the rails 92. At this time, the presence of the guide 90 prevent the insert section 2 from slacking. When one rotation switch of the movement/rotation buttons 98 is depressed, the drum 94 is rotated, causing the entire unit 95 and the insert section 2 to rotate.

The minute bending vibration, the minute moving vibration and the minute rotating vibration are each performed similarly to that in the sixth through eighth embodiments, and hence are not explained here.

With this embodiment, since the endoscope and the device for driving the endoscope are integrated together, handling is facilitated during the operation. Also, because of the provision of the guide 90, the insert section 2 is prevented from slacking.

Furthermore, since the control box 96 is of the push-button type, it can be operated by a single finger.

Other constitution, operation and advantageous effect are similar to those in the sixth or eighth embodiment.

Figure 36:
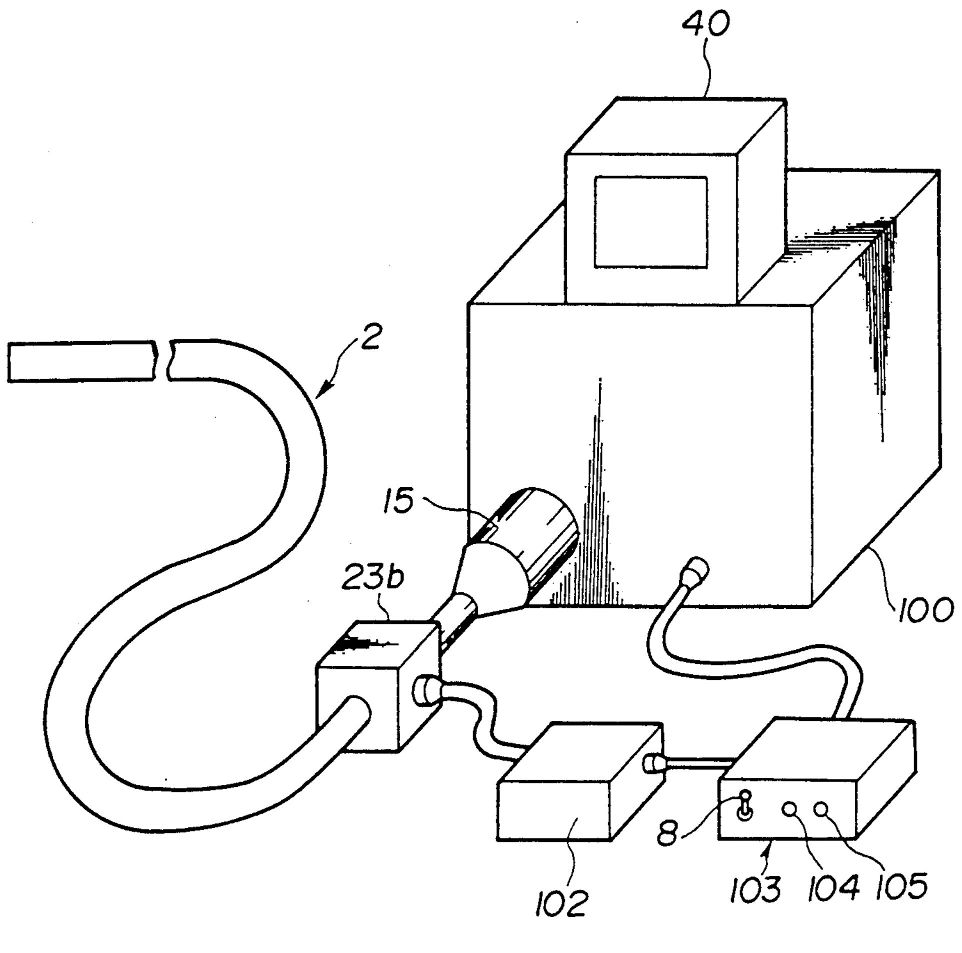

FIGS. 34 through 36 illustrate a tenth embodiment of the present invention.

Note that similar components to those in the sixth embodiment are designated by the same reference numerals, and are not described here.

As shown in FIG. 34, an endoscope apparatus of this embodiment comprises an insert section 2, a bending control and light source unit 100 to which the insert section 2 is connected, a monitor 40 connected to the bending control and light source unit 100, and moving rollers 23 held against the periphery of the insert section 2.

As will be seen in FIGS. 34 and 36, the endoscope 1 of this embodiment includes no operating section as with the seventh embodiment, and a connector 15 is directly provided at the base end of the insert section 2. A bending drive motor 12 is provided in the bending control and light source unit 100, and a bending wire 13 extended through the insert section 2 is attached to the motor 12. A motor driver 101 for driving the motor 12 is also housed in the bending control and light source unit 100. Furthermore, the bending control and light source unit 100 incorporates a lamp 21 and a pump 22 as well.

Separately from the unit 100, there are provided a control box 103 connected to the motor driver 101, and a motor driver 102 controlled by the control box 103 for controlling a motor adapted to drive the moving rollers 23. The control box 103 includes a joy stick 8, an advance switch 104 and a retreat switch 105. The joy stick 8 is to instruct the U, D, R or L bending direction to the motor driver 101.

Operation of this embodiment will be described below with reference to FIG. 35.

When the advance switch 104 on the control box 103 is turned on as shown in FIG. 35(*a*), the control box 103 instructs the minute bending vibration to the motor driver 101. The motor 12 driven by the motor driver 101 is thereby revolved in the U and D directions alternately, as shown in FIG. 35(*c*), to set a minute bending vibration. Simultaneously, the control box 103 instructs rotation of the moving rollers 23 in the advance direction to the motor driver 102. As a result, a bendable portion 7 develops the minute vibration while the insert section 2 is advancing.

On the other hand, when the retreat switch 105 is turned on as shown in FIG. 35(*b*), the control box 103 instructs rotation of the moving rollers 23 in the retreat direction to the motor driver 102, but does not instruct the minute bending vibration to the motor driver 101. As a result, the bendable portion 7 develops no minute vibration while the insert section 2 is retreating. Alternatively, the bendable portion 7 may also develop the minute vibration while the insert section 2 is retreating.

With this embodiment, in the normal state that the insert section is not advancing, the minute vibration will not be developed and hence the view field is kept at a standstill. Accordingly, this embodiment allows the operator to observe the object with certainty and the operator's eyes to be less fatigued.

Further, since the minute vibration is automatically turned on when the insert section 2 is operated to advance, it is not required for the operator to turn on the switch for each on/off switching of the minute vibration, resulting in easier operation. Though not shown, the minute vibration may be turned off during the advance process of the insert section by providing another switch.

The minute vibration is not limited to the minute bending vibration, and may be replaced with the minute moving vibration or the minute rotating vibration, or with an appropriate combination of those minute vibrations. In addition, the minute vibration may be performed during the operation of bending or rotation, instead of during the advance process of the insert section, and the operation of bending or rotation may appropriately be combined with each of the above minute vibrations.

Figure 37:
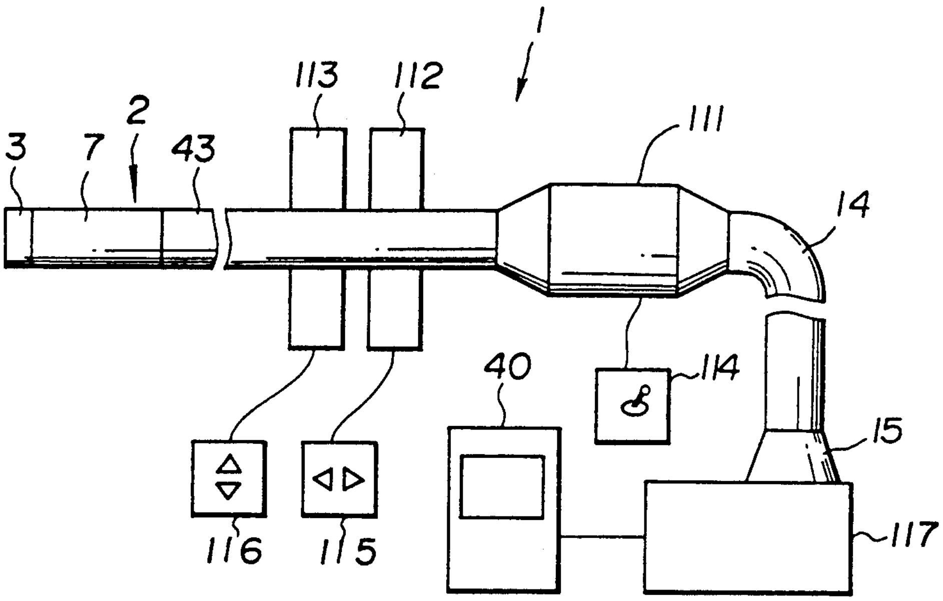
Figure 38:
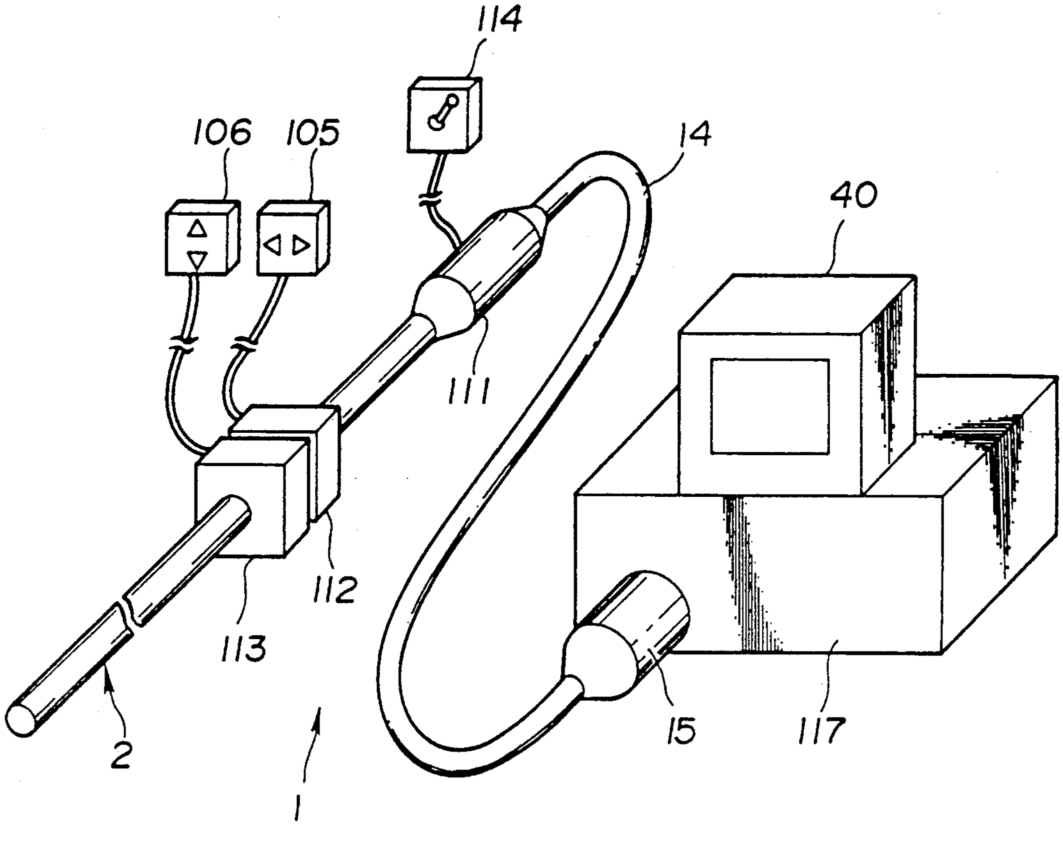

FIGS. 37 and 38 illustrate an eleventh embodiment of the present invention.

An endoscope apparatus of this embodiment comprises an endoscope 1, a controller 117 to which the endoscope 1 is connected, a monitor 40 connected to the controller 117, and a movement device 112 and a rotation device 113 both attached around an insert section 2 of the endoscope 1.

The endoscope 1 comprises the insert section 2, an operating section 111 continuously provided at the rear end of the insert section 2, a universal cable 14 continuously provided at the rear end of the operating section 111, and a connected provided at the end of the universal cable 14. A joy stick 114 is connected to the operating section 111. As with the sixth embodiment, a bending drive motor 12 is provided in the operating section 111. The joy stick 114 is to instruct the bending to the motor 12. The controller 117 incorporates a VP 17, a lamp 21 and a pump 22.

A movement switch 115 and a rotation switch 116 are connected to the movement device 112 and the rotation device 113, respectively. These switches 115, 116 are to instruct the movement and the rotation to the movement device 112 and the rotation device 113, respectively.

The operating section 111, the movement device 112 and the rotation device 113 include respective sections of the bending/movement/rotation control circuit 20 in the sixth embodiment relating to bending control, movement control and rotation control, and can perform the minute bending vibration, the minute moving vibration and the minute rotating vibration by switches (not shown), respectively.

Thus, the devices for driving and controlling the bending, the movement and the rotation are separate from one another. Accordingly, these devices can selectively be used, as required, in an efficient manner.

Other constitution, operation and advantageous effect are similar to those in the sixth embodiment.

Figure 39:
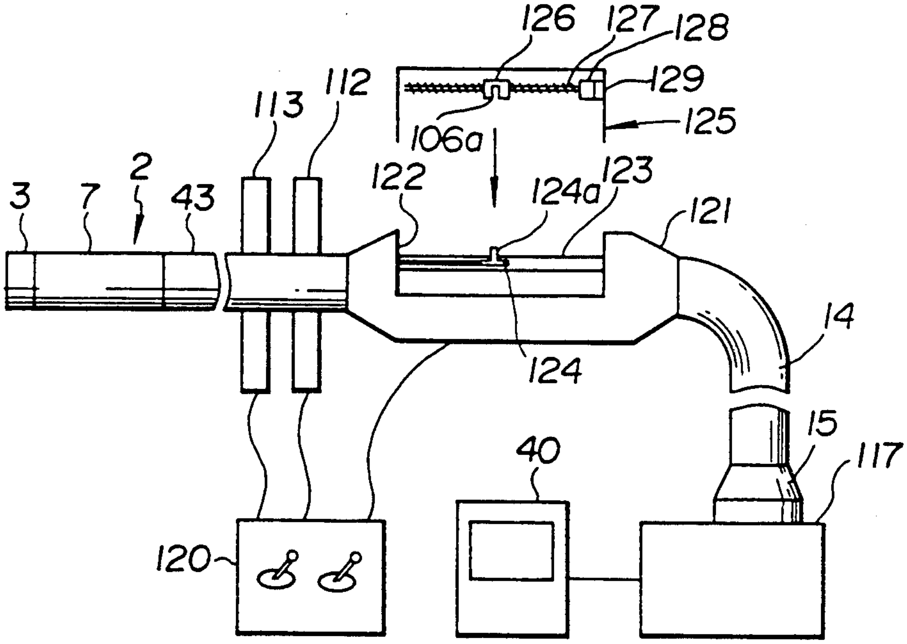
FIG. 39 is an explanatory view showing the constitution of an endoscope apparatus according to a twelfth embodiment of the present invention.

FIG. 39 illustrates a twelfth embodiment of the present invention.

An endoscope of this embodiment has an appearance substantially the same as that of the eleventh embodiment. But, a single centralized joy stick 120 is provided in this embodiment instead of the joy stick 114 and the switches 114, 116 in the eleventh embodiment.

Also, an operating section 121 is provided instead of the operating section 111 in the eleventh embodiment. The operating section 121 has a recess 122 in which a wire guide 123 is extended parallel to the axial direction of the insert section 2. The wire guide 123 is shaped into the form of a cylinder having a slit, with a slider 124 disposed in a slidable manner to advance and retreat along the guide. A bending wire 13 is attached to the slider 124. A projection 124*a* formed on the slider 124 is projecting from the slit of the wire guide 123. A motor unit 125 can be fitted in the recess 123. The motor unit 125 includes a rotatable guide 127 which is formed with male threads on its peripheral surface and extended parallel to the axial direction of the insert section 2. A recessed member 126 is meshed with the guide 127. The guide 127 is rotated by a motor 128, and an encoder 129 is attached to the motor 128. Rotating the guide 127 by the motor 128 causes the recessed member 126 to advance and retreat. By fitting the motor unit 125 in the recess 122 of the operating section 121, a recess 126*a* of the recessed member 126 is engaged with the projection 124*a* of the slider 124.

The operating section 121, the movement device 112 and the rotation device 113 include respective sections of the bending/movement/rotation control circuit 20 in the sixth embodiment relating to bending control, movement control and rotation control, and can perform the bending control, the moving control and the rotating control upon operation of the centralized control joy stick 120, respectively.

The position of the recessed member 126 is recognized by the encoder 129 and, based on the resulting position information, a control circuit provided in the operating section 121 performs control of the bending and the minute bending vibration such as a minute vibration angle.

Other constitution, operation and advantageous effect are similar to those in the sixth or eleventh embodiment.

Figures 40A, 40B, 40C, 40D, 40E, 40F, 40G, 40H, 40I, 40J, 40K, 40L, 40M, 40N, 40O, 40P, 40Q:
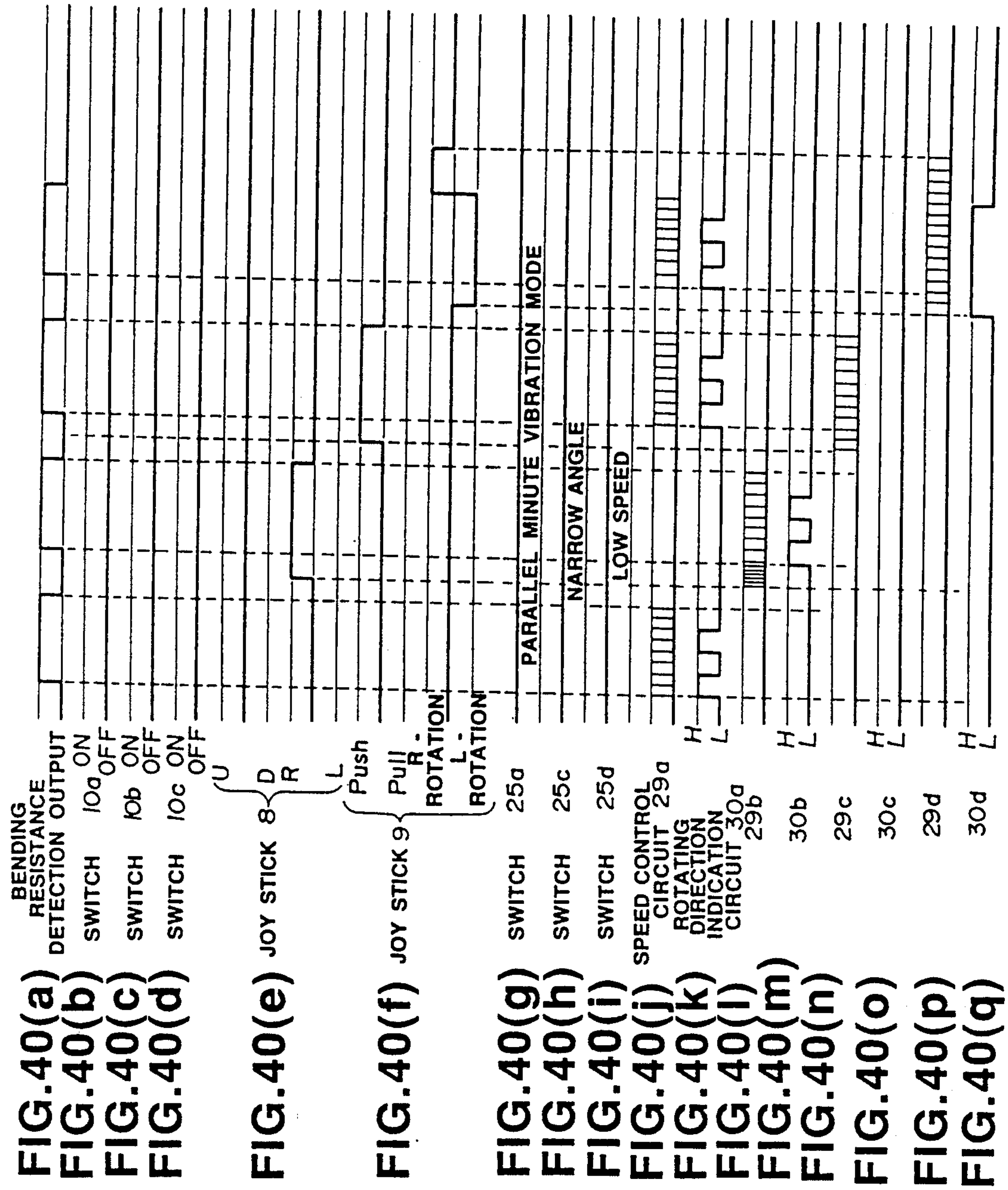
FIG. 40 is a timing chart for explaining operation of an endoscope apparatus according to a thirteenth embodiment of the present invention.
Figures 41A, 41B, 41C, 41D, 41E, 41F, 41G, 41H, 41I, 41J, 41K, 41L, 41M, 41N, 41O, 41P, 41Q:
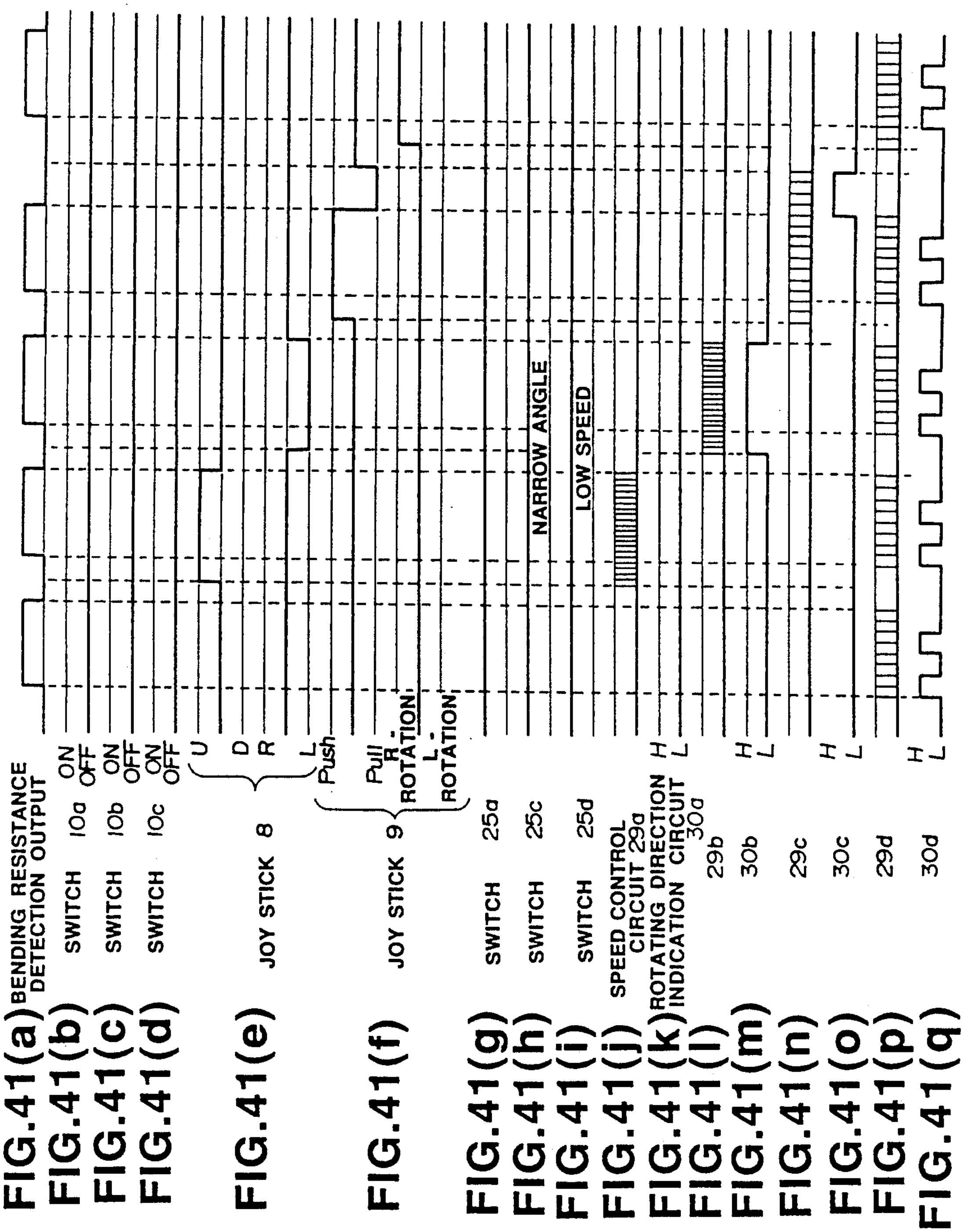
FIG. 41 is a timing chart for explaining operation of an endoscope apparatus according to a fourteenth embodiment of the present invention.
Figures 42L, 42N, 42P:
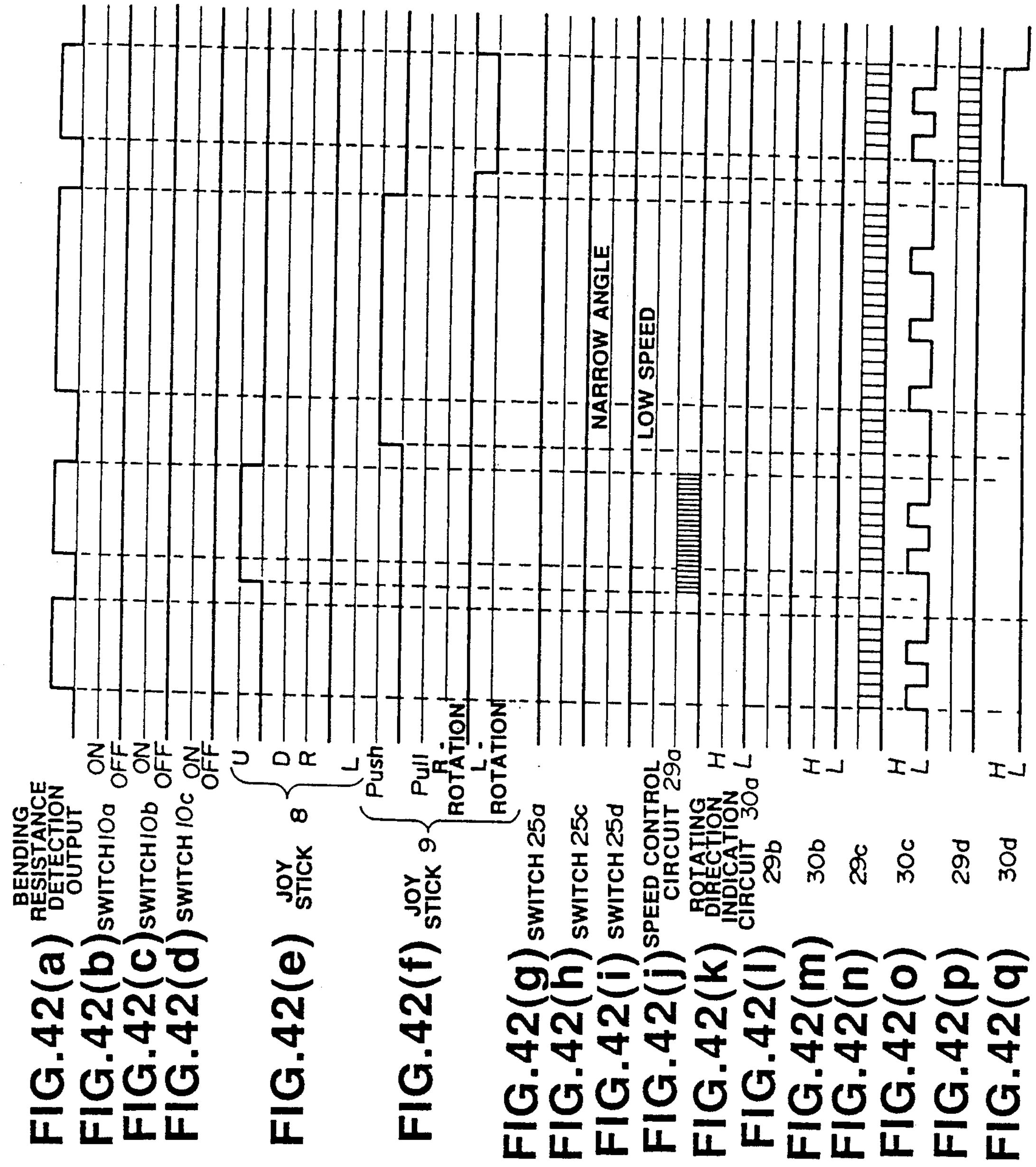
FIG. 42 is a timing chart for explaining operation of an endoscope apparatus according to a fifteenth embodiment of the present invention.

The following thirteenth through fifteenth embodiments shown in FIGS. 40 through 42 are concerned with examples in which the contact pressure, i.e., the bending resistance, exerted on the bendable portion 7 is detected and the minute vibration is automatically actuated when the bending resistance exceeds a predetermined value.

In FIGS. 40 through 42, (a) represents an output of the bending resistance detection circuit 19; (b) through (d) represent operations of the switches 10*a*–10*c*, respectively; (e), (f) represent operations of the joy sticks 8, 9, respectively; and (g) through (i) represent operations of the switches 25*a*, 25*c*, 25*d*, respectively. Furthermore, (j) and (k) represent operations of the speed control circuit 29*a* and the rotating direction indication circuit 30*a* for the bending drive motor 12*a*, respectively. Likewise, (l) and (m) represent operations of the respective circuits 29*b*, 30*b* for the bending drive motor 12*b*; (n) and (o) represent operations of the respective circuits 29*c*, 30*c* for the movement motor 23*a*; and (p) and (q) represent operations of the respective circuits 29*d*, 30*d* for the rotation motor 24*a*, respectively.

FIG. 40 illustrates a thirteenth embodiment of the present invention.

This embodiment is concerned with an example of actuating a minute bending vibration when the bending resistance exceeds a predetermined value.

This embodiment is constituted substantially similarly to the sixth embodiment.

In this embodiment, an output of the bending resistance detection circuit 19 shown in FIGS. 9 and 11 is applied to the control circuit 28 in the bending/movement/rotation control circuit 20. When the output of the bending resistance detection circuit 19 exceeds a predetermined value, the control circuit 28 controls the speed control circuits 29*a*, 29*b* and the rotating direction indication circuits 30*a*, 30*b* for bending, thereby developing the minute bending vibration.

For brevity of explanation, FIG. 40 shows an example in which a parallel minute vibration mode is set as shown at (g) and the minute vibration is set to a narrow-angle, low-speed mode as shown at (h), (i).

When the output of the bending resistance detection circuit 19 exceeds the predetermined value without operating the joy stick 8 as shown in at (a) and (e) in FIG. 40, the rotating direction indication circuit 30*a* outputs pulses in a narrow angle mode as shown at (k), and the speed control circuit 29*a* outputs pulses in a low speed mode as shown at (j). Accordingly, the bendable portion 7 develops a minute bending vibration in the UD directions at a low speed.

On the other hand, when the joy stick 8 is operated in the R direction, for example, and the output of the bending resistance detection circuit 19 does not reach the predetermined value, the speed control circuit 29*b* and the rotating direction indication circuit 30*b* operate in a normal manner as shown at (l), (m) for bending the bendable portion 7 in the R direction. However, as will be seen from (l), the bending speed is faster than the speed during the minute bending vibration. The foregoing also equally applies to the bending in the other U, D or L direction.

Then, when the joy stick 8 is operated in the R direction, for example, and the output of the bending resistance detection circuit 19 exceeds the predetermined value, the rotating direction indication circuit 30*b* output pulses in a narrow angle mode as shown at (m) and the speed control circuit 29*b* output pulses in a low speed mode as shown at (l). Accordingly, the bendable portion 7 develops a minute bending vibration in the RL directions in a narrow-angle, a low-speed mode. The foregoing also equally applies to the case that the output of the bending resistance detection circuit 19 exceeds the predetermined value during the bending operation in the other U, D or L direction.

When the joy stick 9 is operated to perform the movement or the rotation and the output of the bending resistance detection circuit 19 exceeds the predetermined value as shown at (a), (f), the bendable portion 7 develops a minute vibration in the UD directions independently of the operation of movement or rotation as shown at (j), (k) and (n) through (q).

It is needless to say that when an orthogonal minute vibration mode is set, the minute bending vibration occurs in a direction orthogonal to the bending direction, when the output of the bending resistance detection circuit 19 exceeds the predetermined value.

Instead of that the control circuit 28 determines whether or not the output of the bending resistance detection circuit 19 exceeds the predetermined value, the bending resistance detection circuit 19 may be so arranged as to output H when the bending resistance exceeds the predetermined value, and L otherwise.

With this embodiment, as mentioned above, since the minute bending vibration is automatically actuated to reduce the bending resistance when the bending resistance exerted on the bendable portion 7 exceeds the predetermined value, operability of insertion is further improved.

Other constitution, operation and advantageous effect are similar to those in the sixth embodiment.

FIG. 41 illustrates a fourteenth embodiment of the present invention.

This embodiment is concerned with an example of actuating a minute rotating vibration when the bending resistance exceeds a predetermined value.

This embodiment is constituted substantially similarly to the sixth embodiment.

In this embodiment, as with the above thirteenth embodiment, an output of the bending resistance detection circuit 19 shown in FIGS. 9 and 11 is applied to the control circuit 28 in the bending/movement/rotation control circuit 20. When the output of the bending resistance detection circuit 19 exceeds a predetermined value, the control circuit 28 controls the speed control circuit 29*d* and the rotating direction indication circuit 30*d* for rotation, thereby developing the minute rotating vibration.

For brevity of explanation, FIG. 41 shows an example in which the minute vibration is set to a narrow-angle, low-speed mode as shown at (h), (i).

When the output of the bending resistance detection circuit 19 exceeds the predetermined value as shown at (a) in FIG. 40, the rotating direction indication circuit 30*d* outputs pulses in a narrow angle mode as shown at (q), and the speed control circuit 29*d* outputs pulses in a low speed mode as shown at (p). Accordingly, the insert section 2 develops a minute rotating vibration.

When the joy stick 8, 9 is operated to perform the bending or the movement as shown at (e), (f) and the output of the bending resistance detection circuit 19 exceeds the predetermined value, the insert section 2 develops a minute rotating vibration independently of the operation of bending or movement as shown at (j) through (q).

On the other hand, when the joy stick 9 is operated to perform the rotation as shown at (f) and the output of the bending resistance detection circuit 19 exceeds the predetermined value, there develops not the normal rotation, but the minute rotating vibration.

With this embodiment, as mentioned above, since the minute bending vibration is automatically actuated to reduce the bending resistance when the bending resistance exerted on the bendable portion 7 exceeds the predetermined value, operability of insertion is further improved.

Other constitution, operation and advantageous effect are similar to those in the sixth or thirteenth embodiment.

FIG. 42 illustrates a fifteenth embodiment of the present invention.

This embodiment is concerned with an example of actuating a minute moving vibration when the bending resistance exceeds a predetermined value.

This embodiment is constituted substantially similarly to the sixth embodiment.

In this embodiment, as with the above thirteenth embodiment, an output of the bending resistance detection circuit 19 shown in FIGS. 9 and 11 is applied to the control circuit 28 in the bending/movement/rotation control circuit 20. When the output of the bending resistance detection circuit 19 exceeds a predetermined value, the control circuit 28 controls the speed control circuit **29*d* and the rotating direction indication circuit 30*d*** for movement, thereby developing the minute moving vibration.

For brevity of explanation, FIG. 42 shows an example in which the minute vibration is set to a narrow-angle, low-speed mode as shown at (h), (i).

When the output of the bending resistance detection circuit 19 exceeds the predetermined value as shown at (a) in FIG. 40, the rotating direction indication circuit **30*c* outputs pulses in a narrow angle mode as shown at (o), and the speed control circuit 29*c* outputs pulses in a low speed mode as shown at (n). Accordingly, the insert section 2** develops a minute moving vibration.

When the joy stick 8, 9 is operated to perform the bending or the rotation as shown at (e), (f) and the output of the bending resistance detection circuit 19 exceeds the predetermined value, the insert section 2 develops a minute moving vibration independently of the operation of bending or rotation as shown at (j), (k) and (n) through (q).

On the other hand, when the joy stick 9 is operated to perform the advance (push) as shown at (f) and the output of the bending resistance detection circuit 19 exceeds the predetermined value, the rotating direction indication circuit **30*c* outputs pulses with the duration of L being longer than that of H, as shown at (o). As a result, the insert section 2** advances while developing a minute moving vibration.

With this embodiment, as mentioned above, since the minute moving vibration is automatically actuated to reduce the bending resistance when the bending resistance exerted on the bendable portion 7 exceeds the predetermined value, operability of insertion is further improved.

Other constitution, operation and advantageous effect are similar to those in the sixth or thirteenth embodiment.

The following sixteenth through nineteenth embodiments shown in FIGS. 43 through 47 are concerned with examples in which the minute vibration is automatically actuated during the operation of bending, movement or rotation. In FIGS. 44 through 47, (a) through (c) represent operations of the switches **10*a*–10*c*, respectively; (d), (e) represent operations of the joy sticks 8, 9, respectively; and (f) through (h) represent operations of the switches 25*a*, 25*c*, 25*d*, respectively. Furthermore, (i) and (j) represent operations of the speed control circuit 29*a* and the rotating direction indication circuit 30*a* for the bending drive motor 12*a*, respectively. Likewise, (k) and (l) represent operations of the respective circuits 29*b*, 30*b* for the bending drive motor 12*b*; (m) and (n) represent operations of the respective circuits 29*c*, 30*c* for the movement motor 23*a*; and (o) and (p) represent operations of the respective circuits 29*d*, 30*d* for the rotation motor 24*a***, respectively.

Figure 43:
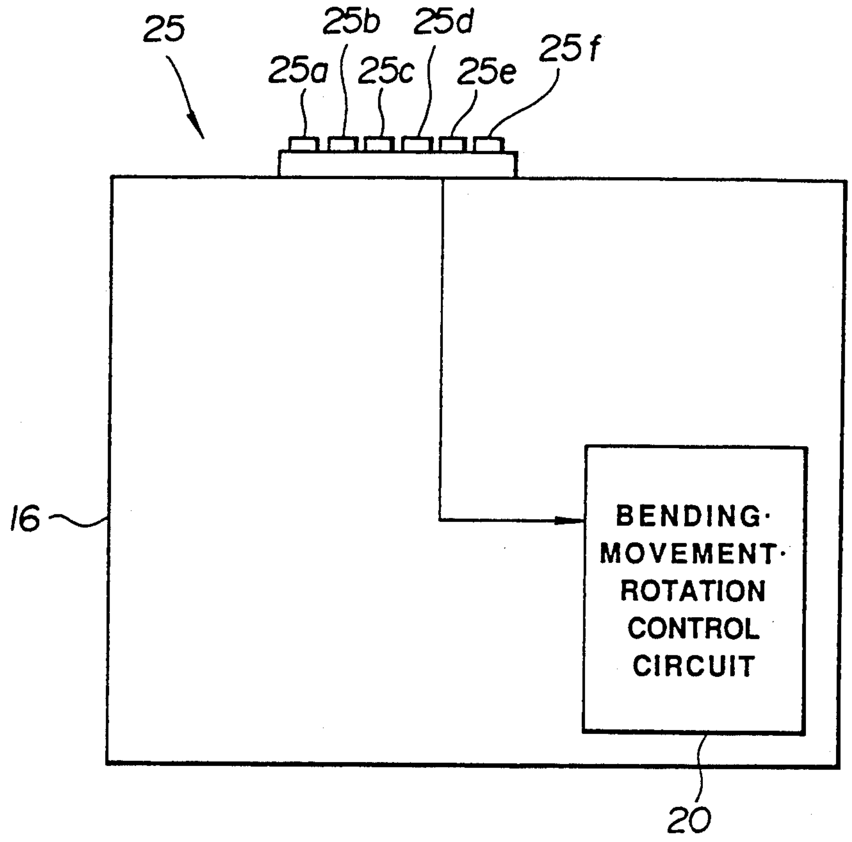
Figures 44A, 44B, 44C, 44D, 44E, 44F, 44G, 44H, 44I, 44J, 44K, 44L, 44M, 44N, 44O, 44P:
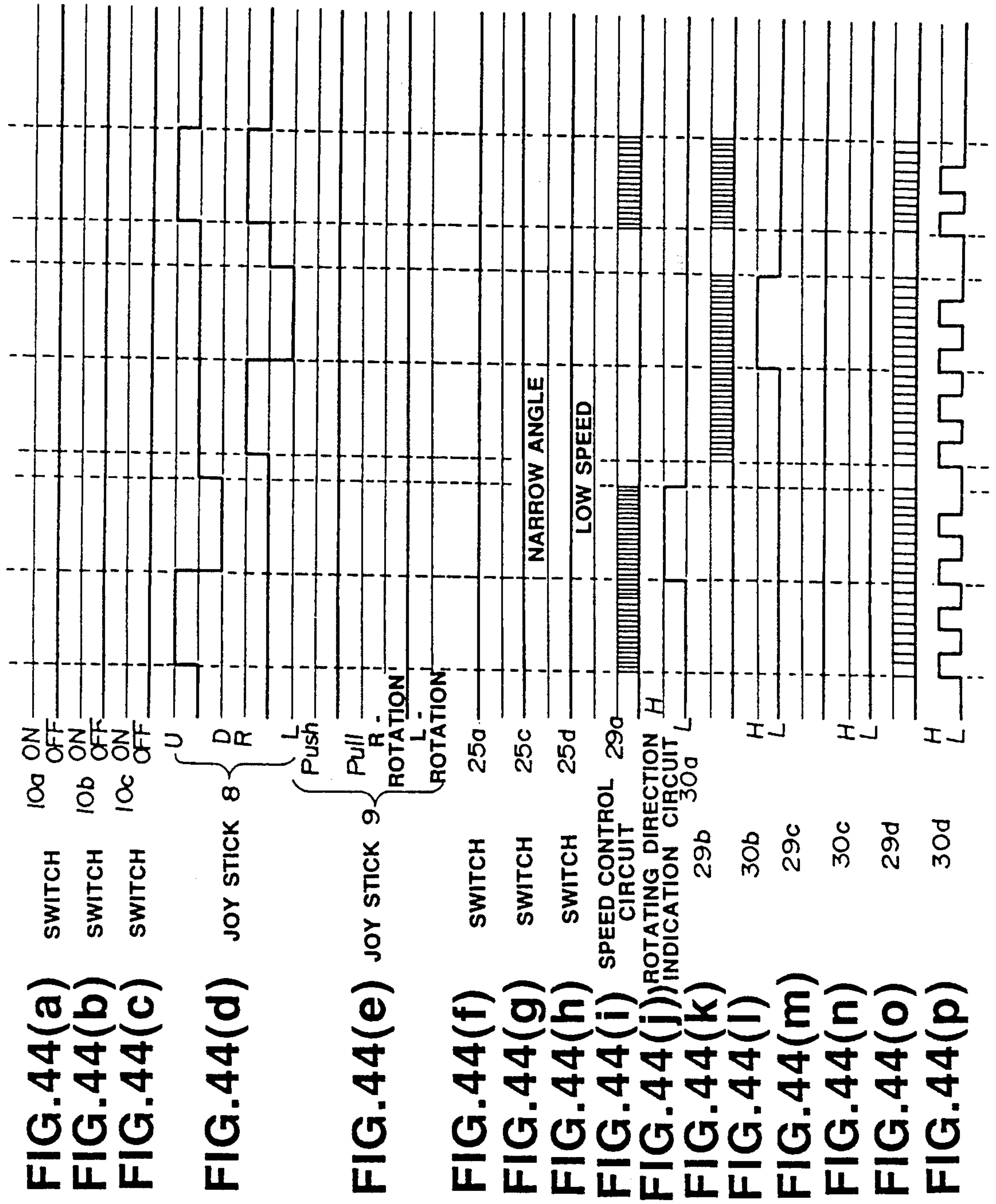

FIGS. 43 and 44 illustrate a sixteenth embodiment of the present invention.

This embodiment is concerned with an example of actuating a minute rotating vibration during the bending operation.

As shown in FIG. 43, in this embodiment, the switch 25 on the controller 16 in the sixth embodiment includes a bending-dependent minute rotating vibration mode setting switch **25*f* in addition to the switches 25*a*–25*f*. When a bending-dependent minute rotating vibration mode is set by this switch 25*f*, the minute rotating vibration is actuated during the bending operation under control of the control circuit 28 in the bending-/movement/rotation control circuit 20**. The remaining constitution of this embodiment is similar to the sixth embodiment.

Operation of this embodiment will be described below with reference to FIG. 44.

For brevity of explanation, FIG. 44 shows an example in which the switch 25 is set to a bending-dependent minute rotating vibration mode and the minute vibration is set to a narrow-angle, low-speed mode as shown at (g), (h).

When the joy stick 8 is operated to perform the bending as shown at (d) in FIG. 44, the normal bending operation is carried out as shown at (i) through (l). At the same time, the rotating direction indication circuit **30*d* outputs pulses in a narrow angle mode as shown at (p), and the speed control circuit 29*d* outputs pulses in a low speed mode as shown at (o). Accordingly, the insert section 2 develops a minute rotating vibration in a narrow-angle, low-speed mode while the bendable portion 7** is subjected to the bending operation.

With this embodiment, as mentioned above, since the minute rotating vibration is automatically actuated to reduce the bending resistance during the bending process of the bendable portion 7, operability of insertion is further improved.

Other operation and advantageous effect are similar to those in the sixth embodiment.

Figures 45K, 45M, 45O:
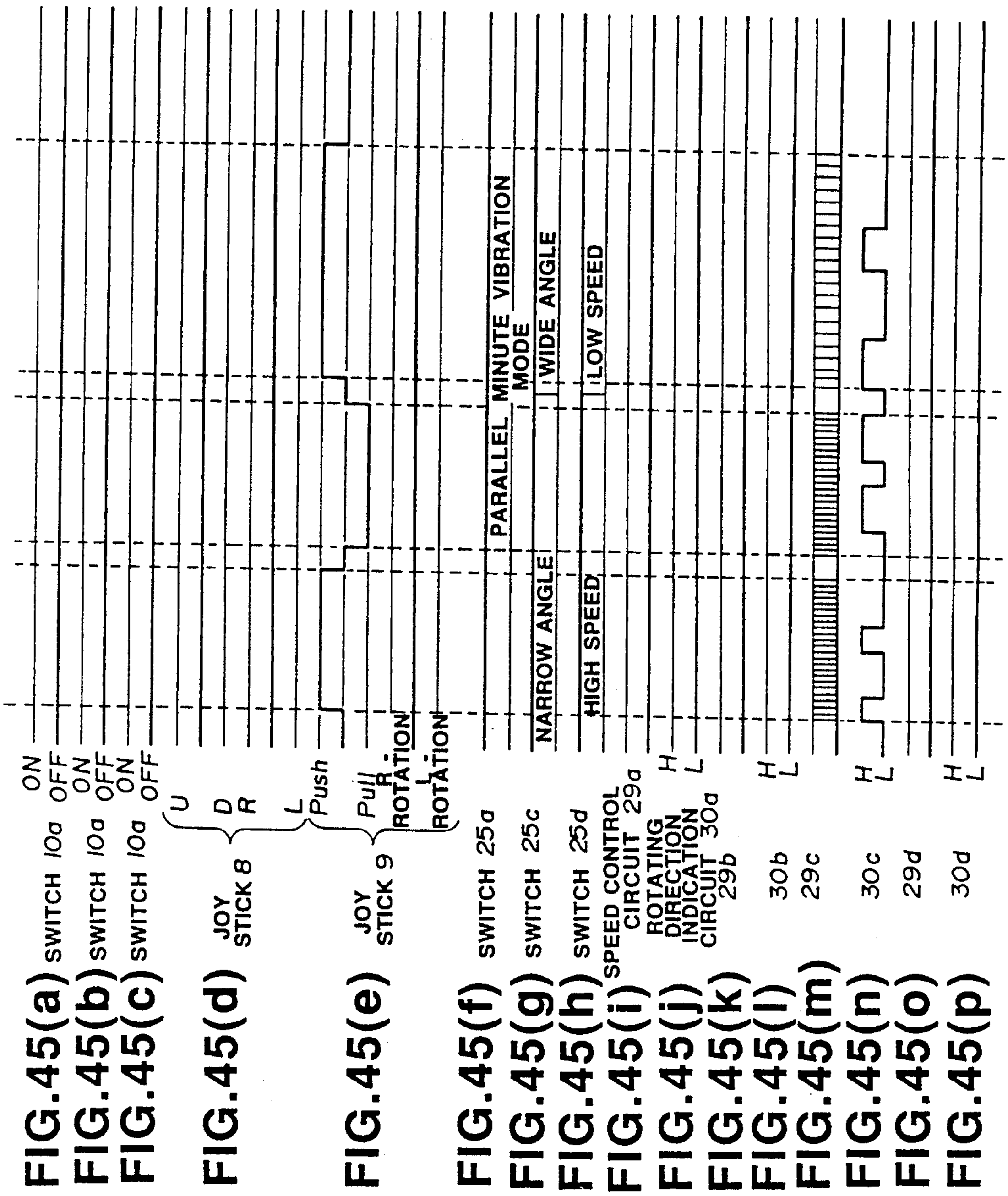
FIG. 45 is a timing chart for explaining operation of an endoscope apparatus according to a seventeenth embodiment of the present invention.

FIG. 45 illustrates a seventeenth embodiment of the present invention.

This embodiment is concerned with an example of actuating a minute moving vibration during the movement operation.

In this embodiment, the switch **25*f* in FIG. 43** is constituted by a movement-dependent minute moving vibration mode setting switch. The remaining constitution is similar to the sixth or sixteenth embodiment.

In this embodiment, when a movement-dependent minute moving vibration mode is set by that switch **25*f*, the minute moving vibration is actuated during the movement operation under control of the control circuit 28 in the bending/movement/rotation control circuit 20**.

When the joy stick 9 is operated to perform the movement as shown at (e) in FIG. 45, the speed control circuit **29*c* outputs pulses, as shown at (m), in accordance with the mode set by the switch 25*d* as shown at (h). Also, the rotating direction indication circuit 30*c* outputs pulses with the duration of L being longer than that of H when the joy stick 9 is operated in the advance (Push) direction, and pulses with the duration of H being longer than that of L when the joy stick 9 is operated in the retreat (Pull) direction. In this respect, the frequency of output pulses from the rotating direction indication circuit 30***c* is varied dependent on the mode set by the switch 25*c* as shown at (g). During the movement operation, therefore, the insert section 2 moves (advances or retreats) while developing a minute moving vibration.

With this embodiment, as mentioned above, since the minute moving vibration is automatically actuated to reduce the bending resistance during the movement process of the bendable portion 7, operability of insertion is further improved.

Other operation and advantageous effect are similar to those in the sixth embodiment.

Figures 46A, 46B, 46C, 46D, 46E, 46F, 46G, 46H, 46I, 46J, 46K, 46L, 46M, 46N, 46O, 46P:
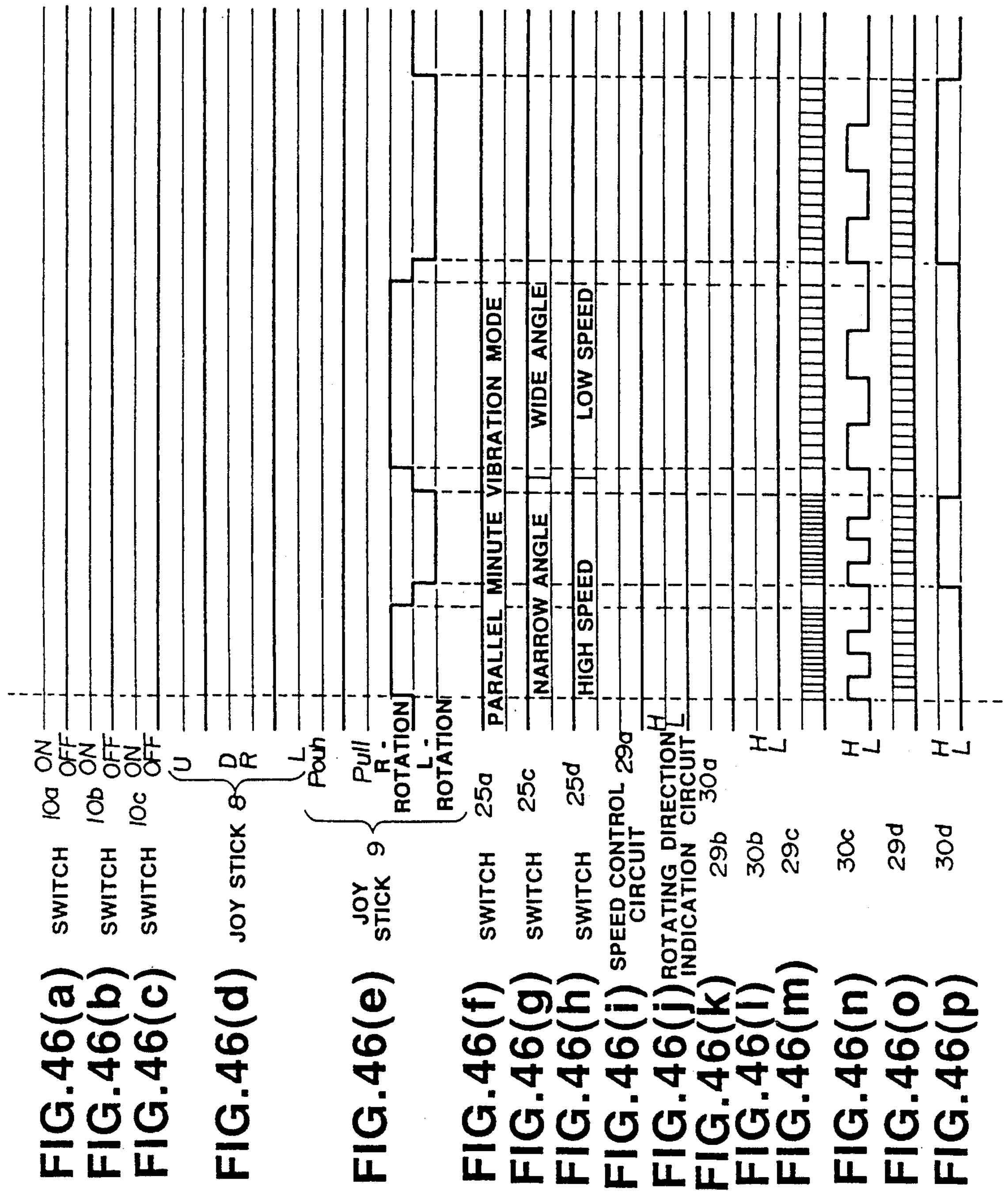
FIG. 46 is a timing chart for explaining operation of an endoscope apparatus according to an eighteenth embodiment of the present invention.

FIG. 46 illustrates an eighteenth embodiment of the present invention.

This embodiment is concerned with an example of actuating a minute moving vibration during the rotation operation.

In this embodiment, the switch 25*f* in FIG. 43 is constituted by a rotation-dependent minute moving vibration mode setting switch. The remaining constitution is similar to the sixth or sixteenth embodiment.

In this embodiment, when a rotation-dependent minute moving vibration mode is set by that switch 25*f*, the minute moving vibration is actuated during the rotation operation under control of the control circuit 28 in the bending/movement/rotation control circuit 20.

When the joy stick 9 is operated to perform the rotation as shown at (e) in FIG. 46, the normal operation is carried out as shown at (o), (p). At the same time, the speed control circuit 29*c* outputs pulses, as shown at (m), in accordance with the mode set by the switch 25*d* as shown at (h). Also, the rotating direction indication circuit 30*c* outputs pulses, as shown at (n), with the frequency dependent on the mode set by the switch 25*c* as shown at (g). During the rotation operation, therefore, the insert section 2 rotates about its own axis while developing a minute moving vibration.

With this embodiment, as mentioned above, since the minute moving vibration is automatically actuated to reduce the bending resistance during the rotation process of the insert section 2, operability of insertion is further improved.

Other operation and advantageous effect are similar to those in the sixth embodiment.

Figures 47A, 47B, 47C, 47D, 47E, 47F, 47G, 47H, 47I, 47J, 47K, 47L, 47M, 47N, 47O, 47P:
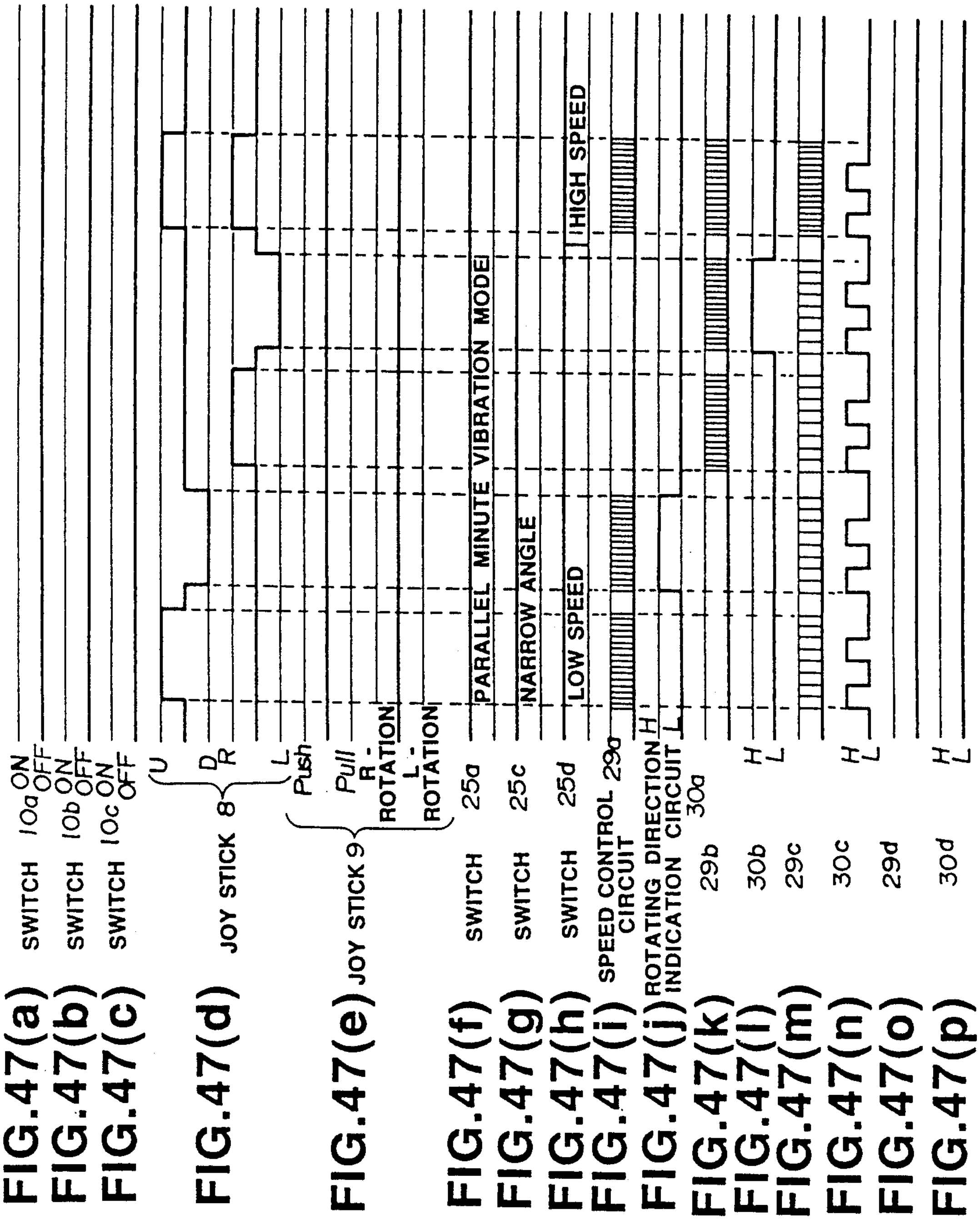
FIG. 47 is a timing chart for explaining operation of an endoscope apparatus according to a nineteenth embodiment of the present invention.

FIG. 47 illustrates a nineteenth embodiment of the present invention.

This embodiment is concerned with an example of actuating a minute moving vibration during the bending operation.

In this embodiment, the switch 25*f* in FIG. 43 is constituted by a bending-dependent minute moving vibration mode setting switch. The remaining constitution is similar to the sixth or sixteenth embodiment.

In this embodiment, when a bending-dependent minute moving vibration mode is set by that switch 25*f*, the minute moving vibration is actuated during the bending operation under control of the control circuit 28 in the bending/movement/rotation control circuit 20.

For brevity of explanation, FIG. 47 shows an example in which a parallel minute vibration mode is set as shown at (f).

When the joy stick 9 is operated to perform the bending as shown at (d) in FIG. 47, the normal bending is carried out as shown at (i) through (l). At the same time, the speed control circuit 29*c* outputs pulses, as shown at (m), in accordance with the mode set by the switch 25*d* as shown at (h). Also, the rotating direction indication circuit 30*c* outputs pulses, as shown at (n), with the frequency dependent on the mode set by the switch 25*c* as shown at (g). During the bending operation, therefore, the insert section 2 is bent while developing a minute moving vibration.

With this embodiment, as mentioned above, since the minute moving vibration is automatically actuated to reduce the bending resistance during the bending process of the insert section 2, operability of insertion is further improved.

Other operation and advantageous effect are similar to those in the sixth embodiment.

It is to be noted that during the operation of bending, movement or rotation, the minute bending, moving or rotating vibration may be actuated in any other combinations other than those shown in the sixteenth through nineteenth embodiments.

Figure 48:
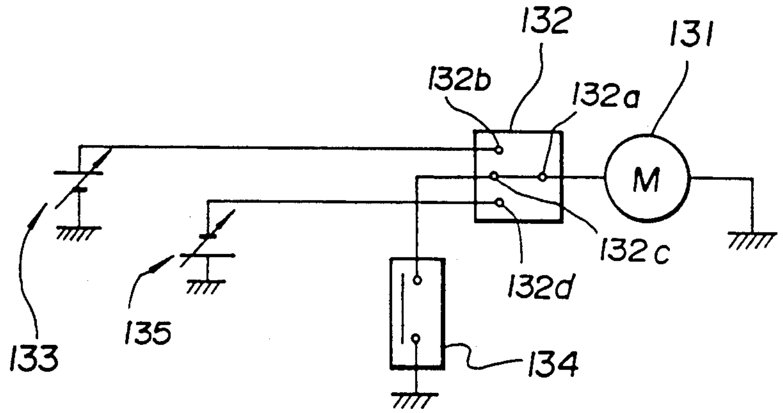
FIG. 48 is a circuit diagram showing a motor and a control circuit of the motor according to a twentieth embodiment of the present invention.

FIG. 48 illustrates a twentieth embodiment of the present invention.

In this embodiment, the bending motors 12*a*, 12*b*, the movement motor 32*a* and the rotation motor 24*a* in the sixteenth through nineteenth embodiments are each constituted by not a stepping motor, but a direct current (DC) motor 131.

The DC motor 131 has one input terminal connected to a movable contact 132*a* of a stop/forward/backward selector switch 132, and the other input terminal grounded. Among three fixed contacts of the selector switch 132, a first fixed contact 132*b* is connected to a positive electrode of a voltage-variable DC power supply 133 of which negative electrode is grounded. A second fixed contact 132*c* of the selector switch 132 is grounded via a free/lock selector switch 134. A third fixed contact 132*d* of the selector switch 132 is connected to a negative electrode of a voltage-variable DC power supply 135 of which positive electrode is grounded.

The selector switch 132 is changed over by each of the rotating direction indication circuit 30*a*-30*d* shown in FIG. 11. When the fixed contact 132*b* or 132*d* is selected, the DC motor 131 is revolved forwards or backwards, respectively. When the fixed contact 132*c* is selected, the DC motor 131 is stopped. Voltages of the power supplies 133, 135 are controlled by each of the speed control circuits 29*a*-29*d*. Thus, by raising or lowering the voltages of the power supplies 133, 135, the DC motor 131 is changed in its speed. The free/lock selector switch 134 is changed over by each of the free/lock switches 31*a*-31*d*. More specifically, when the free/lock selector switch 134 is turned on under a condition that the fixed contact 132*c* of the switch 132 is selected, the DC motor 131 is locked by a counter electromotive force. When the switch 134 is turned off under such a condition, the DC motor 131 is made free.

Other constitution, operation and advantageous effect are similar to those in the sixth through nineteenth embodiments.

In the meanwhile, where the bending motor is disposed at the distal end of the insert section of the endoscope, the distal end portion is increased in weight, which may possibly degrade operability of the endoscope, and tends to enlarge the diameter of the distal end portion.

Therefore, it is conceivable to provide the bending motor in the operating section of the endoscope. In this case, the axis of a pulley to which an angle wire is coupled is generally arranged in orthogonal relation to the axis of the operating section. With this arrangement, the axis of the motor must also be arranged perpendicularly to the axis of the operating section, and hence the tail end of the motor is necessarily projected from a side wall of the operating section.

The above drawback can be avoided by connecting a shaft of the pulley and an output shaft of the motor via bevel gears or the like. However, the provision of such gears increases total weight of the apparatus by an amount corresponding to the gear weight and also complicates the structure, thereby making assembly and maintenance more troublesome.

Further, Japanese Utility Model Laid-Open No. 33402/1984 discloses a technique that a motor is disposed in a connector of a light guide cable connected to a light source unit, a wire is entrained about a pulley fixed to an output shaft of the motor, and the wire is extended through the light guide cable and an insert section toward a distal end portion. But, this prior art necessarily increases an entire length of the wire, resulting in likelihood that the response may be lowered due to slack of the wire and the like.

The following twenty-first and twenty-second embodiments are concerned with examples of an endoscope apparatus which can prevent an increase in the diameter and weight of a distal end portion (component) with simple construction, avoid the trail end of a drive unit from projecting out of a side wall of an operating section, and prevent a reduction in the response.

In the endoscope apparatus according to these embodiments, an operating section disposed at the base end of an insert section is provided on one side with an extended base portion substantially orthogonal to the operating section, a light guide cable is extended through the extended base portion, a driven member is provided in the insert section, and a drive unit for driving the driven member is provided in the extended base portion.

With such constitution, the driven member in the insert section is driven by the drive unit provided in the extended base portion of the operating section through which the light guide cable is extending.

FIGS. 49 through 53 illustrate a twenty-first embodiment of the present invention.

Figure 50:
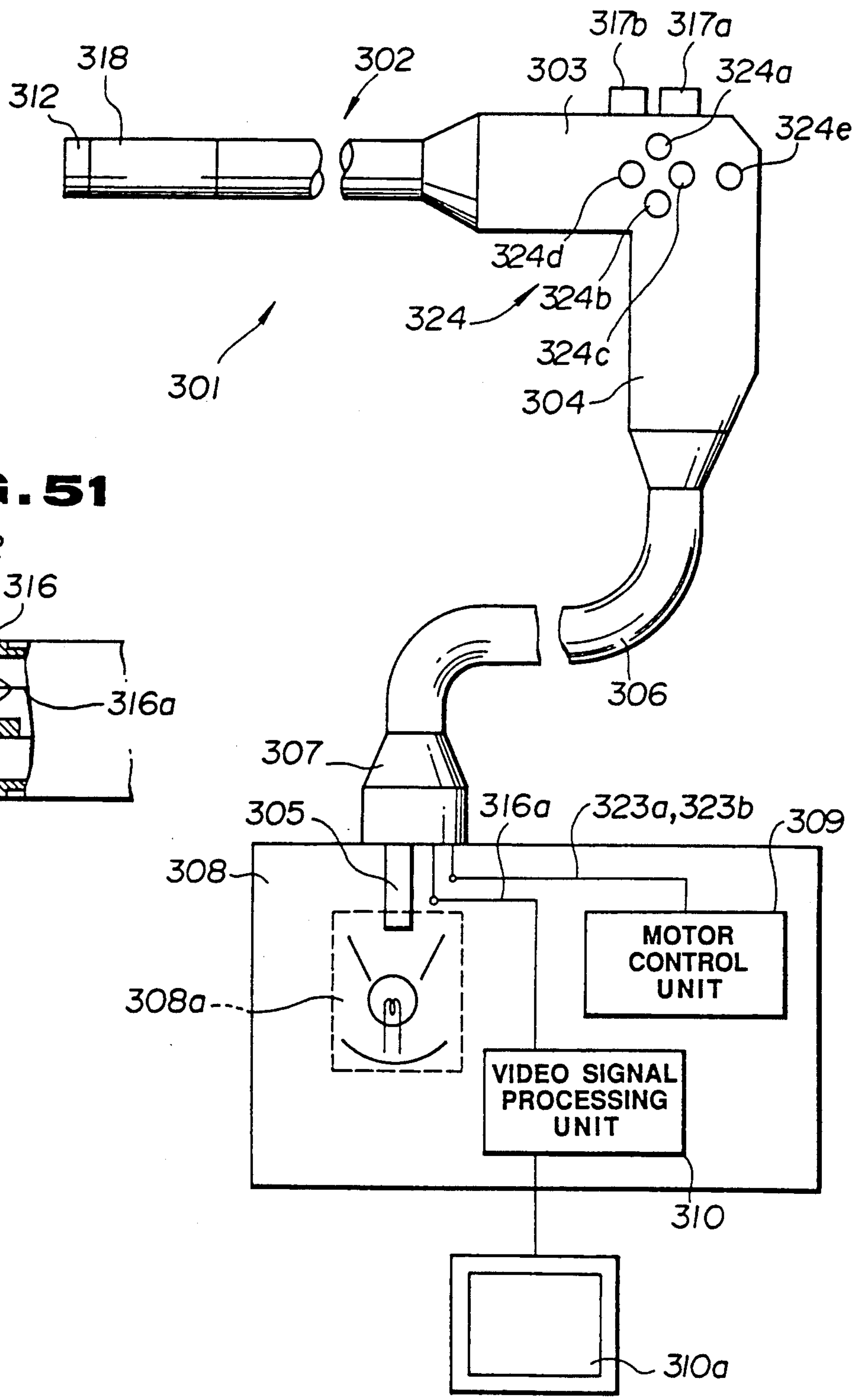
Figure 51:
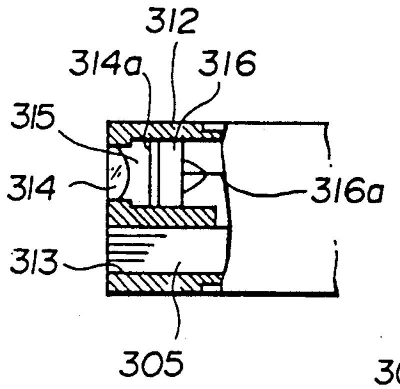

First, an endoscope apparatus of this embodiment will be described briefly with reference to FIG. 50. An endoscope 301 comprises an elongate and flexible insert section 302 which can be inserted into the body cavity or the like, and a relatively large-diameter operating section 303 provided at the based end of the insert section 302.

The insert section 302 is provided at the distal end with a distal end component 312 formed of a hard member. Adjacent the base end of the distal end component 312, there is provided a bendable portion 318, as one example of a driven member, comprising a plurality of articulate pieces which can mutually bend or pivot while expanding and contracting as a whole.

On the other hand, the operating section 303 is formed at the based end with an extended base portion 304 substantially orthogonal to the operating section 303. A light guide cable 306 incorporating a light guide 303 is extended from the end of the extended base portion 304. A connector 307 is provided at the base end of the light guide cable 306, so that the light guide cable 306 is connected to a light source unit 308 via the connector 307. In the state that the connector 307 is connected to the light source unit 308, an incident end of the light guide 305 is positioned opposite to a lamp 308*a*, and a motor control unit 309 and a video signal processing unit 310 both disposed in the light source unit 308 are connected to the endoscope 301 via the connector 307.

The light guide 305 is extended through the insert section 302, and fixed at its one end in an illumination through-hole 313 formed in the distal end component 312 so that a beam of illumination light emitted from the lamp 308*a* is irradiated via the illumination through-hole 313 to a location to be observed. The distal end component 312 is also formed with an observation through-hole 315 which includes an objective optical system 314 fixed therein and extends parallel to the illumination through-hole 313. A solid imaging device 315 such as a CCD is disposed in the focused plane of the objective optical system 314, along with a color mosaic filter 314*a* for color separation. An optical image of the location to be observed, focused by the objective optical system 314, is subjected to photoelectric conversion by the solid imaging device 316, and a resulting video signal is output to the video signal processing unit 310 in the light source unit 308 via a signal line 316*a* fixed to a substrate of the solid imaging device 316. The video signal processing unit 310 is connected to a monitor 310*a*. Thus, the video signal from the solid imaging device 316 is processed by the video signal processing unit 310 and then output to the monitor 310*a* so that the image of the location to be observed can visually be observed on the monitor 310*a*.

The distal end component 312 also includes a suction port and an air-feed/water-feed port (both not shown). By actuating a suction switch 317*a* and an air-feed/water-feed switch 317*b* provided on the operating section 303, it is possible to perform the required operation such as suction or air-feed/water-feed.

Figure 49:
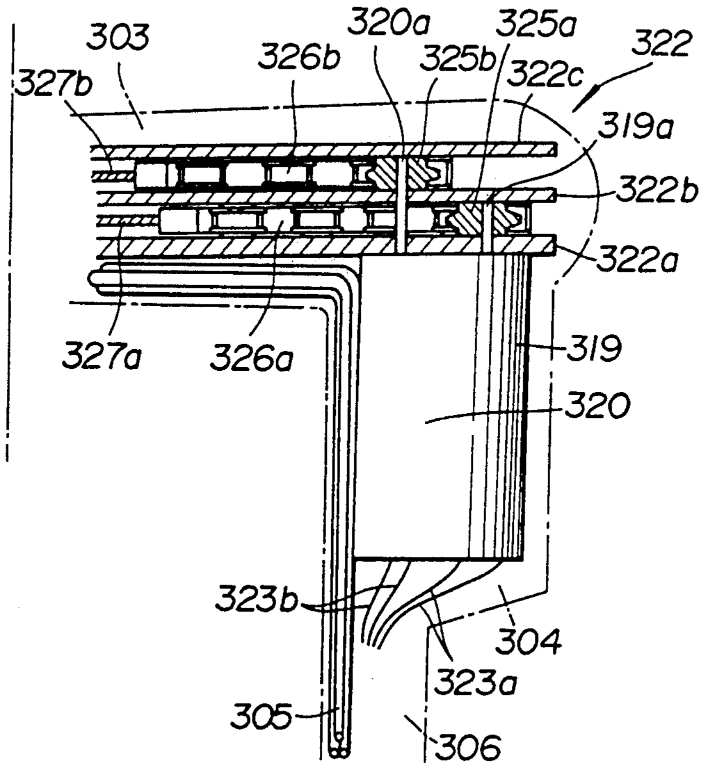

As shown in FIG. 49, a vertically (UD) bending DC motor 319 and a horizontally (RL) bending DC motor 320, as one example of a drive unit, are disposed in the extended base portion 304 parallel to each other. On the base end side of the operating section 303, a frame assembly 322 comprising a first frame 322*a*, a second frame 322*b* and a third frame 322*c* is disposed parallel to the axis of the operating section 303. The vertically bending DC motor 319 and the horizontally bending DC motor 320 are fixed to the first frame 322*a* of the frame assembly 322 which is disposed nearest to the extended base portion 304.

Figure 52:
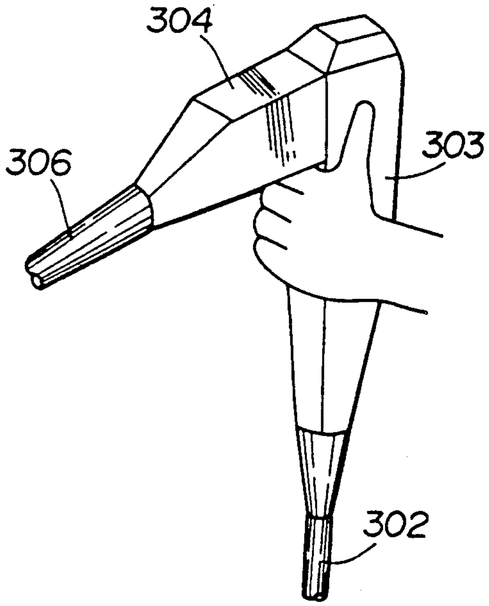

The DC motor 319, 320 are connected to the motor control unit 309 disposed in the light source unit 308 via connecting lines 323*a*, 323*b*, respectively, and are operated by switches 324 disposed on the lateral surface of the operating section 303 and connected to the motor control unit 309. As shown in FIG. 50, the switches 324 comprise four push switches; i.e., a pair of vertically (UD) bending switches 324*a*, 324*b* and a pair of horizontally (RL) bending switches, and a minute bending vibration on/off switch 324*e*, for example. These switches are located in a region where an operator's forefinger can reach when the endoscope 301 is gripped by the left hand at a part midway between the operating section 303 and the extended base portion 304, for example, as shown in FIG. 52. Incidentally, each pair of push switches among the four switches 324*a*–324*d*, which are operated for bending in the opposite directions, are arranged as seesaw switches so that while one of the paired switches is being depressed, the other switch may not be depressed.

On the other hand, an output shaft 319*a* of the vertically bending DC motor 319 penetrates through the first frame 322*a*, and is projected between the first frame 322*a* and the second frame 322*b* in a rotatable manner. An output shaft 320*a* of the horizontally bending DC motor 320 penetrates through the first and second frames 322*a*, 322*b* and is projected between the second frame 322*b* and the third frame 322*c* in a rotatable manner. Pulleys 325*a*, 325*b* are mounted at the ends of the output shafts 319*a*, 320*a*, respectively.

Further, chains 326*a*, 326*b* each having a predetermined length are entrained about the pulleys 325*a*, 325*b*, respectively. Both ends of each of the chains 326*a*, 326*b* are extended toward the insert section 302, and one ends of vertically bending wires 327*a* and horizontally bending wires 327*b* are fixed to the extended ends of the chains 326*a*, 326*b*, respectively. These wires 327*a*, 327*b* are extended through the insert section 302 up to the distal end of the bendable portion 318. The other ends of the horizontally bending wires 327*b* are fixed to corresponding right and left points of the assembly of articulated rings disposed at the distal end of the bendable portion 318, and the other ends of the vertically bending wires 327*a* are fixed to corresponding upper and lower points of that assembly. Therefore, by tensioning and loosening the wires 327*a*, 327*b*, the bendable portion 318 is bent upwards, downwards, rightwards and leftwards, whereby the distal end component 312 can be directed toward the location to be observed.

Figure 53:
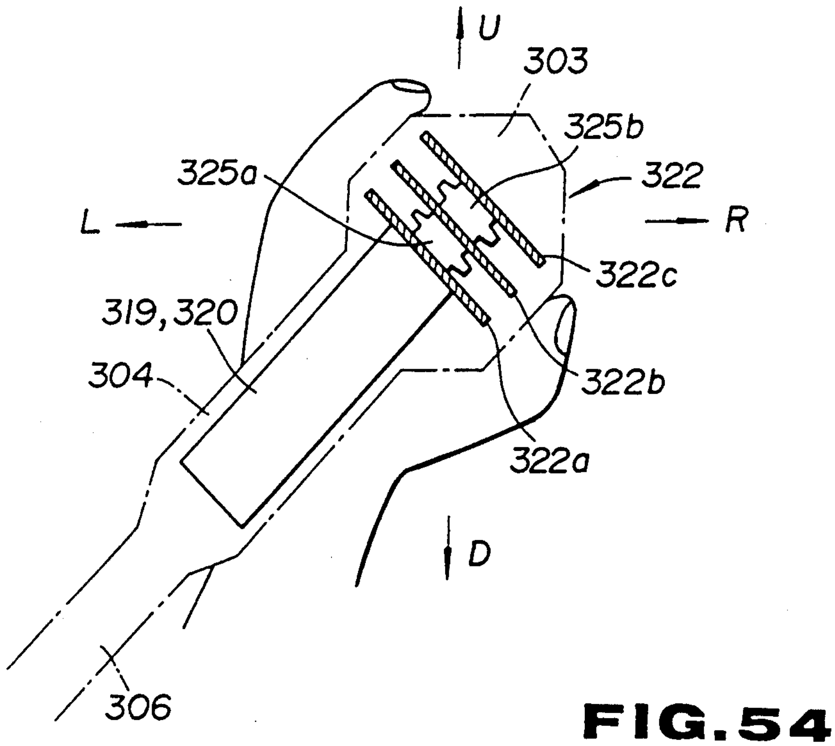

As shown in FIG. 53, the extended base portion 304 housing the DC motors 319, 320 is provided obliquely relative to the bending directions of the bendable portion 318 so that when the operating section 303 is held by the left hand, for example, the extended base portion 304 rests on the back of the gripping hand. As a result, the weight of the DC motors 319, 320, etc. can be supported by the back of the gripping hand, which facilitates supporting and gripping of the operating section 304.

The motor control unit 9 controls the bending (inclusive of the minute bending vibration) in the sixth embodiment, as with a control circuit 70 in the eighth embodiment.

When starting observation by the endoscope 301 thus constituted, the insert section 302 is inserted into the body cavity or the like, the light guide cable 306 is connected to the light source unit 308 via the connector 307, and electric power is supplied to the light source unit 308. Then, a beam of illumination light emitted from the lamp 308*a* in the light source unit 308 is introduced by the light guide 305 to the distal end component 312 and irradiated via the illumination throughhole 313 in the distal end component 312 to the location to be observed.

An optical image of the location to be observed is focused by the objective optical system 314, via the color mosaic filter 314*a* for color separation, into an image area of the solid imaging device 316 and, after photo-electric conversion, applied to the video signal processing unit 31. The signal processed by the video signal processing unit 31 is output to the monitor 310*a* so that the image of the location to be observed can visually be observed on the monitor 310*a*.

In the case where the location to be observed is positioned laterally away from the axis of the insert section 302, the proper switch 324 is operated to bend the bendable portion 318 for directing the distal end component 312 to the location to be observed.

More specifically, by depressing the upwards bending switch 324*a* or the downwards bending switch 324*b*, the vertically bending DC motor 319 is driven via the motor control unit 309 in the light source unit 308, and the pulley 325*a* is rotated via the output shaft 319*a* of the vertically bending DC motor 319. Rotation of the pulley 325*a* moves the chain 326*a* in the axial direction of the operating section 303, whereupon the vertically bending wires 327*a* fixed at one ends to the respective ends of the chain 326*a* are each loosened or tensioned.

Since the other ends of the vertically bending wires 327*a* are fixed to the bendable portion 318 at the upper and lower points on the distal end side thereof, the bendable portion 318 is bent vertically dependent on a rotating angle of the pulley 325*a* upon the upper and lower fixed points being tensioned or loosened. As a result, the distal end component 312 is directed to the location to be observed, allowing that location to be visually observed on the monitor 310*a*.

By releasing the switch 324 from its operated state at the time the distal end component 312 is just directed to the location to be observed, the DC motor 319 is stopped in operation and the bendable portion 318 comes to rest while keeping the bent state (condition), allowing to continue observation of the location to be observed.

The foregoing process is equally applied to not only the case of bending the bendable portion 318 up and down, but also the case of bending it to the right and left.

When it is required to return the bendable portion 319 to the straight form, the bendable portion 319 can easily be returned to the straight form by operating the proper switch 324. In this connection, the state of the bendable portion 318 can be noticed with ease by so arranging as to detect the rotating positions of the pulleys 325*a*, 325*b* and light up an indicator lamp disposed on the operating section 303, for example, when the pulleys 325*a*, 325*b* have returned to their initial states.

In addition, by operating the minute bending vibration on/off switch 324*c*, the bendable portion 318 is caused to develop a minute vibration as with the sixth embodiment.

Although the vertically and horizontally bending DC motors 319, 320 are used as the drive unit in this embodiment, the drive unit is not necessarily limited to the DC motors 319, 320. Alternatively, the drive unit may be of any other type of motors such as AC motors, pulse motors, ultrasonic motors, or fluid motors utilizing a hydraulic pressure.

Further, it is also possible to attach speed reducers to the DC motors 319, 320 for increasing torque produced to perform the bending.

Other operation and advantageous effect are similar to those in the sixth embodiment.

Figure 54:
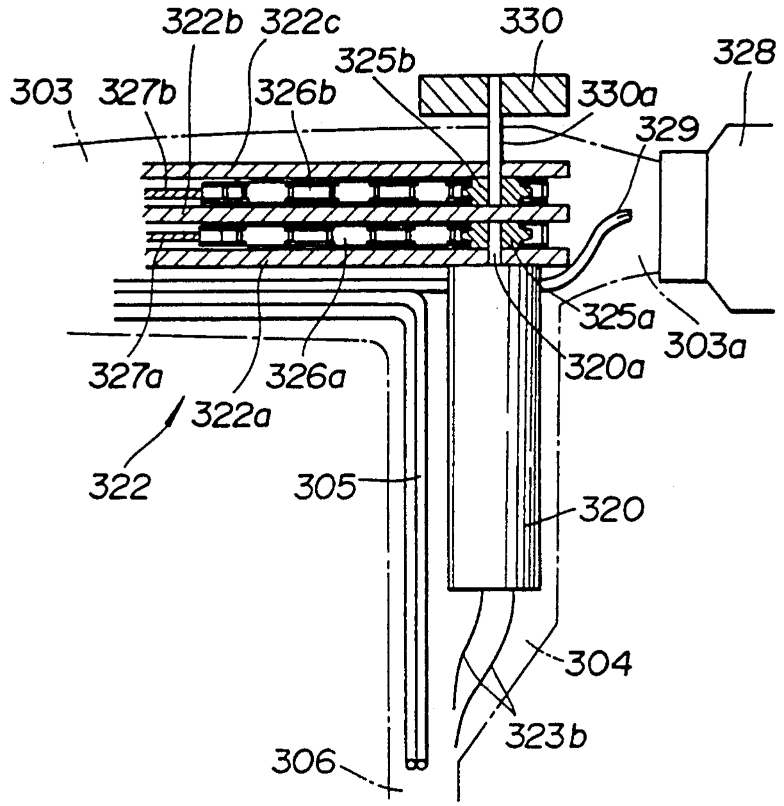
Figure 55:
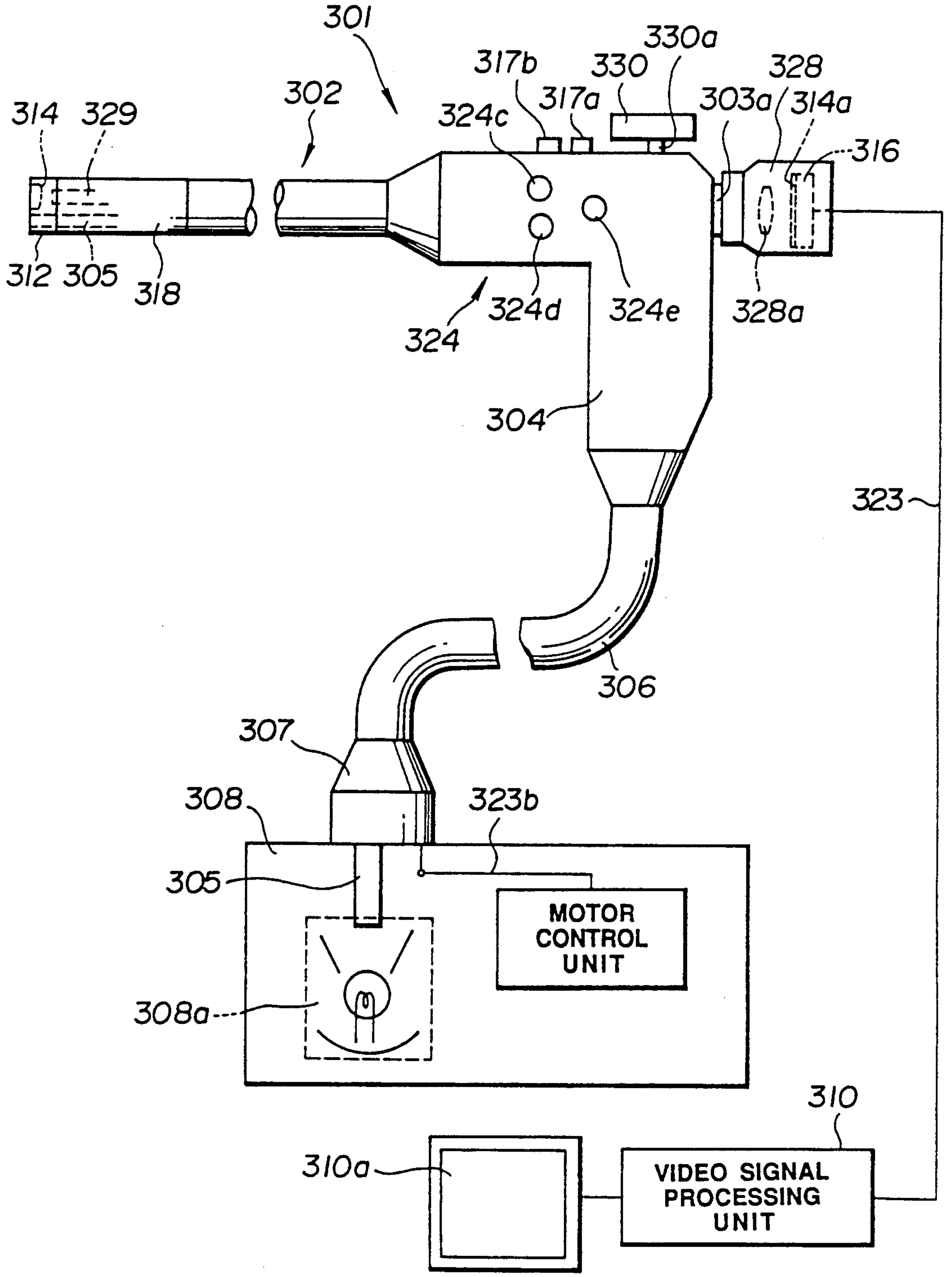

FIGS. 54 and 55 illustrate a twenty-second embodiment of the present invention. The same components as those and components operating similarly to those explained in the above twenty-first embodiment are designated by the same reference numerals, and are not described here.

This embodiment is concerned with an example of a fiber scope. As shown in FIG. 55, an eyepiece portion 303*a* provided on the base end side of an operating section 303 is arranged to permit attachment of a mountable television (TV) camera 328. An image guide 329 is provided opposite to an objective optical system 314 disposed in a distal end component 312 so that the optical image of the location to be observed, focused by the objective optical system 314, is transmitted to the eyepiece portion 303*a* via the image guide 329.

The TV camera 328 incorporates a focusing optical system 328*a*. The optical image of the location to be observed, transmitted to the eyepiece portion 303*a*, is focused by the focusing optical system 328*a* on a solid imaging device 316 via a color mosaic filter 314*a* for color separation. The TV camera 316 is connected via a signal line 323 to a video signal processing unit 310 provided separately from a light source unit 308. The signal resulted from photo-electric conversion by the solid imaging device 316 is processed by the video signal processing unit 310 and output to a monitor 310*a*.

On the other hand, in an extended base portion 304 formed at the based end of the operating section 303 and extending substantially perpendicular to the axis of the operating section 303, there is disposed only a horizontally (RL) bending DC motor 320 as shown in FIG. 54. The horizontally bending DC motor 320 is fixed to a first frame 322*a* of a frame assembly 32 provided in the operating section 303. An output shaft 320*a* of the DC motor 320 is projected between the first frame 322*a* and a second frame 322*b* of the frame assembly 32 in a rotatable manner, with a pulley 325*a* mounted on the projected end of the output shaft 320*a*. The DC motor 320 is connected to a motor control unit 309 in the light source unit 308 via a connecting line 323*b*. By operating a switch 324 which comprises a rightwards bending switch 324*c*, a leftwards bending switch 324*d* and a minute bending vibration on/off switch 324*e* all provided on one lateral side of the operating section 303, the pulley 325*a* is rotated to bend a bendable portion 318.

Another pulley 325*b* is disposed between the second frame 322*b* and a third frame 322*c* of the frame assembly 322 in a rotatable manner. A central axis 330*a* of the pulley 325*b* is projected through the third frame 322*c* to the exterior of the operating section 303. A knob 330 for manually bending the bendable portion 318 up and down is mounted on the projected end of the central axis 330*a*.

With such constitution, by depressing the rightwards bending switch 324*c* or the leftwards bending switch 324*d* to drive the DC motor 320, horizontally bending wires 327*a* are each tensioned or loosened via the pulley 325*a*. On the other hand, by manually rotating the knob 330, vertically bending wires 327*b* are each tensioned or loosened via another pulley 325*b*.

This embodiment is advantageous in that because it includes only one DC motor 320 as one example of the drive unit, the weight of the operating section 303 and the extended base portion 304 is reduced correspondingly, and hence the burden exerted on the operator becomes lighter.

FIGS. 56 through 59 illustrate three examples of driving a driven member other than the bendable portion by a motor provided in the extended base portion 304.

Figure 56:
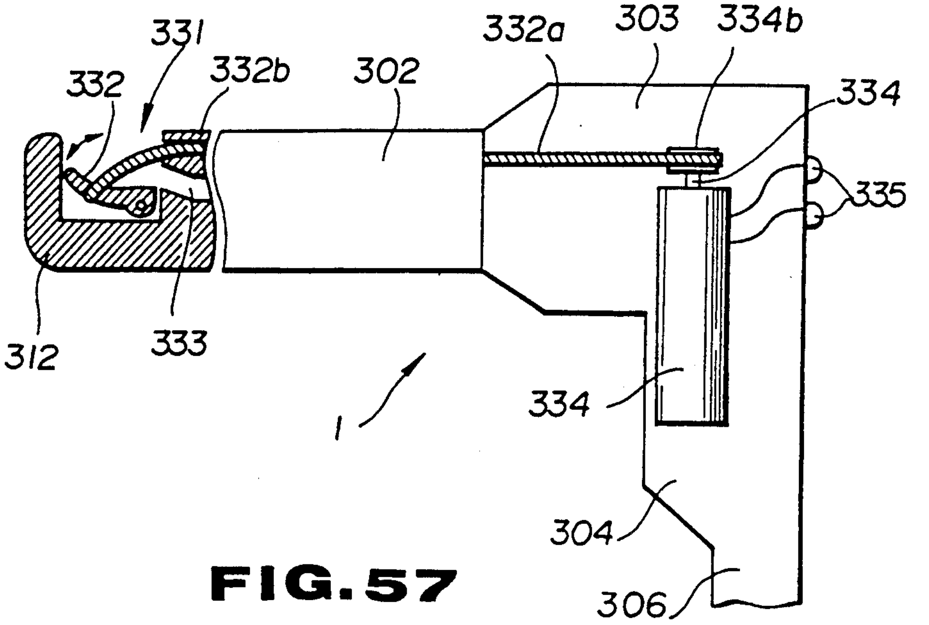
Figure 57:
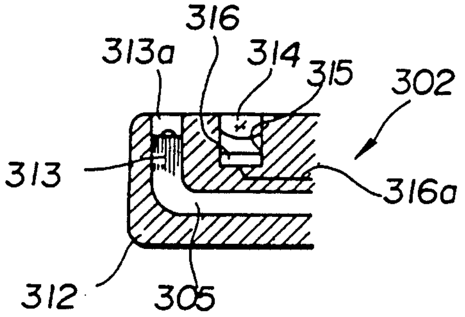

In the first example shown in FIGS. 56 and 57, an endoscope 301 is constituted into the laterally viewing type such that an illumination through-hole 313 in which a light directing lens 313*a* is disposed and an observation through-hole 315 are so formed as to direct laterally of a distal end component 312. Facing the lateral side of the distal end component 312 to which the illumination through-hole 313 and the observation through-hole 315 are directed, there is formed a storage chamber 331 in which a guide member 332 for erecting or raising up a forceps is disposed in a pivotable manner. The guide member 332 is regarded as a driven member in this example.

A forceps channel 333 is communicated with the storage chamber 331. An erection wire 332*a* is coupled to the free end of the guide member 332 and extended toward an operating section 303 through an insertion hole 332*b* bored in the insert section 302. In an extended base portion 304 provided at the base end of the operating section 303, there is disposed a DC motor 334 for raising up the forceps. The erection wire 332*a* is entrained about a pulley 334*b* mounted on an output shaft 334*a* of the DC motor 334.

Further, switches 335 for actuating the DC motor 334 are provided on the outer surface of the distal end of the operating section 303.

With the above consitution, by depressing proper one of the switches 335 to rotate the pulley 334*b*, the erection wire 332*a* entrained about the pulley 334*b* is pulled to raise up the guide member 332.

Figure 58:
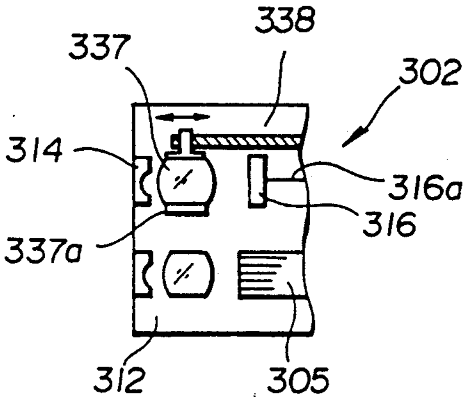

In the second example shown in FIG. 58, a zoom lens 337 is disposed between an objective optical system 314 and a solid imaging device 316 both provided in the distal end component 312. The zoom lens 337 is regarded as a driven member in this example. More specifically, the zoom lens 337 is arranged to be slidable forwards and rearwards along the optical axis of the objective optical system 314. A sliding wire 338 has one end attached to one side of a frame 337*a* for holding the zoom lens 337, and the other end led to a drive unit (not shown).

Upon the sliding wire 338 being pulled by the drive unit, the zoom lens 337 is slid along the optical axis via the frame 337*a* to magnify or reduce the optical image focused on the solid imaging device 316.

Figure 59:
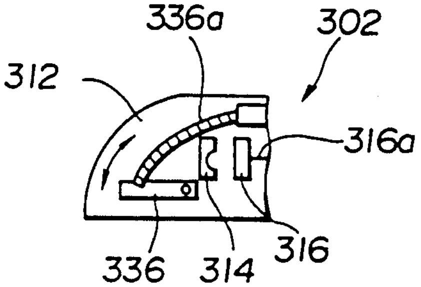

In the third example shown in FIG. 59, the endoscope 301 is constituted to be capable of changing the view field. More specifically, the distal end component 312 is formed of a transparent member, and a mirror 336 as one example of the driven member is provided in front of the objective optical system 314 disposed in the distal end component 312 in a pivotable manner. An operating wire 336*a* has one end attached to the free end of the mirror 336, and the other end led to a drive unit (not shown). By pivoting the mirror 336 via the operating wire 336*a*, the mirror 336 comes into crossing relation with the optical axis of the objective optical system 314.

With such constitution, in a condition that the mirror 336 does not cross the optical axis of the objective optical system 314, an image of the location positioned in front of the central axis of the insert section 302 is focused on the solid imaging device 316. When the mirror 336 is pivoted to cross the optical axis, an image of the location positioned laterally of the optical axis is reflected by the mirror 336 to enter the objective optical system 314. Since the location from which the illumination light is reflected is determined by an angle between the mirror 336 and the optical axis, the viewing direction can be changed in a successive manner by continuously adjusting the inclination angle of the mirror 336.

It is also possible that a pivoting angle of the mirror 336 established by the drive unit is set to 20°, 45°, etc. relative to the optical axis, and the drive unit is energized to change the angle of the mirror 336 for modifying the endoscope 301 into the straightly viewing type, the obliquely viewing type or the laterally viewing type successively.

As described above, the twenty-first and twenty-second embodiments are advantageous in that the construction is simplified, an increase in both the diameter and weight of the distal end component is prevented, the drive unit is avoided from projecting at its tail end out of the lateral side of the operating section, and the response is not lowered.

Inconvenience as encountered when the insert section of an endoscope reaches a bent region of the object to be examined will now be described with reference to FIGS. 60 and 61.

Figure 60:
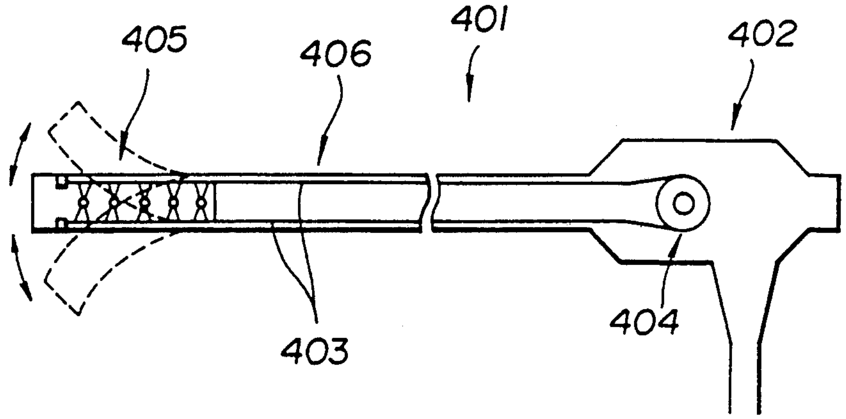
FIG. 60 is an explanatory view showing behavior of a minute bending vibration.

FIG. 60 illustrates a manner of minutely vibrating the bendable portion. An endoscope 401 shown in this drawing comprises an insert section 406 and an operating section 402, the insert section 406 including a bendable portion 405. A bending motor 404 is disposed in the operating section 402. Fixed to the distal end of the bendable portion 405 are both fore ends of an angle wire 403 extended through the insert section 406. The base end of the angle wire 403 is secured to an output shaft of the motor 404. By revolving the motor 404 upon switching operation, the bendable portion 405 can be bent upwards and downwards, for example. Also, by alternately operating a switch up and down to revolve the motor 404 forwards and backwards in a repeated manner, for example, the bendable portion 405 is repeatedly bent in the opposite directions as shown in FIG. 60, which contributes to improve operability of insertion of the insert section into a tract 407 of a living body, such as the large intestine, shown in FIG. 61.

However, when the insert section 406 reaches a bent region of the body tract 407 and a rear part of the bendable portion 405 comes into contact with the body tract 407 to become a pressing part 408 against the tract wall, or when a rear part of the insert section 406 becomes a contact part 409 with the body tract 407, applying a push force to the insert section 406 serves only to increase a pressing force transmitted to the pressing part 408 and a frictional force produced in the contact part 409. This may practically make it difficult to continue the insertion into a deeper place just using the push force. In this case, even if a repeated bending operation (minute vibration) is given to the bendable portion 405 by the motor 404, this would not contribute to improve operability of insertion as indicated by broken lines in FIG. 61.

Figure 61:
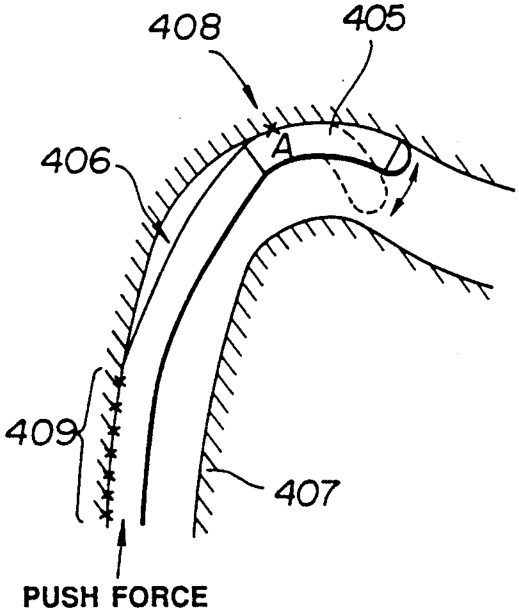
FIG. 61 is an explanatory view showing the state that a rear part of the bendable portion is brought into contact with a tract wall of a living body.

In other words, the repeated bending operation is useful to improve operability of insertion in the case where the pressing part 408 locates in a front part of the bendable portion 405, while the bendable portion 405 only repeats the bending in vain in the case where the bendable portion 405 is brought at its rear part into contact with the body tract 407 as shown in FIG. 61.

The following twenty-third through twenty-fifth embodiments are concerned with examples in which the insert section can be vibrated wavily for solving the foregoing inconvenience.

FIGS. 62 through 66 illustrate a twenty-third embodiment of the present invention.

Figure 64:
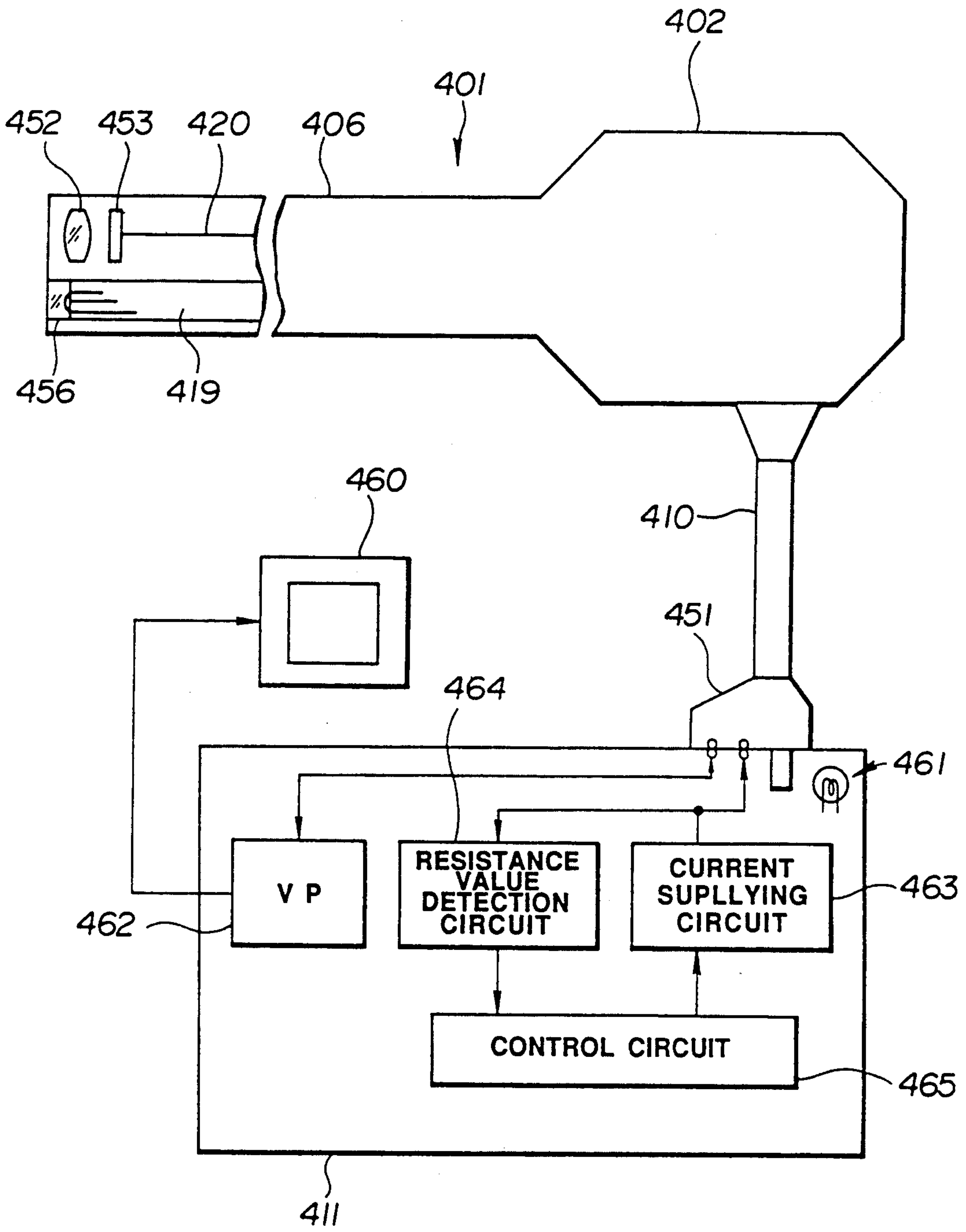

As shown in FIG. 64, an endoscope apparatus of this embodiment comprises an endoscope 401, a controller 411 to which the endoscope 401 is connected, and a monitor 460 connected to the controller 411.

The endoscope 401 comprises an elongate and flexible insert section 406, an operating section 402 continuously provided at the rear end of the insert section 406, and a universal cord 410 extended laterally from the operating section 402. A connector 451 is provided at the end of the universal cord 410 to be freely connectable to the controller 411.

An observation window and an illumination window are formed in the distal end portion of the insert section 406. An objective lens 452 is disposed inside the observation window, and a solid imaging device 453 is disposed at a focus position of the objective lens 452. A signal line 420 connected to the solid imaging device 453 is extended through the insert section 406, the operating section 402 and the universal cord 410 and then connected to the connector 451. A light directing lens 456 is disposed inside the illumination window, and the emergent end of a light guide fiber 419 is located just behind the light directing lens 456. The light guide fiber 419 is extended through the insert section 406, the operating section 402 and the universal cord 410, and has the incident end connected to the connector 451.

The controller 411 incorporates a lamp 461 for supplying a beam of illumination light to the light guide fiber 419, a video processor (hereinafter referred to as VP) 462 connected to the solid imaging device 453 via the connector 451, and a current supplying circuit 463, a resistance value detection circuit 464 and a control circuit 465 (all described later). The solid imaging device 453 is driven by the VP 462, and an output signal of the solid imaging device 453 is subjected to processing for a video signal by the VP 462. The video signal output from the VP 462 is applied to the monitor 460 so that an object image is displayed on the monitor 460.

Figure 62:
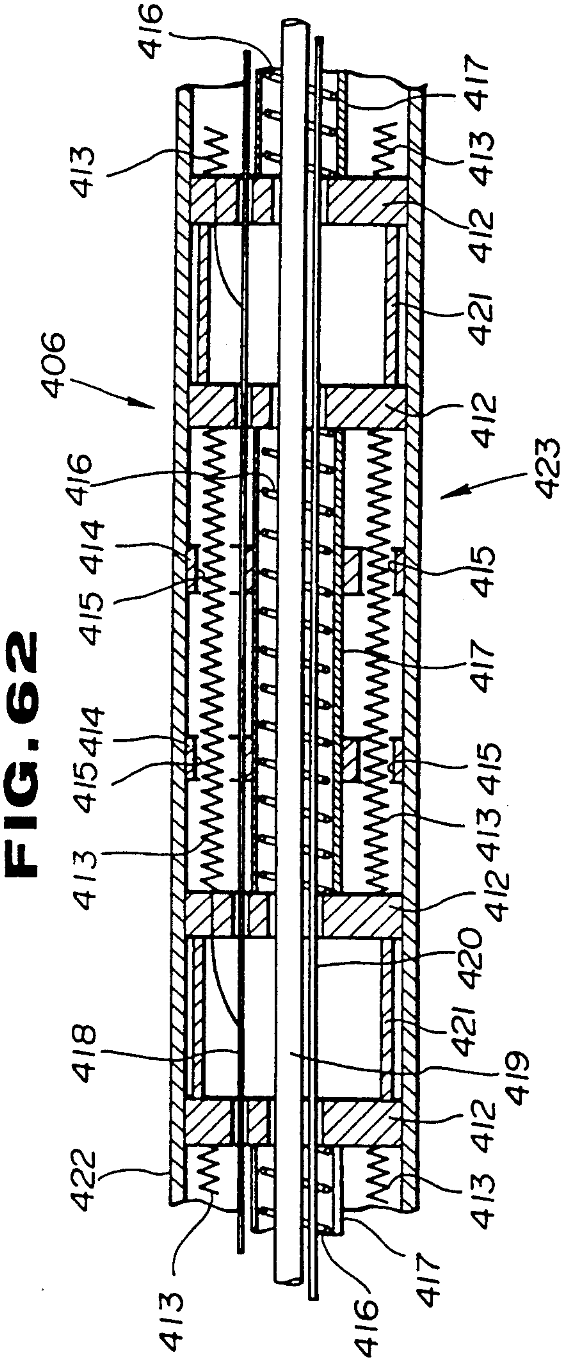
Figure 63:
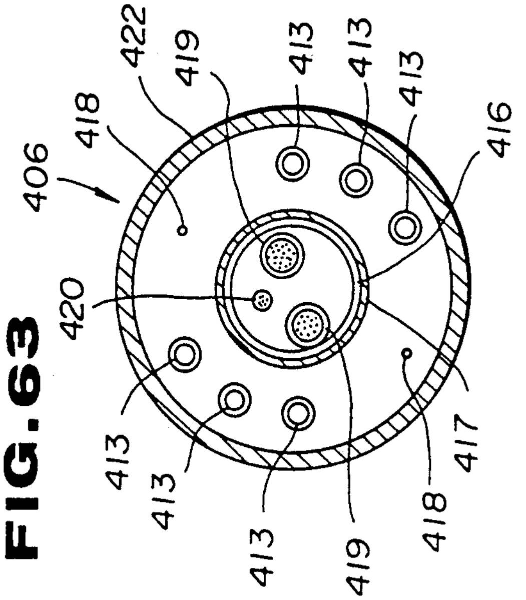

The insert section 406 is constituted as shown in FIGS. 62 and 63.

More specifically, the insert section 406 includes a plurality of bending units 423 which are located in axially different positions and interconnected in a bendable manner independently of each other. The bending units 423 each have flanges 412, 412 at the axial opposite ends, and a plurality of shape memory alloy (hereinafter referred to as SMA) coils 413, which has memorized a closely coiled shape, are fixed between the flanges 412 and 412 in an expanded condition. Between the flanges 412 and 412, there are also provided two intermediate flanges 414, 414. The intermediate flange 414 is formed with a hole or opening 415, and the SMA coils 413 are extended through the hole 415. In addition, a coil spring 416 is fixed at the center between the flanges 412 and 412 along the axis, and an insulating tube 417 covers the outer periphery of the coil spring 416. Lead wires are connected to the opposite ends of each SMA coil 413, respectively, and one of the lead wires is connected to a main lead wire 418. Further, a hole is bored through the flange 412 at the center and, as shown in FIG. 63, the light guide fiber 419 and the signal line 420 are extended through both such flange holes and the coil springs 416.

As will be seen from FIG. 63, the plurality of SMA coils 413 are arranged in parallel in each of opposite areas corresponding to the respective bending directions, and these SMA coils 413 are electrically connected in series. Although FIG. 63 illustrates an arrangement for bending in the two directions, the number of SMA coils 413 may be increased to permit the bending in the four directions, for example, as required.

The bending units 413 each thus constituted are interconnected by respective connecting members 421. An outer cover 422 is provided on the outermost periphery of the insert section 406.

Other than the above mentioned components, an appliance extending channel and/or an air-feed/water-feed channel may be provided in the insert section 406. In an endoscope which includes an image guide for transmitting the object image to the operating section 2, instead of the solid imaging device, the image guide may be disposed in the insert section 406.

The SMA coils 413 are connected to the current supplying circuit 463 and the resistance value detection circuit 464 both disposed in the controller 411 as shown in FIG. 64. When an electric current is supplied to the SMA coils 413 from the current supplying circuit 463, the SMA coils 413 are heated and contracted. Note that current supply to the SMA coils 413 may be performed using an alternating current, a direct current, a PWM (pulse width modulation) current, etc. The resistance value of the SMA coils 413 is detected by the resistance value detection circuit 464, so that the bent amount of the bending unit 423 can be determined by detecting a change in the resistance value upon heating due to supply of the current. Information of the resistance value detected by the resistance value detection circuit 464 is sent to the control circuit 465 and, based on this information, the control circuit 465 controls the amount of current supplied from the current supplying circuit 463, thereby controlling the bent amount of the bending unit 423. Incidentally, the plurality of bending units 423 can be controlled in the bent amount independently of each other.

Figure 65:
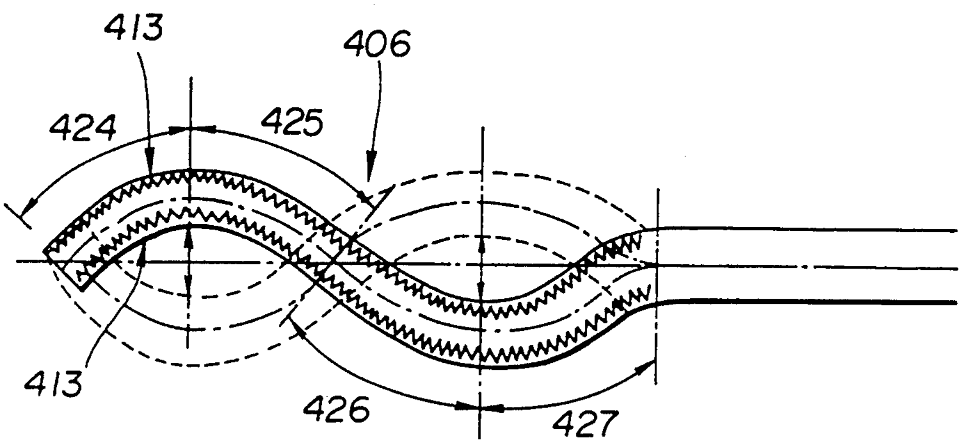

In this embodiment, as shown in FIG. 65, the plurality of bending units 423 are used to form a first bendable portion 424, a second bendable portion 425, a third bendable portion 426 and a fourth bendable portion 427 from the distal end of the insert section 406 in this order. Note that the number of bendable portions is not limited to four, and it may be any desired number as long as a wavy shape of at least a half wave length or more can be imparted to the insert section 406.

Operation of this embodiment will be described below.

Figure 66:
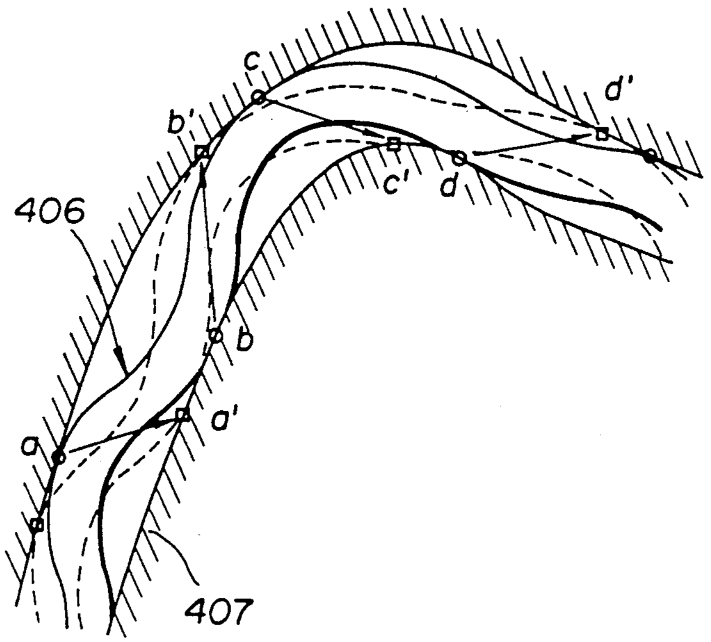

In an attempt to insert the insert section 406 of the endoscope 401 into an object to be examined, such as a tract 407 of a living body, as shown in FIG. 66, when the insert section 406 contacts an inner wall of the body tract 407 to increase the contact resistance of the insert section 406, an electric current is supplied to the SMA coils 413 of each bending unit 423 for heating them, thereby to bend the bending unit 423. Specifically, an electric current is supplied to those SMA coils 413 on one side of each bending unit 423 for heating them, whereby these SMA coils 413 are contracted to bend the bending unit 423. In this respect, as shown in FIG. 65, by varying the directions in which the adjacent bending units 423 are to bend, a sine wave configuration is imparted to the insert section 406. Then, by energizing the respective bending units 423 to bend in the opposite directions to before, a sine wave configuration out of phase 180 degrees from the preceding sine wave configuration is produced as indicated by broken lines in FIG. 65. Then, the above two stages of processes are repeated alternately. This causes the insert section 406 to vibrate in the wavy form as a whole.

When the insert section 406 is inserted into the tract 407 of a living body and reaches such a region as curving steeply with the smaller radius of curvature, as shown in FIG. 66, the foregoing operation is performed so as to wavily vibrate the insert section 406. First, the insert section 406 is brought into the wavy form as indicated by solid lines in FIG. 66. Under this condition, the insert section 406 are in contact with the inner wall of the body tract 407 at points a, b, c, d. Next, the respective bending units 423 are bent in the opposite directions while pushing the insert section 406. With this process, the contact points between the insert section 406 and the body tract 407 are shifted as given by a→a', b→b', c→c', d→d', thereby advancing the insert section 406. By repeating the above process, operability of insertion is improved while surely reducing the contact resistance of the insert section 406, without vibrating the bendable portion in vain as often experienced when the bendable portion is simply vibrated vertically or so. Even in the case of not pushing the insert section 406, vibrating the insert section 406 into the wavy form ensure the advantageous effect of reducing the contact resistance.

Furthermore, since the insert section 406 vibrates of itself in a direction crossing the axial direction thereof even when the insert section 406 is not in contact with the body tract 407, the impact against the body tract 407 is reduced.

Figure 67:
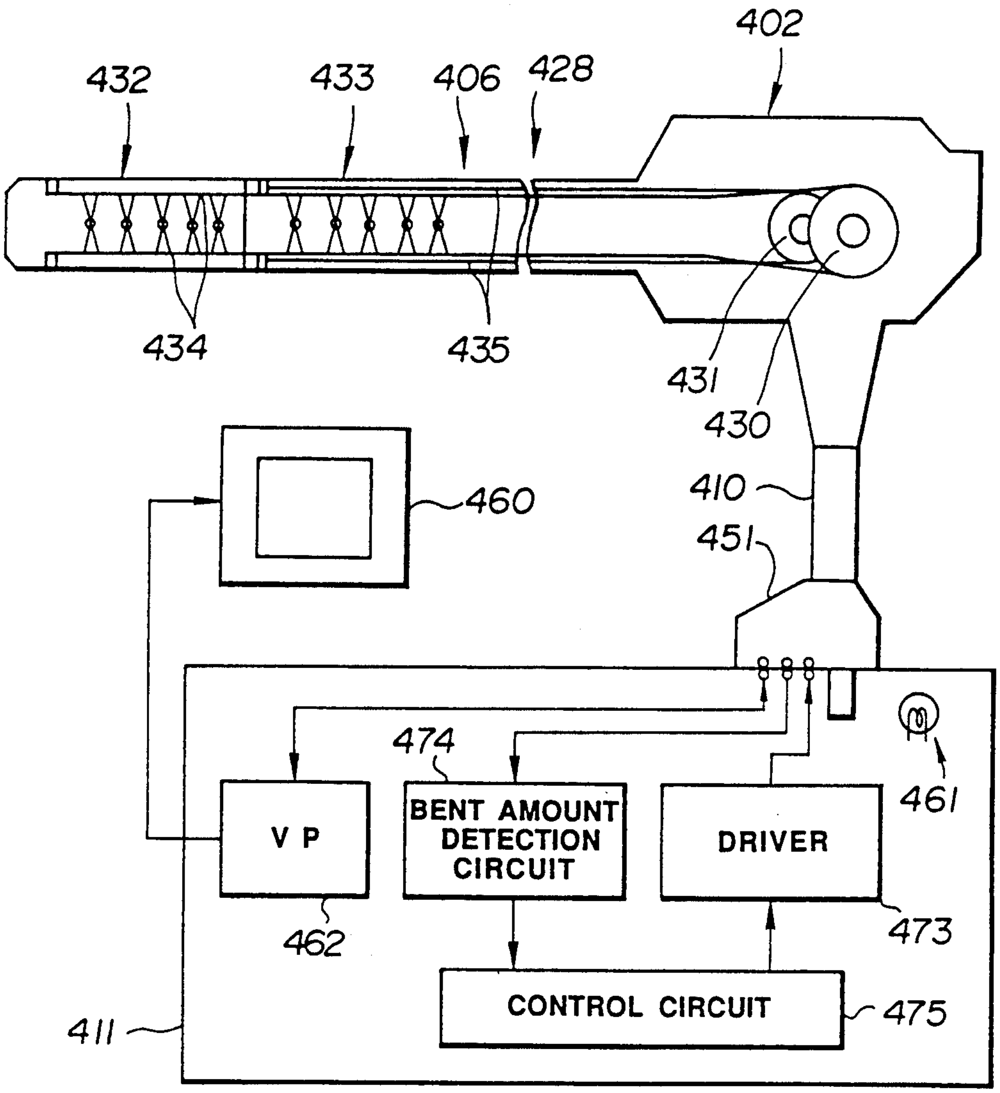
Figure 68:
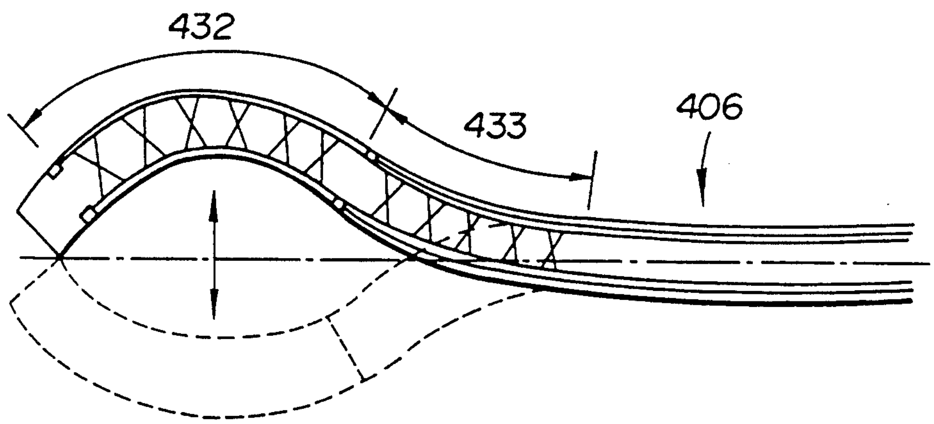
Figure 69:
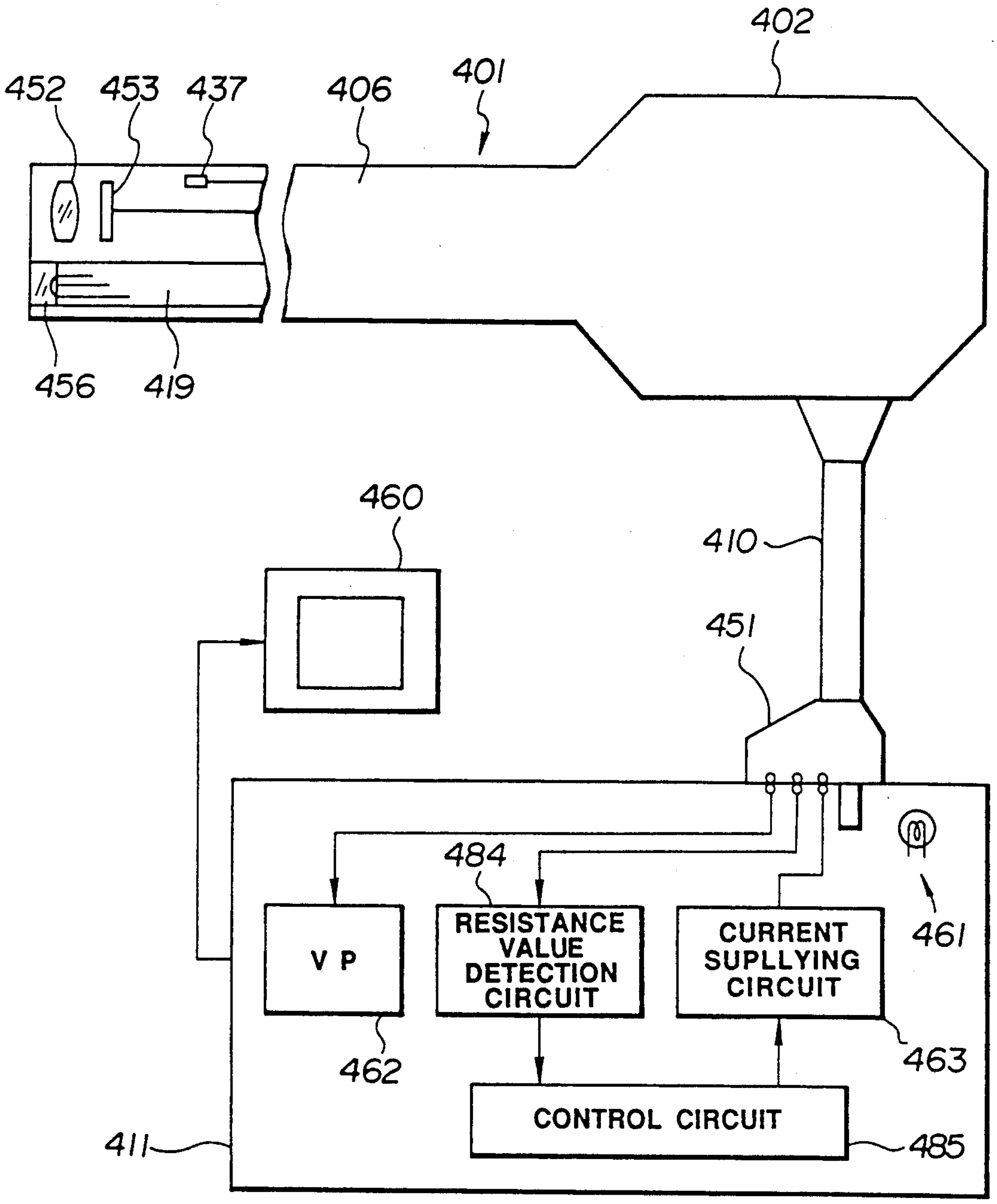

FIGS. 67 and 68 illustrate a twenty-fourth embodiment of the present invention.

An endoscope apparatus of this embodiment comprises, as shown in FIG. 67, an endoscope 428, a controller 411 to which the endoscope 428 is connected, and a monitor 460.

In an insert section 406 of the endoscope 428, there are provided a first bendable portion 432 and a second bendable portion 433 from the distal end side in this order. The bendable portions 432, 433 are each constituted by interconnecting a plurality of cylindrical articulate pieces in a pivotable manner relative to each other. Fixed to the distal end of the first bendable portion 432 are both fore ends of a first angle wire 434 extended through the insert section 406. Also, fixed to the distal end of the second bendable portion 433 are both fore ends of a second angle wire 435 extended through the insert section 406. A first motor 430 and a second motor 431 are disposed in an operating section 402. The base ends of the angle wires 434, 435 are fixed to pulleys mounted on output shafts of the motors 430, 431, respectively. By driving the respective motors 430, 431 to revolve independently of each other, the angle wires 434, 435 are pushed and pulled to bend the respective bendable portions 432, 433 in an independent manner. Encoders (not shown) are attached to the motors 430, 431.

On the other hand, the controller 411 includes, in addition to a lamp 461 and a VP 462, a driver 473 for driving the motors 430, 431, a bent amount detection circuit 474 for detecting the bent amounts of the bendable portions 432, 433 from outputs of the encoders, and a control circuit 475 for controlling the driver 473 based on an output of the bent amount detection circuit 474.

With this embodiment, by bending an adjacent pair of the first bendable portion 432 and the second bendable portion 433 in different directions and repeatedly bending those bendable portions in opposite directions alternately as indicated by solid and broken lines, as shown in FIG. 68, the insert section 406 is caused to vibrate in the wavy form of half wavelength.

Other constitution, operation and advantageous effect are similar to those in the twenty-third embodiment.

FIGS. 69 through 75 illustrate a twenty-fifth embodiment of the present invention.

In this embodiment, a strain gauge 437 is provided as a bent amount sensor in each bending unit 423 for controlling the bent amount in the endoscope 401 of the twenty-third embodiment.

A controller 411 includes, in addition to a lamp 461, a VP 462 and a current supplying circuit 463, a bent amount detection circuit 484 for detecting the bent amount of each bending unit 423 from an output of the strain gauge 437, and a control circuit 485 for controlling the current supplying circuit 463 based on an output of the bent amount detection circuit 484. With such constitution, the bent amount can be maintained at a required value.

Five example of the bending unit 423 provided with the strain gauge 437 will be explained below.

Figure 70:
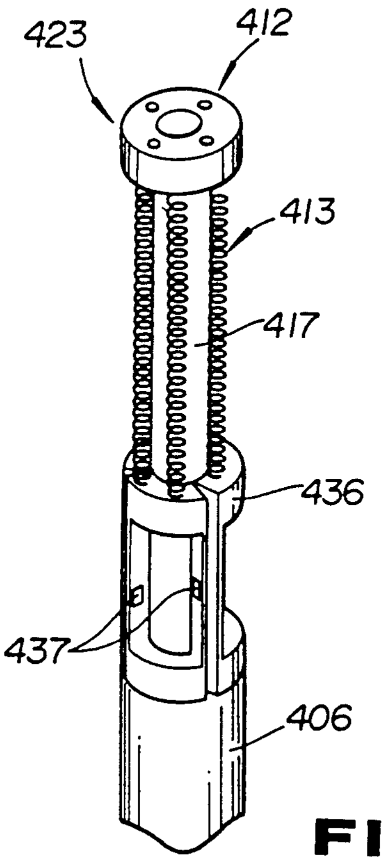

In the first example shown in FIG. 70, each SMA coil 413 has one end fixed to the flange 412, and the other end fixed to a bent amount detection block 436 provided for each of the bending directions. The bent amount detection block 436 is formed of a saddle-like member with its central portion cut away, and has two strain gauges 437, 437, for example, stuck to inner opposite walls of the cut-away portion. With this arrangement, when the SMA coil 423 is contracted under heating, the block 436 on the contracted side is subjected to a tension, and an extent of the resulting strain is detected by the strain gauges 437. By determining the correlation between the extent of strain and the bending angle in advance, the bent amount can be detected from the extent of strain.

Figure 71:
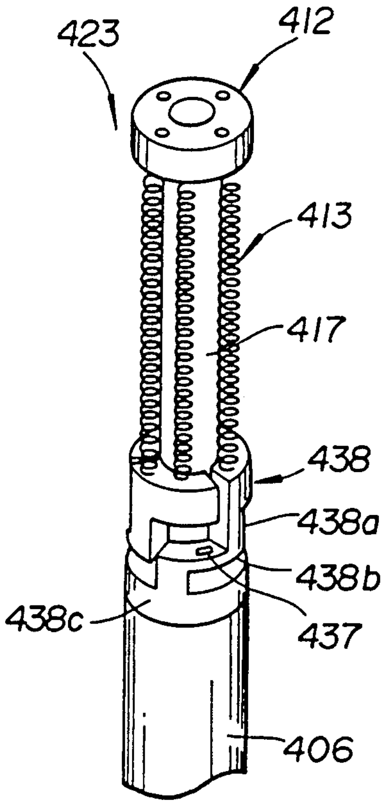

In the second example shown in FIG. 71, each SMA coil 413 has one end fixed to the flange 412, and the other end fixed to a bent amount detection block 438. The bent amount detection block 438 comprises a movable portion 438*a* which is provided for each of the bending directions and to which the other end of the SMA coil 413 is fixed, a strain portion 438*b* extended from the base end of the movable portion 438*a* in the circumferential direction, and a common base portion 438*c* to which the respective strain portions 438*b* are fixed. The strain gauge 437 is stuck to the strain portion 438*b*. With this arrangement, when the SMA coil 423 is contracted under heating, the block 438 on the contracted side is subjected to a tension to produce a bending strain in the strain portion 438*b*, and an extent of the resulting strain is detected by the strain gauge 437.

Figure 72:
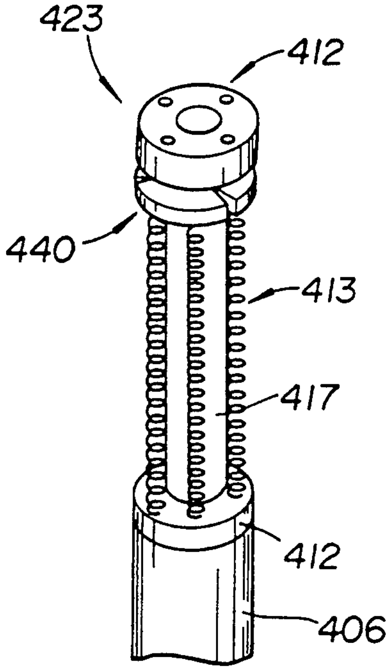
Figure 73:
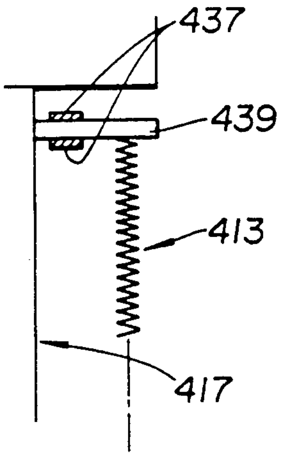

In the third example shown in FIGS. 72 and 73, a bent amount detection block 440 comprising a plurality of plates 439 provided respectively for the bending directions is disposed adjacent one of the opposite flanges on the side facing the SMA coil 413, and one end of each SMA coil 413 is fixed to the corresponding plate 439. As shown in FIG. 73, the strain gauge 437 is stuck to each of opposite surfaces of the plate 439. With this arrangement, when the SMA coil 423 is contracted, the corresponding plate 439 is deformed and this deformation can be detected as a bending strain by the strain gauges 437.

Figure 74:
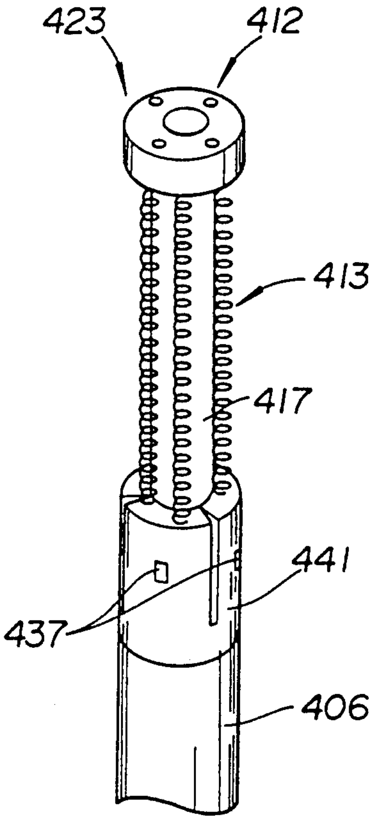

In the fourth example shown in FIG. 74, each SMA coil 413 has one end fixed to the flange 412, and the other end fixed to a bent amount detection block 441. The bent amount detection block 441 is divided by slits on the side facing the SMA coil 413 into separate portions split respectively for the bending directions. The strain gauge 437 is stuck to the outer circumference of each of the split portions. With this arrangement, the force exerted on block 441 can be detected as a tension and a bending strain by the strain gauge 437.

Figure 75:
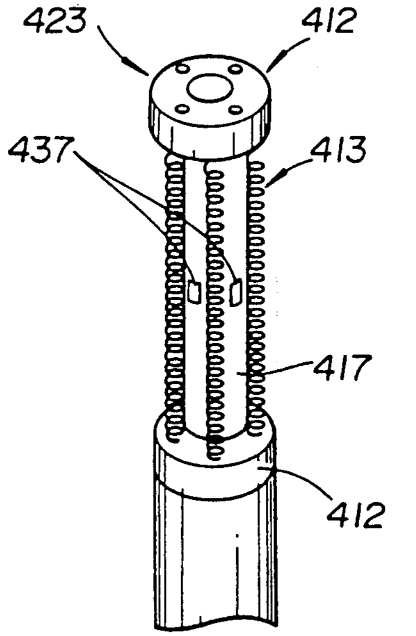

In the fifth example shown in FIG. 75, the strain gauges are directly stuck to the insulating tube 417. With this example, a deformation of the tube 417 due to bending is detected by the strain gauges 437 to determine the bent amount.

Thus, with this embodiment, the force produced upon contraction of the SMA coils 413 under heating can be detected electrically as an extent of strain by the strain gauges 437 stuck to any one of the elastically deformable bent amount detection blocks 436, 438, 440, 441 and the insulating tube 417. By comparing the detected extent of strain with the data correlated in advance to the bent amount, it is possible to determine the bent amount. This permits to control the bent amount of the insert section 406 as desired.

Other constitution, operation and advantageous effect are similar to those in the twenty-third embodiment.

Note that in the twenty-third through twenty-fifth embodiments, the circuit for driving and controlling the bendable portions, etc. may be provided separately from the light source unit.

The wavy form imparted to the insert section is not always required to be the exactly sinusoidal waveform. Also, a plurality of bendable portions may be controlled such that the wavy form developed by the insert section proceeds toward the distal end or base end side.

According to the twenty-third through twenty-fifth embodiments, as described above, the insert section can be fluctuated in the wavy form by bending the plurality of bendable portions provided in the insert section in different directions from one another, which enables to repeatedly change the contact points of the insert section with the object to be examined, in addition to an advantage of reducing the contact resistance through the fluctuations. This results in an advantageous effect of improving operability of insertion while surely reducing the contact resistance of the insert section.

In the meanwhile, where an ultrasonic motor is employed to perform bending in an endoscope, the actuating torque and bending speed could not be controlled in the past, which disabled the bending operation and degraded operability when the load exceeding a predetermined level was applied.

Therefore, FIGS. 76 through 88 illustrate three examples of an endoscope using a vibration wave motor which can continue the bending operation even when the load exceeding a predetermined level is applied.

An endoscope apparatus of these examples comprises a vibration wave motor for bending a bendable portion provided in an insert section, and a motor driver for driving the vibration wave motor, the endoscope apparatus further comprising control means which changes drive frequency of the motor driver to control at least one of a speed and torque of the vibration wave motor.

Thus, in the endoscope apparatus of these examples, the drive frequency of the motor driver for driving the vibration wave motor is changed by the control means to control at least one of a drive speed and actuating torque of the vibration wave motor.

FIGS. 76 through 82 illustrate the first example.

Figure 76:
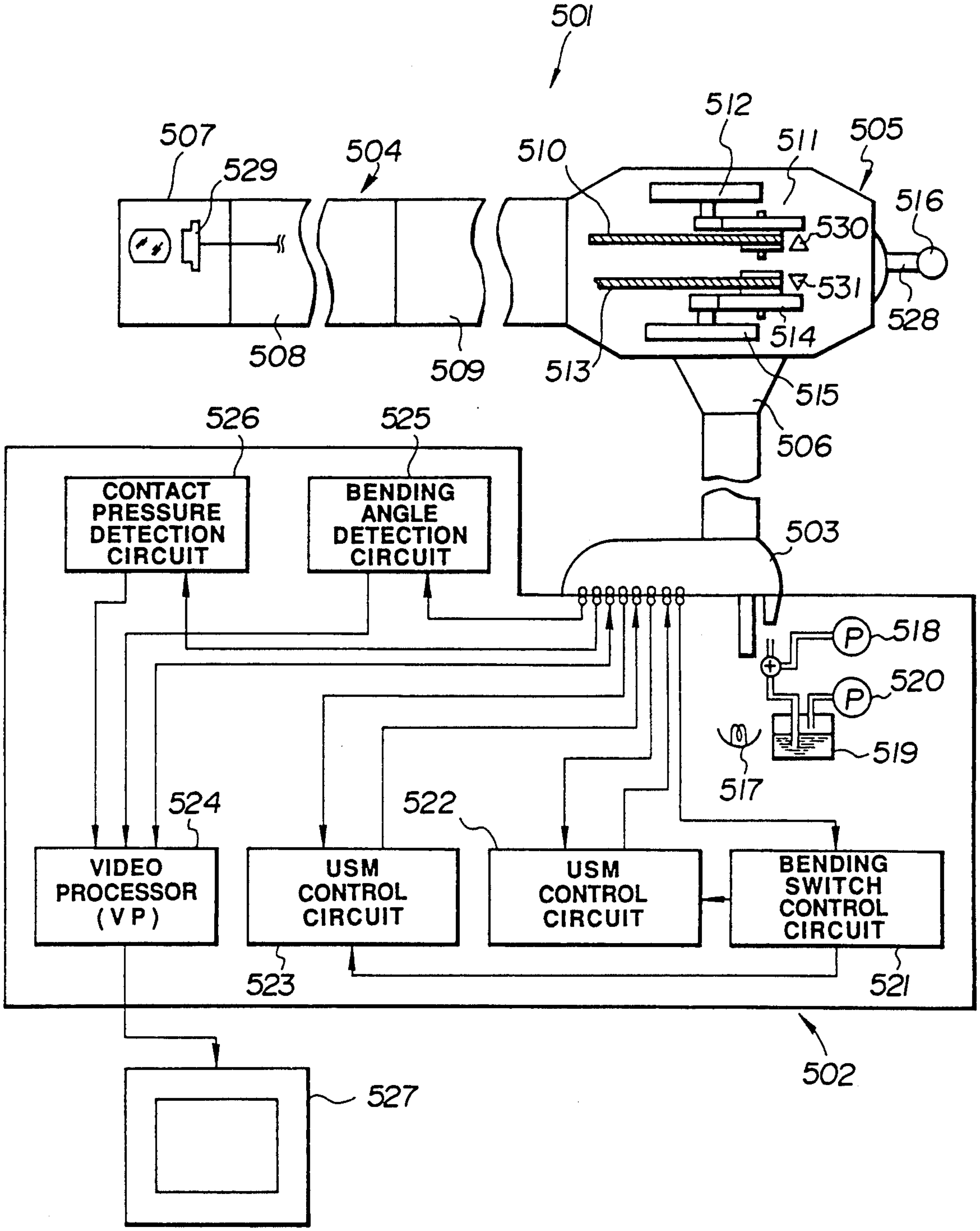

As shown in FIG. 76, a video scope 501 is freely connectable to a universal control apparatus (hereinafter referred to as UCA) 502 via a connector 503.

The video scope 501 comprises an elongate insert section 504 inserted into a living body and being flexible, for example, a larger-diameter grip section 505 continuously provided at the rear end of the insert section 504, a flexible universal cable 506 extended laterally from the rear end of the grip section 505, and the connector 503 provided at the end of the universal cable 506. The insert section 504 comprises a hard distal end component 507 on the frontmost side, and a bendable portion 508 continuously provided on the rear side of the distal end component 507 and capable of bending. Further, a flexible pipe portion 509 is continuously provided behind the bendable portion 508.

In the grip section 505, there are provided an ultrasonic motor (hereinafter referred to as USM) 512, as a vibration motor for the upward/downward (hereinafter referred to as UD) directions, to pull a UD bending wire 510 via a speed reduction gearing 511, and a USM 515 for the rightward/leftward (hereinafter referred to as RL) directions to pull an RL bending wire 513 via a speed reduction gearing 514, along with an air-feed/water-feed button, a suction button, $CO_2$ gas feed button, various switches for a forceps raising mechanism, as well as freezing, releasing and VTR-starting to control a video processor (these buttons and switches being not shown), and a bending switch 516 for controlling the bending direction.

A light guide fiber, an air-feed/water-feed tube, an appliance extending channel and so forth (all not shown) are also incorporated in the video scope 501.

The UCA 502 includes a lamp 517 for supplying a beam of illumination light to the video scope 501, an air-feed pump 518 for feeding air, a tank 519 for storing water to be fed, a water-feed pump 520 for feeding water, a bending switch control circuit 521 for controlling the bending switch 516, USM control circuits 522, 523 for controlling the USM's 512, 515, a video processor 524 for processing a video signal obtained from the video scope, a bending angle detection circuit 525 for detecting an bending angle of the bendable portion 508, and a contact pressure detection circuit 526 for detecting a contact pressure of the insert section with a wall of the body cavity. A monitor 527 is connected to the video processor 524 so that an object image is displayed on the monitor 527.

The bending switch 516 is of the joy stick type that the bending in the vertical (UD) and horizontal (RL) directions is controlled by tilting a lever 528, and changes in a resistance value (the less tilting angle, the smaller the resistance value; and the more tilting angle, the larger the resistance value) are also controlled dependent on the tilting of the lever 528. The bending switch 516 is arranged such that it can be operated in either of the UD and RL directions, but not operated to perform the downward (upward) and leftward (rightward) bending while the upward (downward) and rightward (leftward) bending is being performed. Further, the bending switch 516 can be operated to perform the bending that includes two directions simultaneously, i.e., in any combinations of upward and rightward directions, upward and leftward directions, leftward and rightward directions, and downward and leftward directions. In other words, it is possible to perform the bending obliquely or midway between the four directions.

Note that the bending switch 516 is so arranged as to return to a neutral position under an urging force produced by a spring or the like.

The bending angle detection circuit 525 receives information of the detected bending angle from rotation angle sensors 530, 531 each comprising a photo-reflector or the like, and supplies the information to the video processor 524. The contact pressure detection circuit 526 receives a contact pressure detection signal from a contact pressure sensor (not shown) disposed at an appropriate position of the insert section 504, and detects a contact pressure from the detection signal for supplying it to the video processor 524. The video processor 524 synthesizes the above bending angle information and contact pressure information with the video signal to display them on the monitor 527.

A control mechanism of the USM's 512, 515 will be described below.

Figure 77:
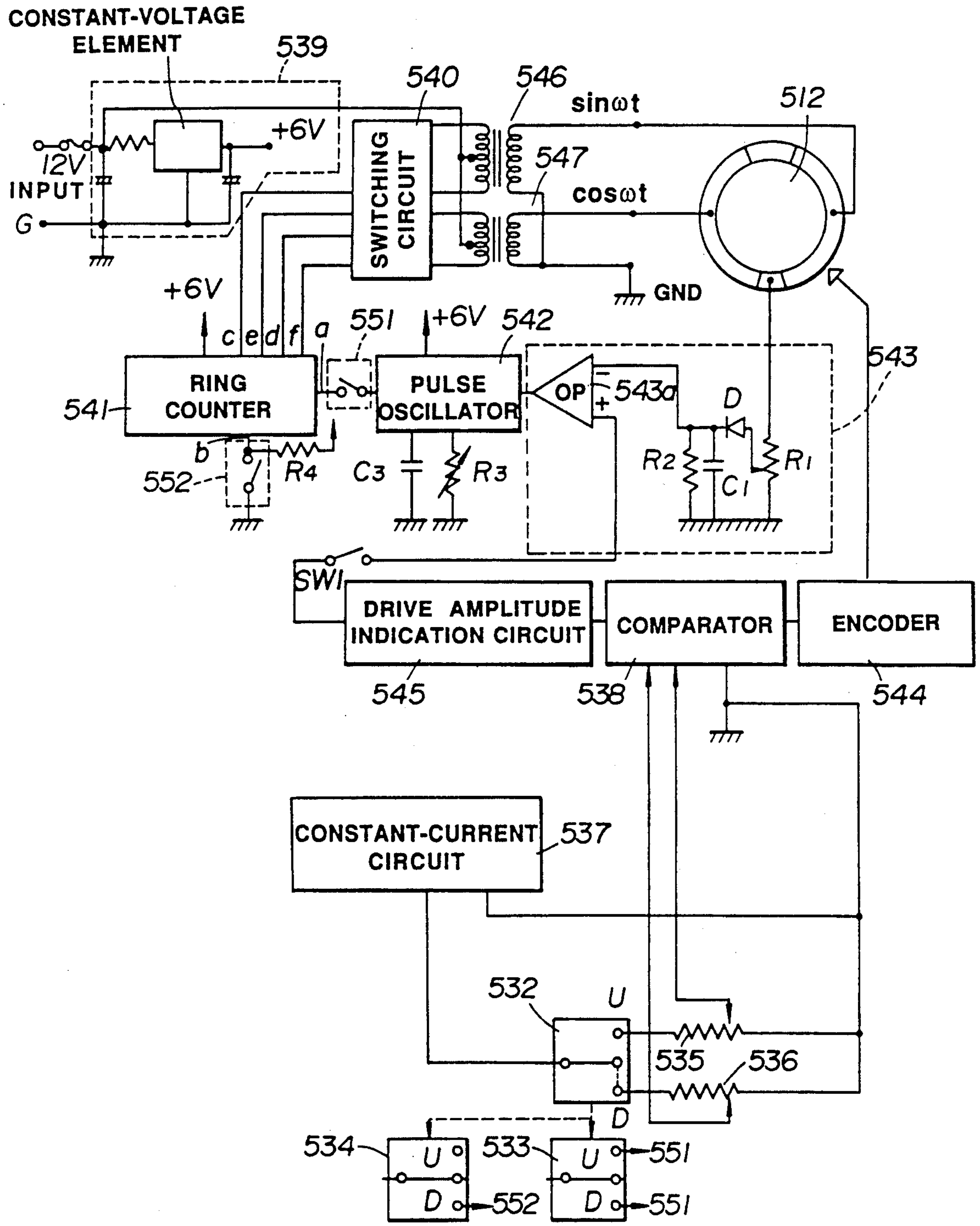

FIG. 77 is a block diagram relating to control of the USM 512 in the UD directions. Control in the RL directions is similar to that in the UD directions, and hence is not described here.

A control mechanism of the switch 516 in the UD directions can be expressed by an equivalent circuit comprising switches 532, 533, 534 and variable resistors 535, 536. Specifically, when the lever 528 of the bending switch 516 is tilted upwards, for example, the switches 532, 533, 534 are shifted upwards in cooperation, and a resistance value of the variable resistor 535 is changed dependent on the tilting of the lever 528.

The bending switch control circuit 521 includes a constant-current circuit 537 which supplies a constant current (e.g., 1 mA) to the switch 532 and the variable resistors 535, 536. Accordingly, respective voltage values dependent on the tilting of the lever 528 in the corresponding directions (i.e., the smaller tilting, the lower voltage values; and the larger tilting, the higher voltage values) are supplied to a comparator 538 from the variable resistors 535, 536.

The USM circuit 523 comprises a power supply circuit 539, a switching circuit 540, a ring counter 541, a pulse oscillator 542, a feedback circuit 643, an encoder 544, the comparator 538, a drive amplitude indication circuit 545 and others.

The switching circuit 540 is constituted by four sets of transistors (not shown) interconnected in the form of Darlington connection, for example. These four transistor sets correspond to four outputs of the ring counter 541. The respective transistor sets are push-pull connected to transformers 546, 547 for supplying a sine wave and a cosine wave of about 100 Vrms to the USM 512.

The ring counter 541 is of a 4-bit, right-and-left shift register of the serial-in/parallel-out type, and its shift direction is changed over upon turning on/off of a switch 552. Thus, when the switch 534 is turned to the downward direction in change-over of the UD directions, the switch 552 is turned on and an L-level signal is supplied to the ring counter 541.

Figure 80:
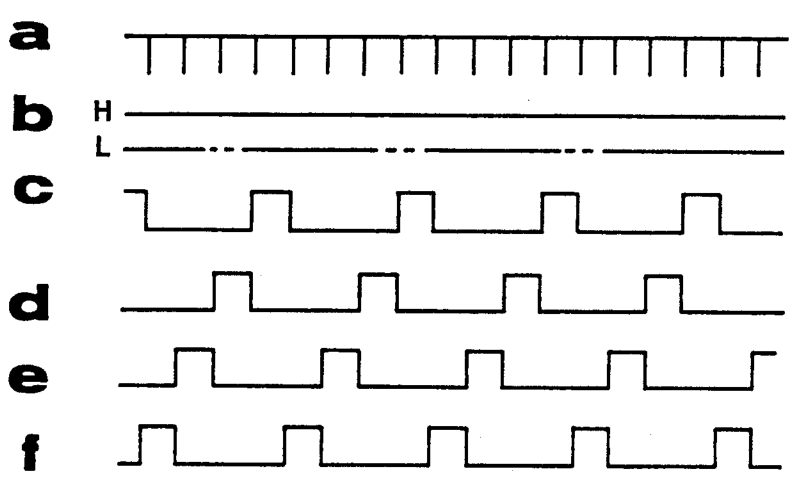
Figure 81:
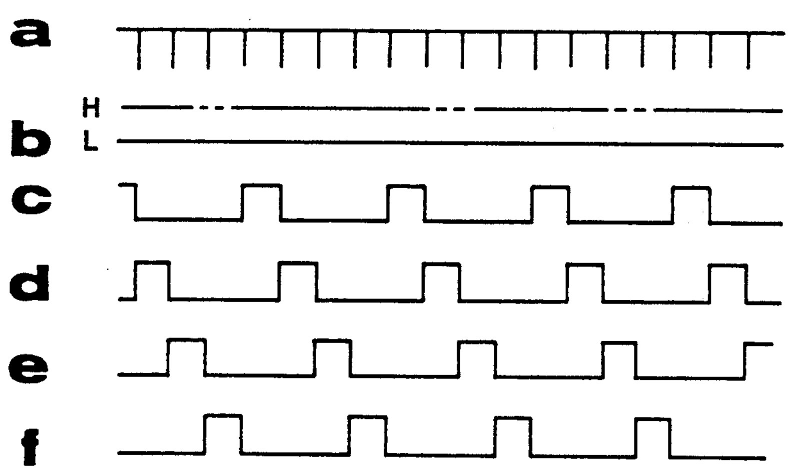

There will now be described the state of respective outputs c, d, e, f under a condition of the switch 552 turning on (upward direction) or off (downward direction) as shown at (b) in FIG. 80 or 81, when pulses shown at (a) in FIGS. 80 or 81 are applied from the pulse oscillator 542 via a switch 551.

Figure 82:
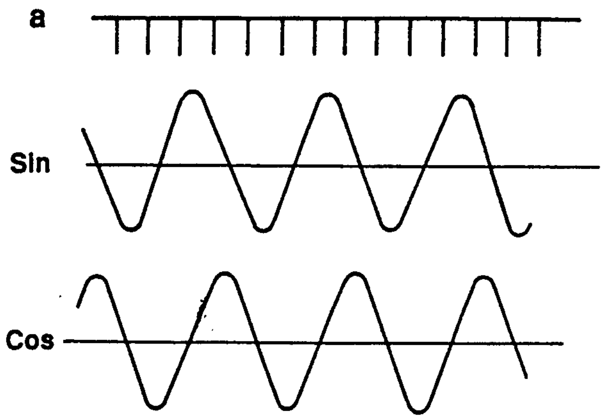

When the switch 551 is turned on and the switch 552 is turned off (i.e., oscillation occurs as shown in FIG. 81), the voltages (electric powers) shown in FIG. 82 are supplied to the USM 512 from the switching circuit 540 and the transformer coils 546, 547.

When oscillation occurs as shown in FIG. 80, the supplied sine wave (sin) and cosine wave (cos) are only reversed in phase relative to those in FIG. 82, and hence are not illustrated.

Figure 78:
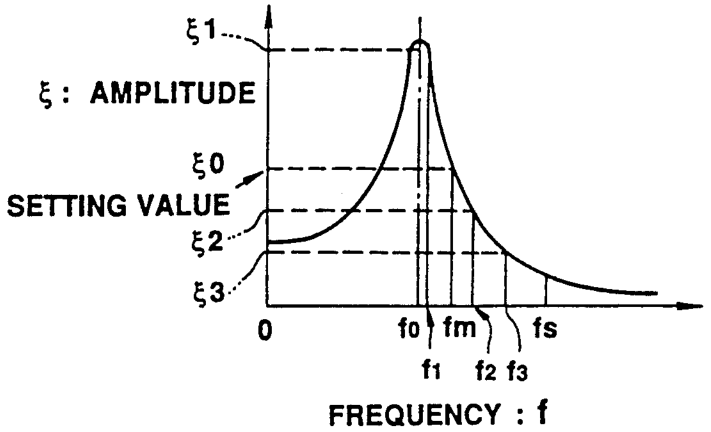

The pulse oscillator 542 oscillates as shown at (a) in FIGS. 80 through 82. The oscillation frequency is variable dependent on an output of the feedback circuit 543. The feedback circuit 543 comprises an operational amplifier 543*a*, a variable resistor $R_1$, a diode D, a capacitor $C_1$, and a resistor $R_2$. Further, as shown in FIG. 78, when the bending switch 516 is not operated, the pulse oscillator 542 oscillates at frequency four times the actuating frequency fs. When the bending switch 516 is operated, the oscillation frequency is quickly lowered to frequency four times the drive frequency fm of the USM 512 as described later. The drive frequency fm of the USM 512 is controlled by the feedback circuit 543. In other words, the feedback circuit 543 controls the drive frequency fm such that the feedback output of the USM 512 coincides with a setting value set by the drive amplitude indication circuit 545.

Incidentally, the pulse oscillator 542 is connected to a ground level via a variable resistor $R_3$ and a capacitor $C_3$ separately.

A revolution speed of the USM 512 is detected by the encoder 544 and input to the comparator 538. The encoder 544 has an F/V conversion function to output a higher voltage with the revolution speed increasing. The comparator 538 compares the voltage value output from the variable resistor 535, 536 of the bending switch 516 with the output value of the encoder 544, and issues the compared result to the indication circuit 545.

The indication circuit 545 outputs a reference voltage to the feedback circuit 543. More specifically, the indication circuit 545 changes the reference voltage such that the output of the encoder 544 coincides with the output voltage of the variable resistor 535, 536. Therefore, when the output voltage of the encoder 544 is lower than the output voltage value of the variable resistor 535, 536 dependent on an operating angle of the bending switch 516 (i.e., the revolution speed of the USM 512 is smaller), the indication circuit 545 changes the reference voltage supplied to the feedback circuit 543 such that the output voltage of the encoder 544 is increased (i.e., the revolution speed of the USM 512 is raised up). Accordingly, the setting value of amplitude for the USM 512 is increased (i.e., the oscillation frequency of the pulse oscillator 542 is decreased).

Note that the pulse oscillator 542 can change the frequency in a range larger than 4 fo and less than 4 fs. ($f1 \leqq f \leqq fs$)

Actual operation of the first example thus constituted will be described below.

When the bending switch 516 is tilted downwards, the associated switches 532, 533, 534 are set to the D side, the switches 551, 552 are turned on, and the variable resistor 536 outputs a predetermined voltage.

Then, the comparator 538 compares the voltage from the variable resistor 536 with the output of the encoder 544, and issues the compared result to the indication circuit 545. When the USM 512 is in a standstill state, the output of the encoder 544 is zero and hence the indication circuit 545 issues the reference voltage to the feedback circuit 543 for increasing the setting value of amplitude $\xi_0$. This causes the USM to start revolving. The setting value of amplitude $\xi_0$ is increased until the compared result in the comparator shows an coincidence. Therefore, as long as the variable resistor 536 continuously outputs a constant voltage value (e.g., $\xi_3$ calculated in terms of the setting value of amplitude of the USM 512), the feedback circuit 543 controls the drive frequency such that the setting value becomes equal to amplitude $\xi_3$.

While the foregoing control process is carried out under a non-load condition, the revolution speed is naturally lowered under a condition of the load being applied. In the case of the USM 512 having characteristics shown in FIG. 79, the USM 512 produces the actuating torque just as high as 2 kg.cm. Thus, if the load exceeding that level is applied, the bending operation would be disabled.

In this example, therefore, when the revolution speed of the USM 512 starts to lower upon application of the load, i.e., when the output of the encoder 544 starts to lower, the indication circuit 545 controls dependent on the output of the comparator 538 such that the amplitude of the USM 512 is increased (i.e., the oscillation frequency of the pulse oscillator 542 is lowered). Accordingly, in the case where the load of 2 kg.cm is applied, for example, the setting value is finally increased to $\xi_2$ ($f=f_2$), thereby obtaining the revolution speed corresponding to the setting value of the variable resistor 536 (even under a condition of the load being applied). When the load is eliminated, the setting value returns to $\xi_3$ ($f=f_3$). Further, when the much larger load is applied, the setting value is increased up to $\xi_1$ ($f=f_1$) at maximum corresponding to a value of the load applied.

Figure 79:
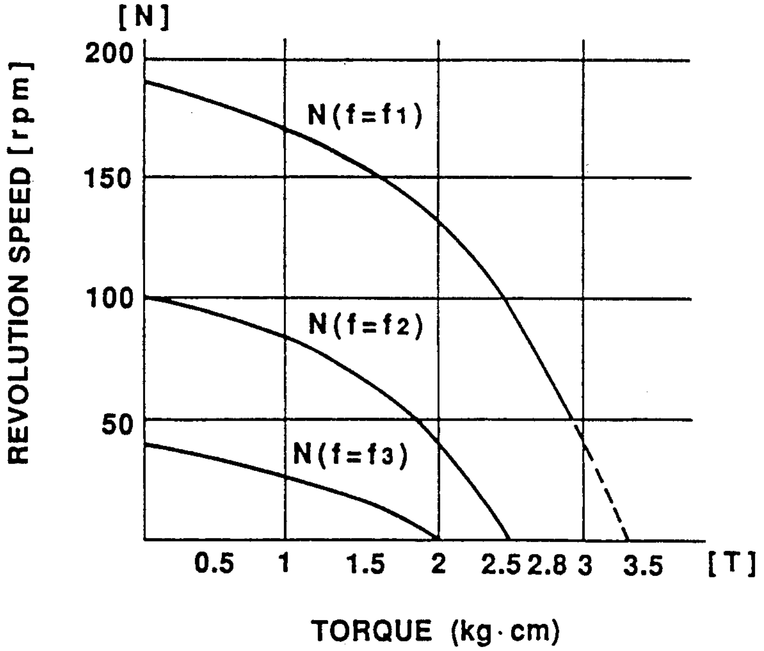

The maximum output voltage of the variable resistor 535, 536 corresponds to the revolution speed 100 rpm of the USM 512, for example. Thus, the highest revolution speed during the bending operation is 100 rpm. It is therefore possible to select any revolution speed in a range from 0 rpm to 100 rpm dependent on the operating angle of the bending switch 516. Furthermore, the maximum torque at any tilting angle of the bending switch 516, i.e., at any revolution speed of the USM 512, is 2.8 kg.cm as shown in FIG. 79 (on an assumption the USM 512 has revolution speed-torque curves as shown in FIG. 79).

The above control process when the bending switch 516 is tilted downwards is equally applied to the case when it is tilted upwards, rightwards or leftwards, and hence the explanation of the latter cases is omitted here. When the bending switch 516 is tilted midway between the upward and rightward directions, the USM's 512, 515 operate similarly to the USM 512 in the foregoing case in parallel. When the bending switch 516 is turned off, the USM's 512, 515 are stopped and their state at that time is maintained by the holding torque.

With this example, as described above, the ultrasonic motor can be controlled to produce the its own maximum actuating torque regardless of whether the revolution speed is fast or slow. In endoscopes, since too earlier bending is dangerous, it is risky to set the setting value to $\xi_1$ ($f=f_1$) at all times for ensuring the large actuating torque. On the other hand, if the amplitude $\xi_0$ is set to provide the satisfactory revolution speed, this leads to an disadvantage that the actuating torque may be too small in some cases.

Not that the USM's 512, 515 of this embodiment may be modified to have the structure capable of generating stationary wave, thereby reducing a degree of the holding torque, so that the bending wires 510, 513 can freely be advanced or retreated by external resistors.

Also, the revolution speed of the motors may be set in a range of 0–50 rpm or 0–180 rpm.

The rotation angle sensors 530, 531 and the encoders of the USM's 512, 515 may be integrated respectively to be used for double purposes.

Although the USM's 512, 515 are provided on the grip section in this example, the installed position is not limited to the grip section and they may be provided at any desired position in the endoscope.

In addition, the outputs from the bending angle detection circuit 525 and the contact pressure detection circuit 526 may be applied to the USM control circuits 522, 523, respectively, for controlling the USM's 512, 515 based on the status of bending angle and contact pressure.

Figure 83A:
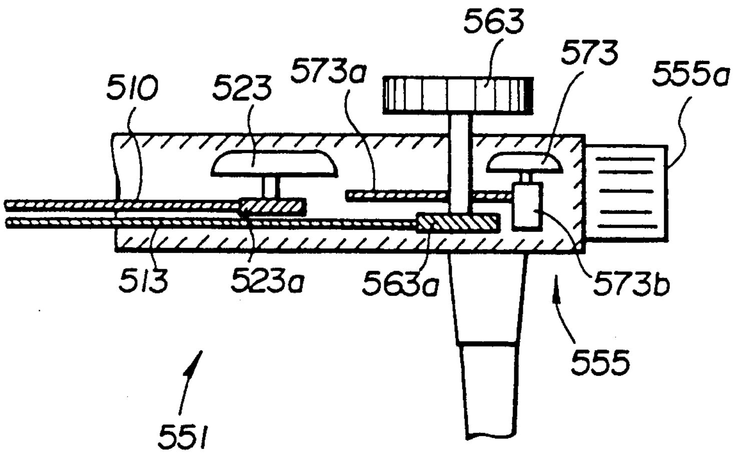
FIG. 83(A) is an explanatory view showing the constitution of an endoscope's operating section.
Figure 83B:
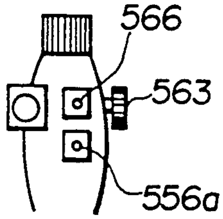
FIG. 83(B) is a front view of the endoscope's operating section.
Figure 84:
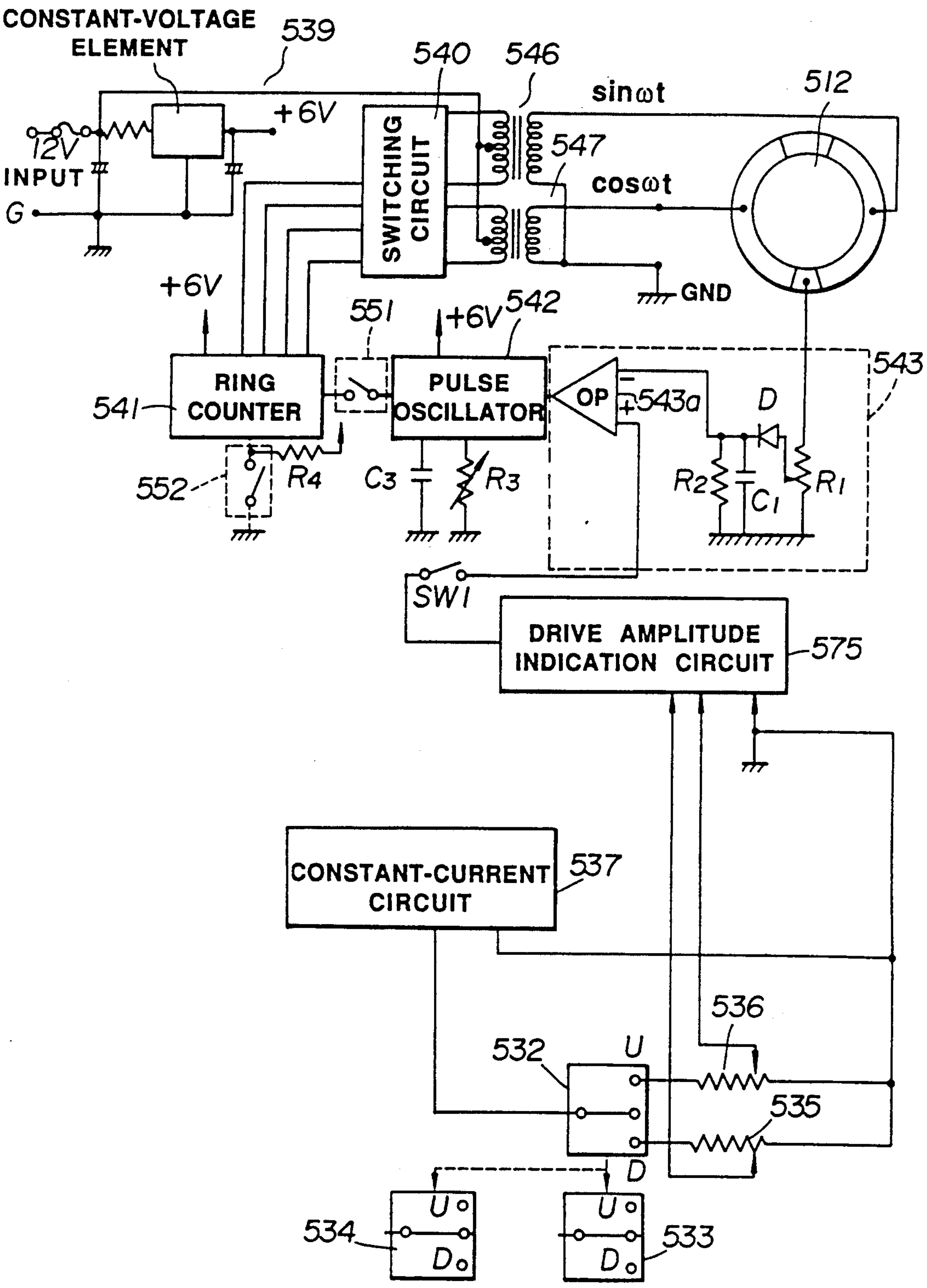
Figure 85:
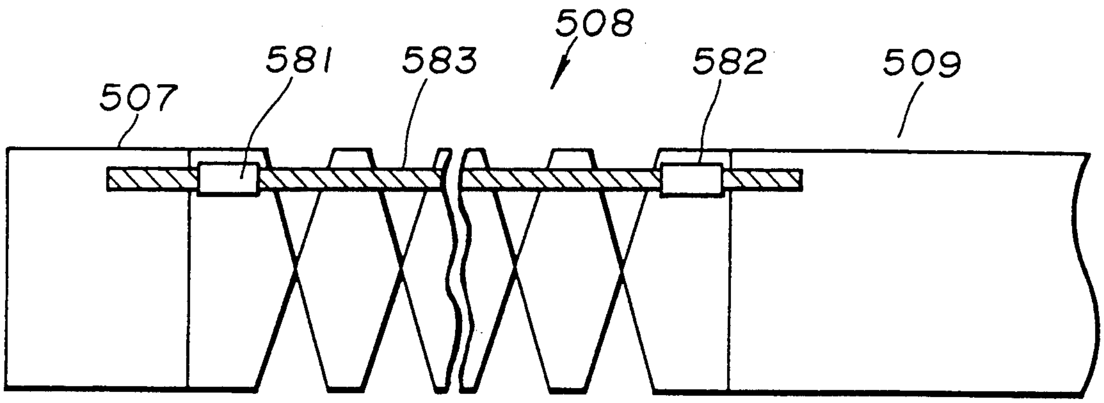

FIGS. 83 and 84 illustrate the second example.

In an endoscope apparatus of this second example, as shown in FIGS. 83(A) and 83(B), a UD bending wire 510, an RL bending wire 513 and a forceps erecting wire 573*a* are housed in a grip section 555 of a fiber scope 551. These wires 510, 513 and 573*a* are entrained about pulleys 523*a*, 563*a* and 573*b* of a USM 523, a manual operation knob 563 and a USM 573, respectively. One end of the wire 573*a* is fixed to the pulley 573*b* by brazing or the like so that as the USM 573 revolves, the wire 573*a* is wound up along a spiral groove in the circumference of the pulley 573*b*.

A bending switch 566 and a forceps erecting switch 566*a* are provided on an operating section 555.

Unlike the above first example, a USM control circuit 523 includes neither the encoder 544 nor the comparator 538. A drive amplitude indication circuit 575 is arranged to receive a voltage from a variable resistor 535, 536, and to set the amplitude $\xi_0$ shown in FIG. 78 dependent on the received voltage value. In other words, when the voltage value from the variable resistor 535, 536 is maximum, the setting value is given by $\xi_1$ ($f=f_1$). When the voltage value is at a ground level, it is given by $f=fs$.

The constitution of the remaining parts of this second example is similar to that in the above first example. The same components as those in the first example are explained by designating them by the same reference numerals.

In this second example, the bendable portion is operated as follows. The bendable portion is bent in the RL directions by manually operating the bending knob 563 so as to push and pull the bending wire 513. Further, for the bending in the UD directions, the bending switch 566 of the two-direction joy stick type is tilted. Then, the reference voltage corresponding to the setting value of amplitude $\xi_0$ dependent on the tilting angle is applied to the feedback circuit 543 to control the drive frequency such that it coincides with the value of $\xi_0$ at that time.

Accordingly, when no load is applied to the motor, the USM 512 is revolved at a speed dependent on the tilting angle of the bending switch 566. When the load is applied to the motor, the bending speed is lowered correspondingly. In this case, therefore, the tilting angle of the bending switch 566 is increased to raise the revolution speed.

The forceps erecting switch 566*a* operates substantially in a like manner to the bending switch 566, and hence its operation is not explained here.

Other operation and advantageous effect of the second example are similar to those in the first example.

FIGS. 85 through 88 illustrate the third example.

In this example, as shown in these drawings, linear type ultrasonic motors (hereinafter referred to as LUM) 581, 582 are disposed in a bendable portion 508 instead of the USM's 512, 515 disposed in the grip section 505 in the above first example.

Figure 86:
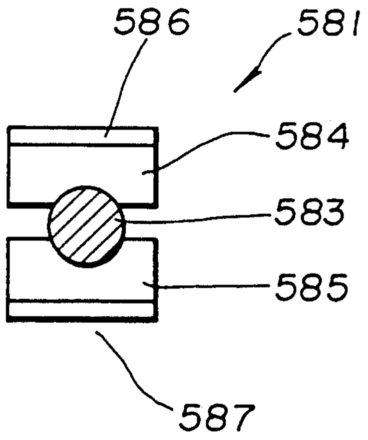

The LUM's 581, 582 are constructed as shown in FIG. 86 (which illustrates only the LUM 581 as a representative). A bending wire 583 is firmly sandwiched by a pair of linear type stators 584, 585. Ceramic plates 586, 587 are bonded to the stators 584, 585, respectively, to produce a progressive wave of plane symmetry on the stators 584, 585 for pulling the wire 583 as a rotor.

An LUM driver (not shown) for driving the LUM 581 is basically similar to the USM control circuit in the second example, but provided in two sets. This example is different from the second example in that the progress wave is produced in the opposite directions by the two sets of drivers so as to pull and push the wire 583.

Thus, by pushing and pulling the single wire 583, the bendable portion 508 can be bent in the UD directions. Further, by adding another wire, it is possible to bend the bendable portion in the RL directions as well.

Actual operation of this example will be explained below.

First, when a bending switch of the two-direction joy stick type (not shown) is tilted upwards, the control process substantially similar to that in the above second example is performed in a non-load condition, whereby the LUM's 581, 582 produce progressive waves in the directions to pull each other at a bending speed dependent on the tilting angle of the bending switch. Accordingly, the bendable portion 508 is bent at a bending speed dependent on the tilting angle of the bending switch.

Now, when the load is applied, the bending speed is lowered correspondingly. In this case, however, the bending speed can be raised up by increasing the tilting angle of the bending switch.

When bending the bendable portion 508 downwards, the LUM's 581, 582 are caused to produce progressive waves in the directions to push away from each other through the control process similar to that as mentioned above.

Figure 87A:
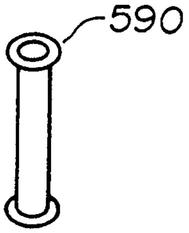
FIG. 87(A) is a perspective view showing an acceleration sensor.
Figure 87B:
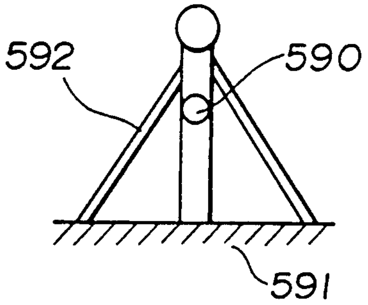
FIG. 87(B) is an explanatory view showing an arrangement of the acceleration sensor.

An acceleration sensor 590 may be disposed at the distal end of the joy stick, as shown in FIG. 87(A), to change the bending speed dependent on changes in an operating speed of the joy stick. Alternatively, as shown in FIG. 87(B), the acceleration sensor 590 may be disposed inside a casing 591 or a watertight cover 592 to protect the acceleration sensor 590 from being damaged such as when subjected to washing.

Figure 88:
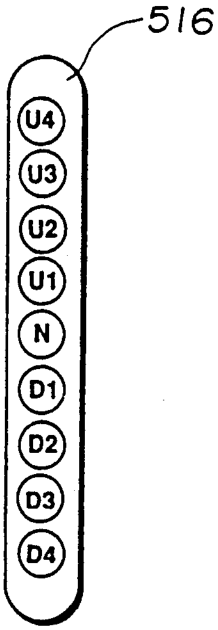

Further, as shown in FIG. 88, the bending switch 516 may be arranged to include a plurality of switches on each side of a neutral N (standstill) position in the UD directions, so that the bending speed is changed dependent on which one of the switches in depressed. For example, the bending speed is set with the relationship of $U1<U2<U3<U4$ and $D1<D2<D3<D4$.

Although the plurality of switches are provided only in the UD directions in FIG. 88, those switches may be in the four directions inclusive of the RL directions as well.

The scope can be used for any purpose in both the medial and industrial fields, and can be applied to fiber scopes as well as electronic scopes.

The bending switch is not limited to the joy stick type, and may be of any other type such as slide type or rotary volume type.

It is also apparent that the foregoing first through third examples can be applied to an endoscope capable of bending in the z-direction.

According to the first through third examples, as mentioned above, since the control means is provided which changes drive frequency of the motor driver for controlling the vibration wave motor, thereby to control at least one of a drive speed and torque of the vibration wave motor, the bending operation can be performed even when the load is applied, and hence operability of the endoscope apparatus is improved.

Meanwhile, in the case of providing a bending motor in the operating section of an endoscope, the axis of a drum to which an angle wire is coupled is generally arranged in orthogonal relation to the axis of the operating section. With this arrangement, the axis of the motor for rotating the drum is also arranged perpendicularly to the axis of the operating section. Therefore, the tail end of the motor is likely to project from an outer wall of the operating section, and the size of the operating section tends to increase. The increased size of the operating section may possibly impair operability of the endoscope apparatus.

In view of the above, FIGS. 89 through 96 illustrate four examples of an endoscope apparatus which can make small the size of the operating section and can achieve a further improvement in operability.

The endoscope apparatus of these examples resides in that an operating section is provided at the base end of an insert section having a bendable portion, a movable member is disposed in the operating section, a pulling member for bending the bendable portion is attached to the movable member, and a motor for driving the movable member is provided in the operating section, wherein the motor is disposed such that the axis of the motor is substantially parallel to the axis of the operating section, and the movable member attached to the pulling member is moved by the motor disposed substantially parallel to the axis of the operating section for bending the bendable portion.

FIGS. 89 through 92 illustrate the first example.

Figure 92:
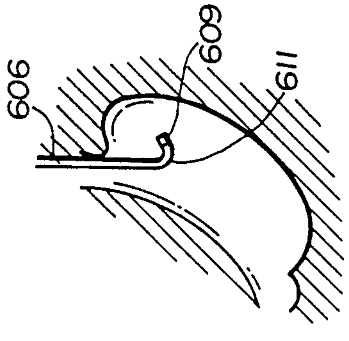

To begin with, an endoscope apparatus of this example will be outlined with reference to FIG. 92. In the drawing, designated by reference numeral 601 is an endoscope and 602 is a light source unit. In the light source unit 602, a lamp 603 is disposed along with a reflecting plate 603*a*.

The endoscope 601 comprises an elongate and flexible insert section 606 which can be inserted into the body cavity or the like, and a tubular operating section 607 of relatively large diameter which is provided at the based end of the insert section 606 and can be gripped by the hand, with a universal cord 608 extended from one lateral side of the operating section 607.

A connector 608*a* is provided at the end of the universal cord 608, so that the universal cord 608 is connected to the light source unit 602 via the connector 608*a*. In the state that the connector 608*a* is connected to the light source unit 602, a motor control unit 604 and a video signal processing unit 605 both disposed in the light source unit 602 are automatically connected to the endoscope 601 via the connector 608*a*, and an incident end 608*b* of illumination light provided in the connector 608*a* is positioned opposite to the lamp 603. A beam of illumination light emitted from the lamp 603 is led to the distal end of the insert section 606 through the universal cord 608.

At the distal end of the insert section 606, there is provided a distal end component 609 which has an observation through-hole and an illumination through-hole formed therein. The illumination light is irradiated via the illumination through-hole to a location to be observed, such as the body cavity.

A video signal from the thus-irradiated location to be observed is transmitted to the video signal processing unit 605 in the light source unit 602 via the universal cord 608. The video signal is then processed by the video signal processing unit 605 and output to a monitor 605*a* so that an image of the location to be observed can visually be observed on the screen of the monitor 605*a*.

Further, midway the insert section 606 at a position nearer to the operating section 607 than the distal end component 609, there is provided a bendable portion 611 comprising a plurality of articulate pieces which can mutually pivot, for example. By operating the bendable portion 611 to bend, the distal end component 609 can be directed to the location to be observed.

Among the plurality of articulate pieces which constitute the bendable portion 611, the articulate piece nearest to the distal end component 609 is fixed to the distal end component 609. One ends of angle wires 612 are fixed to upper, lower, right and left points of that articulate piece in the inner side thereof, respectively. The other ends of the angle wires 612 are extended into the operating section 607 through the insert section 606.

Figure 89:
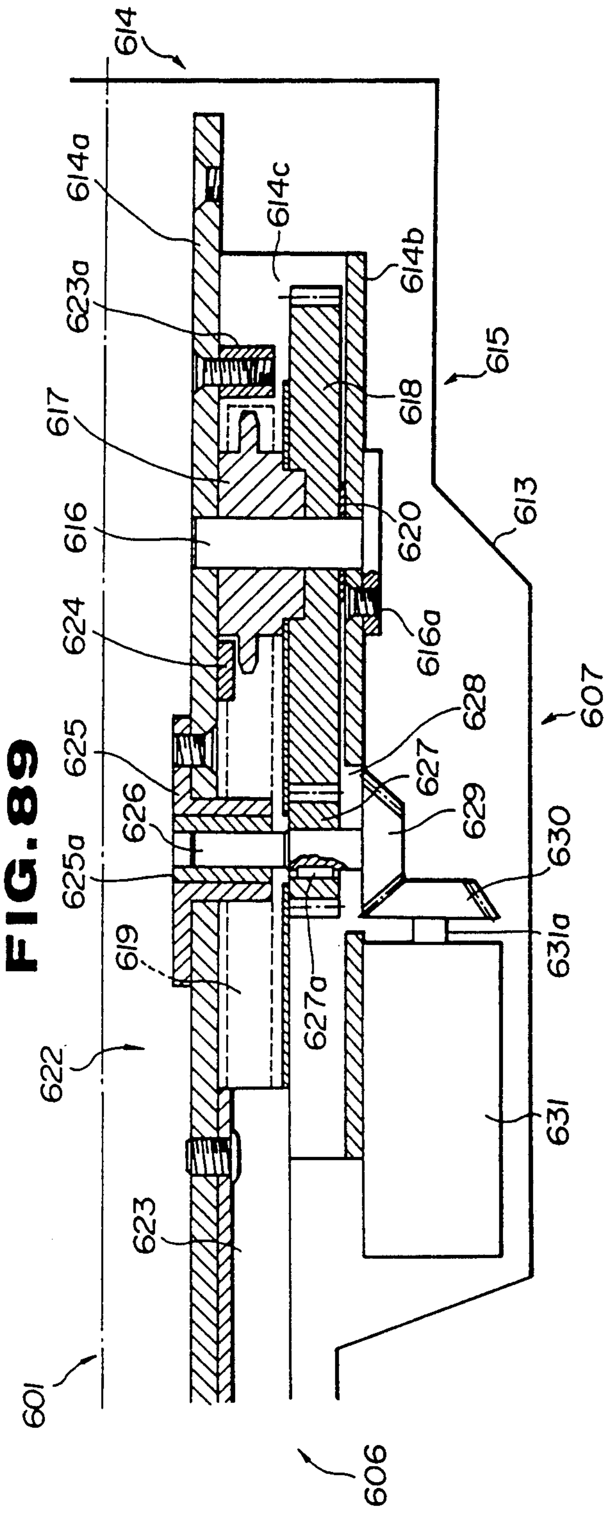
FIGS. 89 through 96 are concerned with four examples of an endoscope apparatus in which the axis of a motor and the axis of an operating section are arranged parallel to each other.

In a case 613 defining the operating section 607, as shown in FIG. 89, there is fixed a frame assembly 614 which comprises a main frame 614*a* disposed substantially parallel to the axis of the operating section 607, and a sub-frame 614*b* secured in parallel to the main frame 614*a* with a certain spacing 614*c* left therebetween.

The frame assembly 614 is provided in pair in transversely symmetrical relation relative to the longitudinal (axial) direction of the operating section 607. A bending actuator 615 for bending the bendable portion 611 up and down (vertically) is mounted on one frame 614, while another bending actuator 615 for bending the bendable portion 611 to the right and left (horizontally) is mounted on the other frame 614 (not shown). Because the pair of bending actuators 615 have the same constitution, the bending actuator 615 for vertically bending the bendable portion 611 will be explained and explanation of the other bending actuator is omitted in this example.

Figure 90:
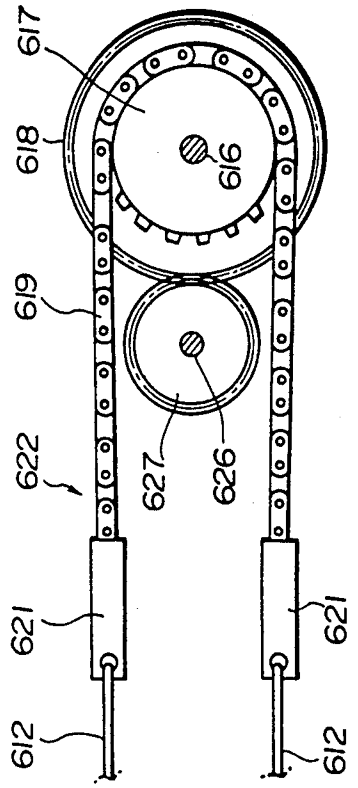

A shaft 616 is inserted through the main frame 614*a* and the sub-frame 614*b* perpendicularly to the axis of the operating section 607 and fixed in place by screws 616*a*. A sprocket 617 as one example of the movable member and a driven gear 618 are rotatably supported over that portion of the shaft 616 which is exposed to the spacing 614*c* between the frames. The sprocket 617 and the driven gear 618 are integrated together by press-fitting or the like, for example. A chain 619 is entrained about the sprocket 617. Further, a plastic member 620 formed of engineered plastic or the like is interposed between the sub-frame 614*b* positioned on the lower side when the endoscope 601 is operated and the driven gear 618 positioned on the side near the sub-frame 614*b*, allowing the driven gear 618 and the sprocket 617 to rotate smoothly. As shown in FIG. 90, both ends of the chain 619 are extended toward the insert section, and the extended ends of the chain 619 are fixed to the one ends of the angle wires 612 via link members 621, respectively.

Therefore, when the sprocket 617 is rotated via the driven gear 618, the angle wires 612 are each tensioned or loosened, whereby the bendable portion 611 is bent to swing the distal end component 609 in the vertical direction, for example, as shown in FIG. 92. Note that the angle wires 612, the chain 619 and the link member 621 jointly constitute the pulling member 622.

The pulling member 622 is surrounded at both lateral sides and the side opposite to the main frame 614*a* by a cover member 623 fixed to the main frame 614*a*. Also, another cover member 623*a* surrounding the sprocket 617 in the form of a semicircle is fixed on the side of the sprocket 617 opposite to the insert section 606. These cover members 623, 623*a* serve to keep the pulling member 622 from contacting other components disposed in the operating section 607 when the pulling member 622 is operated. At a location where the chain 619 engages with and disengages from the sprocket 617, a guide member 624 is disposed to smooth engagement and disengagement of the chain 619 with and from the sprocket 617.

On the other hand, a bearing box 625 is fixed to the main frame 614*a* at a position nearer to the insert section 606 than the position of the sprocket 617. Another shaft 626 parallel to the aforesaid shaft 616 supporting the sprocket 617 is rotatably mounted to the bearing box 625 via a bearing 626*a*.

A drive gear 627 is lockedly fitted via a key 627*a* over the shaft 626 at a location where the shaft 626 is projected toward the sub-frame 614*b* from its portion sandwiched by two runs of the chain 619, the drive gear 627 being held in mesh with the driven gear 618. The diameter of the drive gear 627 is set smaller than that of the driven gear 618 so that rotation of the drive gear 627 is transmitted to the driven gear 618 while being reduced in speed.

One end of the shaft 626 is extended through a hole 628 bored in the sub-frame 614*b* and projected to the side thereof opposite to the main frame 614*a*. A driven bevel gear 629 is formed at the projected end of the shaft 626. A drive bevel gear 630 meshing with the driven bevel gear 629 is provided on an output shaft 631*a* of a motor 631 which is fixed by screws (not shown) or the like to the surface of the sub-frame 614*b* opposite to the main frame 614*a*. Thus, the sprocket 617 is rotated by the motor 631 via a train of the aforesaid gears.

The motor 631 is constituted as a DC motor and fixed with its axis lying parallel to the axis of the operating section 607. This avoids the arrangement of protruding a portion of the motor 631 opposite to the output shaft 631*a* from the case 613 defining the operating section 607, and eliminates the need of bending the corresponding portion of the case outwards. Therefore, the operating section 607 is prevented from increasing in diameter.

Figure 91:
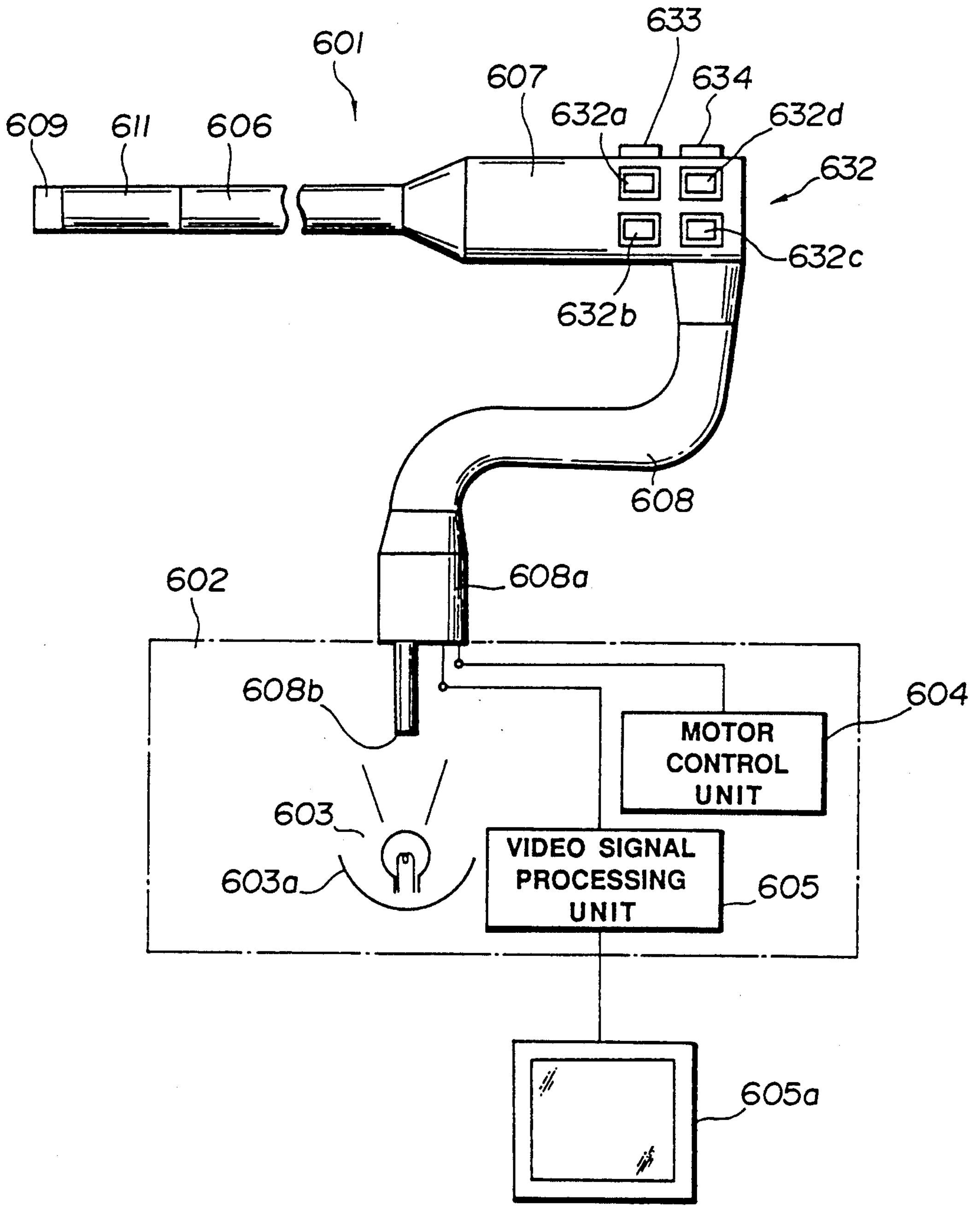

Control buttons 632 for actuating the motor 631 are disposed on the outer surface of the operating section 607. More specifically, as shown in FIG. 91, the control button 632 is provided four in number, for example, on the base end side of the operating section 607, and include an upwards bending button 632*a*, a downwards bending button 632*b*, a rightwards bending button 632*c* and a leftwards bending button 632*d*.

These control buttons 632 are connected to the motor 631 and another motor (not shown) disposed parallel to the motor 631 via the motor control unit 604 in the light source unit 602. By operating any of the control buttons 632 as required, the motor 631 can be driven via the motor control unit 604.

Near the control buttons 632, there are also disposed an air-feed/water-feed button 633, a suction button 534, etc. This allows the operator to operate those buttons without the need of gripping the operating section 632 again for each desired button operation.

Operation of the first example thus constituted will be described below.

When the universal cord 608 is connected to the light source unit 602 via the connector 608*a*, the illumination light incident end 608*b* in the connector 608*a* is positioned opposite to the lamp 603 in the light source unit 602, and the motor control unit 604 and the video signal processing unit 605 are connected to the endoscope 601.

Then, when the insert section 606 of the endoscope 601 is inserted into the body cavity or the like and a power supply of the light source unit 602 is turned on, the illumination light emitted from the lamp 603 and reflected by the reflecting plate 603 is led to the insert section 606 through the incident end 608*b* and irradiated to the location to be observed, such as the body cavity, from the illumination through-hole formed in the distal end component 609.

A video signal from the location to be observed is taken into the endoscope 601 via the observation through-hole and applied to the video signal processing unit 605. The video signal is then processed by the video signal processing unit 605 and output to the monitor 605*a* so that an image of the location to be observed can visually be observed on the screen of the monitor 605*a*.

In the case where the location to be observed is shifted laterally away from the axis of the insert section 606, the distal end component 609 is directed to the location to be observed by operating one of control buttons 632 to bend the bendable portion 611.

More specifically, when the downwards bending button 632*b*, for example, among the control buttons 632 is turned on, an electric current is supplied to the motor 631 of a DC motor via the motor control unit 604 in the light source unit 602, whereupon the output shaft 631*a* of the motor 631 starts rotating in a predetermined direction.

The drive bevel gear 630 is also rotated together with the output shaft 631*a*, and the rotation of the drive bevel gear 630 is transmitted to the shaft 626 via the driven bevel gear 629 for rotating the drive gear 627 together with the shaft 626. Then, the drive gear 627 rotates the driven gear 618, followed by rotating the sprocket 617 integral with the driven gear 618. Upon the rotation of the sprocket 617, the chain 619 is moved in the axial direction of the insert section 607, so that the angle wires 612 fixed to the chain 619 via the link members 621 are each tensioned or loosened.

Because the ends of the angle wires 612 opposite to the link members 621 are fixed to that one of the plural articulate pieces constituting the bendable portion 611 which is nearest to the distal end component 609, the bendable portion 611 is bent downwards, for example, dependent on a rotation angle of the sprocket 617 as shown in FIG. 92, upon the fixed points to that articulate piece being tensioned or loosened. As a result, the distal end component 609 is directed to the location to be observed, allowing that location to be visually be observed on the monitor 605*a*.

By releasing the downwards bending button 632*b* from its operated state at the time the distal end component 609 is just directed to the location to be observed, the motor 632 is stopped in operation and the bendable portion 611 comes to rest while keeping the bent state. This enables to continue observation of the location to be observed under such a condition.

The foregoing operation is equally applied to the case where the bendable portion is bent to the right and left via another bending actuator (not shown).

When it is required to make the bendable portion 611 straight from the above condition, the bendable portion 611 can easily be returned to the straight form by operating the upwards bending button 632*a*. In this connection, the state of the bendable portion 611 can be noticed with ease by so arranging as to detect the rotating position of the sprocket 617 and light up an indicator lamp disposed on the operating section 607 or the like when the rotating position of the sprocket 617 has returned to its initial state.

Although this example has been explained as using a DC motor as the motor 631, the motor 631 is not necessarily limited to a DC motor and may be of any other type such as an AC motor, pulse motor or ultrasonic motor.

Further, in this example, the pulling member 622 is constituted by an assembly comprising the angle wires 612 and the chain 619, and the chain 619 is engaged with the sprocket 617 as one example of the movable member. But, the pulling member 622 and the movable member are not limited to the illustrated ones. For example, it is possible to constitute the movable member in the form of a drum, and to wind a pulling member constituted by the wires 612 alone about the drum. Alternatively, it is also possible that the movable member is constituted as a rack member capable of moving in the axial direction of the operating section 607, and the rack member is moved by a feed screw lying to extend in the axial direction of the operating section 607.

In addition, since the guide member 624 is disposed at a location where the chain 619 engages with and disengages from the sprocket 617 in this example, engagement and disengagement of the chain 619 with and from the sprocket 617 is facilitated, which results in an advantageous effect of smoothing the bending operation of the bendable portion 611 correspondingly.

Figure 93:
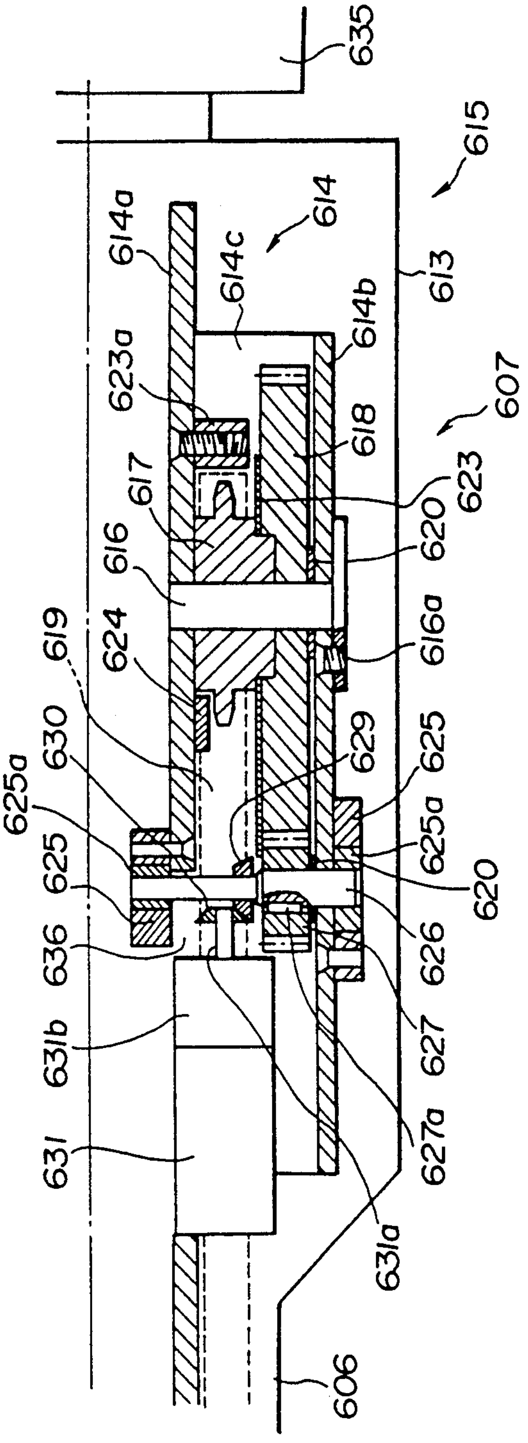
Figure 94:
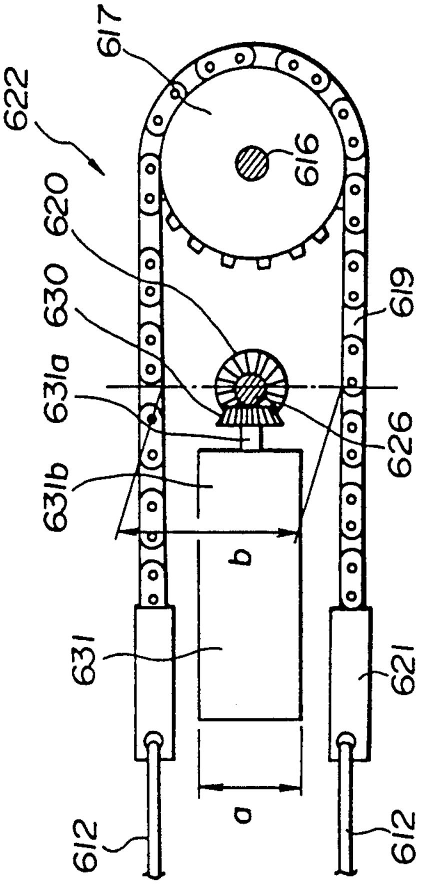

FIGS. 93 and 94 illustrate the second example. Note that the same components as those and components operating similarly to those explained in the above first example are designated by the same reference numerals, and are not described here.

In this second example, a bending actuator is applied to a fiber scope having an eyepiece portion 635, and a motor 631 is disposed in a space defined between two runs of the chain 619.

More specifically, as shown in FIG. 93, an opening 636 is formed in a main frame 614*a* at a position nearer to an insert section 606 than the position of the sprocket 617. The motor 631 is fixed in place with its part fitted into the opening 636. The motor 631 is constituted as a geared motor having a gear head 631*b* at the motor head and capable of rotating an output shaft 631*a* with increased torque.

As shown in FIG. 94, the motor 631 has its diameter a selected to be smaller than the diameter of the sprocket 617, i.e., the distance b between both ends or two runs of the chain 619 entrained about the sprocket 617. A certain gap is left between the lateral sides of the motor 630 and a pulling member 622 including the chain 619 and others so as to keep the pulling member 622 from contacting the motor 630 when the pulling member 622 is operated.

Bearing boxes 625 are secured to the main frame 614*a* and a sub-frame 614*b*, respectively, and a shaft 626 is rotatably mounted in each bearing box 625 via a bearing 625*a*. A driven bevel gear 629 is fixed by press-fitting or the like, for example, to the shaft 626 on its nearly central portion located in a spacing 614*c* between the main frame 614*a* and the sub-frame 614*b*. The driven bevel gear 629 is held in mesh with a drive bevel gear provided on the output shaft 631*a* of the motor 631.

A drive gear 627 is lockedly fitted via a key 627*a* or the like, for example, over the shaft 626 at a location between the driven bevel gear 629 and the sub-frame 614*b*. Further, a plastic member 620 formed of engineered plastic or the like is interposed between the drive gear 627 and the sub-frame 614*b*, allowing the drive gear 627 to rotate smoothly.

The drive gear 627 is held in mesh with a driven gear 618 rotatably disposed in the spacing 614*c*, and a sprocket 617 engaging the chain 619 is integrated with the drive gear 618 by press-fitting or the like.

With such constitution, when the output shaft 631*a* of the motor 631 is rotated via the gear head 630*b* thereof, this rotation is transmitted to the sprocket 617 via the drive gear 627, the driven gear 618 and others. Upon the sprocket 617 being rotated, wires 612 of the pulling member 622 are each tensioned or loosened so that the bendable portion 611 is bent.

As described above, since the motor 631 is not only disposed in the spacing 614*c* between the main frame 614*a* and the sub-frame 614*b*, but also fitted in its part into the opening 636 formed in the main frame 614*a*, this example has an advantageous effect of enabling to reduce size of the operating section 607.

Further, since the motor 631 is constituted as a geared motor, a larger output can be produced with a lower voltage supplied to the motor 631. This permits to reduce size of the motor 631 and make the operating section 607 more compact correspondingly.

Figure 95:
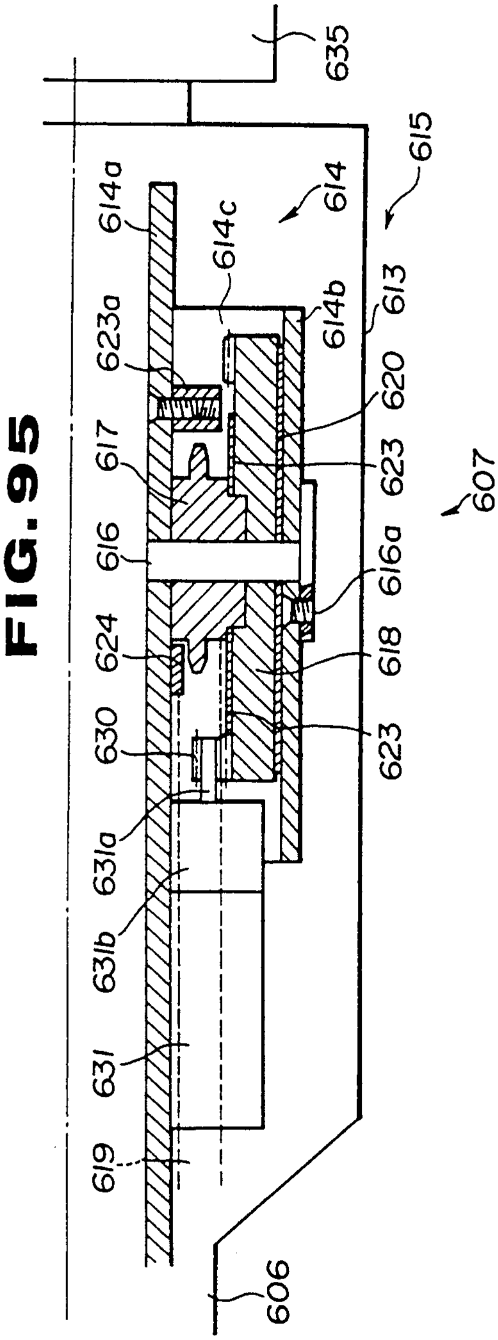

FIG. 95 illustrates the third example.

In this example, the driven gear integrated with a sprocket 617 is constituted as a crown gear 618, while a motor 631 constituted as a geared motor is fixed to the surface of a main frame 614*a* opposite to a sub-frame 614*b*. A pinion 630 meshing with the crown gear 618 is fixedly provided on an output shaft 631*a* of the motor 631 by press-fitting or the like, for example.

When the output shaft 631*a* of the motor 631 is rotated, the pinion 630 on the output shaft 631*a* causes the crown gear 618 to rotate. The sprocket 617 integrated with the crown gear 618 is thereby rotated so that wires of a pulling member 622 are each tensioned or loosened to bend the bendable portion 611.

With this example thus constituted, such members as a driven bevel gear and a drive gear can be omitted. It is hence possible to simplify the structure correspondingly, and to achieve a further reduction in size and weight of the operating section 607.

Note that the means of driving the sprocket 617 by the motor 630 is not limited to the pinion 630 and the crown gear 618 as illustrated in this example, it may be constituted using friction wheels.

Figure 96:
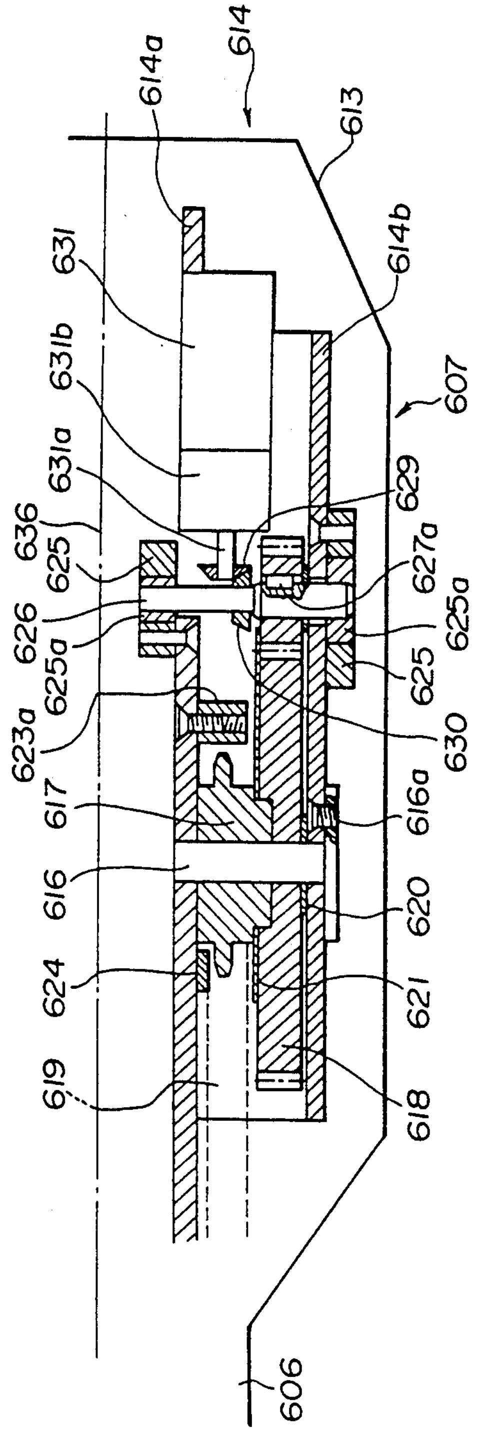

FIG. 96 illustrates the fourth example.

In this example, a sprocket 617 and a driven gear 618 integrated with the sprocket 617 are disposed in an operating section 607 on the side near an insert section 606, while a drive gear 627 and a driven bevel gear 630 both fixedly mounted on a shaft 166 are disposed on the side of the sprocket 617 opposite to the insert section 606. Further, an opening 636 is formed in a main frame 614*a* on the side of the shaft 626 opposite to the insert section 606, and a motor 631 constituted as a geared motor is fixed in place with its part fitted into the opening 636.

With such constitution, since the distance (indicated by "b" in FIG. 94) between both ends or two runs of the chain 619 entrained about the sprocket 617 can be reduced irrespective of the diameter of the motor 631, it is possible to reduce the diameter of the sprocket 617 for making the operating section 607 more compact correspondingly.

According to the above first through fourth embodiments, as described above, since the motor for driving the movable member is disposed substantially parallel to the axis of the operating section, the operating section can be reduced in size, which contributes to improve operability.

Meanwhile, the insert section of a medical endoscope generally has flexibility to be bent or angled in the body cavity. To know the bent state of the insert section in the body cavity is very important in points of alleviating pain imparted to a patient and preventing such a trouble as perforating the cavity wall.

In view of the above situations, Japanese Patent Publication No. 60689/1986 discloses a technique of two-dimensionally displaying the bent state of a flexible tube on an image display.

Also, Japanese Patent Laid-Open No. 292934/1988 discloses a technique of operating a bendable portion dummy provided externally of the body by an operator so as to bend a bendable portion inserted into the body in accordance with the external bendable portion dummy.

However, because the above-cited Japanese Patent Publication No. 60689/1986 displays the bent state in a two-dimensional manner, it was difficult to recognize the three-dimensional state of the insert section. Further, with the technique disclosed in Japanese Patent Laid-Open No. 292934/1988, when the bendable portion strikes against the body wall or the like, there occurs an error between the amount of bending instructed from the bendable portion dummy and the actual bent amount of the bendable portion. It was therefore not ensured to actually bend the bendable portion exactly following the external bendable portion dummy.

In view of the above, FIGS. 97 through 110 illustrate four examples of an endoscope apparatus which permits three-dimensional display of the insert section so that the bent state of the insert section is easily recognized.

The endoscope apparatus of these examples comprises a detector element provided plural in number in an insert section of an endoscope for detecting a degree of bending at the installed position, and annunciator means for displaying the bent state of the insert section based on outputs from the respective detector elements in a three-dimensional manner.

FIGS. 97 through 100 illustrate the first example.

Figure 97:
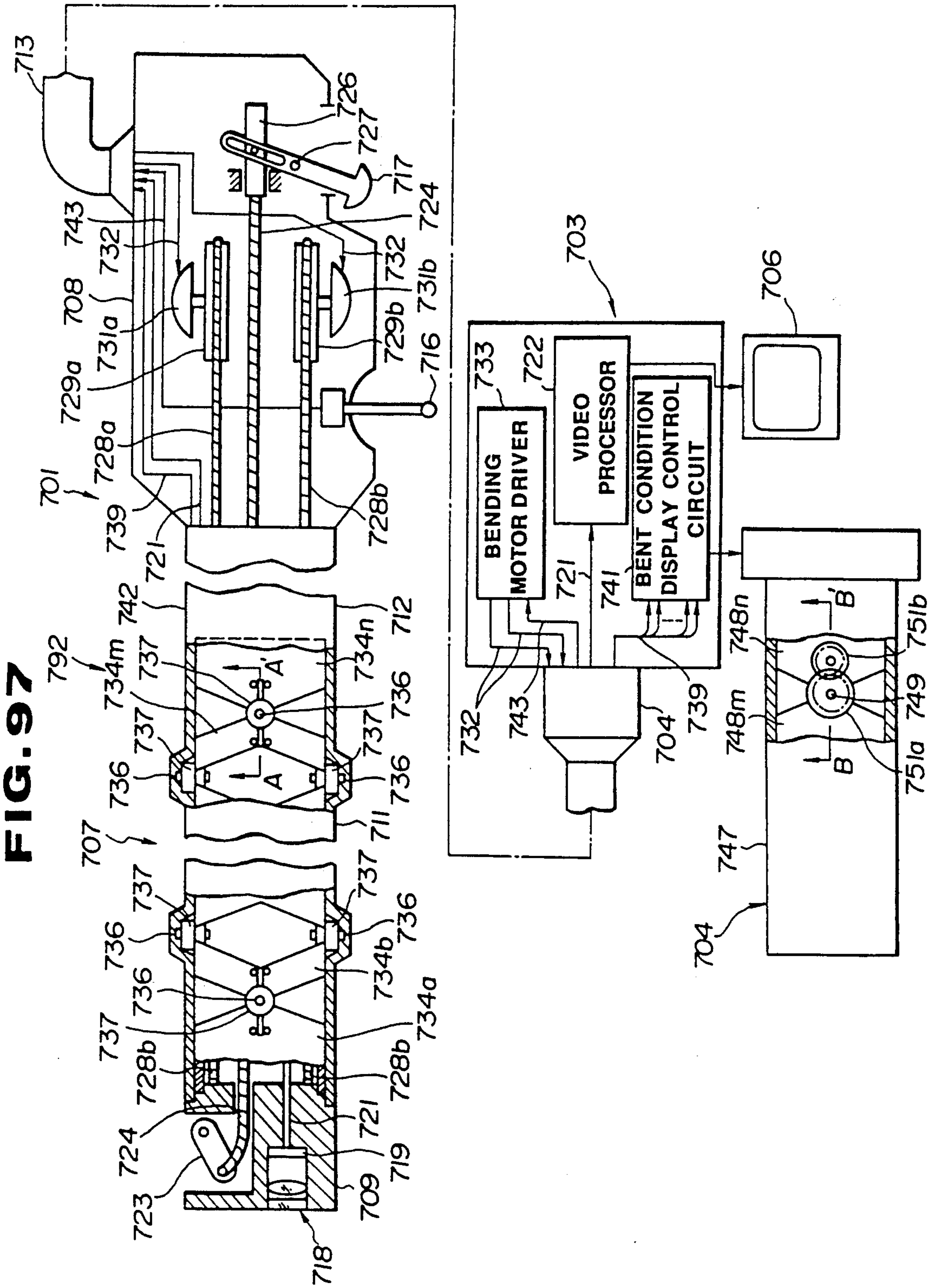
FIGS. 97 through 110 are concerned with four examples of an endoscope apparatus which can notify the bent condition three-dimensionally.

In FIG. 97, an endoscope apparatus 701 of this example comprises an endoscope 702, a centralized controller 703, a bending display 704 as annunciator means, and a TV monitor 706.

The endoscope 701 comprises an elongate insert section 707, and an operating section 708 continuously provided at the rear end of the insert section 707. The insert section 707 includes a distal end component 709, a bendable portion 711 and a flexible pipe portion 708 which are provided in this order from the distal end thereof. The operating section 708 is continuously provided behind the flexible pipe portion 712.

A universal cable 713 is extended from the operating section 708, and a connector 714 provided at the rear end of the universal cable 713 is connected to the centralized controller 703. A bending switch 716 and an appliance erecting stand control lever 717 are provided on the operating section 708.

An objective optical system 718 is provided at the front face of the distal end component 709, and a solid imaging device 719 is provided behind the objective optical system 718 such that the imaging plane of the solid imaging device 719 locates at the focus position of the objective optical system 718. A signal line 721 has one end connected to the solid imaging device 719, and the other end extended through the insert section 707, the operating section 708 and the universal cable 713 and then connected to a video processor 722 in the centralized controller 703.

An appliance erecting stand 723 is provided in the distal end component 709 such that an appliance (not shown) can be adjusted in the projecting direction. An erection wire 724 extended through the insert section 707 and the operating section 708 has one end connected to the appliance erecting stand 723, and the other end connected to a slider 726 in the operating section 708. The slider 726 is provided in such a manner as to slide in the longitudinal direction of the operating section 708, and coupled to one end of the appliance erecting stand control lever 717 which is pivotably provided about a pin 727. By operating the lever 717, the wire 724 is tensioned or loosened to raise up the appliance erecting stand 723.

Further, fixed to the rear end face of the distal end component 709 are one ends of bending wires 728*a*, 728*b* at positions spaced from each other by an angle of almost 90 degrees circumferentially about the longitudinal direction of the insert section 707. These bending wires 728*a*, 728*b* are extended through the insert section 707 and entrained about pulleys 729*a*, 729*b*. Then, the bending wires 728*a*, 728*b* are extended through the insert section 707 again, but now in the reversed direction, and fixed to the distal end component 709 such that the other end of the wire 728*a* is positioned opposite to one end thereof and the other end of the wire 728*b* is positioned opposite to one end thereof, respectively.

The pulleys 729*a*, 729*b* are rotated by ultrasonic motors 731*a*, 731*b*, respectively. Signal lines 732, 732 extended through the universal cable 713 have one ends connected to the ultrasonic motors 731*a*, 731*b*, respectively, and the other ends connected to a bending motor driver 733 in the centralized controller 703.

An outermost first bending piece 734*a* among a plurality of bending pieces 734*a*, 734*b*, . . . which jointly constitute the bendable portion 711 is fixedly fitted to the rear end of the distal end component 709 at the outer periphery thereof. Pivot pins 736, 736 extending radially outwards are provided on the outer periphery of the rear end of the first bending piece 734*a* at positions opposite to each other, and the succeeding second bending piece 734*b* is pivotably coupled to the first bending piece 734*a* by the pivot pins 736, 736. Other pivot pins 736, 736 are provided on the outer periphery of the rear end of the second bending piece 734*b* at positions spaced from the above pivot pins 736, 736 for the first bending piece 734*a* by an angle of 90 degrees, so that the third bending piece 734*c* can be coupled to the second bending piece 734*a* in a pivotable manner. Subsequently, the bending pieces 734*d*, 734*e*, . . . are coupled to each other by pivot pins 736 spaced by an angle of 90 degrees between respective pairs of adjacent bending pieces 734 in a like manner. As a result, the bendable portion 711 can be bent upwards, downwards, rightwards and leftwards.

Figure 98:
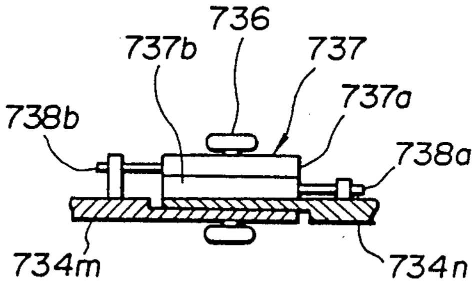

The pivot pins 736, 736, . . . are each provided with a potentiometer 737 as one example of the detector element, as shown in FIG. 98. The potentiometer 737 has cases 737*a* and 737*b* which are arranged one above the other. A pin 738*a* projecting from a peripheral wall of the case 737*a* is fixed to one 734*n* of the bending pieces coupled to each other by the pivot pins 736, while a pin 738*b* projecting from a peripheral wall of the case 737*b* is fixed to the other bending piece 738*m*. With this arrangement, the potentiometer 737 can detect and output respective rotation angles of the bending pieces 734*n*, 734*m*. Signal lines 739, 739, . . . extended through the insert section 707, the operating section 708 and the universal cable 713 have one ends connected to the respective potentiometers 737, and the other ends connected to a bent condition display control circuit 741 in the centralized controller 703.

The bendable portion 711 and the flexible pipe portion 712 are covered at the outer periphery with a covering tube 742.

The bending switch 716 provided on the operating section 708 is arranged to output a signal instructing the bending direction, i.e., in which one of the upward, downward, rightward and leftward directions the bending is to be made. A signal lines 743 extended through the universal cable 713 has one end connected to the bending switch 716, and the other end connected to the bending motor driver 733 in the centralized controller 703.

The video processor 722 is connected to the TV monitor 706 for outputting a video signal.

Figure 99:
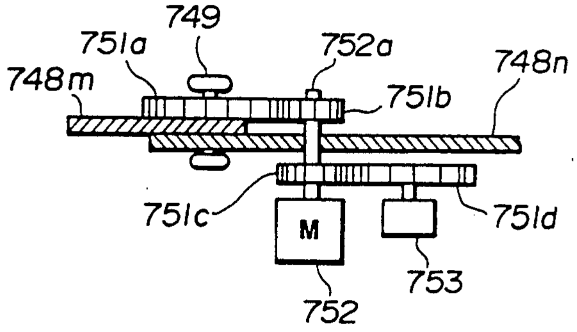
Figure 100:
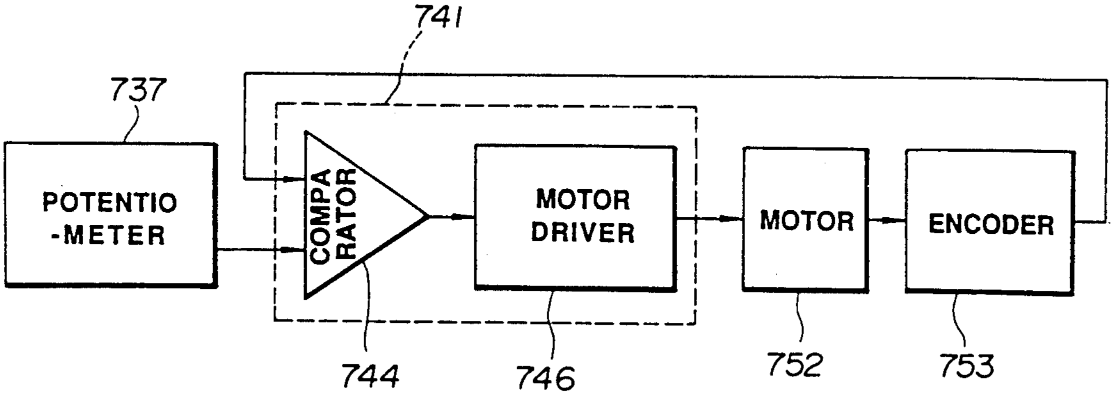

The bent condition display control circuit 741 comprises a pair of comparator 744 and a motor driver 746 as shown in FIG. 100, this pair being provided plural in number. Each pair is connected to one potentiometer 737. The bent condition display control circuit 741 is also connected to the bending display 704. The bending display 704 includes a bending (bendable portion) dummy 747 which reproduces the bent state of the insert section 707 and has miniature size of the bendable portion 711. In the bending dummy 747, there are provided a first bending piece 748*a*, a second bending piece 748*b*, . . . from the distal end thereof in this order. Each joint portion between every adjacent twos of the bending pieces 748*a*, 748*b*, . . . is constituted as shown in FIG. 99.

Every adjacent twos of the plural bending pieces 748 is coupled to each other by a pivot pin 749 in a pivotable manner. This point will now be described in more detail by taking the bending pieces 748*m*, 748*n* among the plural bending pieces 748 as an example. The bending pieces 748*m*, 748*n* are coupled to each other by the pivot pin 749. The pivot pin 749 is fixed to the bending piece 748*m* and is rotatable with respect to the bending piece 748*n*. On the outer side of the bending piece 748*m*, a first gear 751*a* is provided to be coincident with the pivot pin 749 in the center of rotation. The first gear 751*a* is fixed to the bending piece 748*m*.

On the other hand, the bending piece 748*n* is provided with a motor 752 of which drive shaft 752*a* penetrates through a peripheral wall of the bending piece 748*n*. A second gear 751*b* meshing with the first gear 751*a* is mounted over the projected distal end of the drive shaft 752*a*. A third gear 751*c* is also mounted on the drive shaft 752*a*, and a fourth gear 751*d* attached to an encoder 753 is held in mesh with the third gear 751*c*.

The motor 752 is connected to the motor driver 746 of the bent condition display control circuit 741 so that driving of the motor is controlled by the motor driver 746. When the motor 752 is driven under control of the motor driver 746, the bending piece 748*m* is rotated relative to the bending piece 748*n* via the second gear 751*b* and the first gear 751*a*. The rotation of the motor 752 is also transmitted to the encoder 753 via the third gear 751*c* and the fourth gear 751*d*, and the encoder 753 outputs the amount of rotation to the comparator 744 of the bent condition display control circuit 741.

The joint portions of the bending pieces 748*a*, 748*b* . . . are provided in the same number as those of the bending pieces 734*a*, 734*b*, . . . provided in the bendable portion 711. The orientation of each joint portion is also set identical to each other on both sides such that if the joint portion of the first bending piece 734*a* on the side of the bendable portion 711 is lying in the right and left direction (i.e., vertically to the drawing sheet of FIG. 97), the joint portion of the first bending piece 748*a* on the side of the bending dummy 747 is lying similarly in the right and left direction, and so on.

Further, the potentiometer 737 provided between the first bending piece 734*a* and the second bending piece 734*b* on the side of the bendable portion 711 is electrically connected to the motor 752 and the encoder 753 both provided between the first bending piece 748*a* and the second bending piece 748*b* on the side of the bending dummy 747 via the comparator 744 and the motor driver 746. Likewise, the subsequent potentiometers 737 correspond to the subsequent motors 752 and encoders 753, respectively, such that the potentiometer 737 provided between the second bending piece 734*b* and the third bending piece 734*c* on the side of the bendable portion 711 is electrically connected to the motor 752 and the encoder 753 both provided between the second bending piece 748*b* and the third bending piece 748*c* on the side of the bending dummy 747, and so on.

Operation of the endoscope apparatus 701 thus constituted will be described below.

In the case of bending the bendable portion 711 in the right and left direction (i.e., vertically to the drawing sheet of FIG. 97), when the bending switch 716 on the operating section 708 is operated, a signal instructing the rightward and leftward bending is output from the switch 716 to the bending motor driver 733 in the centralized controller 703 via the signal line 743. In response to the instruction signal, the bending motor driver 733 outputs a drive signal to the ultrasonic motor 731*a* via the signal line 732, whereupon the ultrasonic motor 731*a* is driven with the drive signal. When the ultrasonic motor 731*a* is driven, the pulley 729*a* is rotated to tension and loosen the bending wire 728*a* entrained about the pulley 729*a*. Upon the bending wire 728*a* being tensioned and loosened, the cases 737*a*, 737*b* constituting each of the potentiometers 737 provided between the second bending piece 748*b* and the third bending piece 748*c*, between the fourth bending piece 748*d* and the fifth bending piece 748*e*, and so on are rotated by the pins 738*a*, 738*b*, respectively, so that each potentiometer 737 outputs a voltage value given by the resistance value dependent on a relative angle between the adjacent two bending pieces 748. The respective voltage values output from the potentiometers 737, 737, . . . are applied via the signal lines 739, 739, . . . to the respective comparators 744 in the bent condition display control circuits 741 corresponding to the potentiometers 737, 737, . . . , and the comparators 744 output respective voltage signals to the motor drivers 746. The drivers 746, 746, . . . then output drive signals to the motors 752, 752, . . . of the bending dummy 747, respectively. In response to the drive signals, the motors 752, 752, . . . are each revolved to change the relative angle between adjacent two bending pieces 748. Each changed relative angle is fed back from the encoder 753 to the comparator 744. The comparator 744 compares the relative angle fed back and the relative angle output from the potentiometer 737, and continues to output the voltage signal until both the relative angles coincide with each other.

With this example, as described above, since the bent state of the bendable portion 711 which is bent by operating the bending switch 716 on the operating section 708 can be reproduced by use of the bending dummy 747 with high fidelity, it is possible for the operator to readily see the actual bent state of the bendable portion 711 in the body cavity, which state cannot otherwise be observed with the naked eye.

In addition, since the bent state is reproduced three-dimensionally in the form of the bending dummy 747, it is also possible to quickly recognize even the bent state which is difficult to recognize with two-dimensional display.

Figure 101:
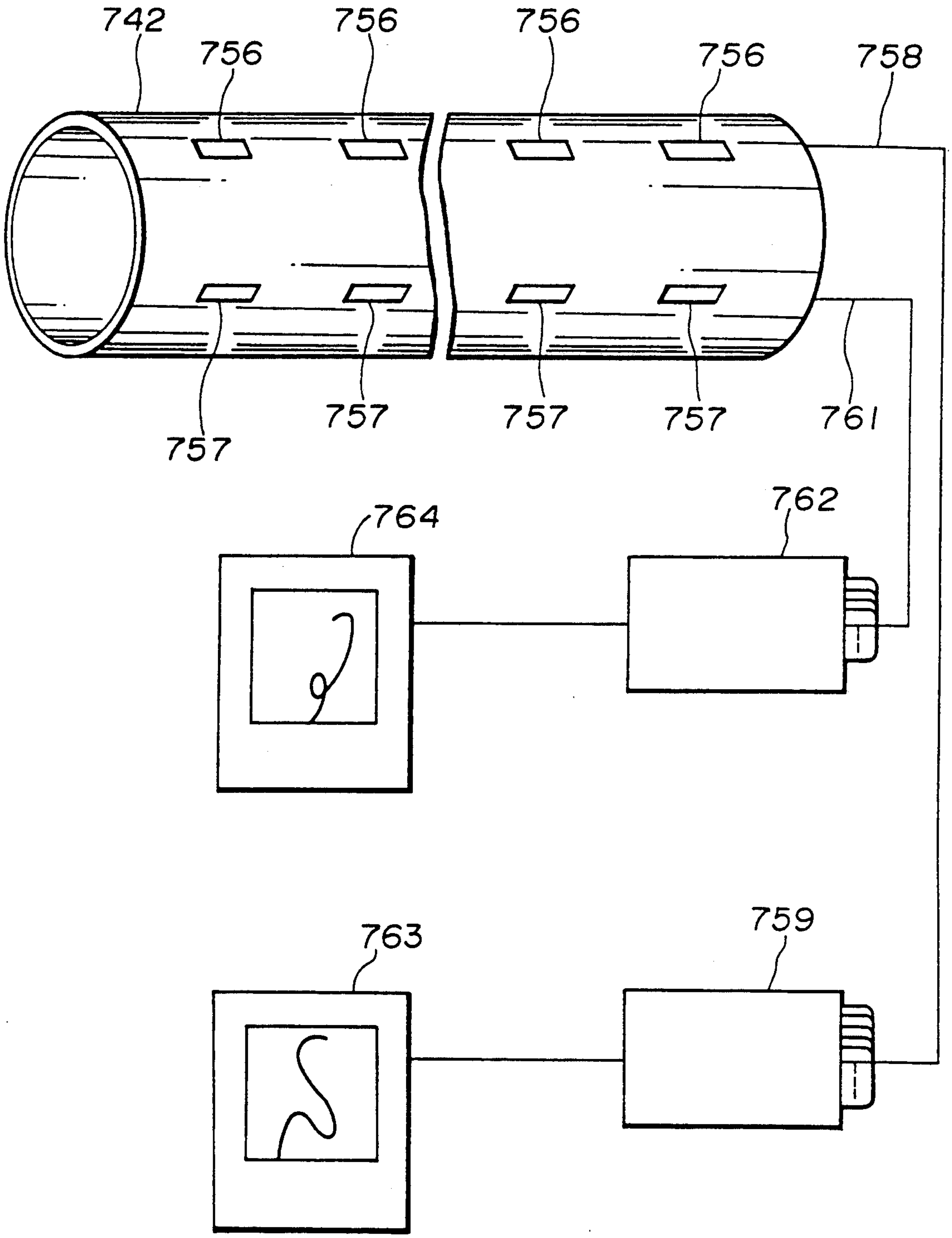
Figure 102:
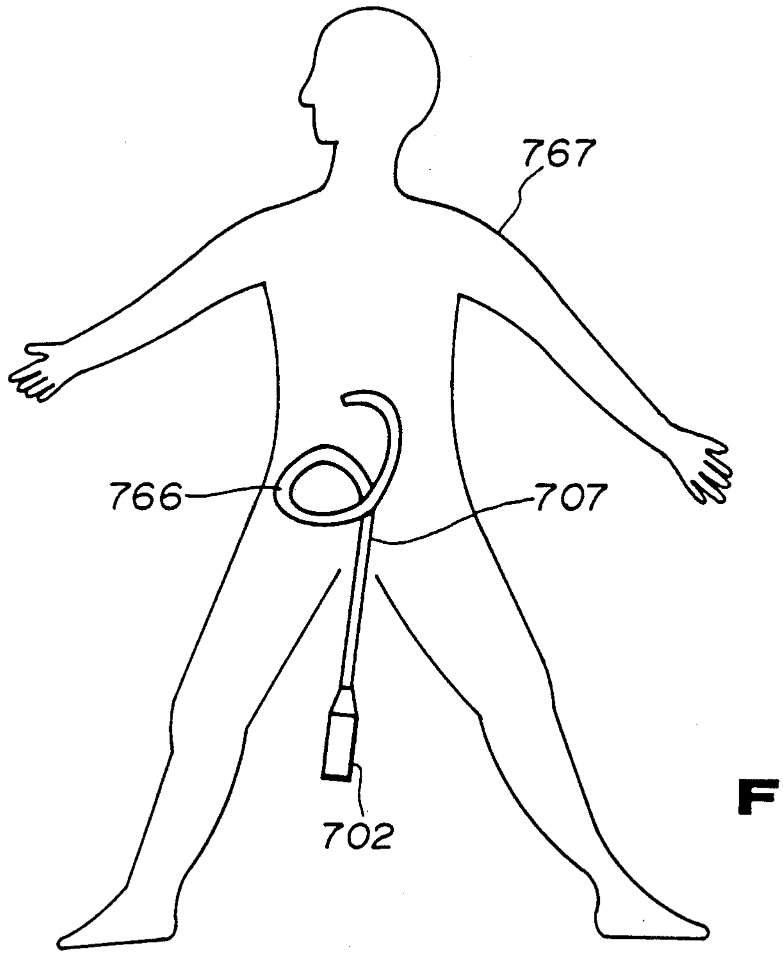
Figure 103:
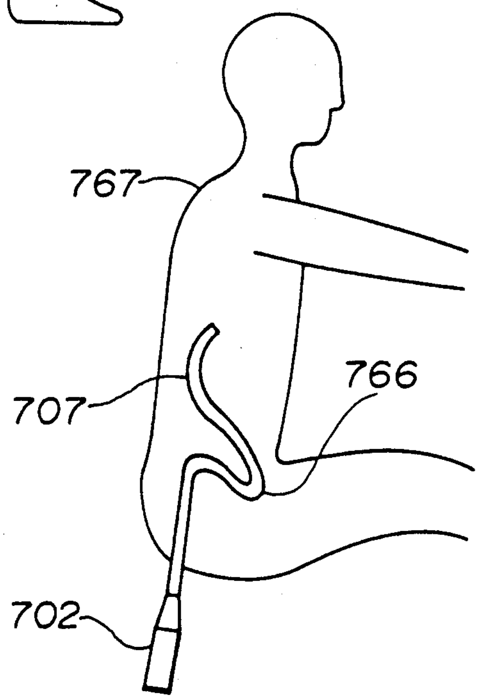
Figure 104:
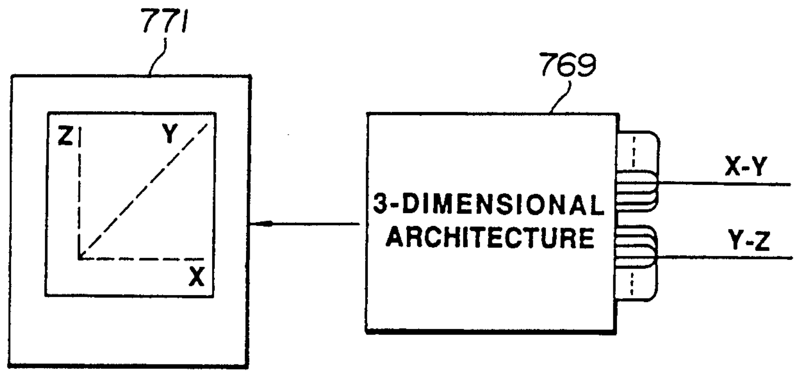

FIGS. 101 through 103 illustrate the second example.

While the potentiometers 737 are provided to the bending pieces 734 of the bendable portion 711 for detecting the bent state of the bendable portion 711 in the first example, pressure sensitive elements as the detector elements are disposed over the entire length of the insert section 707 for detecting the bent state of the insert section 707 in the second example. Note that similar components to those in the first example are designated by the same reference numerals and are not explained here.

On the covering tube 742 of this example, there are provided pressure sensitive elements 756, 756, . . . , 757, 757, . . . such as strain gauges, for example, for detecting the bent state, which are arranged to form a line in the longitudinal direction of the insert section 707 and for each of the vertical and horizontal bending directions of the insert section 707. Signal lines 758, 758, . . . have one ends connected to the pressure sensitive elements 756, 756, . . . for detection of the vertical bending, respectively, and the other ends connected to a vertical bent condition display controller 759. Likewise, signal lines 761, 761, . . . have one ends connected to the pressure sensitive elements 757, 757, . . . for detection of the horizontal bending, respectively, and the other ends connected to a horizontal bent condition display controller 762. Monitors 763, 764 are connected to the display controllers 759, 762, respectively, so that the monitor 763 displays the vertical bent state of the insert section 707 and the monitor 764 displays the horizontal bent state thereof.

Note that the controllers 759, 762 and the monitors 763, 764 jointly constitute the annunciator means.

Operation of this example will be described below.

As shown in FIGS. 102 and 103, the insert section 707 is inserted into the body cavity of a patient 767 while drawing an $\alpha$ loop 66. The pressure sensitive elements 756, 756, . . . , 757, 757, . . . provided in the insert section 707 being bent are changed in their resistance values dependent on the radii of curvature at respective positions where the pressure sensitive elements 756, 756, . . . , 757, 757, . . . are installed, and output corresponding voltage values. These voltage values are input to the bent condition display controllers 759, 762 which execute calculations based on both the input signals and the distances between every adjacent twos of the pressure sensitive elements 756, 756, . . . , 757, 757, . . . , respectively. As a result, the controller 762 displays a continuous curve representing the horizontal bent state, i.e., the bent condition as shown in FIG. 102, on the monitor 764, while the controller 759 displays a continuous curve representing the vertical bent state, i.e., the bent condition as shown in FIG. 103, on the monitor 763.

The operator confirms the bent state of the insert section 707 while observing the monitors 763, 764, and removes the $\alpha$ loop 66 by twisting the endoscope 702 clockwise. Afterward, the operator continues operation to further insert the insert section 707 into the body cavity of the patient 767.

With this example, since the bent state of the insert section 707 can be observed in the two directions different from each other by 90 degrees, it is possible to understand the three-dimensional bent state of the insert section 707 at a glance.

Further, by applying arithmetic operation such as coordinate conversion to the vertical bending information and the horizontal bending information, the bent state can be displayed in any desired two directions. Of course, display as observed in three or more directions is also possible.

In addition, instead of using the pressure sensitive elements 756, 756, . . . , 757, 757, . . . , information from two X-rays images photographed in the two directions shifted from each other by 90 degrees, for example, may be used. In this case, the information may also be displayed in any desired two directions.

Other constitution, operation and advantageous effect are similar to those in the first example.

FIGS. 104 through 107 illustrate the third example.

In this example, the output signals of the pressure sensitive elements 756, 756, . . . , 757, 757, . . . mentioned in the second example are input to a three-dimensional architecture circuit 769.

The signals, including the bending information, output from the pressure sensitive elements 756, 756, . . . , 757, 757, . . . are input to the three-dimensional architecture circuit 769 which calculates the bent state of the insert section 707 and display it on a monitor 771.

Note that the three-dimensional architecture circuit 769 and the monitor 771 jointly constitute the annunciator means.

In this example, the vertical bent state is derived from both the radii of curvature of the regions near the pressure sensitive elements 756, 756, . . . , which radii are calculated from changes in the resistance values of the pressure sensitive elements 756, 756, . . . , and the distances between every adjacent twos of the pressure sensitive elements 756, 756, . . . , while the horizontal bent state is derived from both the radii of curvature of the regions near the pressure sensitive elements 757, 757, . . . , which radii are calculated from changes in the resistance values of the pressure sensitive elements 757, 757, . . . , and the distances between every adjacent twos of the pressure sensitive elements 757, 757, . . . , respectively. The horizontal bent state and the vertical bent state are input two the three-dimensional architecture circuit 769 as Y—X axis information and Y—Z information, respectively, so that these information are reconstructed into the three-dimensional form and displayed on the monitor 771.

Other constitution, operation and advantageous effect are similar to those in the first example.

Figure 105:
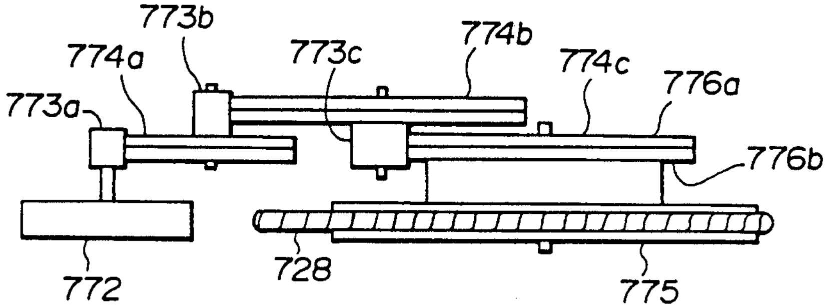

Furthermore, a bending control mechanism of this example is constituted as shown in FIG. 105. A stepping motor 772 transmits torque to a pulley 775 mounted on a third scissors gear 774c via a first gear 773a, a first scissors gear 774a, a second gear 773b, a second scissors gear 774b, a third gear 773d and the third scissors gear 774c. A bending wire 728 is entrained about the pulley 775, so that the bending wire 728 is tensioned and loosened by revolving the stepping motor 772.

It is to be noted that each scissors gear 774 comprises two gears which are arranged one above the other in back-to-back relation and biased in opposite directions to each other for reducing backlash. For example, the third scissors gear 774c comprises two gears 776a, 776b which are superposed in back-to-back relation under a condition that they are biased in opposite directions, both of the gears 776a, 776b being held in mesh with the third gear 773c.

Figure 106:
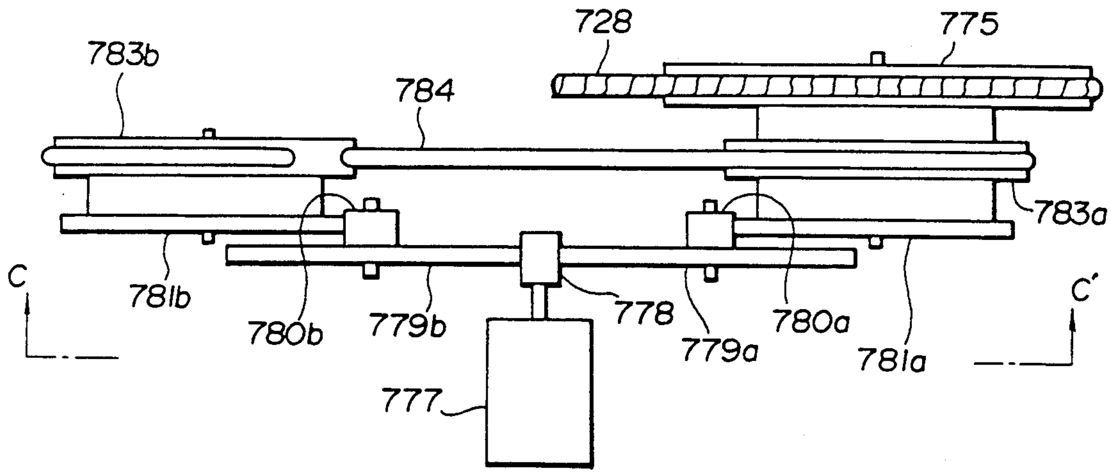

Alternatively, backlash may be eliminated with an arrangement shown in FIG. 106.

Figure 107:
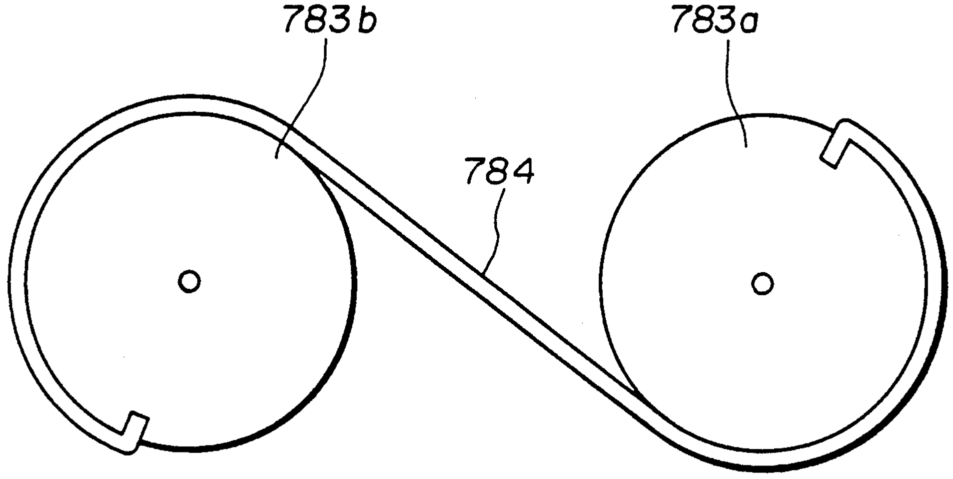

In FIG. 106, a DC motor 777 transmits torque to a pulley 775 mounted on a gear 781a via a train of gears 778, 779a, 780a and 781a. A bending wire 728 is entrained about the pulley 775, so that the bending wire 728 is tensioned and loosened by revolving the DC motor 777. Further, gears 779b, 780b, 781b having the same number of teeth as the gears 779a, 780a, 781a are held in mesh with the gear 778, and disks 783a, 783b having the same diameter are mounted on the gears 781a, 781b, respectively. As shown in FIG. 107, an elastic wire member 784 such as a rubber wire is entrained about both the disks 783a, 783b in form of nearly an 8-shape, and has the opposite ends fixed to the outer peripheral surfaces of the respective disks 783a, 783b so that the wire member 784 is biased in the contracting direction at all times. Thus, the line member 784 serves to always apply torque to the gears 779a, 780a, 781a in a predetermined direction for preventing the occurrence of backlash.

In addition, this example can be utilized not only to simply display the bent state, but also to offer an information source for achieving motor-powered bending apparatus and motor-powered moving/twisting (automatic inserting) apparatus.

Figure 108:
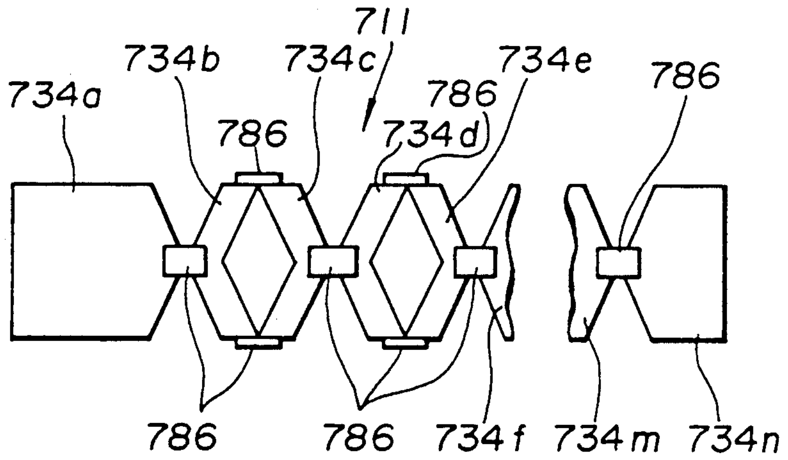
Figure 109:
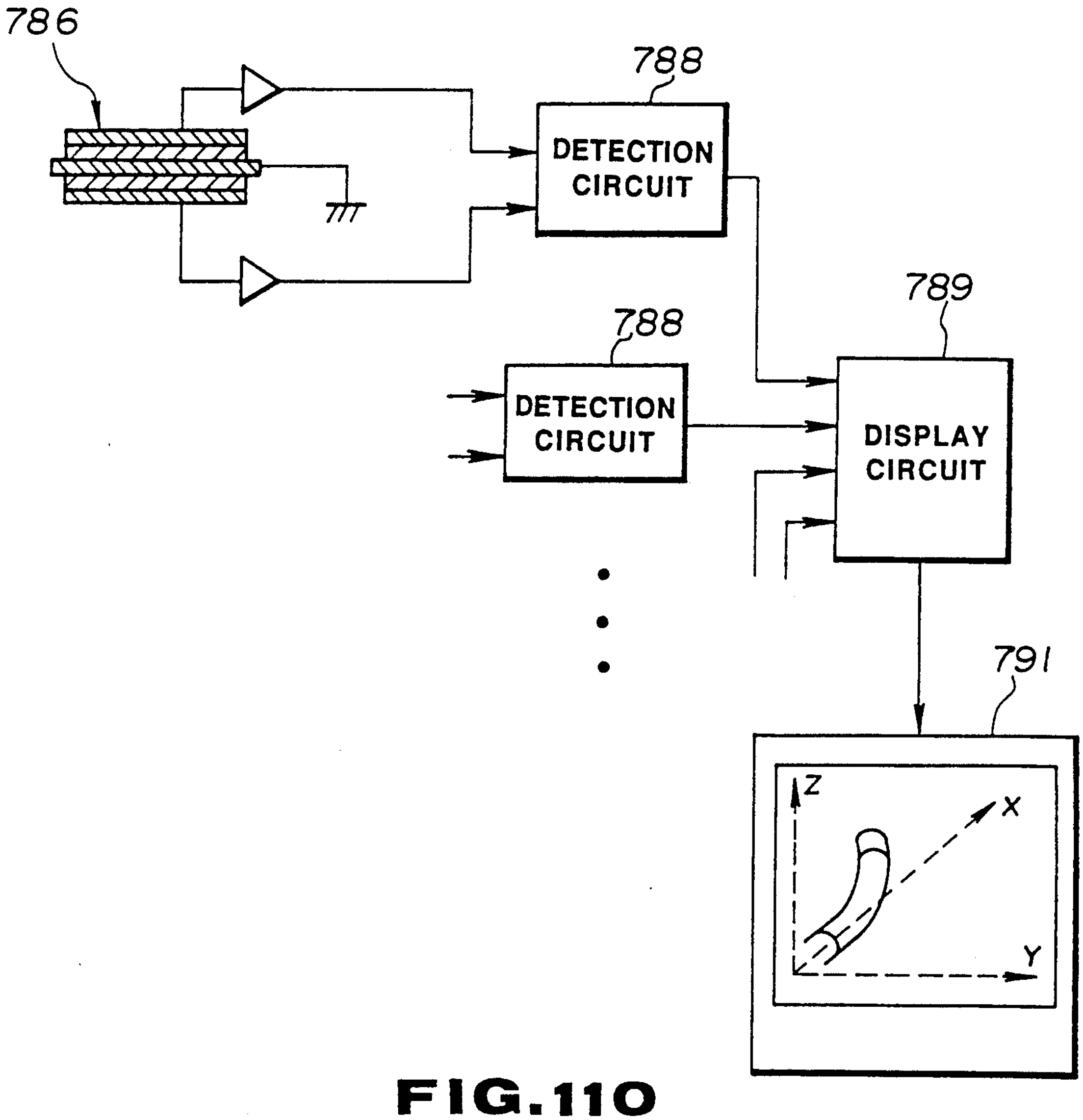
Figure 110:
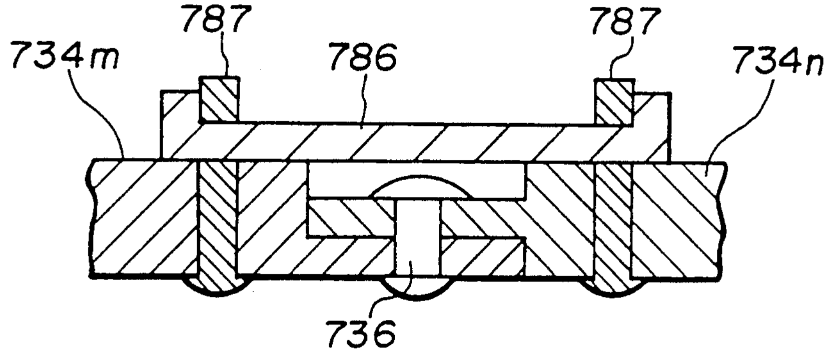

FIGS. 108 through 110 illustrate the fourth example.

In this example, the bent amount is detected using a bimorph piezoelectric element as the detector element.

A plurality of bending pieces 734a, 734b, . . . which constitute the bendable portion 711 are coupled to each other by respective pivot pins 736, 736 in a pivotable manner, with a bimorph piezoelectric element 786 provided at each joint portion between the bending pieces. For example, the joint portion between the bending pieces 734m and 734n is constituted as shown in FIG. 110. More specifically, in the joint portion between the bending pieces 734m and 734n coupled to each other by the pivot pin 736 in a pivotable manner, the bimorph piezoelectric element 786 is fixed at one end to the bending piece 734m and at the other end to the bending piece 734n by respective set pins 787, 787.

The bimorph piezoelectric elements 786, 786, . . . provided at the joint portions are connected to detection circuits 788, 788, . . . , respectively, which are in turn connected to a display circuit 789. The display circuit 789 is connected to a monitor 791 for outputting the bending information to the monitor 791.

Note that the detection circuits 788, 788, . . . , the display circuit 789 and the monitor 791 jointly constitute the annunciator means.

With this example, when the bendable portion 711 is bent, the bimorph piezoelectric elements 786, 786, . . . provided at the joint portions between every adjacent twos of the bending pieces 734a, 734b, . . . output the bending information at installed positions of the bimorph piezoelectric elements 786, 786, . . . to the detection circuits 788, 788, . . . , respectively. Each detection circuit 788 holds a differentiated voltage output from the bimorph piezoelectric element 786 and executes addition (subtraction) of the holding voltage, followed by outputting the result to the display circuit 789. The display circuit 789 issues a signal including the bending information output from the respective bimorph piezoelectric elements 786, 786, . . . to the monitor 791 so that the monitor 791 displays the three-dimensional bending information.

Other constitution, operation and advantageous effect are similar to those in the first example.

According to the first through four examples, as described above, it is possible to effect three-dimensional display of the insert section and hence to easily recognize the bent state of the insert section.

Meanwhile, in the case where a motor is used as bending drive means, when the distal end component provided at the distal end of the insert section of the endoscope is brought into contact with a wall of the body cavity or the like upon bending of the bendable portion, the motor load is increased. This raises a problem that the amount of heat produced by the motor is too increased under an overload condition.

Therefore, FIGS. 111 through 118 illustrate five examples of an endoscope apparatus which can inform the endoscope operator of an increase in the amount of heat produced by the motor, or can control driving of the motor upon an increase in the amount of heat produced by the motor.

These examples include detection means for detecting a temperature of the motor and means of informing a detection signal from the detection means. With this constitution, a rise in the motor temperature is informed to the endoscope operator.

Figure 111:
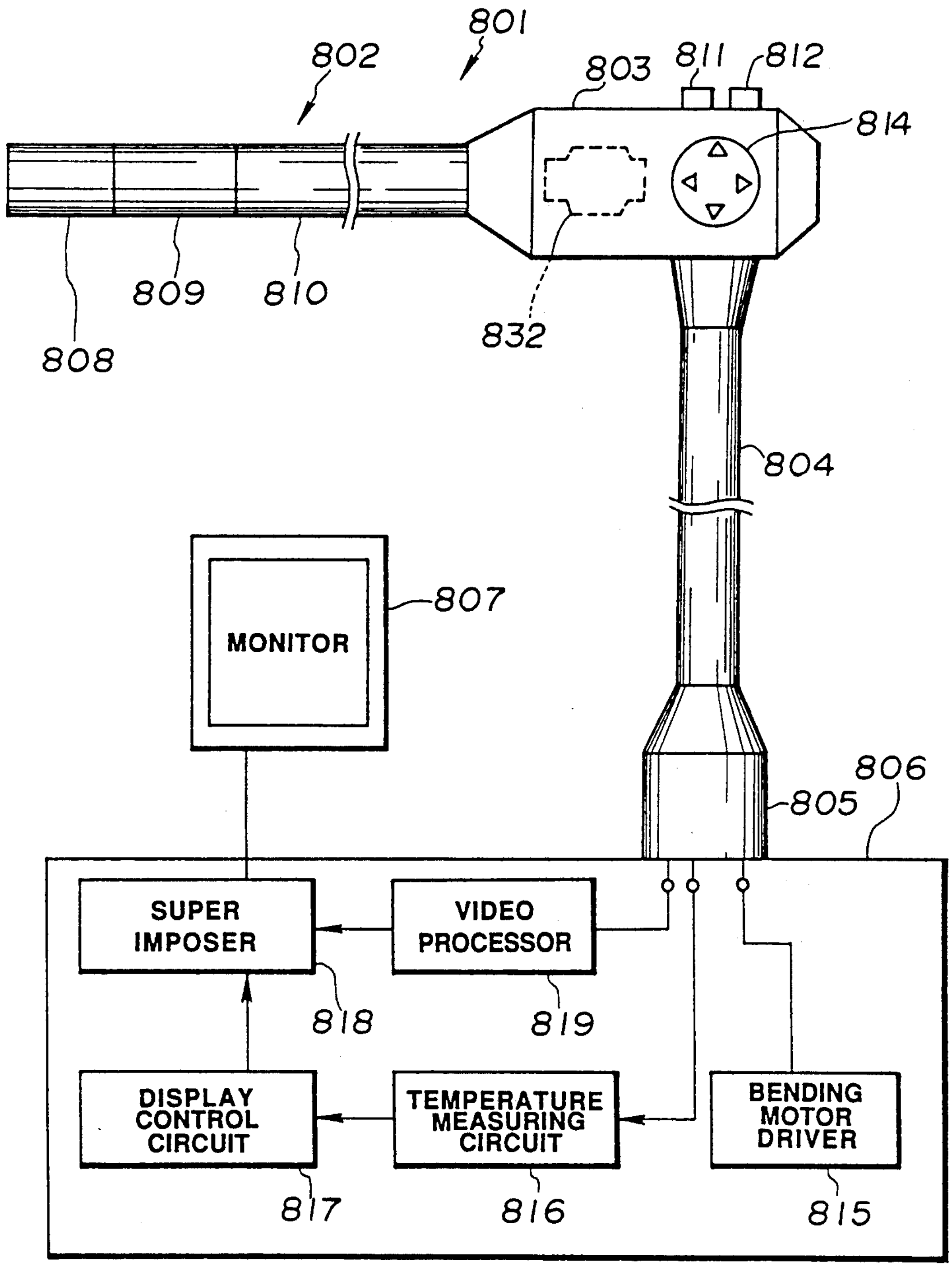
Figure 112:
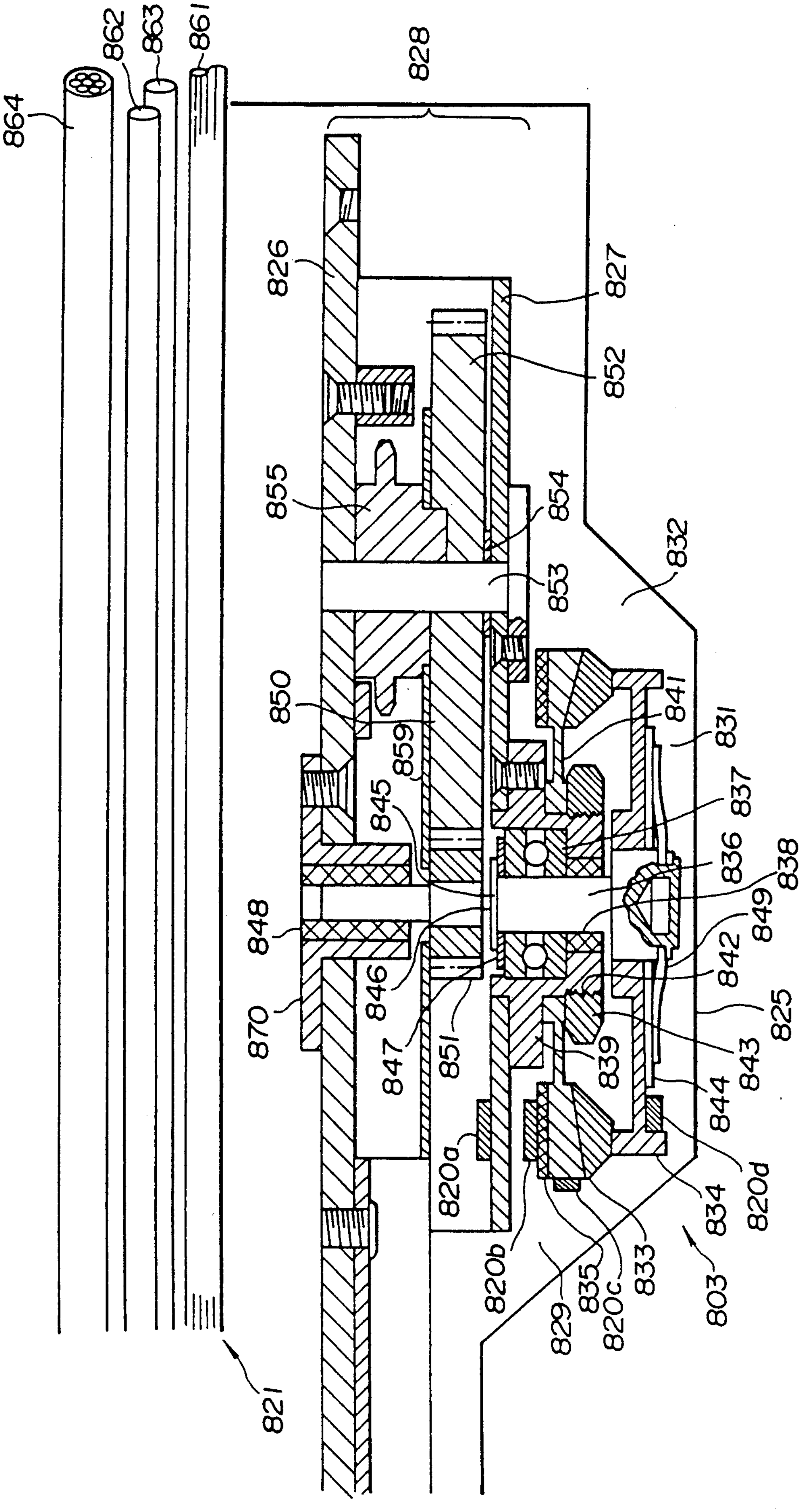

FIGS. 111 through 113 illustrate the first example.

An endoscope apparatus comprises, as shown in FIG. 111, an endoscope 801 formed into an elongate shape to be capable of being inserted into the body cavity, for example, a controller 806 including a video processor 819 (described later) 819 and connectable to a universal cord 804 from the endoscope 801 via a connector 805, and a monitor 807 for producing an image of an object, such as the required internal location of the body cavity, based on an output signal of the video processor 819.

The endoscope 801 comprises an elongate insert section 802, a larger-diameter operating section 803 continuously provided at the rear end of the insert section 802, the universal cord 804 extended laterally from the operating section 803, and the connector 805 provided at the end of the universal cord 804. The insert section 802 comprises a distal end component 808 in which the emergent end face of a light guide (not shown), an imaging device for imaging an object, etc. are disposed, a bendable portion 809 continuouly provided at the rear end of the distal end component 808 and capable of bending vertically (up and down) and horizontally (to the right and left), and a flexible pipe portion 810 continuously provided at the rear end of the bendable portion 809.

The operating section 803 incorporates an ultrasonic motor (hereinafter referred to as USM) 832 as a motor for driving the bendable portion 809 to bend, and also includes an air-feed/water-feed switch 811, a suction switch 812, and a bending switch 814 to output a control signal for controlling the USM 832.

The light guide is extended through the insert section 802, the operating section 803 and the universal cord 804, and has its incident end face projecting out of the connector 805.

The controller 806 includes a light source unit (not shown) for supplying a beam of illumination light to the light guide (not shown) which is extended through the endoscope 801 and projected out of the connector 805, a bending motor driver 815 for driving the motor based on the control signal from the bending switch 814, a temperature measuring circuit 816 for processing an electric signal from a thermometer (described later) to measure a temperature of the USM 832, a display control circuit 817 for converting a measured temperature signal from the temperature measuring circuit 816 to a signal capable of being input to a superimposer 818 (described later), a video processor 819 for carrying out conversion and various steps of signal processing of an image pick-up signal from the imaging device disposed in the distal end component 808 to produce a video signal, and a superimposer 818 for synthesizing the video signal of the video processor 819 and the output signal of the display control circuit 817 to issue the resulting signal as a composite video signal to the monitor 807.

Within a case 825 incorporated in the operating section 803, as shown in FIG. 112, there are disposed two sets of frame assemblies (only one of them being shown as the frame assembly 828) which are positioned in laterally symmetrical relation and each of which comprises a main frame 826 and a sub-frame 827 arranged parallel to each other with a certain distance or space defined therebetween. A built-in component storage space 821 is formed between both the frames. Then, a bending actuator 829 for the vertical bending is mounted to one frame assembly 828, while another bending actuator (not shown) for the horizontal bending is mounted to the other frame assembly.

In the built-in component storage space 821, there are disposed a light guide 861, an air-feed tube 862, a water-feed tube 863, an electric signal line 864 between the imaging device and the video processor 819, and others.

Because the bending actuators for the vertical and horizontal bending have the same structure, only one bending actuator 829 for the vertical bending will be explained below. A USM unit 831 is mounted to the sub-frame 827 supported by the main frame 826. The USM 832 in the USM unit 831 comprises a substantially disk-like stator 833, and a rotor 834 held in intimate contact with the surface of the stator 833 facing the case 825 in the peripheral portion of the stator. A piezoelectric element 835 is fixedly bonded to the surface of the stator 833 opposite to the rotor 834 in the peripheral portion of the stator. The rotor 834 is fitted and fixed to the distal end of a rotary shaft 836. The rotary shaft 836 is supported at its intermediate portion by a thrust bearing 837 and a first radial bearing 838. The thrust bearing 837 and the first radial bearing 838 are stored and supported in the same first bearing box 839. The first bearing box 839 is joined to the sub-frame 827 and secured thereto by screws 841. The stator 833 is fitted over the outer periphery of the first bearing box 839, and fixedly fastened by a nut 843 meshed with male threads 842 formed on the outer peripheral surface of the first bearing box 839. Thus, the stator 833 is fixed in place and unable to rotate.

The thrust bearing 837 is supported by a snap ring 845 at a predetermined position to the outer periphery of the rotary shaft 836 via a washer 847, the snap ring 845 being fitted into a groove 846 formed in the outer peripheral surface of the rotary shaft 836. The inner end portion of the rotary shaft 836 is supported by a second radial bearing 848 held in a second bearing box 870 which is mounted to the main frame 826.

On the other hand, to the outer end of the rotary shaft 836 thus supported is attached a belleville (conical plate) spring 849 by caulking. The belleville spring 849 serves to strongly biases the rotor 834 in the direction in which the rotor 834 is pressed against the stator 833. A rubber sheet 844 is interposed between the rotor 834 and the belleville spring 849 for protecting the rotor 834 from damages and preventing a slippage between the rotor 834 and the rotary shaft 836.

Further, a drive gear 851 of a transmission gear mechanism, e.g., a transmission gear train 850, is fixedly mounted on the rotary shaft 836 of the USM unit 831 by means of press-fitting or the like at an intermediate position between the first radial bearing 838 and the second radial bearing 848. The drive gear 851 is held in mesh with a driven gear 852. The driven gear 852 is supported by a shaft 853 provided between the main frame 826 and the sub-frame 827 to be rotatable about the shaft 853. A washer 854 made of resin, for example, is interposed between the driven gear 852 and the sub-frame 827 for smoothing rotation of the driven gear 852. A sprocket 855 as a rotatable member for pulling operation is supported between the driven gear 852 and the main frame 826 in such a manner as freely rotatable about the shaft 853. The sprocket 855 is engaged with or joined by screws (not shown) or the like to the driven gear 852 for corotation therewith. A chain (not shown) is entrained about the sprocket 855, and a partition 859 is provided on the side of the transmission gear train 850 facing the chain to prevent interference between the transmission gear train 850 and the chain.

The aforesaid thermometer is given by a thermometer 820*a* stuck to the sub-frame 827 of the USM 832, a thermometer 820*b* stuck to the piezoelectric element 835 of the USM 832, a thermometer 820*c* stuck to the stator 833 of the USM 832, or a thermometer 820*d* stuck to the rotor 834 of the USM 832. In the following explanation, these thermometers 820*a*–820*d* are collectively referred to as the thermometer 820.

The thermometer 820 is formed of a platinum resistor, thermistor or positor which is changed in its resistance value, for example, dependent on the environmental or ambient temperature of each thermometer 820.

Figure 113A:
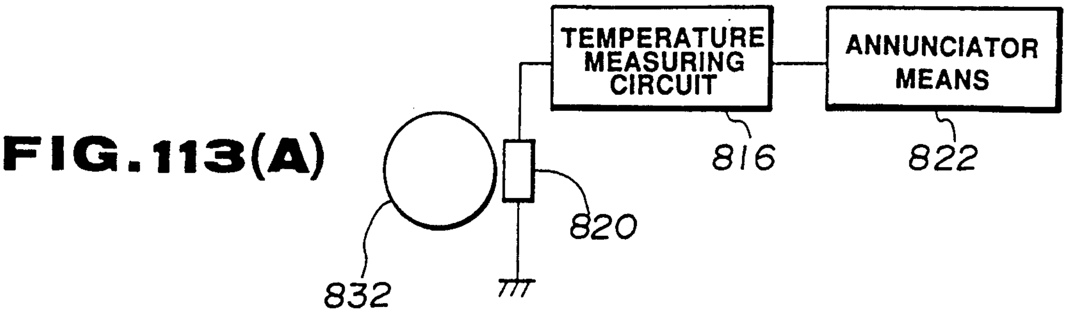
FIGS. 113(A)-113(C) are each a circuit diagram showing means of detecting a motor temperature.

The thermometer 820 and the temperature measuring circuit 816 are practically constituted as shown in FIG. 113(A). More specifically, an example of FIG. 113(A) comprises the thermometer 820 disposed in contact with or close to the USM 832 as the motor and having one end grounded, the temperature measuring circuit 816 having its input terminal to which the other end of the thermometer 820 is connected, and annunciator means 822 to which an output terminal of the temperature measuring circuit 816 is connected. In this example, the annunciator means 822 is constituted by the display control circuit 817 and the superimposer 818.

Figure 113B:
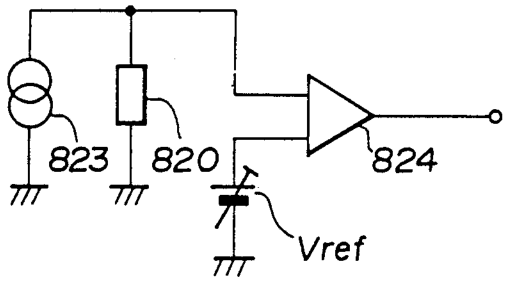

The temperature measuring circuit 816 comprises, as shown in FIG. 113(B), a constant-current source 823 having one end grounded, a thermometer 820 having one end grounded, and a comparator 824 having a first input terminal to which the other ends of both the constant-current source 823 and the thermometer 820 are connected and a second input terminal to which a comparative (reference) voltage source Vref is connected.

Figure 113C:
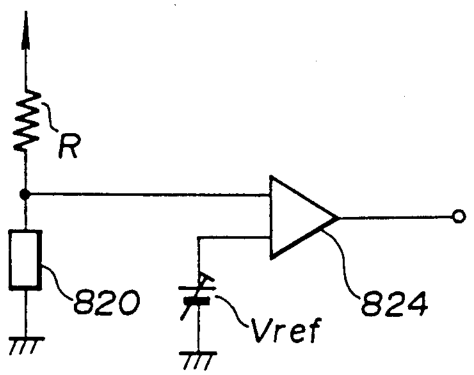

Alternatively, the temperature measuring circuit 816 may comprise, as shown in FIG. 113(C), a resistor R having one end connected to a power supply, a thermometer 820 having one end connected to the other end of the resistor R and the other end grounded, and a comparator 824 having a first input terminal to which the junction between the resistor R and the thermometer 820 are connected and a second input terminal to which a comparative (reference) voltage source Vref is connected.

Operation of the electronic endoscope apparatus thus constituted will be described below.

In the electronic endoscope apparatus, as shown FIG. 111, when the endoscope 801 is connected to the controller 806 via the connector 805, the incident end face of the light guide (not shown in FIG. 111) is positioned opposite to the light source unit (not shown), and the endoscope 801 is connected to the bending motor driver 815, the temperature measuring circuit 816 and the video processor 819.

Then, by applying electric power to the controller 806, the illumination light from the light source unit is supplied to the incident end face of the light guide, led through the light guide, and irradiated to the internal location of the body cavity or the like from the emergent end face in the distal end component 808. An image of the object irradiated by the illumination light is focused to the photo-electric conversion plane of a solid imaging device (not shown) by an objective lens (not shown) disposed in the distal end component 808, for producing a photo-electrically converted signal. This signal is input to the video processor 819 which carries out conversion to a video signal and various steps of signal processing, and the resulting signal is output to the superimposer 818.

The thermometer 820 converts the temperature of the USM 832 to an electric signal and outputs it to the temperature measuring circuit 816. The temperature measuring circuit 816 converts the electric signal to a measured temperature signal and outputs it to the display control circuit 817. The display control circuit 817 converts the measured temperature signal to an indication signal in the form of 8-bit codes, for example, and outputs it to the superimposer 818.

The superimposer 818 synthesizes the indication signal with the aforesaid video signal of the object and outputs a resulting composite video signal to the monitor 807.

Accordingly, the monitor 807 displays both the image of the object and an alarm indication for rise in temperature of the USM 832, for example.

As an alternative, the temperature of the USM 832 may be displayed on the monitor 807 in the form of numerals, for example.

Thus, this example has an advantageous effect of allowing the operator to recognize a rise in temperature of the USM 832 as a motor.

Figure 114:
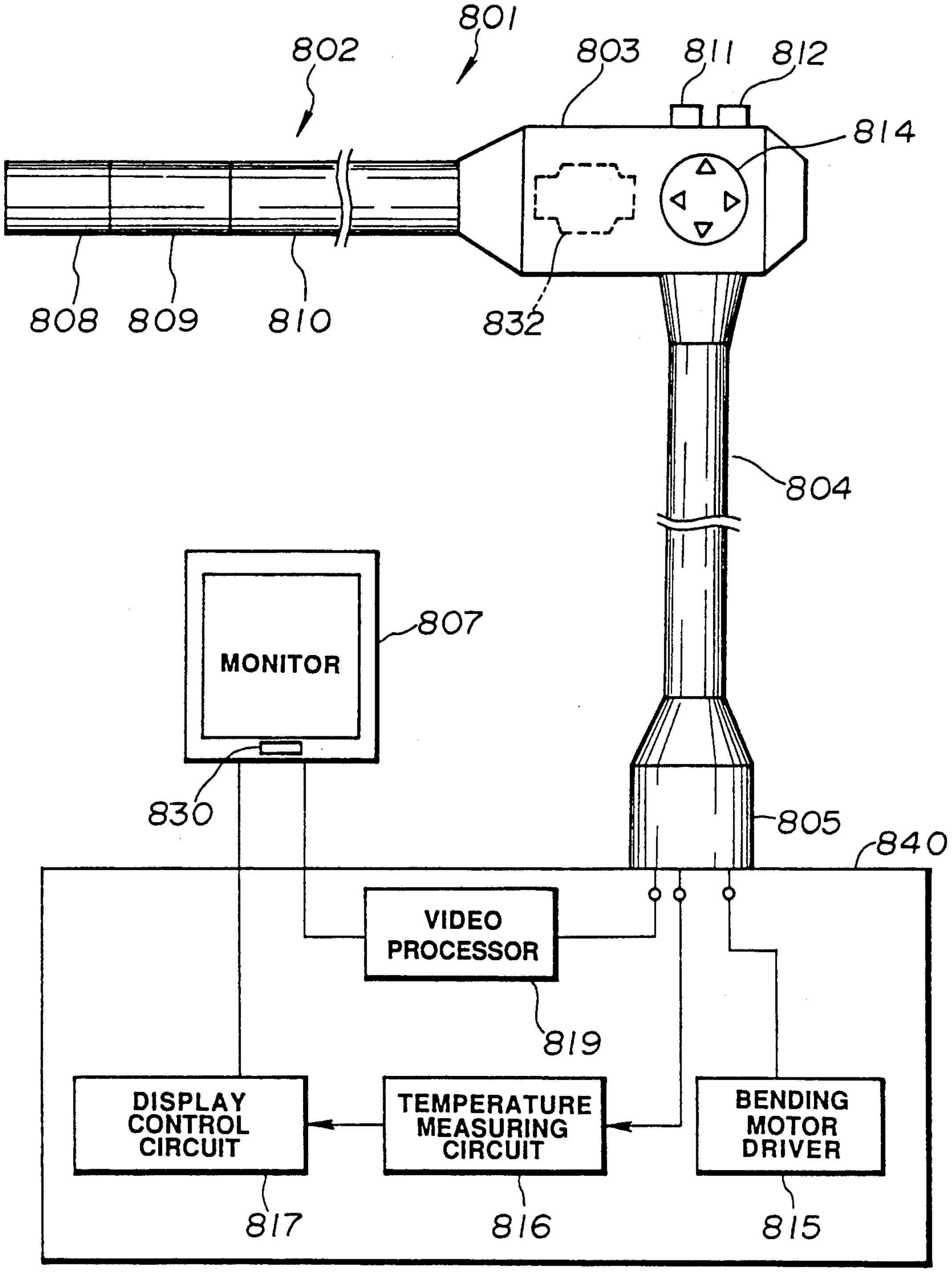

FIGS. 114 and 115 illustrate the second example. Note that the same components as those and components operating similarly to those in the first example are designated by the same reference numerals and are not explained here.

An electronic endoscope apparatus comprises an endoscope 801, a controller 840, and a monitor 807.

The controller 840 is constituted by excepting the superimposer 818 from the controller 806 explained in the first example, and outputs a video signal of the video processor 819 and an output signal of the display control circuit 817 to the monitor 807.

Figure 115A:
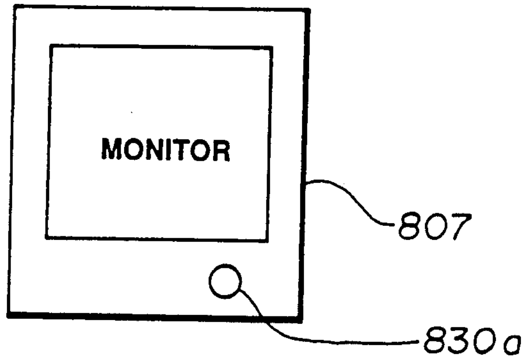
FIGS. 115(A)-115(C) are each an explanatory view showing a monitor.
Figure 115B:
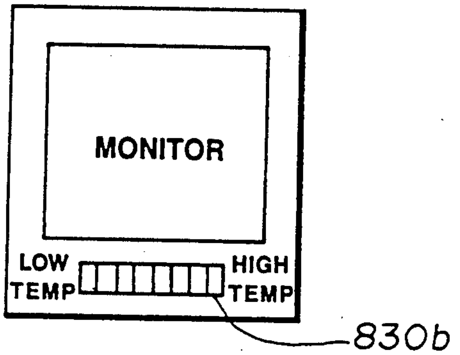
Figure 115C:
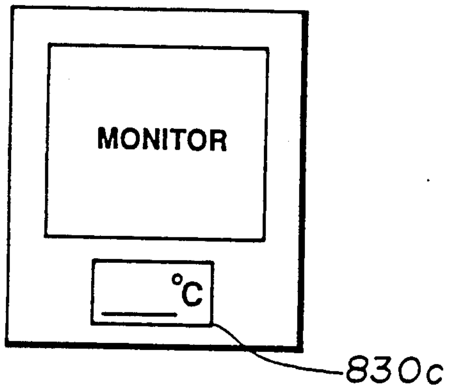

The monitor 807 is provided with a temperature display 830. This temperature display 830 comprises an indicator 830*a* formed of a light emitting diode or the like as shown in FIG. 115(A), or an indicator 830*b* formed of plural light emitting diodes or the like arrayed in the order of blue, yellow and red, for example, as shown in FIG. 115(B), or an indicator 830*c* formed of light emitting diodes or the like arranged to inform numerals, as shown in FIG. 115(C).

Operation of the electronic endoscope apparatus thus constituted will be described below.

The temperature measuring circuit 816 monitors the temperature of the USM 832 based on the electric signal from the thermometer 820 at all times, and outputs the measured temperature signal to the display control circuit 817 when the temperature of the USM 832 exceeds a predetermined value. In response to the measured temperature signal, the display control circuit 817 causes the indicator 830*a* of the temperature display 830 to light up or blink, i.e., flash on/off.

Accordingly, the operator can recognize a rise in temperature of the USM 832 as a motor at a glance from illumination or blinking of the indicator 830*a* of the temperature display 830.

Alternatively, the temperature measuring circuit 816 converts the temperature of the USM 832 to the measured temperature signal based on the electric signal from the thermometer 820 at all times, and outputs the measured temperature signal to the display control circuit 817. In response to the measured temperature signal, the display control circuit 817 drives the indicator 830*b* of the temperature display 830 to light up or blink the blue light emitting diode when the temperature of the USM 832 is at 50 degrees, the yellow light emitting diode when it is at 70 degrees, and the red light emitting diode when it is over 100 degrees, for example.

Accordingly, the operator can always recognize a temperature condition of the USM 832 as a motor from illumination or blinking of the indicator 830*b* in different colors.

As an alternative, the temperature measuring circuit 816 converts the temperature of the USM 832 to the measured temperature signal based on the electric signal from the thermometer 820 at all times, and outputs the measured temperature signal to the display control circuit 817. In response to the measured temperature signal, the display control circuit 817 drives the indicator 830*c* of the temperature display 830 to inform the temperature of the USM 832 in the form of numerals, for example.

Accordingly, the operator can always recognize the temperature of the USM 832 as a motor by just seeing the indicator 830*c* of the temperature display 830.

Furthermore, this example is also applicable to an endoscope apparatus using an image guide by providing the temperature display 830 as a separate unit.

In short, as with the first example, this example also has an advantageous effect that the operator can recognize a rise in temperature of the USM 832 as a motor.

Figure 116:
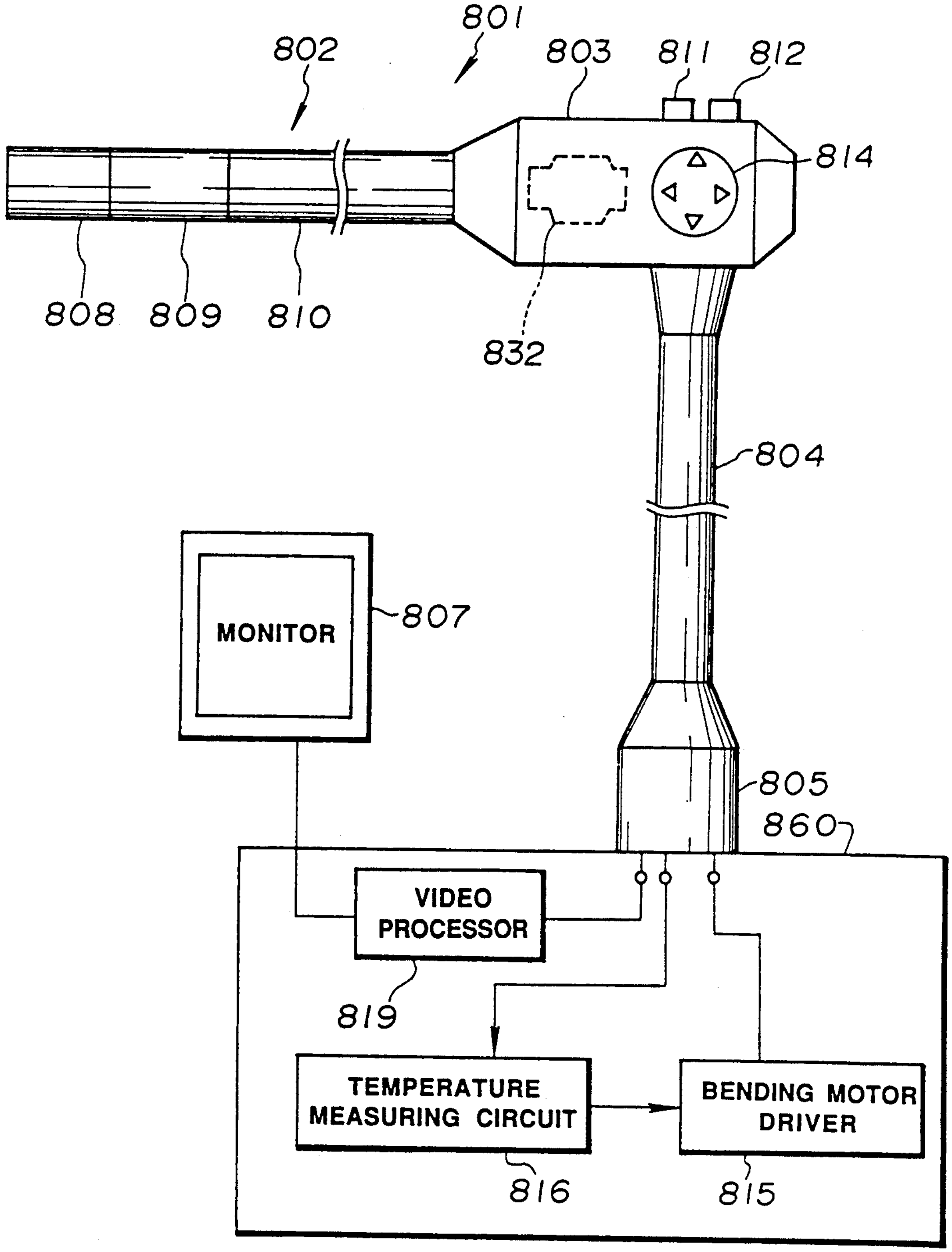

FIG. 116 illustrates the third example. Note that the same components as those and components operating similarly to those in the foregoing examples are designated by the same reference numerals and are not explained here.

An endoscope apparatus comprises an endoscope 801, a controller 860, and a monitor 807.

The controller 860 comprises a bending motor driver 815, a temperature measuring circuit 816, a video processor 819, and annunciator means (not shown).

An output terminal of the temperature measuring circuit 816 which outputs a measured temperature signal therefrom is connected to both the bending motor driver 815 and the annunciator means.

The annunciator means may be constituted by any one as explained in the above examples, or any other one explained in the following examples.

Operation of the endoscope apparatus thus constituted will be described below.

The temperature measuring circuit 816 monitors the temperature of the USM 832 based on the electric signal from the thermometer 820 at all times, and outputs a measured temperature signal to both the bending motor drive circuit 815 and the annunciator means when the temperature of the USM 832 exceeds a predetermined value.

In response to the measured temperature signal, the bending motor drive circuit 815 limits a current or voltage of the drive power supplied to the USM 832, and makes control for suppressing the amount of heat produced by the USM 832 and keeping constant or lowering the drive force of the USM 832.

Simultaneously, the annunciator means (not shown) is actuated to inform the operator of the current condition.

This example has an advantageous effect of suppressing the amount of heat produced by the USM 832 and keeping constant or lowering the drive force of the USM 832 to reduce the bending resistance.

Other advantageous effect is similar to that in the foregoing examples.

FIG. 117 illustrates the fourth example.

Figure 117A:
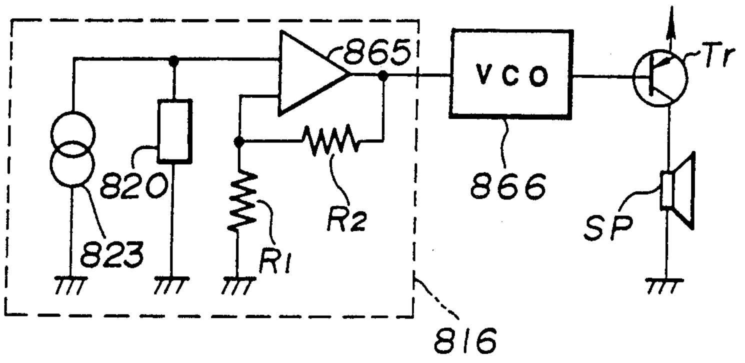
FIGS. 117(A) and 117(B) are each a circuit diagram showing annunciator means of the fourth example.

Annunciator means comprises, as shown in FIG. 117(A), temperature measuring means 816 which consists of a constant-current source 823, a thermometer 820, a resistor $R_1$, a resistor $R_2$ and an amplifier 865 for outputting an electric signal of the thermometer 820 in the form of voltage, a VCO 866 as an oscillator of which oscillation frequency is changed dependent on the voltage, a transistor Tr, and a loudspeaker SP.

Figure 117B:
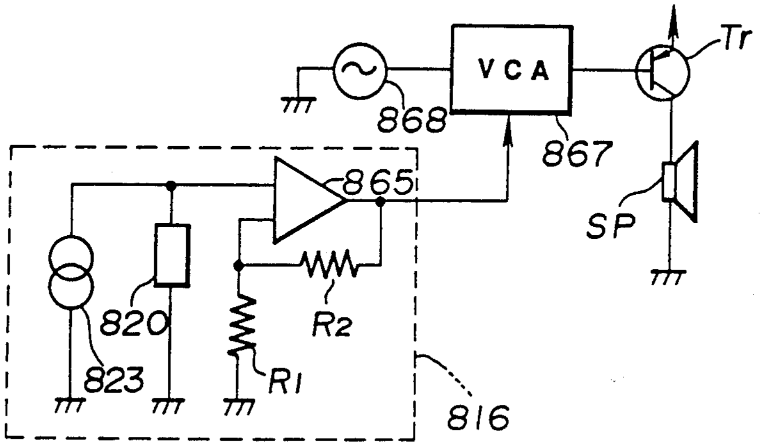

Alternatively, the annunciator means may comprise, as shown in FIG. 117(B), the aforesaid temperature measuring means 816, an audible frequency oscillator 868, a VCA 867 as an amplifier of which amplitude is changed dependent on the voltage, a transistor Tr, and a loudspeaker SP.

An output terminal of the temperature measuring means 816 is connected to a control terminal of the VCO 866 or the VCA 867, and an output terminal of the VCO 866 or VCA 867 is connected to the base of the transistor Tr. The transistor Tr has the collector connected to a power supply and the emitter grounded via the loudspeaker SP, and sounds the loudspeaker SP in response to a signal applied to the base.

Operation of the annunciator means thus constituted will be described below.

When a constant current is supplied to the thermometer 820 from the constant-current source 823, the thermometer 820 produces a voltage dependent on the ambient temperature in the area where the thermometer 820 is installed. The voltage of the thermometer 820 is amplified by the amplifier 865 to an appropriate level and input to the VCO 866 or the VCA 867.

As a result, the oscillation frequency is controlled in the case of the VCO 866. More specifically, by setting the VCO 866 to oscillate and output audible frequency when the motor temperature is increased as mentioned above, the operator can recognize a rise in temperature of the motor.

Alternatively, the degree of amplification is controlled in the case of the VCA 867. More specifically, by setting the VCA 867 to appropriately amplify and issue the output of the audible frequency oscillator 868 when the motor temperature is increased as mentioned above, the operator can recognize a rise in temperature of the motor.

In short, this example has an advantageous effect of enabling to recognize a rise in temperature of the motor with audible sounds.

Figure 118:
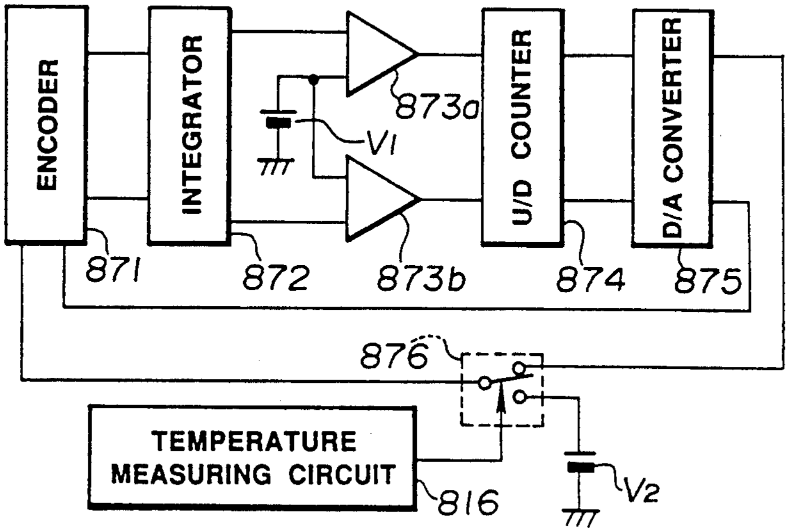

FIG. 118 illustrates the fifth example.

Annunciator means in this example is arranged such that a switch 876 and a voltage source $V_2$ are provided in a white balance circuit (describer later) in turn provided in the video processor, and an output terminal of the temperature measuring circuit 816 is connected to a control terminal of the switch 876.

The white balance circuit comprises an encoder 871 for converting a video signal in accordance with the RGB system to a video signal in accordance with the NTSC system, for example, an integrator 872 to which color difference signals $(R-Y, B-Y)$ from the encoder 871 are applied, comparators 873*a*, 873*b* for comparing output signals of the integrator 872 with a comparative (reference) voltage $V_1$, an up/down counter (hereinafter referred to as a U/D counter) 874 for adding or subtracting the count in response to output signals of the comparators 873*a*, 873*b*, and a D/A converter 875 for converting digital signals from the U/D counter 874 to analog signals. The D/A converter 875 has a first output terminal connected to a first feedback terminal of the encoder 871, and a second output terminal connected to a break point of the switch 876. A transfer terminal of the switch 876 is connected to a second feedback terminal of the encoder 871. A make contact of the switch 876 is connected to a positive terminal of the voltage source $V_2$, and a negative terminal of the voltage source $V_2$ is grounded.

Operation of the annunciator thus constituted will be described below.

Usually, a color tone of the photographed subject image is reproduced by the white balance circuit with exact fidelity. Therefore, those endoscope apparatus for observing an inner location of the body cavity produce red-based images, and those endoscope apparatus for observing other objects produce images based on the color of the object to be observed.

Now, when the temperature measuring circuit 816 detects that the amount of heat produced by the motor exceeds a predetermined value as mentioned above, the temperature measuring circuit 816 changes over the switch 876. This causes the voltage source $V_2$ to be connected to the second feedback terminal of the encoder 871 via the transfer terminal and the make contact of the switch 876. Upon this switching, the white balance circuit changes the color of the observed screen or background to any other one based on green or the like in those endoscope apparatus for observing the inner location of the body cavity, for example.

In short, this example has an advantageous effect of allowing the operator to recognize a rise in temperature of the motor while seeing the screen for observation.

FIG. 112 also illustrates the sixth example as well as the first example. Note that the internal structure of the sixth example is similar to that of the first example, and hence only the parts relating to the sixth example will be explained here.

In this example, a paint of which color is changed dependent on temperatures (hereinafter referred to as a thermopaint) is applied onto the case 825 of the USM 832. The operating section of the endoscope is formed with a window formed of a transparent window so that the operator can confirm the area of the case 825 where the thermopaint is applied.

Instead of forming the above window in the operating section, a heat conducting member may be provided between the operating section and the case 825, and the thermopaint may be applied onto the operating section.

In short, this example has an advantageous effect of allowing the operator to recognize a rise in temperature of the motor from a change in color of the thermopaint.

Note that the motor is not limited to a USM in the above respective examples, and may be of any other type such as a DC motor or AC motor.

According the first through sixth examples, as described above, by allowing the operator to recognize an increase in the amount of heat produced by a motor, e.g., an overload condition of the motor, it is possible to avoid such an overload condition of the motor and ensure the stable operation.

Meanwhile, bending means of a conventional endoscope is arranged such that a bending wire extended through an insert section is manually pushed and pulled in an operating section. Accordingly, the operator is able to know the bent amount by resorting to a hand feeling only, and cannot obtain exact information of the bent amount.

Therefore, with a view of exactly detecting the bent amount, Japanese Utility Model Publication No. 37923/1988 or Japanese Utility Model Laid-Open No. 10661/1985 discloses a technique that a rotary potentiometer is provided in a drive mechanism for a bending wire, or a technique that a resistance member of a variable resistor is attached to an outer tube of an operating section and a slidable member is attached to a bending wire, thereby constituting a potentiometer.

Further, Japanese Patent Laid-Open No. 99827/1988 or Japanese Patent Laid-Open No. 122834/1986 discloses a technique of providing a conductive rubber or a magnetic resistance element in the distal end portion of an endoscope.

However, the provision of the conductive rubber, the magnetic resistance element or the like in the distal end portion to detect the bent amount results in drawbacks of increasing the outer diameter of the distal end portion, forcing a patient to suffer much pain during examination, and restricting a range of use in which insertion of the endoscope is allowable.

Also, if the potentiometer or the like is provided in the operating section like the above conventional technique, the operating section is enlarged in size and operability is impaired.

Therefore, FIGS. 119 through 126 illustrate three examples of an endoscope apparatus in which a device for detecting the bent amount can be provided in an operating section of an endoscope without enlarging size of the operating section and degrading operability.

In these examples, a part of a bent amount detection device such as a bent amount sensor is disposed in the space surrounded by both a rotatable member provided in an operating section for the bending operation and a pulling member having its part wound around the rotatable member and being pulled to bend a bendable portion upon rotation of the rotatable member, thereby enabling to detect the bent amount without enlarging size of the operating section.

Figure 120:
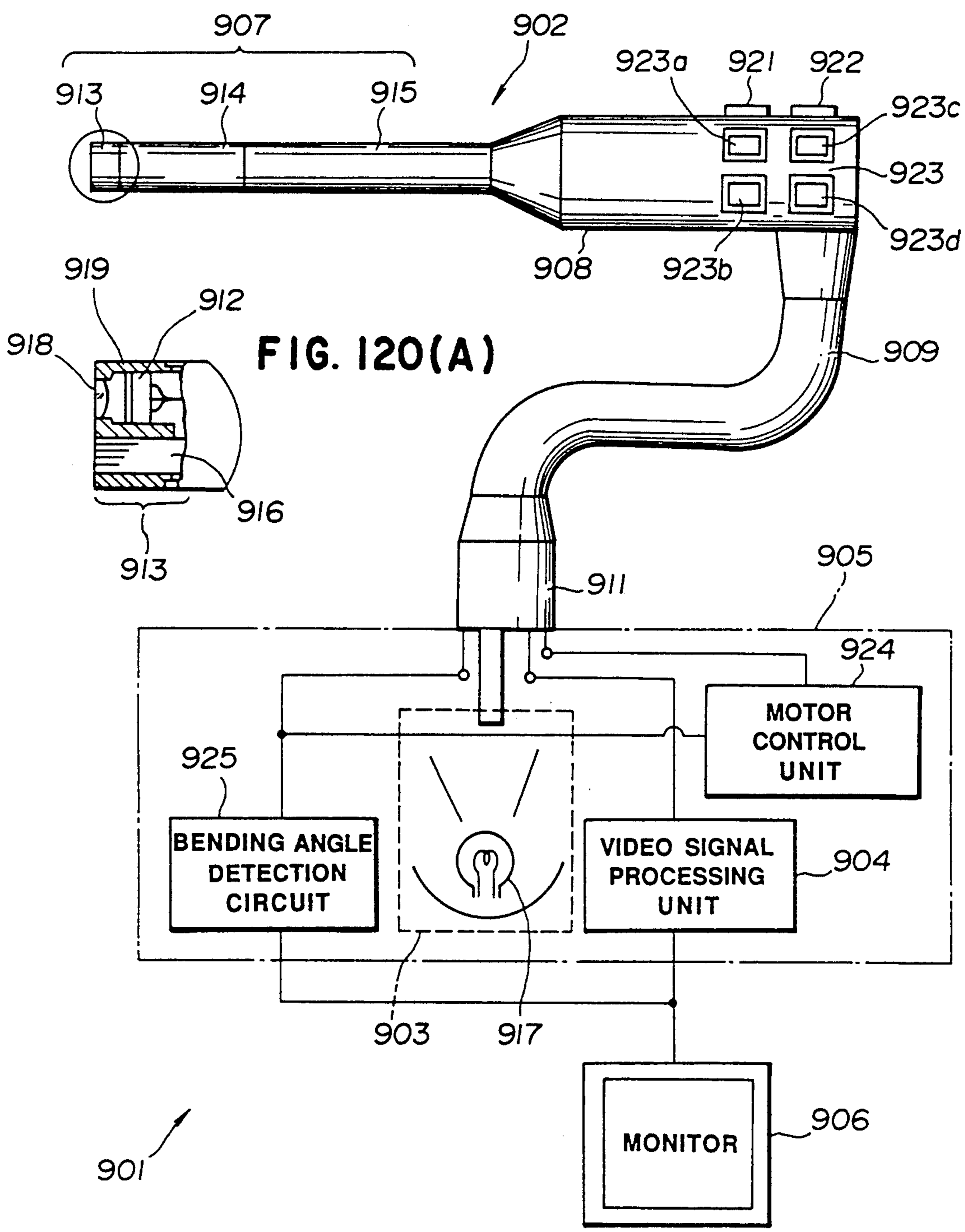
FIGS. 119 through 126 are concerned with three examples of an endoscope apparatus in which a device for detecting the bent amount of a bendable portion is provided in an operating section.
Figure 119:
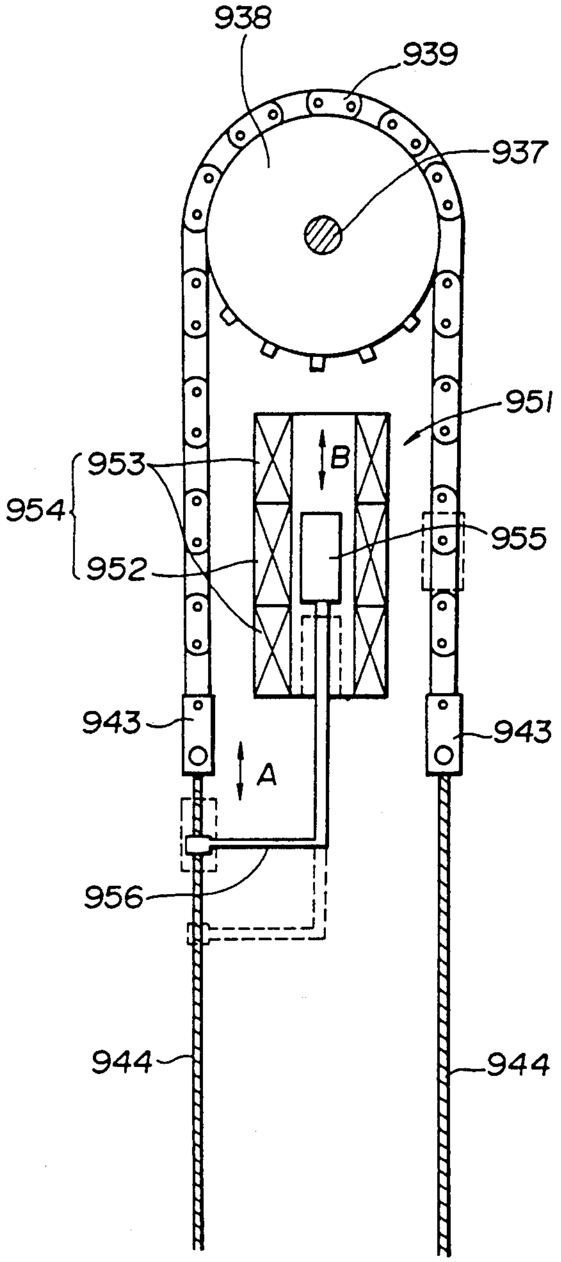
Figure 121:
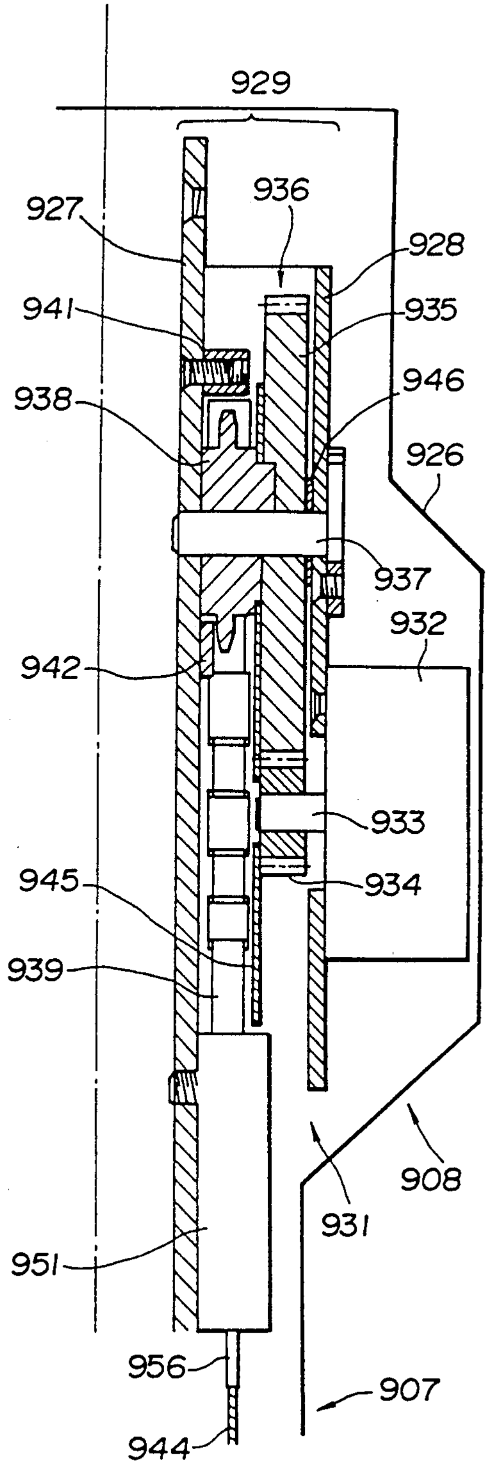

FIGS. 119 through 121 illustrate the first example.

An endoscope apparatus 901 of the first example comprises, as shown in FIG. 120, an electronic endoscope 802, a video processor 905 incorporating both a light source unit 903 to supply a beam of illumination light to the electronic endoscope 902 and a video signal processing control unit 904, and a monitor 906 for displaying a standard video signal produced from the video signal processing control unit 904.

The electronic endoscope 902 comprises an insert section 907 which is so flexible and elongate as to allow its insertion into the body cavity or the like, a larger-diameter operating section 908 formed at the rear end of the insert section 907, a universal cord 909 extended laterally from the operating section 908, and a connector 911 provided at the end of the universal cord 909. The connector 911 is freely connectable to the video processor 905 in a detachable manner.

The insert section 907 comprises a hard distal end component 913 in which a CCD 912 and others are disposed, a bendable portion 914 provided adjacent the distal end component 913 on the rear side thereof, and an elongate, flexible pipe portion 915 provided at the rear end of the bendable portion 914.

In the insert section 907, there extends a light guide 916 for transmitting the illumination light. The light guide 916 is further extended through the operating section 908 and then the universal cord 909. Thus, under a condition that the connector 911 is connected to the video processor 905, the illumination light emitted from a lamp 917 in the light source unit 903 is supplied to the end face of the light guide 916. The light guide 916 transmits the illumination light emitted from the lamp 917, and radiates it forwards from the end face of the distal end component 913. An optical image of an object irradiated by the emergent light is focused by an objective lens 918 provided in the distal end component 913 onto the CCD 912 located in the focus plane of the objective lens 918. A color mosaic filter 919 for color separation is attached to the imaging plane of the CCD 912 to carry out color separation for each pixel. A signal subjected to photo-electric conversion by the CCD 912 is input via a signal line to the video signal processing unit 904 which executes various steps of signal processing for conversion to a standard video signal. Based on this video signal, the object image is displayed on the monitor 906.

On the operating section 908 of the electronic endoscope 902, there are provided an air-feed/water-feed switch button 921, a suction switch button 922, and a set of bending switches 923.

The set of bending switches 923 include an upward switch button 923*a*, a downward switch button 923*b*, a leftward switch button 923*c*, and a rightward switch button 923*d*.

When one of the bending switches 923 is depressed to bend the bendable portion 914, a motor control unit 924 and a bending angle detection circuit 925 both in the video processor 905 are operated to control a drive motor for bending the bendable portion 914 and detect a bending angle.

A bending actuator as shown in FIG. 121 is assembled in the operating section 908.

Within a case 926 of the operating section 908, there are disposed two sets of frame assemblies 929, 929 (only one of them being shown in FIG. 121) which are positioned in laterally symmetrical relation and each of which comprises a main frame 927 and a sub-frame 928 arranged parallel to each other with a space defined therebetween.

A bending actuator 931 for the vertical (upward/-downward) bending is mounted to one frame assembly 929, while another bending actuator (not shown) for the horizontal (rightward/leftward) bending is mounted to the other frame assembly 929.

The bending actuator 931 for the vertical bending shown in FIG. 121 will be explained in detail below.

A DC motor 932 is mounted to the sub-frame 928 supported by the main frame 927. A drive gear 934 is secured to a drive shaft 933 of the DC motor 932 by press-fitting or the like, and is held in mesh with a driven gear 935 on the side of the drive gear 934 opposite to the insert section 907, thereby constituting a transmission gear train 936.

The driven gear 935 is rotatably attached to a shaft 937 and coaxially joined with a sprocket 938 which is rotatably supported on the shaft 937 at a position near the main frame 927. The shaft 937 is fixed screwed to the sub-frame 928, so that the driven gear 935 and the sprocket 938 are rotated about the shaft 937 together.

The sprocket 938 constitutes a rotatable member for pulling operation, and a chain 939 is entrained about the sprocket 938. Around the outer circumference of the chain 939 entrained about the sprocket 938, chain guides 941, 942 for guiding and preventing the chain 939 from slipping out of the sprocket 938 are fixedly screwed to the main frame 927.

As shown in FIG. 119, both ends of the chain 939 entrained about the sprocket 938 are coupled to bending wires 944, 944 via joint pieces 943, 943, respectively. Thus, the chain 939, the joint pieces 943, 943, and the bending wires 944, 944 jointly constitute a pulling member. These bending wires 944, 944 are extended through the insert section 907 and coupled to the front end of the bendable portion 914 or the rear end of the distal end component 913. As the sprocket 938 rotates, the bending wires 944, 944 are pushed and pulled (or loosened and tensioned) dependent on the rotating direction of the sprocket 938 such that one wire 944 is pushed and the other wire 944 is pulled, thereby enabling to bend the bendable portion 914.

Further, as shown in FIG. 121, a partition 945 is provided between the chain 939 and the transmission gear train 936 for preventing the chain 939 from striking against the transmission gear train 936.

Moreover, in order to prevent the transmission gear train 936 from directly striking against the sub-frame 928, a cushion member 946 is fitted around the shaft 937 at a position therebetween.

In this example, as shown in FIG. 119, means of detecting the bent amount of the bendable portion 914, i.e., a differential transformer 951 constituting a bent amount sensor, is disposed in the space defined between the sprocket 938 and both ends or two runs of the chain 939 entrained about the sprocket 938 and extending substantially parallel to each other with a spacing or distance corresponding to the diameter of the sprocket 938. The differential transformer 951 is fixedly screwed to the main frame 927 as shown in FIG. 121.

The differential transformer 951 has a coil unit 954 which comprises a primary coil 952 having a substantially cylindrical outer configuration, and a pair of secondary coils 953 each provided on either side of the primary coil 952. The central axis of the coil unit 954 is arranged substantially parallel to the direction in which the chain 939 is moved. A core 955 is located inside the coil unit 954 and fixed to the distal end an L-shaped arm 956 which is in turn fixed to one bending wire 944 by soldering or the like. When that bending wire 944 moves as indicated by arrow A, the core 955 is also moved as indicated by arrow B in interlock with the movement of the bending wire 944 in the same direction and by the same distance.

The coil unit 954 of the differential transformer 951 is connected to the bending angle detection circuit 925 in the video processor 905. By applying a voltage of constant frequency to the primary coil 952 and detecting a difference between respective voltages induced in the secondary coils 953, 953, the bending angle detection circuit 925 can determine the direction and distance of movement of the core 955, i.e., the direction and distance of movement of the bending wire 944, based on the polarity and extent of the detected voltage difference. The bending angle detection circuit 925 calculates the bending angle (bent amount) of the bendable portion 911 from the above direction and distance of movement of the core, and displays it on the monitor 906.

In addition, the set of bending switches 923 and the DC motor 932, 932 (only one of them being shown in FIG. 121) are connected to the motor control unit 924. Depending on one of the bending switches 923 being operated, the motor control unit 924 supplies a drive current necessary for desired control including the rotating direction of the DC motors 932, 932.

Operation of this first example will be described below.

After inserting the insert section 907 of the electronic endoscope 902 into the body cavity, when it is desired to bend the bendable portion 914 upwards, the operator depresses the upward switch button 923*a* among the set of bending switches 923.

Upon the switch operation, the DC motor 932 is revolved to rotate the drive gear 934 secured to the drive shaft 933 of the DC motor 932, whereby the driven gear 935 held in mesh with the drive gear 934 and the sprocket 938 corotatable with the driven gear 935 are rotated. As the sprocket 938 rotates, the chain 939 is turned to pull the upper bending wire 944 coupled to one end of the chain 939 and let out the lower bending wire 944. As a result, the bendable portion 911 is forcibly bent upwards.

As the upper bending wire 944 is pulled to move in either direction, the arm 956 secured at one end to the wire 944 is also moved in the same direction so that the core 955 fixed to the arm 956 is moved through the coil unit 954 in interlock relation.

Upon the movement of the core 955, the degree of electromagnetic coupling between the primary coil 952 and the two secondary coils 953, 953 is changed to produce a potential difference between the two secondary coils 953 and 953 which is proportional to the displaced amount of the core 955. This potential difference is detected by the bending angle detection circuit 925 and then converted to the direction and distance of movement of the bending wire 944. Based on this distance of movement, the bending angle is determined through the arithmetic processing and displayed on the monitor 906.

With this first example, since the differential transformer 951 as a sensor for detecting the bent amount of the bendable portion 914 is disposed in the space defined at a position adjacent the sprocket 938 as the rotatable member for operating the pulling member and in a region between both ends or two runs of the chain 939 extending substantially parallel to each other and coupled to the bending wires 944, 944, respectively, the bent amount sensor can be stored without increasing size of the operating section 908. Accordingly, it is possible to prevent a reduction in operability.

Although the DC motor 932 is used as drive means for driving the sprocket 938 to rotate in the foregoing first example, the drive means is not limited to the DC motor. It may be of any other rotary type motor such as a ultrasonic motor, stepping motor or AC motor.

Figure 122:
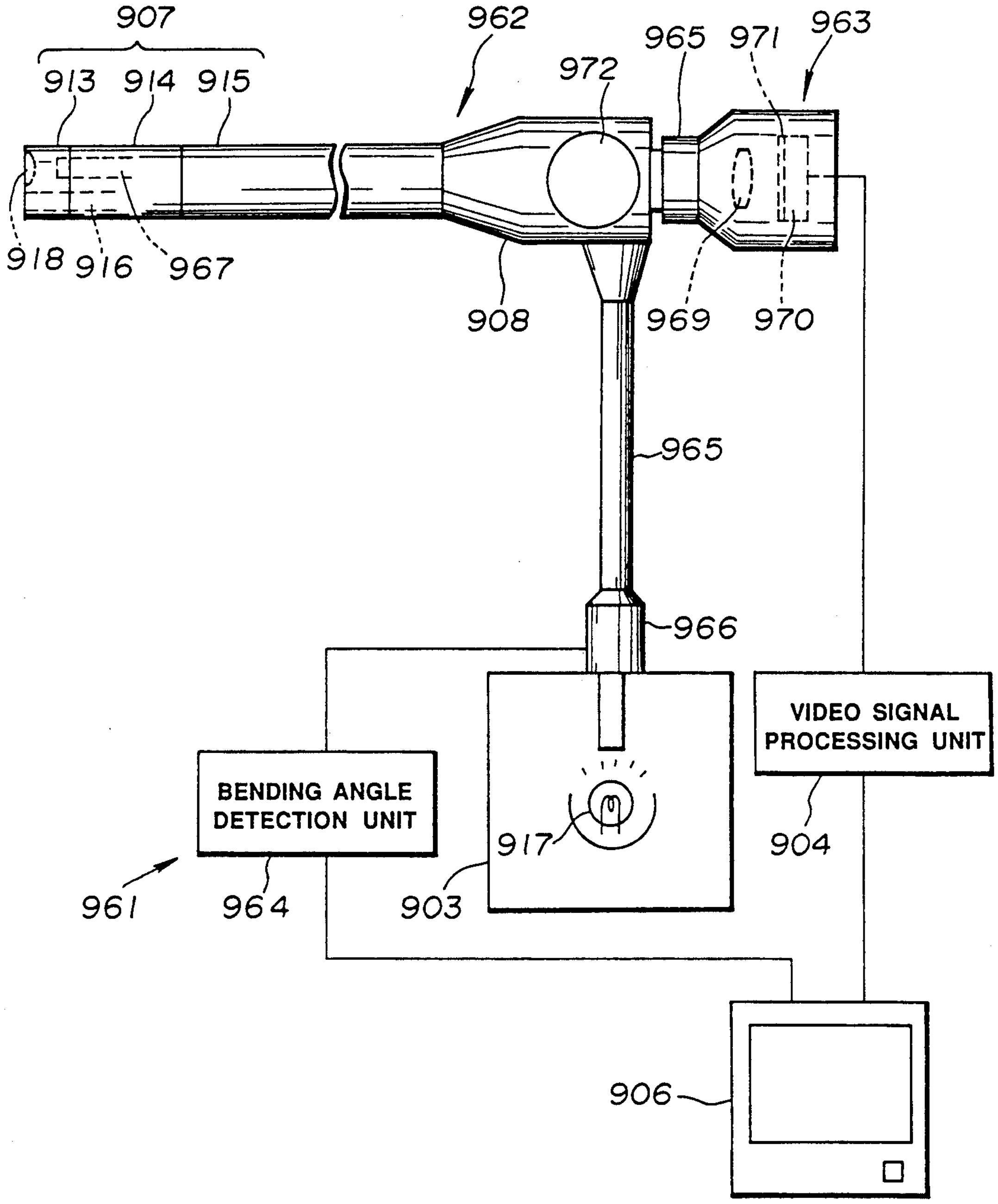

FIG. 122 illustrates the second example.

Note that the identical components to those in the first example are designated by the same reference numerals. An endoscope apparatus 961 of this example comprises a fiber scope 962, a mount type television (TV) camera 963 fitted to the fiber scope 962, a light source unit 903 for supplying a beam of illumination light to the fiber scope 962, a video signal processing unit 904 for processing a signal from the TV camera 963, a monitor 906 for displaying a video signal produced by the video signal processing unit 904, and a bending angle detection unit 964 for detecting the bent amount of a bendable portion 914.

As with the electronic endoscope 802, the fiber scope 962 has an insert section 907 comprising a distal end component 913, the bendable portion 914 and a flexible pipe portion 915, and an operating section 908. An eyepiece portion 965 is formed at the rear end of the operating section 908, and the TV camera 963 is detachably fitted to the eyepiece portion 965.

A light guide 916 is extended through the insert section 907 of the fiber scope 962 and further through a light guide cable 965 which is extended to the exterior from the operating section 908. By connecting a connector 966 to the light source unit 903, the illumination light of a lamp 917 is supplied to the light guide 916.

An objective lens 918 is attached to the distal end component 913 of the insert section 907, and the front end face of an image guide 967 is located in the focus plane of the objective lens 918. The image guide 967 serves to transmit an optical image to the rear end face thereof located in the eyepiece portion 965. An eyepiece is disposed opposite to the rear end face of the image guide 967 so that the operator can observe the optical image transmitted and magnified through the eyepiece by the naked eye.

Further, a focusing lens 969 is disposed in the TV camera 963 so as to focus the optical image onto a CCD 970. A mosaic filter 971 for color separation is attached to the imaging plane of the CCD 970.

A bending control knob 972 is provided on the operating section 908 of the fiber scope 961. By turning the knob 972, the bendable portion 914 can be bent manually.

Figure 123:
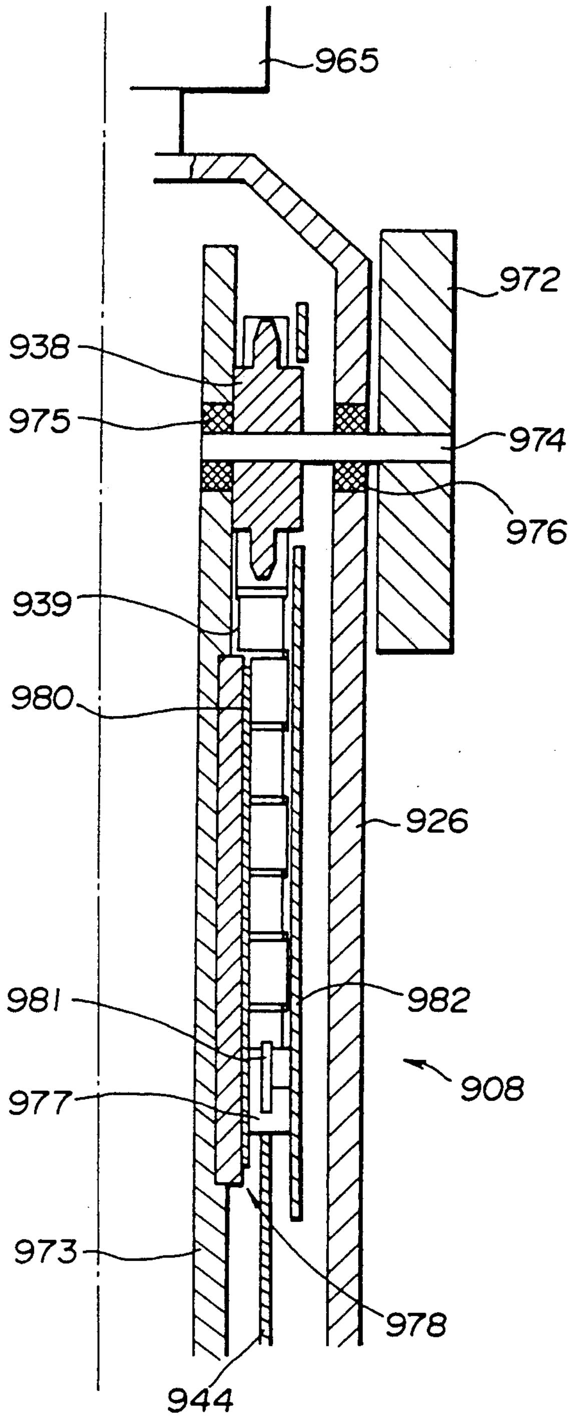

FIG. 123 shows the structure of a bending actuator inside the operating section 908.

Within a case 926 of the operating section 908, there is disposed a frame 973 facing the inner surface of the case 926. A sprocket 938 is mounted to the frame 973 in facing relation to the inner surface of the case 926, and secured to a shaft 974 by screws (not shown) or the like. The shaft 974 is rotatably supported at one end near the frame 973 by a bearing 975 built in the frame 973, and at its intermediate portion by another bearing 976 built in the case 926, with the other end of shaft 974 projected to the exterior. The knob 972 is secured to the projected end of the shaft 974.

Accordingly, the sprocket 938 can be rotated by turning the knob 972.

Figure 124:
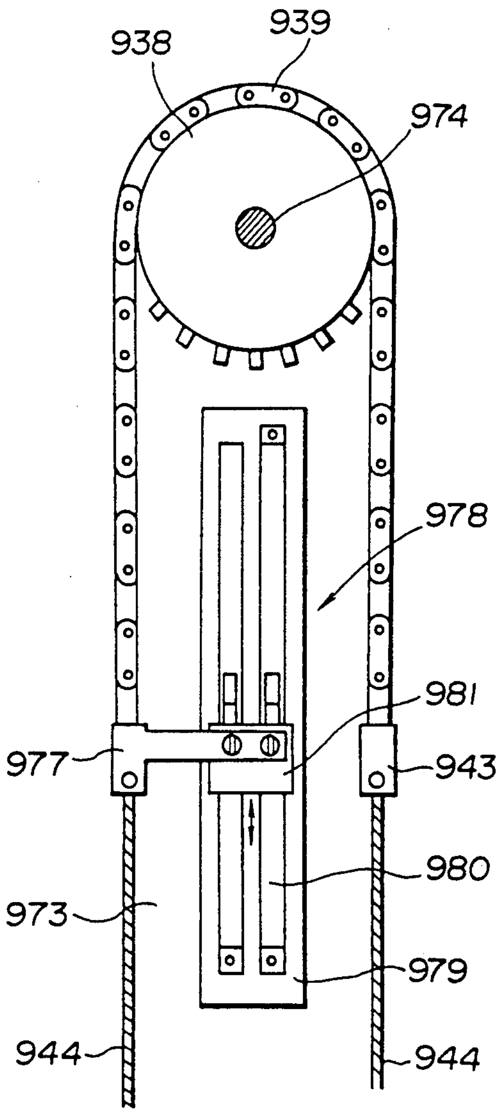
Figure 125:
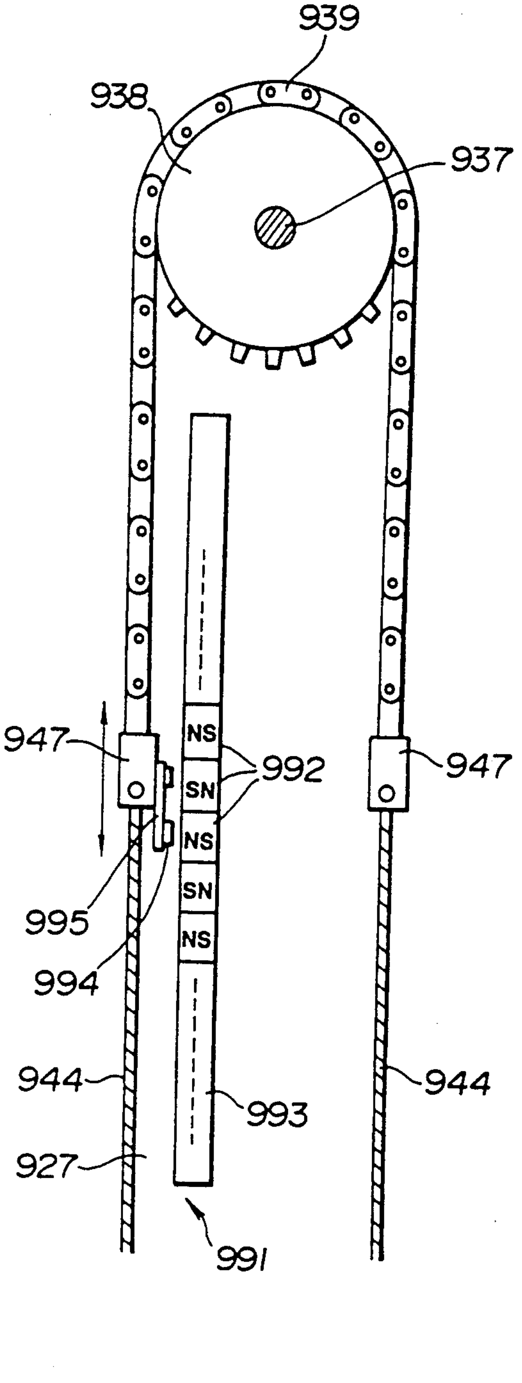

As shown in FIG. 124, a chain 939 is entrained about the sprocket 938. A joint piece 943 and an arm-fitted joint piece 977 are attached to both ends of the chain 930, respectively. Bending wires 944, 944 are coupled to both ends of the chain 930 via the pieces 943, 977, respectively.

A linear type potentiometer 978 as a bent amount sensor is disposed in the space surrounded by the sprocket 938, the chains 939 entrained about the sprocket 938, and the bending wires 944, 944 coupled to both ends of the chain 939 via the joint pieces 943, 977.

More specifically, as shown in FIG. 124, a resistance element base plate 979, which constitutes the linear type potentiometer 978, is built in the frame 973 such that the longitudinal direction of the base plate 979 is parallel to the direction of movement of the chain 939. On the resistance element base plate 979, an elongate resistance element 980 is attached to extend in the longitudinal direction of the base plate 979 so that a brush 981 secured to the arm-fitted joint piece 977 by screws or the like can smoothly slide over the resistance element 980.

As shown in FIG. 123, the brush 981 is kept by a hold plate 982 in a contact state with the resistance element 980 at all times even during movement of the brush.

While FIG. 123 shows the bending actuator for the vertical bending by way of example, another bending actuator (not shown) of the same structure, but for the horizontal bending, is provided on the left side on the drawing.

The linear type potentiometer 978 is connected to the bending angle detection unit 964 via a signal line (not shown), extended through the light guide cable 965 shown in FIG. 122, and the connector 966. Thus, depending on the distance of movement of the arm-fitted joint piece 977, the resistance between the brush 981 and the end of the resistance element 980 is changed, and this change in the resistance is converted by the bending angle detection unit 964 to the bending direction and the distance of movement. Then, the bending angle is determined from that distance of movement through the process of calculations and displayed on the monitor 906.

Operation of this second example will be described below.

After inserting the insert section 907 of the fiber scope 962 into the body cavity, when it is desired to bend the bendable portion 914 upwards, the operator turns the knob 972 in a direction corresponding to the upward bending direction, whereby the sprocket 938 is rotated about the shaft 974. As the sprocket 938 rotates, the chain 939 is turned to pull the upper bending wire 944 coupled to one end of the chain 939 and let out the lower bending wire 944. As a result, the bendable portion 914 is forcibly bent upwards.

During the above bending operation, as the chain 939 is turned and moved, the brush 981 secured to the arm-fitted joint piece 977 is also moved over the resistance element 980 on the base plate 979 concurrently. Thus, the pick-up resistance is changed proportional to the distance between the brush 981 and the resistance element 980.

This change in the resistance is converted by the bending angle detection unit 964 to the bending direction and the distance of movement. Then, the bending angle is determined from that distance of movement through the process of calculations and displayed on the monitor 906.

In this second example, use of the linear type potentiometer 978 enables to reduce its height and hence achieve a reduction in size of the operating section 908.

Since the resistance element base plate 979 is built in the frame 973, it is possible to facilitate manufacture, reduce the required height, and hence achieve a reduction in both size and thickness of the operating section 908.

Where the resistance element base plate 979 is molded using plastics, the entire weight can be reduced.

Further, an optical linear type potentiometer may instead be used by forming the resistance element 980 of a photoconductive material and employing an LED or light guide end in place of the brush 981. This modification makes it possible to detect the distance of movement in a contactless manner for calculating the bending angle, prevent erroneous detection of the bending angle due to contact failure or other causes, and reduce the power necessary for the bending operation.

In addition, an Induct-thin utilizing electromagnetic induction may be used instead of the linear type potentiometer 978.

Figure 25:
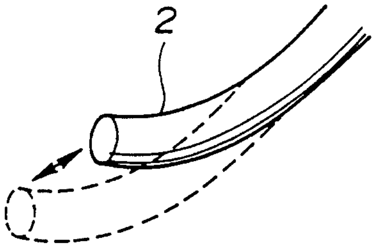
Figure 26:
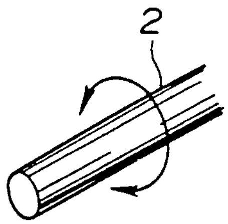

FIG. 25 illustrates the third example.

This example is to employ a magnetic linear type encoder 991 instead of the differential transformer 951 in the above first example.

A linear magnetic scale 993 formed by a train of small magnets (indicated at 992), which can be magnetized in such a manner as to alternately produce N and S poles at the desired pitch, is attached to a main frame 927 in the space surrounded by a sprocket 938, a chain 939 entrained about the sprocket 938 and others, as well as over a range where one end of the chain 939 is movable, such that the scale 993 extends parallel to the direction of movement of the chain 938. In this connection, a groove or recess in which a part of the linear magnetic scale 992 is to be built may be formed in the main frame 927.

On the other hand, a base plate 995 mounting a Hall IC 994 thereon is secured to a joint piece 943 by screws or the like. The Hall IC 994 is positioned to face the magnetic scale 993 with a spacing of about 0.5 mm–1 mm therebetween, for example. Thus, as the Hall IC 994 moves together with the joint piece 943, it intersects the magnetic fields produced by the small magnets 992, . . . constituting the magnetic scale 993, and hence generates pulse-like signals proportional to the number of magnetized magnets, which number in turn corresponds to the distance of movement of the Hall IC. These pulse-like signals are detected by the bending angle detection circuit 925 shown in FIG. 120 to determine the bending angle.

Operation of this third example will be described below.

As the sprocket 938 rotates, the chain 939 is moved and the joint piece 943 is also moved together. Therefore, the Hall IC 994 on the base plate 995 secured to the joint piece 943 moves over the magnetic scale 993 and generates the pulse-like signals proportional to the number of magnetized magnets and hence corresponding to the distance of movement of the Hall IC. Based on the pulse-like signals, the bending angle detection circuit 925 calculates the distance of movement of the chain 939, i.e., the bending angle, and displays it on the monitor 906.

The bending direction may be detected by taking out the signal representing the revolving direction of the motor from the motor control unit 924.

With this third example, the size and weight can be reduced by using the Hall IC 994.

Because of the contactless detection, the power necessary for the bending operation is not increased and a motor of relatively small size and torque can be used to drive the sprocket to rotate.

Further, a magnetic resistance element may be used instead of the Hall IC 994. In this case, a magnetic substance may be applied onto the main frame 927, and a magnetic scale may be formed in the main frame body. This contributes to further reduce the size and weight.

Figure 126:
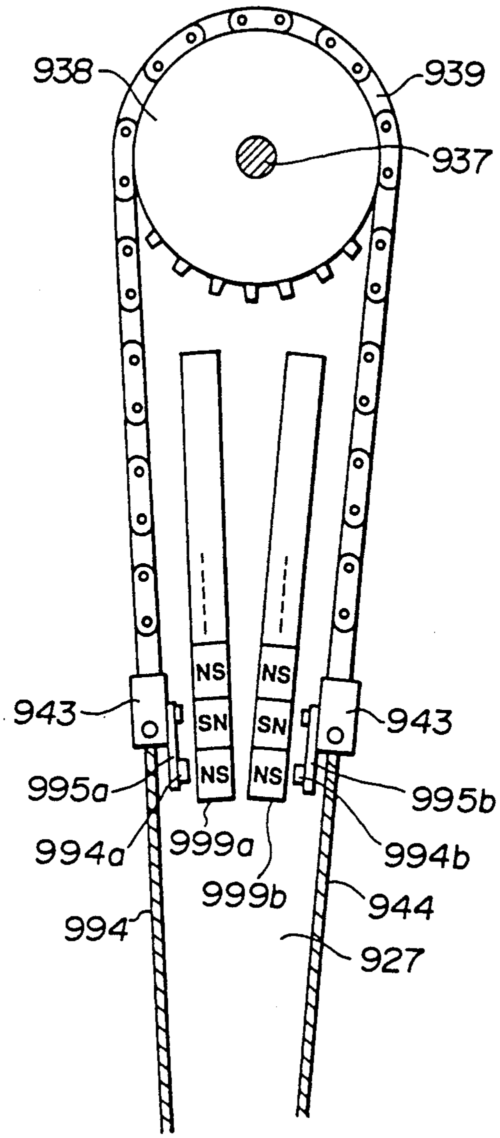

FIG. 126 illustrates a principal part of a modification of the third example. In this modification, a pair of magnetic scales 999*a*, 999*b*, each of which is obtained by reducing the length of the magnetic scale 991 of the third example to nearly half of the original one, are fixed to the main frame 927 over a length to cover about half of the range where each end of the chain 939 is movable, such that the scales 999*a*, 999*b* extend parallel to the direction of movement of the chain.

Hall IC's 994*a*, 994*b* are attached to the joint pieces 943, 943 via base plates 995*a*, 995*b*, respectively.

Those Hall IC's 994*a*, 994*b* are connected to the bending angle detection circuit 925, and used such that one Hall IC 994*b* detects the bent amount of zero and in the upward direction, and the other Hall IC 994*a* detects the bent amount in the downward direction.

By thus employing the two magnetic scales 999*a*, 999*b* and the two Hall IC's 994*a*, 994*b* each for either bending direction, the operating section 908 can be reduced in its length.

Note that in this modification, the wires 944, 944 are arranged to have a narrower spacing therebetween.

Moreover, utilization of the space defined by the sprocket 938, the chain 939 and others is not limited to install a sensor as the bent amount detection means therein. At least a part of the bending angle detection device, such as a part of the bending angle detection circuit 925, may be disposed in that space.

According to the first through third examples, as described above, since sensor means of the bending detection means for detecting the bent amount of the bendable portion of the insert section is disposed in the space surrounded by the rotatable member for pulling operation and the pulling member, an increase in size of the operating section resulted from providing the bending detection means can be prevented effectively.

Meanwhile, for the purpose of forcibly bending a bendable portion in an insert section of an endoscope, when an electric motor is mounted into an operating section of the endoscope and a pulling member for bending operation is pulled by utilizing power of the electric motor to remotely bend the bendable portion, the operating section tends to increase in size because the electric motor is stored in the operating section. This may cause a problem of impairing operability.

It is therefore conceivable to use a plurality of gears for compensating torque, thereby to make the motor as small as possible in size correspondingly, as proposed in the specification of DE 2504663 C2.

In many cases, however, the proposed technique is not so effective in making the operating section more compact with its sole use, because of the presence of gear bodies and members for supporting the gears. If a complicated or elaborate gear mechanism, in particular, is adopted from the need of relatively large drive force for the bending operation, the entire size would be increased on the contrary. Thus, there has been experienced a difficulty in mounting a motor into the operating section compactly.

Further, since both of the vertical bending operation and the horizontal bending operation are performed in usual endoscopes, two sets of bending actuators for carrying out the bending operation in the respective directions must be installed in the operating section, and hence the size of the operating section is increased all the more.

Figure 135:
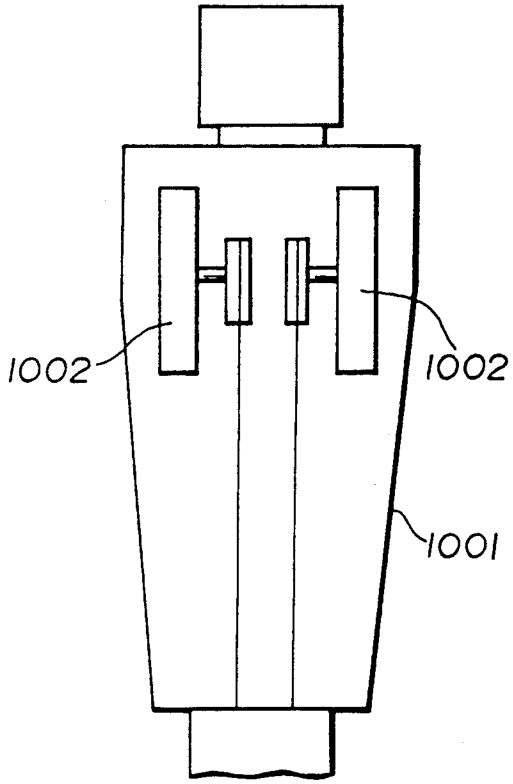
Figure 136:
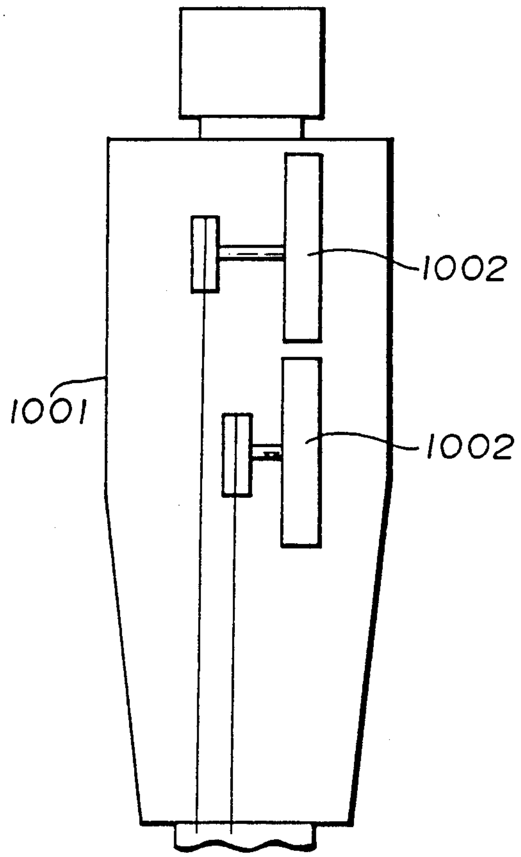

The manner of mounting those two bending actuators into an operating section 1001 of the endoscope can be practiced by arranging two motors 1002, 1002 in laterally symmetrical relation as shown in FIG. 135, or by arranging two motors 1002, 1002 to be offset in the longitudinal or back and forth direction of an operating section 1001 as shown in FIG. 136.

But, the laterally symmetrical arrangement of the two motors 1002, 1002 as shown in FIG. 135 is disadvantageous in enlarging the diameter of the operating section 1001 of the endoscope too much. The axially offset arrangement of the two motors 1002, 1002 in the longitudinal direction of an operating section 1001 is also disadvantageous in increasing the length of the operating section 1001 too much. Thus, either arrangement is not effective in achieving the easy operation.

In view of the above, FIGS. 127 through 134 illustrate five examples of a bending actuator for an endoscope using a motor as drive source, which can realize the compact structure by using a transmission gear mechanism to transmit power to a rotatable member for bending operation and by uniquely designing its layout structure.

The bending actuator for the endoscope of these examples comprises a bending drive motor installed in an operating section of the endoscope, a transmission gear mechanism driven by the bending drive motor to rotate, a rotatable member for pulling operation driven by the bending drive motor via the transmission gear mechanism to rotate, and a pulling member wound around the rotatable member for pulling operation and extended through the insert section of the endoscope toward the distal end thereof for bending a bendable portion of the insert section when the pulling member is pulled upon rotation of the rotatable member, wherein a bearing to receive a rotary shaft of at least one of those gears constituting the transmission gear mechanism is disposed in the space surrounded by the rotatable member and the pulling member.

With this constitution, therefore, the layout structure of the transmission gear mechanism and others for increasing drive torque can be compacted.

Further, the bending actuator for the endoscope of these examples includes two bending actuators installed in an operating section of the endoscope, and each of these bending actuators comprises a bending drive motor, a transmission gear train driven by the bending drive motor to rotate, a rotatable member for pulling operation driven by the bending drive motor via the transmission gear train to rotate, and a pulling member wound around the rotatable member for pulling operation and extended through the insert section of the endoscope toward the distal end thereof for bending a bendable portion of the insert section when the pulling member is pulled upon rotation of the rotatable member, wherein the rotatable member for pulling operation in each bending actuator is located on the side of its own transmission gear train near to the other bending actuator.

With this constitution, therefore, the drive force can be increased by the transmission gear train, and the bending drive motor can be made smaller in size as far as possible. Also, since the rotatable member is arranged inside the transmission gear train so that the transmission gear train is located on the outer side, the operating section of the endoscope can be compacted without increasing the length and thickness or diameter of the operating section.

FIGS. 127 through 130 illustrate the first example.

Figure 130:
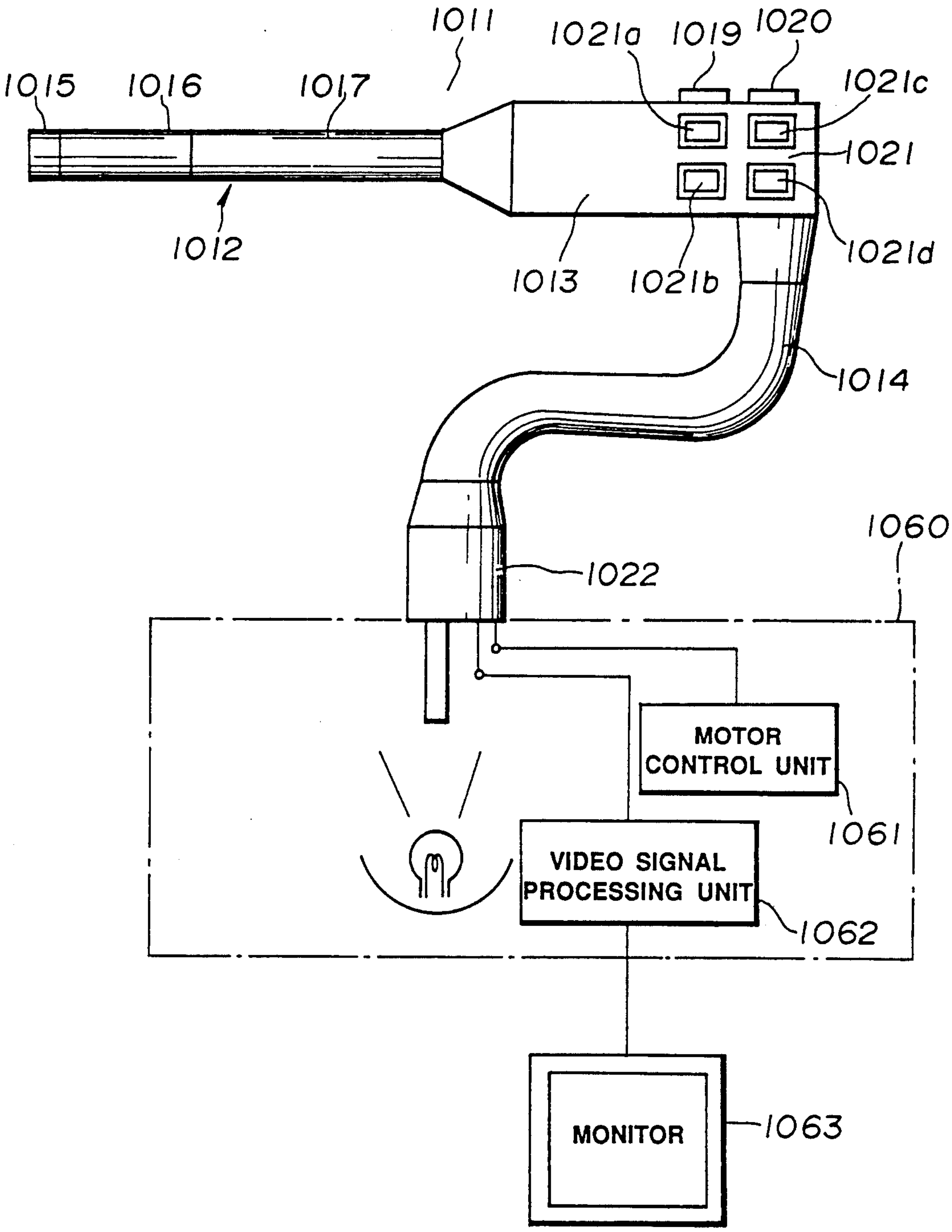

An endoscope 1011, entirety of which is shown in FIG. 130, comprises an insert section 1012, an operating section 1013, and a universal cord 1014 for light guide. The insert section 1012 comprises a distal end component 1015, a bendable portion 1016, and a flexible pipe portion 1017. This endoscope 1011 is of the electronic type. On the operating section 1013, there are provided an air-feed/water-feed switch button 1019, a suction switch button 1020, a bending switch area 1021 and others. The bending switch area 1021 includes an upward switch button **1021*a*, a downward switch button 1021*b*, a leftward switch button 1021*c*, and a rightward switch button 1021*d*, which are used for bending the bendable portion 1016 as described later. Furthermore, a connector 1022 for connection to an illumination light source unit 1060 (described later) is attached to the extended end of the universal cord 1014** for light guide.

In the body of the illumination light source unit 1060, there are disposed a motor control unit 1061 and a video signal processing unit 1062. By connecting the connector 1022 of the endoscope 1011 to the illumination light source unit 1060, those units 1061, 1062 are automatically connected to the side of the endoscope 1011. Then, a video signal processed by the video signal processing unit 1062 is sent to a monitor 1063.

Note that the motor control unit 1061 may be provided separately from the illumination light source unit 1060.

Figure 127:
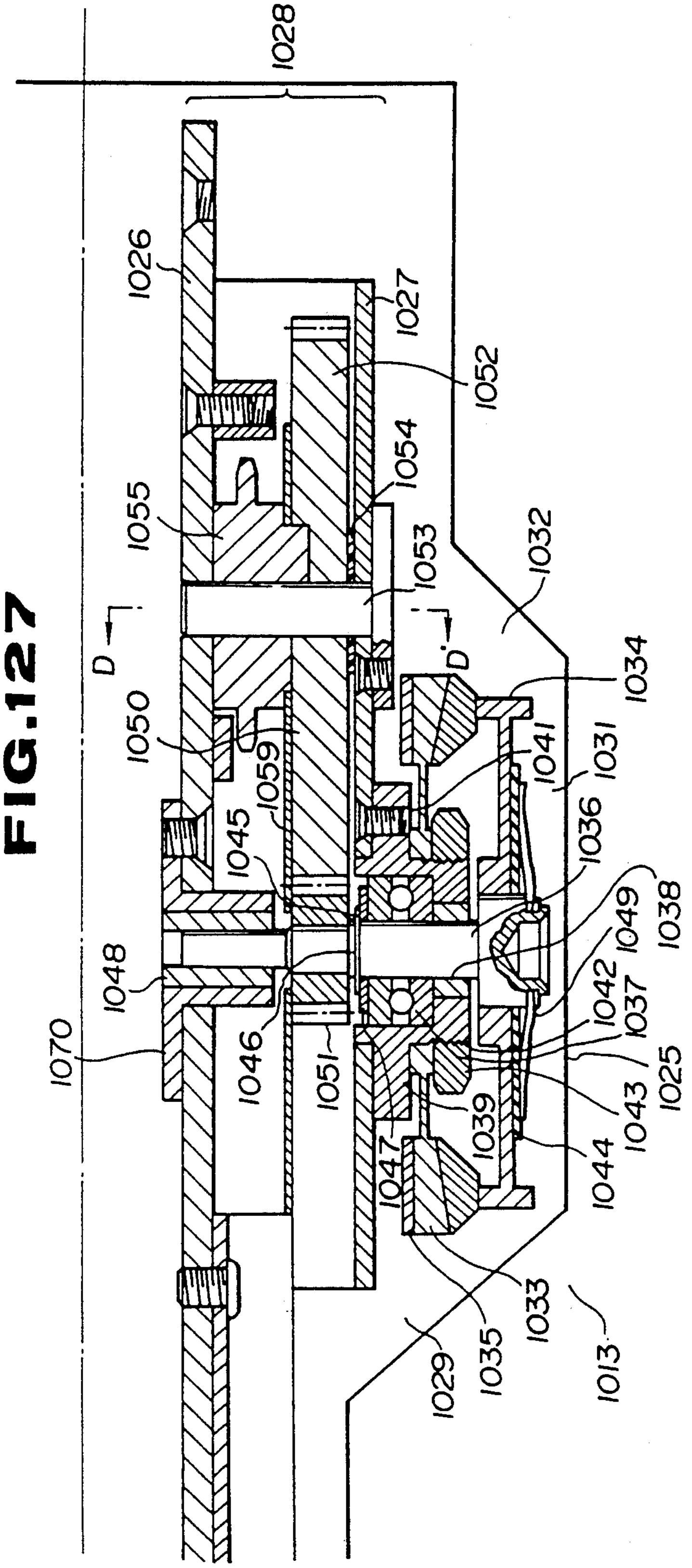
FIGS. 127 through 136 are concerned with five examples of a bending operation device of an endoscope apparatus in which a bending motor is disposed in an operating section and the operating section is made compact.
Figure 128:
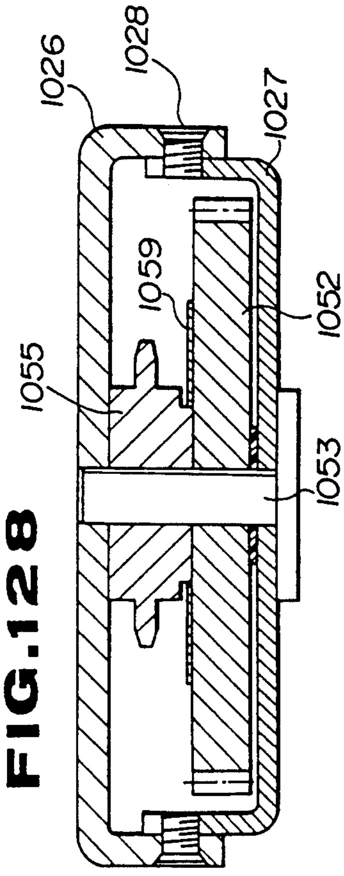

FIGS. 127 and 128 show the structure of a bending actuator incorporated in the operating section 1013 of the endoscope 1011. Within a case 1025 of the operating section 1013, there are disposed two sets of frame assemblies 1028, 1028 which are positioned in laterally symmetrical relation and each of which comprises a main frame 1026 and a sub-frame 1027 arranged parallel to each other with a certain distance or space defined therebetween. Then, a bending actuator 1029 for the vertical bending is mounted to one frame assembly 1028, while another bending actuator (not shown) for the horizontal bending is mounted to the other frame assembly 1028. FIG. 127 shows only one bending actuator 1029 for the vertical bending.

Because both of the bending actuators have the same structure, one bending actuator 1029 will be explained in detail below. A ultrasonic motor unit 1031 is mounted to the sub-frame 1027 supported by the main frame 1026. A ultrasonic motor 1032 in the ultrasonic motor unit 1031 comprises a disk-like stator 1033, and a rotor 1034 held in intimate contact with the surface of the stator 1033 facing the case 1025 in the peripheral portion of the stator. A piezoelectric element 1035 is fixedly bonded to the surface of the stator 1033 opposite to the rotor 1034 in the peripheral portion of the stator. The rotor 1034 is fitted and fixed to the distal end of a rotary shaft 1036. The rotary shaft 1036 is supported at its intermediate portion by a thrust bearing 1037 and a first radial bearing 1038. The thrust bearing 1037 and the first radial bearing 1038 are stored and supported in the same first bearing box 1039. The first bearing box 1039 is joined to the sub-frame 1027 and secured thereto by screws 1041. The stator 1033 is fitted over the outer periphery of the first bearing box 1039, and fixedly fastened by a nut 1043 meshed with male threads 1042 formed on the outer peripheral surface of the first bearing box 1039. Thus, the stator 1033 is fixed in place and unable to rotate.

The thrust bearing 1037 is supported by a snap ring 1047 at a predetermined position to the outer periphery of the rotary shaft 1036 via a washer 1047, the snap ring 1047 being fitted into a groove 1046 formed in the outer peripheral surface of the rotary shaft 1036. The inner end portion of the rotary shaft 1036 is supported by a second radial bearing 1048 held in a second bearing box 1070 which is mounted to the main frame 1026.

On the other hand, to the outer end of the rotary shaft 1036 thus supported is attached a belleville spring 1049 by caulking. The belleville spring 1049 serves to strongly biases the rotor 1034 in the direction in which the rotor 1034 is pressed against the stator 1033. In this respect, any desired biasing force can be selected by changing a thickness and/or the number of washer(s) 1047 used. A rubber sheet 1044 is interposed between the rotor 1034 and the belleville spring 1049 for protecting the rotor 1034 from damages and preventing a slippage between the rotor 1034 and the rotary shaft 1036.

Further, a drive gear 1051 of a transmission gear mechanism, e.g., a transmission gear train 1050, is fixedly mounted on the rotary shaft 1036 of the ultrasonic motor unit 1031 by means of shrinkage-fitting or the like at an intermediate position between the first radial bearing 1038 and the second radial bearing 1048. The drive gear 1051 is held in mesh with a driven gear 1052. The driven gear 1052 is supported by a shaft 1053 provided between the main frame 1026 and the sub-frame 1027 to be freely rotatable about the shaft 1053. A washer 1054 made of resin, for example, is interposed between the driven gear 1052 and the sub-frame 1027 for smoothing rotation of the driven gear 1052. A sprocket 1055 as a rotatable member for pulling operation is supported between the driven gear 1052 and the main frame 1026 in such a manner as freely rotatable about the shaft 1053. The driven gear 1052 and the sprocket 1055 are engaged with or joined by screws (not shown) or the like to each other for corotation.

Figure 129:
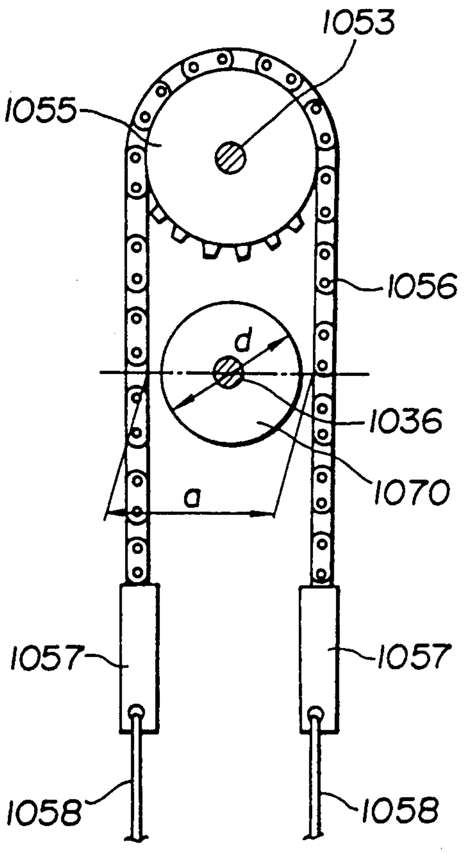

As shown in FIG. 129, a chain 1056 is entrained about the sprocket 1055, and bending wires 1058, 1058 are coupled to both ends of the chain 1056 via joint pieces 1057, 1057, respectively. Thus, the chain 1056 and the bending wires 1058, 1058 jointly constitute a pulling member. These bending wires 1058, 1058 are extended through the insert section 1012 and coupled to the front end of the bendable portion 1016 or the rear end of the distal end component 1015. As the sprocket 1055 rotates as described later, the bending wires 1058, 1058 are pushed and pulled dependent on the rotating direction of the sprocket 1055 to bend the bendable portion 1016. In addition, a partition 1059 is provided between the transmission gear train 1050 and the chain 1056, as shown in FIGS. 127 and 128, to prevent interference therebetween.

On the other hand, as shown in FIG. 129, the rotary shaft 1036 and the sprocket 1055 are arranged to be offset or away from each other in the axial direction of the operating section 1013. The width or spacing a between two runs of the chain 1056, which corresponds to the outer diameter of the sprocket 1055, is larger than the outer diameter d of the second bearing box 1070 located in the region of the width a. Accordingly, the second bearing box 1070 can be arranged between two runs of the chain 1056 with a proper allowance. Also, the second bearing box 1070 is kept from contacting the chain 1056.

Operation of the bending actuator 1029 will be described below. After inserting the insert section 1012 of the endoscope 1011 into the body cavity, when it is desired to bend the bendable portion 1016 upwards, the operator depresses the upward switch button **1021*a* in the bending switch area 1021. Upon the switch operation, the controlled drive voltage is applied to the piezoelectric element 1035 on the stator 1033, and a progressive wave in the predetermined direction is produced on the stator 1033. As a result, the rotor 1034 is rotated with the progressive wave in the predetermined direction. The rotation of the rotor 1034 is transmitted to the rotary shaft 1036 to rotate the drive gear 1051 secured to the rotary shaft 1036. Then, the rotation of the drive gear 1051 is transmitted to the driven gear 1052 for driving the sprocket 1055 integral with the driven gear 1052 to rotate. Accordingly, the chain 1056 is turned to pull the upper bending wire 1058 coupled to one end of the chain 1056 and let out the lower bending wire 1058. As a result, the bendable portion 1016 of the insert section 1012** is forcibly bent upwards.

Since the diameter of the driven gear 1052 is sufficiently smaller than the diameter of the drive gear 1051, the transmission gear train 1050 can increase the drive force based on the resulting transmitted rotation ratio. Also, since the drive gear 1051 and the sprocket 1055 are arranged to be offset or away from each other in the axial direction of the operating section 1013, and the width or spacing a between two runs of the chain 1056 corresponding to the outer diameter of the sprocket 1055 is set larger than the outer diameter d of the second bearing box 1070 supporting the rotary shaft 1036 of the drive gear 1051, as shown in FIG. 129, the chain 1056 is prevented from contacting the second bearing box 1070 and from failing to move.

When it is desired to bend the bendable portion 1016 downwards, the downward switch button **1021*b* in the bending switch area 1021 is depressed; when it is desired to bend the bendable portion 1016 leftwards, the leftward switch button 1021c in the bending switch area 1021 is depressed; and when it is desired to bend the bendable portion 1016 rightwards, the rightward switch button 1021c in the bending switch area 1021 is depressed. Upon such switch operation, the bendable portion 1016 is bent in the desired direction in a like manner to the above case. Note that when the bendable portion 1016 is bent in the rightward and leftward directions, it is operated by another bending actuator (not shown) which is provided in laterally symmetrical relation to the above bending actuator 1016**.

Although the sprocket 1055 and the chain 1056 are respectively used as the rotatable member and the pulling member in this first example, it is also possible to use a pulley and a pulling wire instead of the sprocket 1055 and the chain 1056, respectively.

Figure 131:
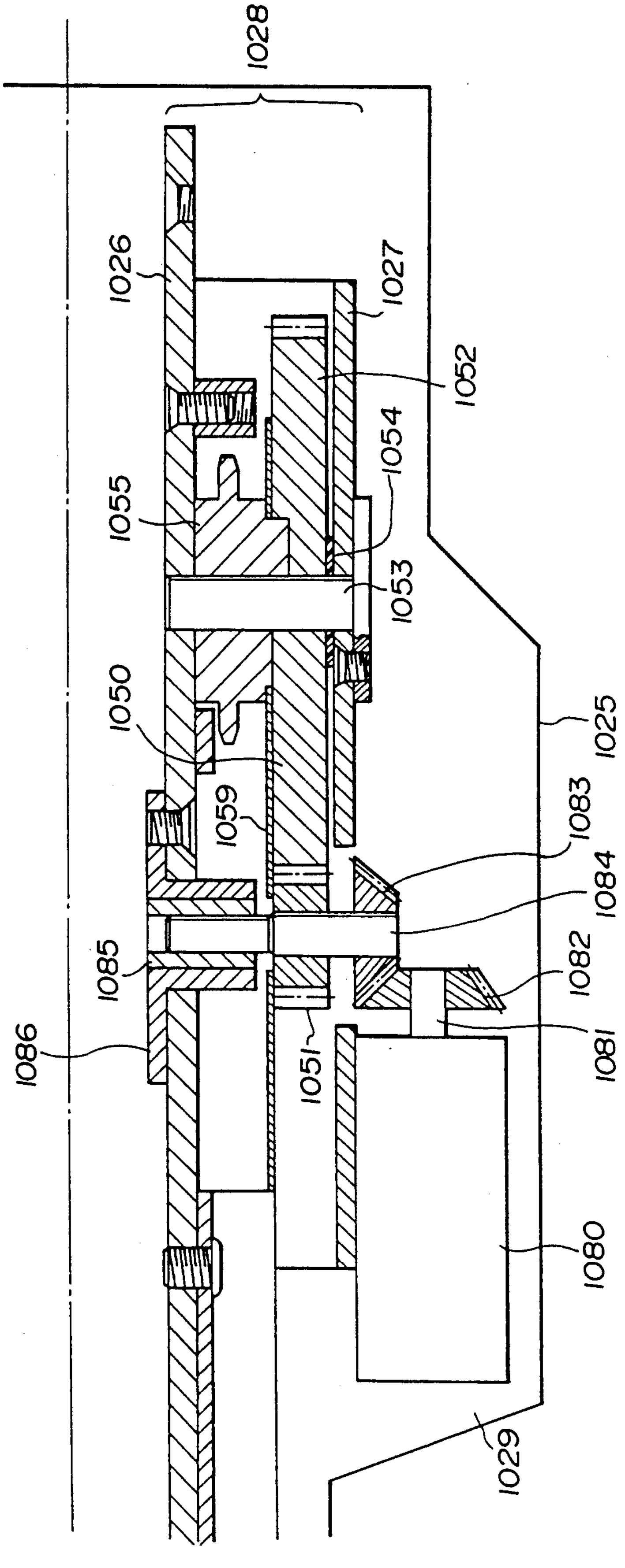

FIG. 131 illustrates the second example. In this example, a DC motor 1080 is used instead of the ultrasonic motor 1032 in the first example. A rotary shaft 1081 of a DC motor 1080 is arranged to lie in the axial direction of the operating section 1013 of the endoscope 1011, and attached to the outer surface of the sub-frame 1027. A bevel gear 1082 is fitted over the distal end of the rotary shaft 1081. Another bevel gear 1083 is held in mesh with the bevel gear 1082. Another bevel gear 1083 is attached to the outer end of a drive shaft 1084 arranged perpendicularly to the rotary shaft 1081. The drive shaft 1084 is supported by a bearing 1085 in turn held in a bearing box 1086 which is attached to the main frame 1026.

Further, a drive gear 1051 of a transmission gear train 1050 is secured to an intermediate portion of the drive shaft 1084 by means of shrinkage-fitting or the like, for example, and is held in mesh with a driven gear 1052. The drive gear 1051 and the driven gear 1052 cooperatively constitute the transmission gear train 1050 which has the small transmitted rotation ratio. The remaining constitution is similar to that of the above first example.

Now, when the upper switch button 1021a in the bending switch area 1021 is depressed, the rotary shaft 1081 of the DC motor 1080 is rotated and the resulting torque is transmitted from the drive gear 1051 to the driven gear 1052 of the transmission gear train 1050 via the bevel gears 1082, 1083 meshing with each other. The sprocket 1055 integral with the driven gear 1052 is then rotated. Subsequent operation proceeds in a like manner to the above first example. Specifically, as the chain 1056 is turned, the upper bending wire 1058 is pulled while letting out the lower bending wire 1058, whereby the bendable portion 1016 of the insert section 1012 is bent.

With this example, since the DC motor 1080 is used as a bending drive source, the drive voltage can be lowered in comparison with the case of using the aforesaid ultrasonic motor. This improves safety and economic efficiency. Even in the case of using a motor which is long in the axial direction, the operating section 1013 can be reduced in its thickness or diameter.

Furthermore, the drive motor may be of any other rotary type such as an AC motor or pulse motor. In addition, the above mentioned motor can be located at any desired position as long as the bevel gear 1082 fitted over the end of the rotary shaft 1081 of the motor is held in mesh with the bevel gear 1083.

Figure 132:
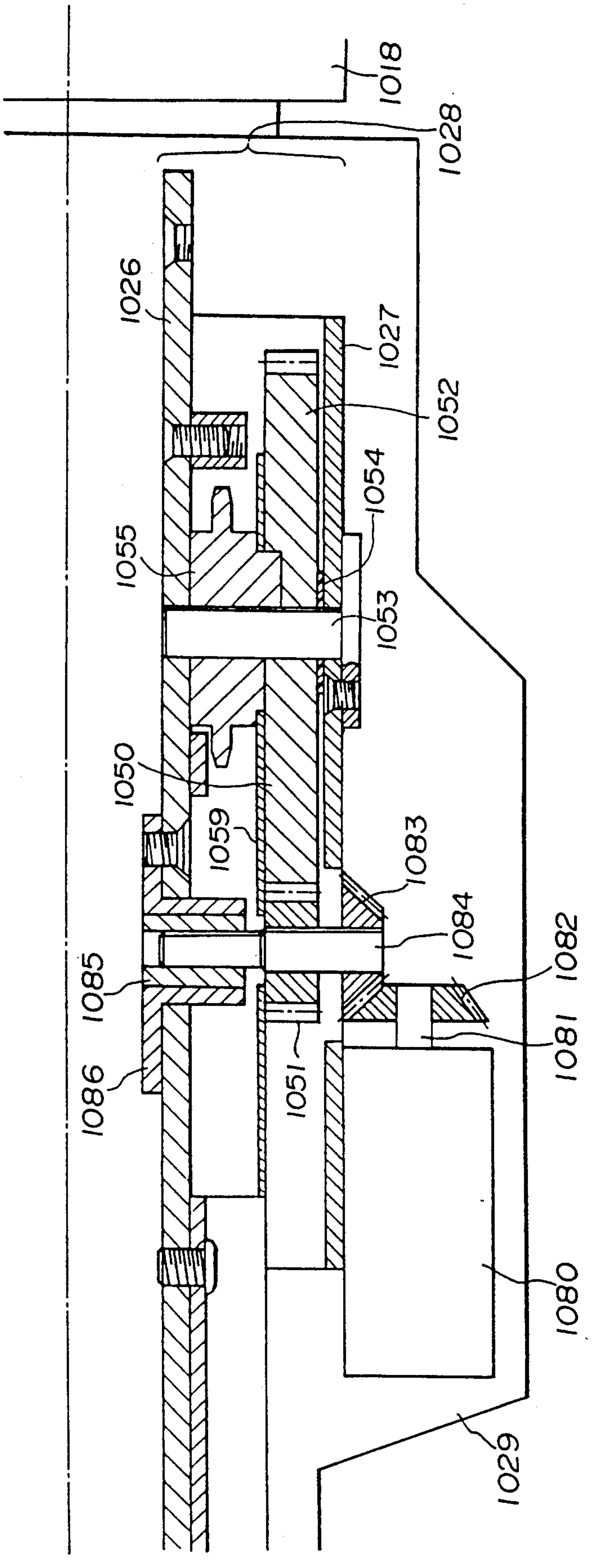

FIG. 132 illustrates the third example. In this example, the structure of the above second example is applied to a fiber scope in which an endoscope 1011 itself has an eyepiece portion 1018.

Figure 133:
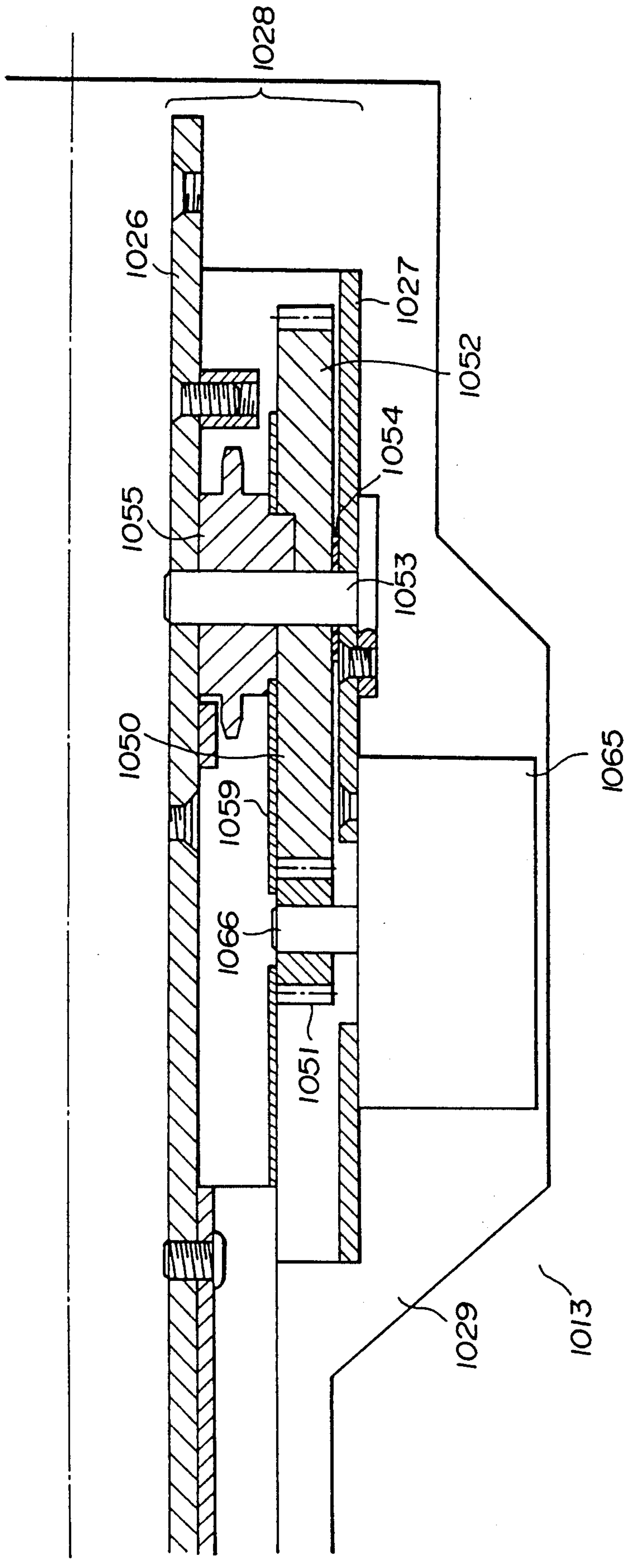

FIG. 133 illustrates the fourth example. In this example, a DC motor 1065 is used instead of the ultrasonic motor unit 1031 in the above first example. A drive gear 1051 similar to that as explained above is secured to a rotary shaft 1066 of the DC motor 1065.

By using the DC motor 1065, the drive voltage can be lowered in comparison with the case of using the aforesaid ultrasonic motor. This improves safety, economic efficiency and other factors.

Figure 134:
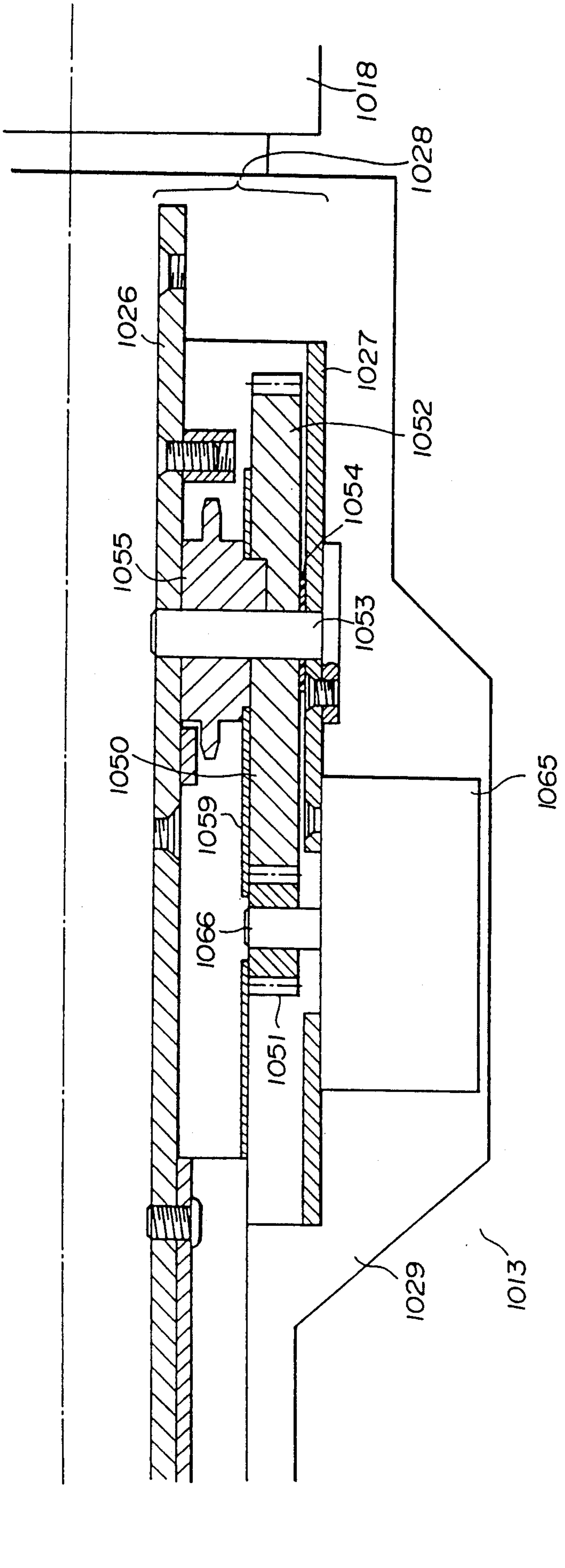

FIG. 134 illustrates the fifth example. In this example, the endoscope 1011 of the above fourth example is constituted as the fiber scope type. Therefore, an eyepiece portion 1018 is associated with the operating section 1013.

In the foregoing first through fifth examples, the transmission gear mechanism can be constituted by utilizing many variations such as in the number and combinations of gears used. The bending drive motor may be of any other type of vibration wave motor, or any other rotary type such as an AC motor or pulse motor.

According to the first through fifth examples, as described above, since a bearing to receive a rotary shaft of at least one of those gears constituting the transmission gear mechanism, which transmits rotation of the bending drive motor to the rotatable member for pulling operation, is disposed in the space surrounded by the rotatable member and the pulling member wound around the rotatable member, it is possible to suppress the entire length in the axial direction of the motor rotary shaft and achieve the compact structure even in the case of using the transmission gear mechanism to perform bending operation by a motor.

Moreover, according to the first through fifth examples, since in two bending actuators arranged side by side, the respective transmission gear trains are disposed on the outer side and the respective rotatable member for bending operation are disposed on the inner side, the operating section can be compacted without increasing the length and thickness or diameter of the operating section. Also, the drive force can be increased by the transmission gear train, and hence the bending drive motor can be made smaller in size as far as possible.

The present invention is not limited to that electronic endoscope which incorporates the solid imaging device in the distal end portion of the insert section, and also applicable to those types of endoscopes in which the object image focused by the objective lens is transmitted to the base end of the insert section through the image guide, and the transmitted image is observed by the naked eye in the eyepiece portion or picked up by imaging means.

Further, the present invention can be applied to not only endoscopes, but also various catheters for blood vessels or bile and pancreatic ducts. The present invention is not limited to medical purposes, and also applicable to endoscopes for industrial, engineering and other purposes.

It will be apparent that various and different embodiments of the present invention can be made in a wide range from the foregoing disclosure of the invention without departing from the spirit and scope of the invention. The present invention is defined by only the attached claims and is not restricted from the specific embodiments of the invention.

What is claimed is:

1. An endoscope apparatus comprising:

an elongate insert section including an observation window in the distal end portion and inserted into an object to be observed;

observation means for producing an endoscope image, said observation means including a focusing optical system which receives an incident light from said object through said observation window to focus said endoscope image; and vibration means for vibrating at least a part of said insert section in a direction crossing the axial direction of said insert section, said vibration means including a vibration unit capable of vibrating in itself to vibrate at least the part of said insert section even under a condition that said insert section is not contact with said object.

2. An endoscope apparatus according to claim 1, further comprising a bendable portion provided in a part of said insert section and capable of bending, and drive means for driving said bendable portion to bend, said vibration means including control means for controlling said drive means to vibrate said bendable portion as said vibration unit.

3. An endoscope apparatus according to claim 1, wherein said vibration means is provided outside said insert section.

4. An endoscope apparatus according to claim 1, wherein said vibration means is provided inside said insert section.

5. An endoscope apparatus according to claim 1, wherein said vibration unit is provided on the base end side of said insert section opposite to said distal end portion thereof.

6. An endoscope apparatus according to claim 1, wherein said vibration means vibrates at least the part of said insert section in one direction crossing the axial direction of said insert section in said part.

7. An endoscope apparatus according to claim 1, wherein said vibration means vibrates at least the part of said insert section in a combination of vibrations in plural directions crossing the axial direction of said insert section in said part.

8. An endoscope apparatus according to claim 1, further comprising drive means to reciprocate said insert section in the axial direction of said insert section.

9. An endoscope apparatus according to claim 1, further comprising drive means to rotate said insert section in a reciprocal manner about the axial direction of said insert section.

10. An endoscope apparatus according to claim 1, further comprising drive means to reciprocate said insert section in the axial direction of said insert section, and drive means to rotate said insert section in a reciprocal manner about the axial direction of said insert section.

11. An endoscope apparatus according to claim 1, wherein said vibration means vibrates said insert section in the wavy form.

12. An endoscope apparatus according to claim 1, wherein said vibration means includes a switching means to change over between the vibrating state and the non-vibrating state.

13. An endoscope apparatus according to claim 1, wherein said vibration means includes drive means able to vibrate at least the part of said insert section in plural modes, and selector means for selecting one or more of said vibrations modes of said drive means to actuate the selected vibration form.

14. An endoscope apparatus according to claim 1, wherein said vibration means includes control means for controlling conditions of vibration.

15. An endoscope apparatus according to claim 1, further comprising second vibration means to vibrate at least the part of said insert section in the mode different from the vibration mode produced by said vibration means.

16. An endoscope apparatus according to claim 15, wherein the vibration mode produced by said second vibration means includes at least one of the mode of reciprocating said insert section in the axial direction of said insert section, and the mode of rotating said insert section in a reciprocal manner about the axial direction of said insert section.

17. An endoscope apparatus according to claim 15, further comprising selector means to select one or more of the vibration mode(s) produced by said vibration means and the vibration mode(s) produced by said second vibration means.

18. An endoscope apparatus according to claim 15, further comprising control means to control at least one of vibrating conditions given by said vibration means and vibrating conditions given by said second vibration means.

19. An endoscope apparatus according to claim 1, further comprising detection means to detect a pressure exerted on at least a part of said insert section, and vibration control means to cause said vibration means to start vibration when said pressure detected by said detection means exceeds a predetermined value.

20. An endoscope apparatus according to claim 2, further comprising an operating section continuously provided at the base end of said insert section opposite to said distal end portion thereof, and connection means to connect between said operating section and an external device, said drive means being provided in said connection means.

21. An endoscope apparatus according to claim 20, wherein said drive means is provided in the end portion of said connection means on the same side as said operating section.

22. An endoscope apparatus comprising:

an abutment portion held in abutment with at least a part of an insert section of an endoscope; and fluctuation means for fluctuating said abutment portion such that at least the part of said insert section is vibrated in a direction crossing the axial direction of said insert section.

23. An insert apparatus for an object suitable for observing, examining or treating the object, comprising:

an elongate insert section inserted into the object; and vibration means for vibrating at least a part of said insert section in a direction crossing the axial direction of said insert section, said vibration means including a vibration unit capable of vibrating in itself to vibrate at least the part of said insert section even under a condition that said insert section is not contact with said object.

24. An endoscope apparatus comprising:

an elongate insert section including an observation window in the distal end portion and inserted into an object to be observed;

observation means for producing an endoscope image, said observation means including a focusing optical system which receives an incident light from said object through said observation window to focus said endoscope image;

vibration means for vibrating at least a part of said insert section in a direction crossing the axial direction of said insert section, said vibration means including a vibration unit capable of vibrating in itself to vibrate at least the part of said insert section even under a condition that said insert section is not contact with said object; and at least one of drive means for moving said insert section in the axial direction of said insert section, and drive means for rotating said insert section about the axial direction of said insert section.

25. An endoscope apparatus comprising:

an elongate insert section including an observation window in the distal end portion and inserted into an object to be observed;

an operating section continuously provided at the base end of said insert section opposite to said distal end portion thereof;

observation means for producing an endoscope image, said observation means including a focusing optical system which receives an incident light from said object through said observation window to focus said endoscope image;

a bendable portion provided in at least a part of said insert section and capable of bending;

drive means provided in said operating section for driving said bendable portion to bend; and control means for controlling said drive means to vibrate said bendable portion.

26. An endoscope apparatus comprising:

an endoscope body which has an elongate insert section including an observation window in the distal end portion and inserted into an object to be observed, observation means for producing an endoscope image, said observation means including a focusing optical system which receives an incident light from said object through said observation window to focus said endoscope image, and a bendable portion provided in at least a part of said insert section and capable of bending;

drive means provided in an external device to which said endoscope body is connected, for driving said bendable portion to bend; and control means for controlling said drive means to vibrate said bendable portion.

27. An endoscope apparatus comprising:

an endoscope body which has an elongate insert section including an observation window in the distal end portion and inserted into an object to be observed, observation means for producing an endoscope image, said observation means including a focusing optical system which receives an incident light from said object through said observation window to focus said endoscope image, a bendable portion provided in at least a part of said insert section and capable of bending, and a connector connected to an external device;

drive means provided in said connector for driving said bendable portion to bend; and control means for controlling said drive means to vibrate said bendable portion.

28. A method of reducing contact resistance of an insert section of an endoscope against an object to be observed, comprising the step of:

vibrating at least a part of said insert section in a direction crossing the axial direction of said insert section such that at least the part of said insert section vibrates in itself even under a condition that said insert section is not contact with the object, thereby reducing the contact area between said insert section and the object.

29. An insert apparatus for the body cavity to be inserted from the descending colon to the transverse colon, comprising:

an elongate insert section inserted into the body cavity; and vibration means for vibrating at least a part of said insert section in a direction crossing the axial direction of said insert section, said vibration means including a vibration unit capable of vibrating in itself to vibrate at least the part of said insert section even under a condition that said insert section is not contact with the body cavity.

* * * * *